United States Patent
Zhou et al.

(10) Patent No.: US 11,471,519 B2
(45) Date of Patent: *Oct. 18, 2022

(54) METHODS OF CANCER TREATMENT USING TUMOR ANTIGEN-SPECIFIC T CELLS

(71) Applicants: SYZ Cell Therapy Co., Guangdong (CN); HRYZ (Shenzhen) Biotech Co., Guangdong (CN)

(72) Inventors: Xiangjun Zhou, Shenzhen (CN); Yanyan Han, Shenzhen (CN); Xihe Chen, Shenzhen (CN); Xiaoling Liang, Shenzhen (CN)

(73) Assignees: SYZ Cell Therapy Co., Shenzhen (CN); HRYZ (Shenzhen) Biotech Co., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/571,430

(22) Filed: Jan. 7, 2022

(65) Prior Publication Data

US 2022/0125904 A1 Apr. 28, 2022

Related U.S. Application Data

(63) Continuation of application No. 17/047,057, filed as application No. PCT/CN2019/082407 on Apr. 12, 2019, now Pat. No. 11,219,676.

(30) Foreign Application Priority Data

Apr. 13, 2018 (WO) ................ PCT/CN2019/082407

(51) Int. Cl.
*A61K 39/00* (2006.01)
*A61P 35/00* (2006.01)
*C12N 5/0783* (2010.01)

(52) U.S. Cl.
CPC ............. *A61K 39/001157* (2018.08); *A61K 39/001149* (2018.08); *A61K 39/001153* (2018.08); *A61K 39/001186* (2018.08); *A61P 35/00* (2018.01); *C12N 5/0636* (2013.01); *A61K 2039/5158* (2013.01); *C12N 2501/24* (2013.01); *C12N 2501/515* (2013.01); *C12N 2502/1121* (2013.01)

(58) Field of Classification Search
CPC .... A61K 39/001157; A61K 39/001186; A61K 39/001153; A61K 2039/5158; C12N 5/0636
See application file for complete search history.

(56) References Cited

U.S. PATENT DOCUMENTS

| | | | |
|---|---|---|---|
| 5,399,346 A | 3/1995 | Anderson | |
| 5,580,859 A | 12/1996 | Felgner | |
| 5,589,466 A | 12/1996 | Felgner | |
| 6,326,193 B1 | 12/2001 | Liu | |
| 7,999,092 B2 | 8/2011 | Han | |
| 10,967,054 B2 | 4/2021 | Xiangjun et al. | |
| 11,219,675 B2 | 1/2022 | Zhou et al. | |
| 11,219,676 B2 * | 1/2022 | Zhou | A61K 39/001186 |
| 11,229,689 B2 | 1/2022 | Zhou et al. | |
| 11,248,208 B2 | 2/2022 | Zhou et al. | |
| 11,390,659 B2 | 7/2022 | Zhou et al. | |
| 2018/0078624 A1 | 3/2018 | Zhou | |
| 2021/0017495 A1 | 1/2021 | Zhou | |
| 2021/0113676 A1 | 4/2021 | Zhou et al. | |
| 2021/0154285 A1 | 5/2021 | Zhou et al. | |
| 2021/0198341 A1 | 7/2021 | Zhou et al. | |
| 2021/0268083 A1 | 9/2021 | Zhou et al. | |
| 2022/0211829 A1 | 7/2022 | Zhou et al. | |

FOREIGN PATENT DOCUMENTS

| | | |
|---|---|---|
| CN | 104946588 A | 9/2015 |
| EP | 2215220 B1 | 1/2018 |
| WO | 2001029058 A1 | 4/2001 |
| WO | 200196584 A2 | 12/2001 |
| WO | 2008033403 A2 | 3/2008 |
| WO | 2016145578 A1 | 9/2016 |
| WO | 2016146035 A1 | 9/2016 |
| WO | 2016154508 A1 | 9/2016 |
| WO | 2016189104 A1 | 12/2016 |
| WO | 2019183924 A1 | 10/2019 |
| WO | 2019185041 A1 | 10/2019 |

(Continued)

OTHER PUBLICATIONS

Han et al., Dynamic and specific immune responses against multiple tumor antigens were elicited in patients with hepatocellular carcinoma after cell-based immunotherapy, J Transl Med., 15(1):64, Publication Date: Mar. 22, 2017 (Year: 2017).*
Bernal, M. et al. (Sep. 2012, e-pub Jul. 26, 2012). "Implication Of The β2-microglobulin Gene In The Generation Of Tumor Escape Phenotypes" Cancer Immunol. Immunother 61(9):1359-1371.
Bissinger, A.L. et al. (2007). "Isolation And Expansion Of Human Cytomegalovirusspecific Cytotoxic T Lymphocytes Using Interferon-Secretion Assay," Experimental Hematology 30:1178-1184.
Brosterhus, H. et al. (1999). "Enrichment And Detection Of Live Antigen-Specific CD4+ And CDS+ T Cells Based on Cytokine Secretion," Eur. J. Immunol 29:4053-4049.
Datta, R. et al. (Nov. 1992). "Ionizing Radiation Activates Transcription of the EGR1 Gene Via CArG Elements," Proc. Natl. Acad. Sci. USA 89(1):10149-10153.
Davis, M.M. et al. (Apr. 1998). "Ligand Recognition By αβ T Cell Receptors," Annu Rev Immunol 16:(15):523-544.

(Continued)

*Primary Examiner* — Peter J Reddig
*Assistant Examiner* — Cheng Lu
(74) *Attorney, Agent, or Firm* — Morrison & Foerster LLP

(57) ABSTRACT

The present application provides methods of preparing tumor antigen-specific T cells comprising enriching activated T cells from a first co-culture comprising a first population of antigen-loaded dendritic cells loaded and a population of T cells, and co-culturing the enriched activated T cells with a second population of antigen-loaded dendritic cells. Also provided are methods of treating cancer in an individual using the tumor antigen-specific T cells, pharmaceutical compositions and kits for cell-based cancer immunotherapy.

20 Claims, 47 Drawing Sheets

(56) References Cited

FOREIGN PATENT DOCUMENTS

| WO | 2019196087 A1 | 10/2019 |
|---|---|---|
| WO | 2019196088 A1 | 10/2019 |
| WO | 2019196924 A1 | 10/2019 |

OTHER PUBLICATIONS

Davis, M.M. et al. (Aug. 4, 1988). "T-Cell Antigen Receptor Genes and T-Cell Recognition," Nature 334:395-402.

Edgar, R.C. (2004, e-pub. Mar. 19, 2004). "Muscle: Multiple Sequence Alignment With High Accuracy And High Throughput," Nucleic Acids Research 32(5):1792-1797.

Edgar, R.C. (Aug. 19, 2004). "Muscle: A Multiple Sequence Alignment Method With Reduced Time And Space Complexity," BMC Bioinformatics 5(113):1-19.

Gingrich, J.R. et al. (1998). "Inducible Gene Expression in the Nervous System of Transgenic Mice," Annual Rev. Neurosci. 21:377-405.

Han, Y. et al. (Mar. 22, 2017). "Dynamic and Specific Immune Responses Against Multiple Tumor Antigens Were Elicited In Patients With Hepatocellular Carcinoma After Cell-Based Immunotherapy," J. Transl. Med. 15(1):64, 13 pages.

IMGT Scientific Chart (Created Mar. 25, 1997). Located at http://www.imgt.org/IMGTScientificChart/Nomenclature/IMGT-FRCDRdefinition.html, last visited on Jan. 22, 2021, 2 pages.

International Search Report and Written Opinion of the International Searching Authority dated Jul. 17, 2019, for International Patent Application No. PCT/CN2019/082407, filed Apr. 12, 2019, 9 pages.

IPAR AnalyzerTM User's Guide. Brochure from iRepertoire Inc., V20200916, located at https://irepertoire.com/wp-content/uploads/2020/02/20200916-iPair-demo_CRBedits.pdf last visited Jan. 22, 2021, 19 pages.

Kim, J.H. et al. (Apr. 2011). "High Cleavage Efficiency of a 2A Peptide Derived from Porcine Teschovirus-1 in Human Cell Lines, Zebrafish and Mice," PLOS One 6(4):e18556, 8 pages.

Larche, M. (2008). "Determining MHC Restriction of T-Cell Responses," No. 6 in Methods Mol. Med., Jones, M.G et al. eds., Humana Press, Totowa, New Jersey, USA, 138:57-72, 27 pages.

Lefranc, M.-P. (1999). "The IMGT Unique Numbering For Immunoglobulins, T-Cell Receptors, and Ig-Like Domains," The Immunologist 7(4):132-136.

Mader, S. et al. (Jun. 1993). "A Steroid-Inducible Promoter for the Controlled Overexpression of Cloned Genes in Eukaryotic Cells." Proc. Natl. Acad. Sci. USA 90:5603-5607.

Manome, Y. et al. (Oct. 1993). "Coinduction of c-jun Gene Expression and Internucleosomal DNA Fragmentation by Ionizing Radiation," Biochemistry 32(40):10607-10613.

Melero, I. et al. (Aug. 2015). "Evolving Synergistic Combinations Of Targeted Immunotherapies To Combat Cancer," Nature Review Cancer 15:457-472.

Restifo, N.P. et al. (Apr. 2012). "Adoptive Immunotherapy For Cancer: Harnessing The T Cell Response," Nat. Rev. Immunol. 12:269-281.

Shukla, S.A. et al. (Nov. 2015; e-published on Sep. 15, 2015). "Comprehensive Analysis of Cancer-Associated Somatic Mutations in Class I HLA Genes," Nature Biotechnology 33(11):1152-1158.

Spencer, D. M. et al. (Nov. 12, 1993). "Controlling Signal Transduction with Synthetic Ligands," Science 262 (5136):1019-1024.

U.S. Appl. No. 17/668,746, filed Feb. 10, 2022, by Zhou.(Copies of U.S. Patent Applications are not submitted herewith pursuant to the waiver of 37 C.F.R. § 1.98(a)(2)(iii) issued by the Office dated Sep. 21, 2004).

U.S. Appl. No. 17/843,912, filed Jun. 17, 2022, by Zhou.(Copies of U.S. Patent Applications are not submitted herewith pursuant to the waiver of 37 C.F.R. § 1.98(a)(2)(iii) issued by the Office dated Sep. 21, 2004).

U.S. Appl. No. 17/843,916, filed Jun. 17, 2022, by Zhou.(Copies of U.S. Patent Applications are not submitted herewith pursuant to the waiver of 37 C.F.R. § 1.98(a)(2)(iii) issued by the Office dated Sep. 21, 2004).

U.S. Appl. No. 17/843,917, filed Jun. 17, 2022, by Zhou.(Copies of U.S. Patent Applications are not submitted herewith pursuant to the waiver of 37 C.F.R. § 1.98(a)(2)(iii) issued by the Office dated Sep. 21, 2004).

U.S. Appl. No. 17/843,920, filed Jun. 17, 2022, by Zhou.(Copies of U.S. Patent Applications are not submitted herewith pursuant to the waiver of 37 C.F.R. § 1.98(a)(2)(iii) issued by the Office dated Sep. 21, 2004).

Ui-Tel, K. et al. (2000). "Sensitive Assay of RNA Interference in Drosophila and Chinese Hamster Cultured Cells Using Firefly Luciferase Gene As Target," FEBS Letters 479:79-82.

Vigneron, N. et al. (Jul. 15, 2013). "Database of T Cell-Defined Human Tumor Antigens: the 2013 Update," Cancer Immunity 13:15, pp. 1-6.

Wolfl, M. et al. (Apr. 2014, e-pub. Mar. 27, 2014). "Antigen-Specific Activation And Cytokine-Facilitated Expansion Of Naive, Human CD8+ T Cells," Nature Protocols 9(4):950-966, 38 pages.

Yang, X. et al. (2009; e-published on Dec. 19, 2008). "An Introduction to Epitope Prediction Methods and Software" Rev. Med. Virol. 19(2):77-96.

\* cited by examiner

METHODS OF CANCER TREATMENT USING TUMOR ANTIGEN-SPECIFIC T CELLS

CROSS-REFERENCE TO RELATED APPLICATIONS

This application is a Continuation Patent Application of U.S. patent application Ser. No. 17/047,057, which adopts an international filing date of Apr. 12, 2019, and is a national phase application under 35 U.S.C. § 371 of International Application No. PCT/US2019/082407, filed internationally on Apr. 12, 2019, which claims the priority benefit of International Patent Application No. PCT/CN2018/082945, filed Apr. 13, 2018, the contents of each of which are incorporated herein by reference in their entirety.

FIELD OF THE INVENTION

The present application relates to the field of cancer immunotherapy. More specifically, this application provides methods, compositions and kits for treating cancer in an individual using tumor antigen-specific T cells.

BACKGROUND OF THE INVENTION

The human body has an elaborate immune system to defend itself against diseases. Unleashing the body's own immunity against cancer has been a long-standing ideal in oncology. Natural immune response against a tumor is elicited by tumor antigens. Antigen presenting cells (APCs), notably dendritic cells (DCs), can process and present the tumor antigens on their cell surface. Upon maturation, DCs loaded with tumor antigens can trigger T cell response, which involves cytotoxic T cells, helper T cells, and functionally distinct effecter and memory T cells against cancer cells expressing the tumor antigens. A particularly powerful type of T cell response involves production of cytotoxic T cells that can kill cancer cells by releasing cytokines, enzymes, and cytotoxins, or by inducing pro-apoptosis signaling cascades via cell-cell interactions.

Cell-based cancer immunotherapy seeks to treat cancer by administering to patients immunity-mediating cells prepared to target tumor antigens. FDA-approved PROVENGE® (sipuleucel-T) is a DC-based therapy, comprising exposing a patient's peripheral blood mononuclear cells (PBMCs) to a fusion protein comprising a tumor-derived antigen coupled to a cytokine, and then infusing the PBMCs, presumably containing activated DCs that can present the tumor-derived antigen to T cells, to the patient. See, U.S. Pat. No. 6,210,662. Adoptive T-cell therapy involves isolating tumor-infiltrating lymphocytes (TIL) from a patient's tumor, expanding the TILs ex vivo, and infusing the TILs back to the patient after depleting the patient's native non-myeloid lymphocytes. See, Restifo N P et al. (2012) *Nat. Rev. Immunol.* 12: 269-81. T cells with engineered T cell receptors (TCR-T) or chimeric antigen receptors (CAR-T) further expand the capacity of adoptive T-cell therapy methods by modifying the microenvironment of T cell-tumor interactions. Recently, a Multiple Antigen Specific Cell Therapy ("MASCT") method has been designed to harness the therapeutic capacity of both DCs and activated T cells in order to provide a safe, durable and customizable treatment to cancer patients. See, International Patent Application Publication No. WO2016145578A1. Improved MASCT methods have been described in International Patent Application No. PCT/CN2018/081338.

The disclosures of all publications, patents, patent applications and published patent applications referred to herein are hereby incorporated herein by reference in their entirety.

BRIEF SUMMARY OF THE INVENTION

The present application provides methods of preparing tumor antigen-specific T cells, and methods of treating cancer in an individual using the tumor antigen-specific T cells.

One aspect of the present application provides a method of preparing a population of tumor antigen-specific T cells, the method comprising: a) a first co-culturing step, comprising co-culturing a first population of dendritic cells ("DCs") loaded with a plurality of tumor antigen peptides with a population of T cells to obtain a first co-culture comprising activated T cells; b) an enrichment step, comprising subjecting the first co-culture to an enrichment process to obtain an enriched population of activated T cells; and c) a second co-culturing step, comprising co-culturing the enriched population of activated T cells with a second population of DCs loaded with one or more tumor antigen peptides from the plurality of tumor antigen peptides (e.g., a tumor antigen peptide from the plurality of tumor antigen peptides, or the plurality of tumor antigen peptides) to obtain a population of tumor antigen-specific T cells. In some embodiments, the first co-culturing step is carried out for no more than about 7 days (such as about 1 to about 3 days, about 2 days or about 3 days) prior to the enrichment step.

In some embodiments according to any one of the methods described above, the ratio between the population of T cells to the first population of DCs loaded with the plurality of tumor antigen peptides is no more than about 30:1 (such as about 10:1 to about 20:1, or about 15:1 or about 20:1). In some embodiments, the first population of DCs loaded with the plurality of tumor antigen peptides and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., an anti-PD-1 antibody, such as SHR-1210). In some embodiments, the first co-culture medium comprises IL-2 and an anti-PD-1 antibody. In some embodiments, the first co-culture medium comprises IL-2, IL-7, IL-15 and IL-21 and an anti-PD-1 antibody.

In some embodiments according to any one of the methods described above, the enrichment step comprises contacting the first co-culture with antigen presenting cells (APCs, such as PBMCs) loaded with the plurality of tumor antigen peptides to obtain a stimulated co-culture, and isolating from the stimulated co-culture a population of enriched activated T cells using a ligand that specifically recognizes a cytokine (e.g., IFNγ). In some embodiments, the enrichment step comprises contacting the first co-culture with APCs (e.g., PBMCs) loaded with the plurality of tumor antigen peptides to obtain a stimulated co-culture, and isolating from the stimulated co-culture a population of enriched activated T cells using a ligand that specifically recognizes a cell surface molecule. In some embodiments, the ratio between the enriched population of activated T cells and the second population of DCs loaded with one or more tumor antigen peptides from the plurality of tumor antigen peptides is about 1:1 to about 20:1 (e.g., about 1:1, about 2:1 or about 4:1). In some embodiments, the enriched population of activated T cells and the second population of DCs loaded with the plurality of tumor antigen peptides are co-cultured for about 12 to 25 days (such as about 15 days to 21 days).

In some embodiments according to any one of the methods described above, the second co-culturing step comprises co-culturing the second population of DCs loaded with one or more tumor antigen peptides from the plurality of tumor antigen peptides with the enriched population of activated T cells in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the one or more cytokines is added to the second co-culture no more than about 3 days (e.g., about 2 days) after the second co-culturing step starts. In some embodiments, the one or more cytokines comprises IL-2. In some embodiments, the one or more cytokines comprises IL-2, IL-7, IL-15 and IL-21. In some embodiments, the immune checkpoint inhibitor is an anti-PD-1 antibody (e.g., SHR-1210).

In some embodiments according to any one of the methods described above, the method further comprises a third co-culturing step comprising co-culturing a population of the tumor antigen-specific T cells with a population of antigen presenting cells (APCs) loaded with one or more tumor antigen peptides from the plurality of tumor antigen peptides (e.g., a tumor antigen peptide from the plurality of tumor antigen peptides, or the plurality of tumor antigen peptides) to obtain a second population of tumor antigen-specific T cells. In some embodiments, the APCs are PBMCs. In some embodiments, the APCs are DCs. wherein the ratio between the population of tumor antigen-specific T cells and the population of APCs loaded with one or more tumor antigen peptides from the plurality of tumor antigen peptides is about 1:1 to about 20:1 (e.g., about 1:1, about 2:1 or about 4:1). In some embodiments, the population of tumor antigen-specific T cells and the third population of DCs loaded with one or more tumor antigen peptides from the plurality of tumor antigen peptides are co-cultured for about 5 to 9 days (such as about 7 days). In some embodiments, the population of tumor antigen-specific T cells and the population of APCs loaded with one or more tumor antigen peptides from the plurality of tumor antigen peptides are co-cultured in a third co-culture medium comprising one or more cytokines (such as IL-2 or a plurality of cytokines, e.g., IL-2, IL-7, and IL-15) and an anti-CD3 antibody (e.g., OKT3). In some embodiments, the third co-culture medium comprises IL-2 and OKT3. In some embodiments, the third co-culture medium comprises IL-2, IL-7, IL-15 and OKT3. In some embodiments, the third co-culturing step is repeated, e.g., once, twice or three times.

In some embodiments according to any one of the methods described above, the first co-culturing step further comprises contacting a population of DCs with a plurality of tumor antigen peptides to obtain the first population of DCs loaded with the plurality of tumor antigen peptides. In some embodiments, the second co-culturing step further comprises contacting a population of DCs with one or more tumor antigen peptides from the plurality of tumor antigen peptides to obtain the second population of DCs loaded with the plurality of tumor antigen peptides. In some embodiments, the first co-culturing step comprises culturing the first population of DCs loaded with the plurality of tumor antigen peptides in a DC maturation medium comprising a toll-like receptor (TLR) agonist. In some embodiments, the second co-culturing step comprises culturing the second population of DCs loaded with one or more tumor antigen peptides from the plurality of tumor antigen peptides in a DC maturation medium comprising a toll-like receptor (TLR) agonist. In some embodiments, the DC maturation medium comprises INFγ, MPLA and PGE2. in some embodiments, the population of DCs is obtained by inducing differentiation of a population of monocytes from PBMCs In some embodiments according to any one of the methods described above, the population of T cells in the first co-culturing step is present in a population of PBMCs. In some embodiments, the population of DCs and the population of T cells are obtained from the same individual, e.g., the individual being treated.

In some embodiments according to any one of the methods described above, the plurality a tumor antigen peptides is a plurality of synthetic tumor antigen peptides. In some embodiments, the plurality of tumor antigen peptides is not obtained from a cell sample.

In some embodiments according to any one of the methods described above, the plurality of tumor antigen peptides comprises general tumor antigen peptide(s), cancer-type specific antigen peptide(s), and/or neoantigen peptides. In some embodiments, the plurality of tumor antigen peptides comprises one or more neoantigen peptides. In some embodiments, the plurality of tumor antigen peptides comprises (e.g., consists of) neoantigen peptides. In some embodiments, the plurality of tumor antigen peptides comprises at least about 5 (e.g., at least about 10, 20, 30, 40 or more) different tumor antigen peptides.

Another aspect of the present application provides an isolated population of cells prepared using any one of the methods described above. In some embodiments, the isolated population of cells comprises at least about 3% of tumor antigen-specific T cells that secrete INF-γ upon stimulation with the plurality of tumor antigen peptides. In some embodiments, the isolated population of cells comprises at least about 3% of tumor antigen-specific T cells that secrete TNF-α upon stimulation with the plurality of tumor antigen peptides.

Also provided is a method of treating a cancer in an individual, comprising administering to the individual an effective amount of the tumor antigen-specific T cells prepared by any one of the methods described above. In some embodiments, the method further comprises administering to the individual an effective amount of DCs loaded with the plurality of tumor antigen peptides. In some embodiments, the DCs and the tumor antigen-specific T cells are derived from the individual being treated. In some embodiments, the method further comprises freezing a population of the tumor antigen-specific T cells to obtain a frozen stock, co-culturing a thawed population of tumor antigen-specific T cells from the frozen stock with a population of APCs (e.g., DCs or PBMCs) loaded with one or more tumor antigen peptides from the plurality of tumor antigen peptides to provide a second population of tumor antigen-specific T cells, and administering an effective amount of the second population of tumor antigen-specific T cells. In some embodiments, the method comprises one or more cycles of: (a) co-culturing a population of tumor antigen-specific T cells from a stock of the tumor antigen-specific T cells with a population of APCs (e.g., DCs or PBMCs) loaded with one or more tumor antigen peptides from the plurality of tumor antigen peptides to provide a further population of tumor antigen-specific T cells, and (b) administering an effective amount of the tumor antigen-specific T cells from the further population. In some embodiments, the tumor antigen-specific T cells are administered intravenously. In some embodiments, the DCs loaded with the plurality of tumor antigen peptides are administered subcutaneously.

In some embodiments according to any one of the methods of treatment described above, the individual is a human individual. In some embodiments, the individual has previously received an immunotherapy. In some embodiments, the individual is immunologically responsive to the immunotherapy. In some embodiments, the immunotherapy is selected from the group consisting of an immune checkpoint inhibitor, an adoptive immune cell therapy, a cancer vaccine, an oncolytic virus and combinations thereof. In some embodiments, the individual is capable of developing a specific immune response against the plurality of tumor antigen peptides. In some embodiments, the individual has clinically benefited from a Multiple-Antigens Stimulating Cellular Therapy (MASCT, including "improved MASCT" and other variant MASCT methods) comprising administering to the individual an effective amount of activated T cells prepared b co-culturing a population of T cells with a population of DCs loaded with the plurality of tumor antigen. In some embodiments, the individual has partial response (PR), complete response (CR), or stable disease (SD) for at least 6 months (e.g., at least one year, 2 years or more) after receiving the MASCT.

Further provided are pharmaceutical compositions, kits, and articles of manufacture for use in any one of the methods described above.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE DRAWINGS

FIG. 2B shows consistently strong immune response by the patient's PBMCs against the HPV18-E7, RGS-5 and CPA peptides.

DETAILED DESCRIPTION OF THE INVENTION

Figure 1:
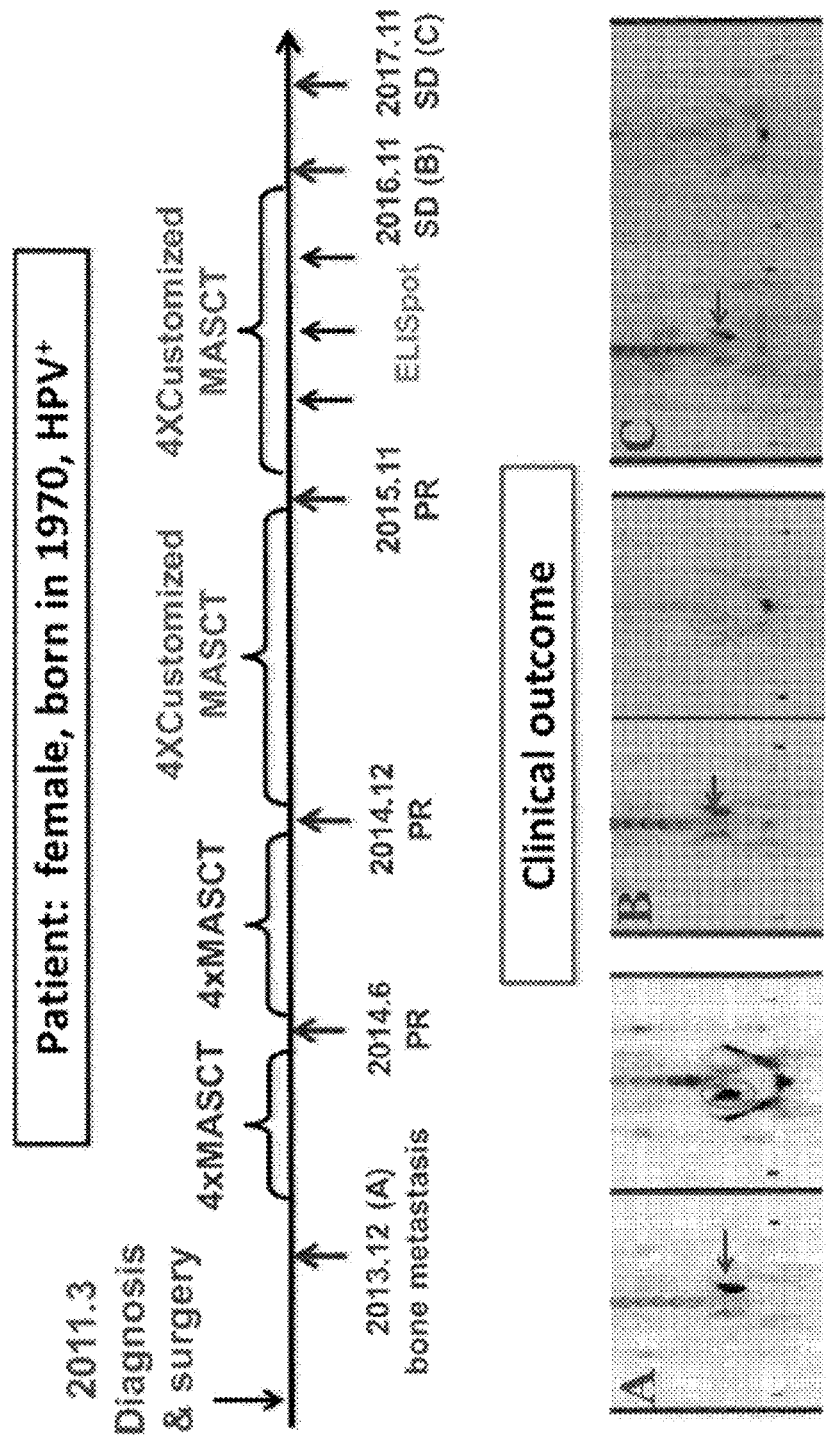
FIG. 1 shows clinical data of a patient with metastatic cervical cancer treated with MASCT. The bottom panel shows ECT results of the patent taken in December 2013 (prior to any MASCT treatments), in November 2016 (after achieving Stable Disease status on MASCT), and in November 2017. The arrows and circles point to the metastasis site on the right sacroiliac joint bone, showing reduction of the metastatic tumor and no additional metastasis in response to MASCT treatments.

The present application provides methods of preparing tumor antigen-specific T cells for cancer treatment. The methods described herein comprise enrichment of activated T cells from a co-culture of cells with antigen-loaded dendritic cells ("DCs"), followed by co-culturing of the enriched activated T cells with antigen-loaded DCs, thereby providing tumor antigen-specific T cells. In some embodiments, a population of the tumor antigen-specific T cells (e.g., from a frozen stock) is further co-cultured with antigen presenting cells (APCs) loaded with one or more tumor antigen peptides from the plurality of tumor antigen peptides to provide further populations of tumor antigen-specific T cells. The methods described herein enable preparation of tumor antigen-specific T cells at a high concentration in the co-culture and with high yield to satisfy the need for a sustainable source of efficacious tumor antigen-specific T cells in Multiple Antigen Specific Cell Therapy methods ("MASCT") or variations thereof.

Accordingly, one aspect of the present application provides a method of preparing a population of tumor antigen-specific T cells, the method comprising: a) a first co-culturing step, comprising co-culturing a first population of DCs loaded with a plurality of tumor antigen peptides with a population of T cells to obtain a first co-culture comprising activated T cells; b) an enrichment step, comprising subjecting the first co-culture to an enrichment process to obtain an enriched population of activated T cells; and c) a second co-culturing step, comprising co-culturing the enriched population of activated T cells with a second population of DCs loaded with one or more tumor antigen peptides from the plurality of tumor antigen peptides to obtain a population of tumor antigen-specific T cells. In some embodiments, the method further comprises a third co-culturing step, comprising co-culturing a population of the tumor antigen-specific T cells with a third population of APCs (e.g., DCs or PBMCs) loaded with one or more tumor antigen peptides from the plurality of tumor antigen peptides to provide a second population of tumor antigen-specific T cells. In some embodiments, the third co-culturing step is repeated for one or more times.

Tumor antigen-specific T cells prepared using the methods described herein, methods of treating cancer, compositions, kits, and articles of manufacture are also provided.

I. Definitions

Terms are used herein as generally used in the art, unless otherwise defined as follows.

As used herein, "a plurality of tumor antigen peptides," "multiple tumor antigen peptides," "a pool of tumor antigen peptides" and "a tumor antigen peptides pool" are used interchangeably to refer to a combination of two or more tumor antigen peptides.

As used herein, "antigen presenting cells loaded with a plurality of tumor antigen peptides" and "antigen presenting cells loaded with one or more tumor antigen peptides" are also referred to as "antigen-loaded antigen presenting cells." Antigen presenting cells ("APCs") loaded with a plurality of tumor antigen peptides are APCs that have enhanced presentation of one or more tumor antigen peptides or fragments thereof among the plurality of tumor antigen peptides. In some embodiments, the antigen-loaded APCs are antigen-loaded DCs. In some embodiments, the antigen-loaded APCs are antigen-loaded PBMCs.

As used herein, "activated T cells" refer to a population of monoclonal (e.g. encoding the same TCR) or polyclonal (e.g. with clones encoding different TCRs) T cells that have T cell receptors that recognize at least one tumor antigen peptide. Activated T cells may contain one or more subtypes of T cells, including, but not limited to, cytotoxic T cells, helper T cells, natural killer T cells, γδ T cells, regulatory T cells, and memory T cells.

"Tumor antigen-specific T cells" and "tumor specific T cells" are used herein interchangeably.

As used herein, "immune checkpoint inhibitor" refers to an agent (including an antibody) that inhibits or blocks an inhibitory immune checkpoint molecule on an immune cell (such as T cell) or a tumor cell. "Immune checkpoint molecules" include molecules that turn up an immune signal (i.e., "co-stimulatory molecules"), or molecules that turn down an immune signal (i.e., "inhibitory immune checkpoint molecules") against a tumor cell.

As used herein, treatment or "treating" is an approach for obtaining beneficial or desired results including clinical results. For purposes of this invention, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread (e.g., metastasis) of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The terms "individual," "subject" and "patient" are used interchangeably herein to describe a mammal, including humans. An individual includes, but is not limited to, human, bovine, horse, feline, canine, rodent, or primate. In some embodiments, the individual is human. In some embodiments, an individual suffers from a disease, such as cancer. In some embodiments, the individual is in need of treatment.

As is understood in the art, an "effective amount" refers to an amount of a composition (e.g. antigen-loaded DCs, or tumor antigen-specific T cells) sufficient to produce a desired therapeutic outcome (e.g., reducing the severity or duration of, stabilizing the severity of, or eliminating one or more symptoms of cancer). For therapeutic use, beneficial or desired results include, e.g., decreasing one or more symptoms resulting from the disease (biochemical, histologic and/or behavioral), including its complications and intermediate pathological phenotypes presented during development of the disease, increasing the quality of life of those suffering from the disease, decreasing the dose of other medications required to treat the disease, enhancing effect of another medication, delaying the progression of the disease, and/or prolonging survival of patients.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "combination therapy" means that a first agent is administered in conjunction with another agent. "In conjunction with" refers to administration of one treatment modality in addition to another treatment modality, such as administration of the tumor antigen-specific T cells described herein in addition to administration of another agent (such as an immune checkpoint inhibitor) to the same individual. As such, "in conjunction with" refers to administration of one treatment modality before, during, or after delivery of the other treatment modality to the individual. Such combinations are considered to be part of a single treatment regimen or regime.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to an individual without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The following definitions may be used to evaluate response based on target lesions: "complete response" or "CR" refers to disappearance of all target lesions; "partial response" or "PR" refers to at least a 30% decrease in the sum of the longest diameters (SLD) of target lesions, taking as reference the baseline SLD; "stable disease" or "SD" refers to neither sufficient shrinkage of target lesions to qualify for PR, nor sufficient increase to qualify for PD, taking as reference the nadir SLD since the treatment started; and "progressive disease" or "PD" refers to at least a 20% increase in the SLD of target lesions, taking as reference the nadir SLD recorded since the treatment started, or, the presence of one or more new lesions.

The following definitions of response assessments may be used to evaluate a non-target lesion: "complete response" or "CR" refers to disappearance of all non-target lesions; "stable disease" or "SD" refers to the persistence of one or more non-target lesions not qualifying for CR or PD; and "progressive disease" or "PD" refers to the "unequivocal progression" of existing non-target lesion(s) or appearance of one or more new lesion(s) is considered progressive disease (if PD for the individual is to be assessed for a time point based solely on the progression of non-target lesion(s), then additional criteria are required to be fulfilled.

As used herein, the terms "cell", "cell line", and "cell culture" are used interchangeably and all such designations include progeny. It is understood that all progeny may not be precisely identical in DNA content, due to deliberate or inadvertent mutations. Variant progeny that have the same function or biological activity as the original cells are included.

The term "peptide" refers to a polymer of amino acids no more than about 100 amino acids (including fragments of a protein), which may be linear or branched, comprise modified amino acids, and/or be interrupted by non-amino acids. The term also encompasses an amino acid polymer that has been modified naturally or by intervention, including, for example, disulfide bond formation, glycosylation, lipidation, acetylation, phosphorylation, or any other manipulation or modification. Also included within this term are, for example, peptides containing one or more analogs of an amino acid (including, for example, unnatural amino acids, etc.), as well as other modifications known in the art. The peptides described herein may be naturally-occurring, i.e., obtained or derived front a natural source (e.g., blood) or synthesized (e.g., chemically synthesized or by synthesized by recombinant DNA techniques).

The term "antibody" used herein is used in the broadest sense and specifically covers monoclonal antibodies (including full length monoclonal antibodies), multispecific antibodies (e.g., bispecific antibodies), and antibody fragments so long as they exhibit the desired biological activity.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragments.

As use herein, the term "specifically binds to," "recognizes," "specifically recognizes," "targets," or is "specific for" refers to measurable and reproducible interactions such as binding between a target and an antibody, or a receptor and a ligand, or a receptor and an epitope/MHC complex, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to an antigen peptide (or an epitope) has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

The term "about X-Y" used herein has the same meaning as "about X to about Y."

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "an," and "the" include plural referents unless the context clearly dictates otherwise.

II. Methods of Preparing Tumor Antigen-Specific T Cells

The present application provides methods of preparing a population of tumor antigen-specific T cells comprising co-culturing a population of enriched activated T cells or a population of stock tumor antigen-specific T cells with a population of antigen-presenting cells (APCs) loaded with one or more tumor antigen peptides (referred herein as "antigen-loaded APCs"). In some embodiments, the APCs are DCs. In some embodiments, the APCs are PBMCs. In some embodiments, the T cells and APCs are obtained from an individual that has previously received MASCT. In some embodiments, the individual has clinically benefitted from the MASCT.

In some embodiments, there is provided a method of preparing tumor antigen-specific T cells comprising co-culturing an enriched population of activated T cells with a population of DCs loaded with one or more tumor antigen peptides, wherein the enriched population of activated T cells is prepared by subjecting a first co-culture to an enrichment process, and wherein the first co-culture comprises a population of T cells and a first population of DCs loaded with a plurality of tumor antigen peptides comprising the one or more tumor antigen peptides. In some embodiments, the ratio between the enriched population of activated T cells and the population of antigen-loaded DCs is about 1:1 to about 20:1 (e.g., about 1:1 or about 2:1). In some embodiments, the enriched population of activated T cells and the population of antigen-loaded DCs are co-cultured for about 12 to 25 days. In some embodiments, the method comprises co-culturing the population of antigen-loaded DCs with the enriched population of activated T cells in an initial co-culture medium comprising one or more cytokines (e.g., a plurality of cytokines and an immune checkpoint inhibitor (e.g., anti-PD-1 antibody) to provide a co-culture; and adding an anti-CD3 antibody (e.g., OKT-3) to the co-culture to obtain a population of tumor antigen-specific T cells. In some embodiments, the anti-CD3 antibody is added to the co-culture no more than about 3 days (e.g., about 2 days) after the co-culturing step starts. In some embodiments, the antigen-loaded DCs and T cells are derived from the same individual, e.g., PBMCs from an individual that has previously received MASCT. In some embodiments, the individual has clinically benefitted from the MASCT.

In some embodiments, there is provided a method of preparing tumor antigen-specific T cells comprising: a) subjecting, a first co-culture to an enrichment process to obtain an enriched population of activated T cells, wherein the first co-culture comprises a first population of DCs loaded with a plurality of tumor antigen peptides and a population of T cells; and b) co-culturing the enriched population of activated T cells with a second population of DCs loaded with one or more tumor antigen peptides from the plurality of tumor antigen peptides to obtain a population of tumor antigen-specific T cells. In some embodiments, the enrichment process comprises contacting the first co-culture with APCs (e.g., PBMCs) loaded with the plurality of tumor antigen peptides to obtain a stimulated co-culture, and isolating an enriched population of activated T cells from the stimulated co-culture using a ligand that specifically recognizes a cytokine (such as IFNγ) or a cell surface molecule. In some embodiments, the ratio between the enriched population of activated T cells and the second population of antigen-loaded DCs is about 1:1 to about 20:1 (e.g., about: 1:1 or about 2:1). In some embodiments, the enriched population of activated T cells and the second population of antigen-loaded DCs are co-cultured for about 12 to 25 days. In some embodiments, the method comprises co-culturing the second population of antigen-loaded DCs with the population of T cells in comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the antigen-loaded DCs and T cells are derived from the same individual, e.g., PBMCs from an individual that has previously received MASCT. In some embodiments, the individual has clinically benefitted from the MASCT.

In some embodiments, there is provided a method of preparing tumor antigen-specific T cells comprising: a) a first co-culturing step, comprising co-culturing a first population of DCs loaded with a plurality of tumor antigen peptides with a population of T cells to obtain a first co-culture comprising activated T cells; b) an enrichment step, comprising subjecting the first co-culture to an enrichment process to obtain an enriched population of activated T cells; and c) a second co-culturing step, comprising co-culturing the enriched population of activated T cells with a second population of DCs loaded with one or more tumor antigen peptides from the plurality of tumor antigen peptides to obtain a population of tumor antigen-specific T cells. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines such as IL-2 or a plurality of cytokines, IL-2, IL-7, IL-15 and IL-21) and an immune checkpoint inhibitor (e.g., anti-PD-1 antibody). In some embodiments, the ratio between the enriched population of activated T cells and the second population of antigen-loaded DCs is about 1:1 to about 20:1 (e.g., about 1:1 or about 2:1). In some embodiments, the enriched population or activated T cells and the second population of antigen-loaded DCs are co-cultured for about 12 to 25 days. In some embodiments, the method comprises co-culturing the second population of antigen-loaded DCs with the population of T cells in an initial second co-culture medium comprising an immune checkpoint inhibitor and optionally one or more cytokines IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the one or more cytokines is added to the second co-culture no more than about 3 days (e.g., about 2 days) after the second co-culturing step starts. In some embodiments, the population of T cells in the first co-culturing step is present in a population of PBMCs. In some embodiments, the antigen-loaded DCs and T cells are derived from the same individual, e.g., PBMCs from an individual that has previously received MASCT. In some embodiments, the individual has clinically benefitted from the MASCT.

In some embodiments, there is provided a method of preparing tumor antigen-specific T cells comprising: a) a first co-culturing step, comprising co-culturing a first population of DCs loaded with a plurality of tumor antigen peptides with a population of T cells to obtain a first co-culture comprising activated T cells; b) an enrichment step, comprising contacting the first co-culture with APCs (e.g., PBMCs) loaded with the plurality of tumor antigen peptides to obtain a stimulated co-culture, and isolating an enriched population of activated T cells from the stimulated co-culture using a ligand that specifically recognizes a cytokine (such as IFNγ) or a cell surface molecule, and c) a second co-culturing step, comprising co-culturing the enriched population of activated T cells with a second population of DCs loaded with one or more tumor antigen peptides from the plurality of tumor antigen peptides to obtain a population of tumor antigen-specific T cells. In some embodiments, the first co-culturing step is carried out for no more than about 7 days such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-7, IL-15 and IL-21) and an immune checkpoint inhibitor (e.g., anti-PD-1 antibody). In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days. In some embodiments, the method comprises co-culturing the second population of antigen-loaded DCs with the population of T cells in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the one or more cytokines is added to the second co-culture no more than about 3 days (e.g., about 2 days) after the second co-culturing step starts. In some embodiments, the population of T cells in the first co-culturing step is present in a population of PBMCs. In some embodiments, the antigen-loaded DCs and T cells are derived from the same individual, e.g., PBMCs from an individual that has previously received MASCT. In some embodiments, the individual has clinically benefitted from the MASCT.

In some embodiments, there is provided a method of preparing tumor antigen-specific T cells comprising: a) a first co-culturing step, comprising co-culturing a first population of DCs loaded with a plurality of tumor antigen peptides with a population of T cells to obtain a first co-culture comprising activated T cells; b) an enrichment step, comprising subjecting the first co-culture to an enrichment process to obtain an enriched population of activated T cells; and c) a second co-culturing step, comprising co-culturing the enriched population of activated T cells with a second population of DCs loaded with one or more tumor antigen peptides from the plurality of tumor antigen peptides in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines or a plurality of cytokines) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the one or more cytokines is added to the second co-culture no more than about 3 days (e.g., about 2 days) after the second co-culturing step starts. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody). In some embodiments, the enrichment process comprises contacting the first co-culture with APCs (e.g., PBMCs) loaded with the plurality of tumor antigen peptides to obtain a stimulated co-culture, and isolating an enriched population of activated T cells from the stimulated co-culture using a ligand that specifically recognizes a cytokine (such as IFNγ) or a cell surface molecule. In some embodiments, the ratio between the enriched population of activated T cells and the second population of antigen-loaded DCs is about 1:1 to about 2.0:1 (e.g., about 1:1 or about 2:1). In some embodiments, the enriched population of activated T cells and the second population of antigen-loaded DCs are co-cultured for about 12 to 25 days. In some embodiments, the population of T cells in the first co-culturing step is present in a population of PBMCs. In some embodiments, the antigen-loaded DCs and T cells are derived the same individual, e.g., PBMCs from an individual that has previously received MASCT. In some embodiments, the individual has clinically benefitted from the MASCT.

In some embodiments, there is provided a method of preparing tumor antigen-specific T cells comprising: a) contacting a first population of DCs with a plurality of tumor antigen peptides to obtain a first population of DCs loaded with a plurality of tumor antigen peptides; b) a first co-culturing step, comprising co-culturing the first population of DCs loaded with the plurality of tumor antigen peptides with a population of T cells to obtain a first co-culture comprising activated T cells; c) an enrichment step, comprising subjecting the first co-culture to an enrichment process to obtain an enriched population of activated T cells; d) contacting a second population of dendritic cells with one or more tumor antigen peptides from the plurality of tumor antigen peptides to obtain a second population of DCs loaded with one or more tumor antigen peptides from the plurality of tumor antigen peptides; and e) a second co-culturing step, comprising co-culturing the enriched population of activated T cells with the second population of DCs loaded with one or more tumor antigen peptides from the plurality of tumor antigen peptides in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the one or more cytokines is added to the second co-culture no more than about 3 days (e.g., about 2 days) after the second co-culturing step starts. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of cells are co-cultured sin a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody). In some embodiments, the enrichment process comprises contacting the first co-culture with APCs (e.g., PBMCs) loaded with the plurality of tumor antigen peptides to obtain a stimulated co-culture, and isolating an enriched population of activated T cells from the stimulated co-culture using a ligand that specifically recognizes a cytokine (such as IFNγ) or a cell surface molecule. In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days. In some embodiments, the population of T cells in the first co-culturing, step is present in a population of PBMCs. In some embodiments, the antigen-loaded DCs and T cells are derived from the same individual, e.g., PRMCs from an individual that has previously received MASCT. In some embodiments, the individual has clinically benefitted from the MASCT.

In some embodiments, there is provided a method of preparing tumor antigen-specific T cells comprising: a) contacting a first population of DCs with a plurality of tumor antigen peptides to obtain a first population of DCs loaded with the plurality of tumor antigen peptides; b) culturing the first population of DCs loaded with the plurality of tumor antigen peptides in a DC maturation medium comprising a toll-like receptor (TLR) agonist; c) a first co-culturing step, comprising co-culturing the first population of DCs loaded with the plurality of tumor antigen peptides with the population of T cells in a first co-culture medium comprising one or more cytokines (such as IL-2 or a plurality of cytokines, e.g., IL-2, IL-7, IL-15 and IL-21), an immune checkpoint inhibitor (e.g., anti-PD-1 antibody) to obtain a first co-culture comprising activated T cells; d) an enrichment step, comprising contacting the first co-culture with PBMCs loaded with the plurality of tumor antigen peptides to obtain a stimulated co-culture, and isolating an enriched population of activated T cells from the stimulated co-culture using a ligand that specifically recognizes a cytokine (such as IFNγ) or a cell surface molecule; e) contacting a second population of DCs with one or more tumor antigen peptides from the plurality of tumor antigen peptides to obtain a second population of antigen-loaded DCs; f) culturing the second population of antigen-loaded DCs in a DC maturation medium comprising a toll-like receptor (TLR) agonist; and g) a second co-culturing step, comprising co-culturing the enriched population of activated T cells with the second population of DCs loaded with the plurality of tumor antigen peptides in a second initial co-culture medium comprising one or more cytokines (e.g., a plurality of cytokines) and an immune checkpoint inhibitor (e.g., anti-PD-1 antibody) to obtain a second co-culture, and adding an anti-CD3 antibody (e.g., OKT3) to the second co-culture to provide a population of tumor antigen-specific T cells. In some embodiments, the anti-CD3 antibody is added to the second co-culture no more than about 3 days (e.g., about 2 days) after the second co-culturing step starts. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., antibody). In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days. In some embodiments, the population of T cells in the first co-culturing step is present in a population of PBMCs. In some embodiments, the DC maturation medium comprises INFγ, MPLA and PGE2. In some embodiments, the first population of DCs and/or the second population of DCs is obtained by inducing differentiation of a population of monocytes from PBMCs. In some embodiments, the antigen-loaded DCs and T cells are derived from the same individual, e.g., PBMCs from an individual that has previously received MASCT. In some embodiments, the individual has clinically benefitted from the MASCT.

In some embodiments, there is provided a method of preparing tumor antigen-specific T cells comprising: co-culturing a population of tumor antigen-specific T cells with a population of APCs (e.g., PBMCs, DCs, or cell line APCs) loaded with one or more tumor antigen peptides. In some embodiments, the population of tumor antigen-specific T cells is obtained from a frozen stock of the tumor antigen-specific T cells prepared using any one of the methods described above. In some embodiments, the population of tumor antigen-specific T cells is obtained from the PBMCs of an individual that has clinically benefitted from a MASCT. In some embodiments, the ratio between the population of tumor antigen-specific T cells and the population of antigen-loaded APCs is about 1:1 to about 20:1 (e.g., about 1:1, 1:2 or 1:4). In some embodiments, the population of tumor antigen-specific T cells and the population of antigen-loaded APCs are co-cultured for about 5 to 9 (e.g., about 7) days. In some embodiments, the population of tumor antigen-specific T cells and the population of antigen-loaded APCs are co-cultured in a third co-culture medium comprising one or more cytokines (such as IL-2 or a plurality of cytokins, e.g., IL-2, IL-7, and IL-15) and an anti-CD3 antibody (e.g., OKT3). In some embodiments, the co-culturing is repeated, e.g., once or twice. In some embodiments, the population of the tumor antigen-specific T cells is obtained from a frozen stock of the tumor antigen-specific T cells.

In some embodiments, there is provided a method of preparing tumor antigen-specific T cells comprising: co-culturing a thawed population of frozen tumor antigen-specific T cells with a population of APCs (e.g., PBMCs, DCs, or cell line APCs) loaded with one or more tumor antigen peptides, wherein the frozen tumor antigen-specific T cells are prepared by freezing the tumor antigen-specific T cells prepared by any one of the methods described above. In some embodiments, the frozen tumor antigen-specific T cells are prepared by: a) a first co-culturing step, comprising co-culturing a first population of DCs loaded with a plurality of tumor antigen peptides with a population of T cells to obtain a first co-culture comprising activated T cells; b) an enrichment step, comprising subjecting the first co-culture to an enrichment process to obtain an enriched population of activated T cells; c) a second co-culturing step, comprising co-culturing the enriched population of activated T cells with a second population of DCs loaded with one or more tumor antigen peptides from the plurality of tumor antigen peptides to obtain a population of tumor antigen-specific T cells; and d) freezing the population of tumor antigen-specific T cells.

In some embodiments, there is provided a method of preparing tumor antigen-specific T cells comprising: a) a first co-culturing step, comprising co-culturing a first population of DCs loaded with a plurality of tumor antigen peptides with a population of T cells to obtain a first co-culture comprising activated T cells; b) an enrichment step, comprising subjecting the first co-culture to an enrichment process to obtain an enriched population of activated T cells; c) a second co-culturing step, comprising co-culturing the enriched population of activated T cells with a second population of DCs loaded with one or more tumor antigen peptides from the plurality of tumor antigen peptides to obtain a first population of tumor antigen-specific T cells; d) a third co-culturing step, comprising co-culturing a sub-population of tumor antigen-specific T cells from the first population of tumor antigen-specific T cells with a third population of APCs (e.g., DCs or PBMCs) loaded with one or more tumor antigen peptides from the plurality of tumor antigen peptides, thereby providing the tumor antigen-specific T cells. In some embodiments, the ratio between the subpopulation of tumor antigen-specific T cells and the third population of antigen-loaded DCs is about 1:1 to about 20:1 (e.g., about 1:1, 1:2 or 1:4). In some embodiments, the subpopulation of tumor antigen-specific T cells and the third population of antigen-loaded DCs are co-cultured for about 5 to 9 (e.g., about 7) days. In some embodiments, the subpopulation of tumor antigen-specific T cells and the third population of antigen-loaded DCs are co-cultured in a third co-culture medium comprising one or more cytokines (such as IL-2 or a plurality of cytokines, e.g., IL-2, IL-7, and IL-15) and an anti-CD3 antibody (e.g., OKT3). In some embodiments, the third co-culturing step is repeated, e.g., once, twice or three times. In some embodiments, the subpopulation of tumor antigen-specific T cells is obtained from a frozen stock of the first population of tumor antigen-specific T cells. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody). In some embodiments, the ratio between the enriched population of activated T cells and the second population of antigen-loaded DCs is about 1:1 to about 20:1 (e.g., about 1:1 or about 2:1). In some embodiments, the enriched population of activated T cells and the second population of antigen-loaded DCs are co-cultured for about 12 to 25 days. In some embodiments, the method comprises co-culturing the second population of antigen-loaded DCs with the population of T cells in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the one or more cytokines is added to the second co-culture no more than about 3 days (e.g., about 2 days) after the second co-culturing step starts. In some embodiments, the population of T cells in the first co-culturing step is present in a population of PBMCs. In some embodiments, the antigen-loaded DCs and T cells are derived from the same individual, e.g., PBMCs from an individual that has previously received MASCT. In some embodiments, the individual has clinically benefitted from the MASCT.

Exemplary methods for preparing tumor antigen-specific T cells are illustrated in FIGS. 3, 6, 9, 12, 15, 18 and 21A-21B and described in Examples 2-6.

Figure 3:
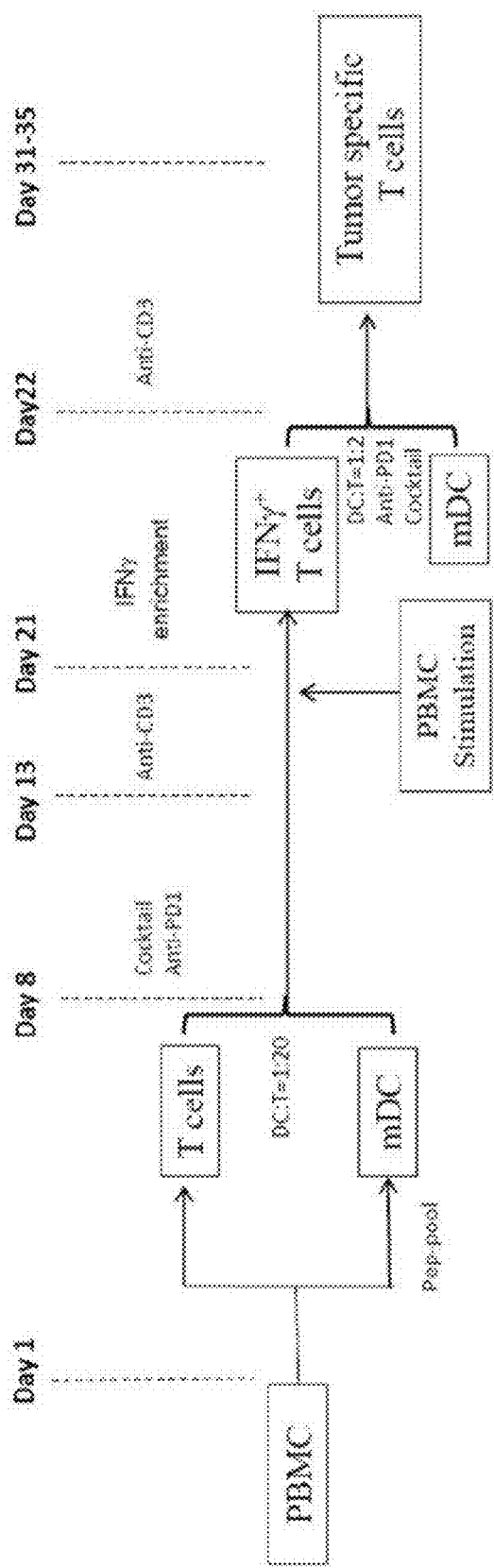
FIG. 3 shows an exemplary method for preparing tumor antigen-specific T cells as described in Example 2.

In some embodiments, there is provided a method of preparing tumor antigen-specific T cells comprising: (a) contacting a population of DCs derived from a population of PBMCs from an individual with at plurality of tumor antigen peptides to obtain a first population of antigen-loaded DCs; (b) a first co-culture step comprising co-culturing a population of T cells (e.g., present in PBMCs) and the first population of antigen-loaded DCs in an initial first co-culture medium comprising one or more cytokines (e.g., a plurality of cytokines) and an immune checkpoint inhibitor (e.g., anti-PD-1 antibody), and adding an anti-CD3 antibody to the first co-culture no more than about 7 days (e.g., about 5 days) after the first-co-culture starts to obtain a first co-culture; (c) an enrichment step comprising contacting the first co-culture with PBMCs loaded with the plurality of tumor antigen peptides to obtain a stimulated co-culture, and isolating an enriched population of activated T cells from the stimulated co-culture using a ligand that specifically recognizes a cytokine (such as IFNγ) to obtain an enriched population of activated T cells; (d) a second co-culture step comprising co-culturing the enriched population of activated T cells and a second population of DCs loaded with the plurality of tumor antigen peptides in as co-culture medium comprising one or more cytokines (e.g., as plurality of cytokines), an immune checkpoint inhibitor (e.g., anti-PD-1 antibody) and an anti-CD3 antibody, thereby providing the tumor antigen-specific T cells. In some embodiments, the ratio between the population of T cells and the first population of antigen-loaded DCs is about 20:1. In some embodiments, the population of T cells and the population of antigen-loaded DCs are co-cultured for about 13-14 days. In some embodiments, the ratio between the enriched population of activated T cells and the second population of antigen-loaded DCs is about 2:1. In some embodiments, the enriched population of activated T cells and the second population of antigen-loaded DCs are co-cultured for about 9-13 days. An exemplary method is shown in FIG. 3.

Figure 6:
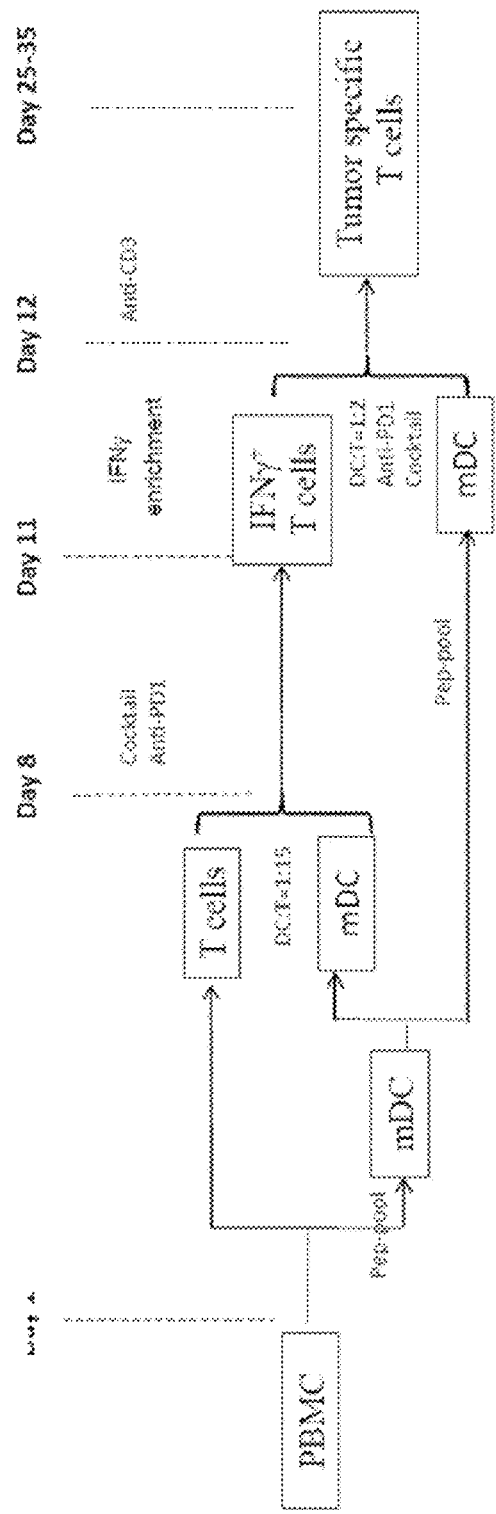
FIG. 6 shows an exemplary method ("Method 2") for preparing tumor antigen-specific T cells as described in Example 3.

In some embodiments, there is provided a method of preparing tumor antigen-specific T cells comprising: (a) contacting a population of DCs derived from a population of PBMCs from an individual with a plurality of tumor antigen peptides to obtain antigen-loaded DCs; (b) a first co-culture step comprising co-culturing a population of T cells (e.g., present in PBMCs) and a first population of the antigen-loaded DCs in an initial first co-culture medium comprising one or more cytokines (e.g., a plurality of cytokines) and an immune checkpoint inhibitor (e.g., anti-PD-1 antibody); (c) an enrichment step comprising contacting the first co-culture with PBMCs loaded with the plurality of tumor antigen peptides to obtain a stimulated co-culture, and isolating an enriched population of activated T cells from the stimulated co-culture using a ligand that specifically recognizes a cytokine (such as IFNγ) to obtain an enriched population of activated T cells; (d) a second co-culture step comprising co-culturing the enriched population of activated T cells and a second population of the antigen-loaded DCs in a co-culture medium comprising one or more cytokines (e.g., a plurality of cytokines), all immune checkpoint inhibitor (e.g., anti-PD-1 antibody) and an anti-CD3 antibody, thereby providing the tumor antigen-specific T cells. In some embodiments, the antigen-loaded DCs are cultured in a DC maturation medium comprising a toll-like receptor (TLR) agonist. In some embodiments, the DC maturation medium comprises INFγ, MPLA and PGE2. In some embodiments, the antigen-loaded DCs are cultured in the DC maturation medium for about 8 to about 12 days. In some embodiments, the ratio between the population of T cells and the first population of the antigen-loaded DCs is about 15:1. In some embodiments, the population of T cells and the population of antigen-loaded DCs are co-cultured for about 3-4 days. In some embodiments, the ratio between the enriched population of activated T cells and the second population of antigen-loaded DCs is about 2:1. In some embodiments, the enriched population of activated T cells and the second population of antigen-loaded DCs are co-cultured for about 13-23 days. An exemplary method is shown in FIG. 6.

Figure 9:
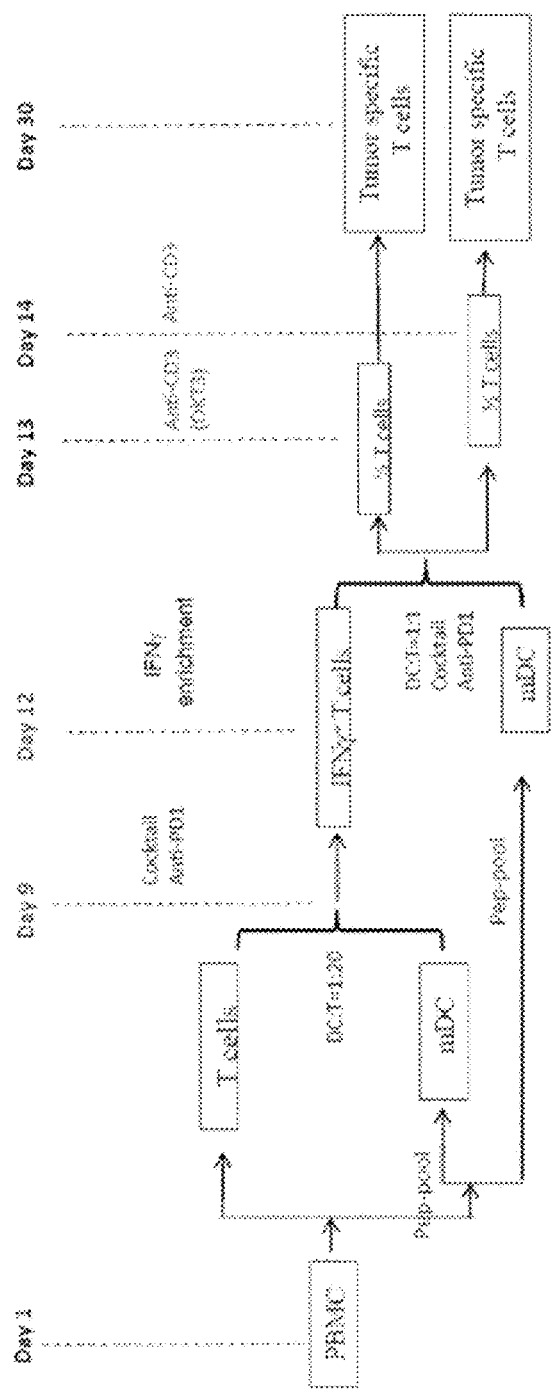
FIG. 9 shows optimization the exemplary method of FIG. 6 ("Method 2m") for preparing tumor antigen-specific T cells as described in Example 3.

In some embodiments, there is provided a method of preparing tumor antigen-specific T cells comprising: (a) contacting a population of DCs derived from a population of PBMCs from an individual with a plurality of tumor antigen peptides to obtain antigen-loaded DCs; (b) a first co-culture step comprising co-culturing a population of T cells (e.g., present in PRMCs and a first population of the antigen-loaded dendritic cells in an initial first co-culture medium comprising one or more cytokines (e.g., a plurality of cytokines) and an immune checkpoint inhibitor (e.g., anti-PD-1 antibody); (c) an enrichment step comprising contacting the first co-culture with PBMCs loaded with the plurality of tumor antigen peptides to obtain a stimulated co-culture, and isolating an enriched population of activated T cells from the stimulated co-culture using a ligand that specifically recognizes a cytokine (such as IFNγ) to obtain an enriched population of activated T cells; (d) a second co-culture step comprising co-culturing the enriched population of activated T cells and a second population of the antigen-loaded DCs in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines IL-2 or a plurality of cytokines) to the second co-culture about 1 to 3 days (e.g., about 2 days) after the second co-culturing step starts, thereby providing the tumor antigen-specific T cells. In some embodiments, the antigen-loaded DCs are cultured in a DC maturation medium comprising a toll-like receptor (TLR) agonist. In some embodiments, the DC maturation medium comprises INFγ, MPLA and PGE2. In some embodiments, the antigen-loaded DCs are cultured in the DC maturation medium for about 8 to about 12 days. In some embodiments, the ratio between the population of T cells and the first population of the antigen-loaded DCs is about 20:1. In some embodiments, the population of T cells and the population of antigen-loaded DCs are co-cultured for about 2-3 days. In some embodiments, the ratio between the enriched population of activated T cells and the second population of antigen-loaded DCs is about 1:1. In some embodiments, the enriched population of activated T cells and the second population of antigen-loaded DCs are co-cultured for about 15-20 days (e.g., about 16 days). An exemplary method is shown in FIG. 9.

Figure 12:
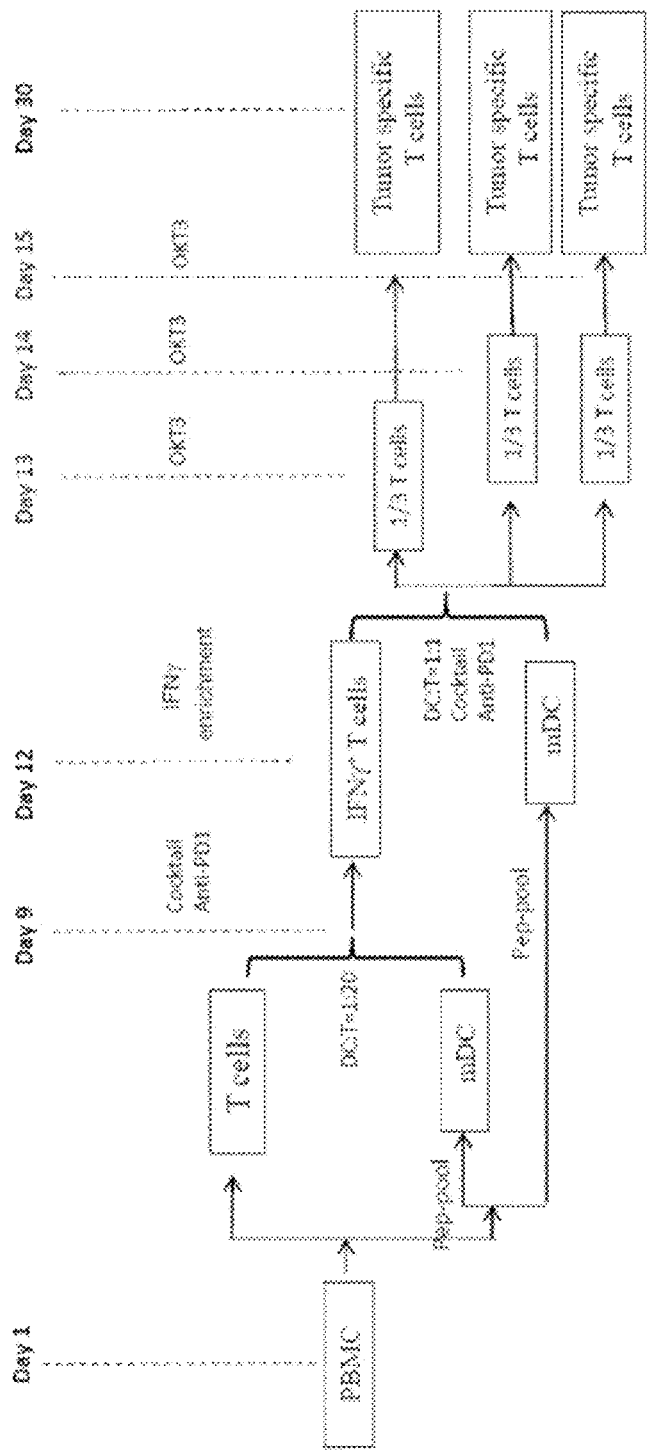
FIG. 12 shows optimization of the exemplary method of FIG. 9 for preparing tumor antigen-specific T cells as described in Example 3.

In some embodiments, there is provided a method of preparing tumor antigen-specific T cells comprising: (a) contacting a population of DCs derived from a population of PBMCs from an individual with a plurality of tumor antigen peptides to obtain antigen-loaded DCs; (b) as first co-culture step comprising co-culturing a population of T cells (e.g., present PBMCs) and a first population of the antigen-loaded DCs in an initial first co-culture medium comprising one or more cytokines (e.g., a plurality of cytokines) and an immune checkpoint inhibitor (e.g., anti-PD-1 antibody); (c) an enrichment step comprising contacting the first co-culture with PBMCs loaded with the plurality of tumor antigen peptides to obtain a stimulated co-culture, and isolating an enriched population of activated T cells from the stimulated co-culture using a ligand that specifically recognizes a cytokine (such as IFNγ) to obtain an enriched population of activated T cells; (d) a second co-culture step comprising co-culturing the enriched population of activated T cells and a second population of the antigen-loaded DCs in an initial second co-culture medium comprising an immune checkpoint inhibitor and optionally one or more cytokines (e.g., IL-2 or a plurality of cytokines) to obtain a second co-culture, and adding an anti-CD3 antibody (e.g., OKT3) and optionally one or more cytokines (e.g., IL-2 or a plurality of cytokines) to the second co-culture about 1 day to about 3 days (e.g., about 2 days) after the second co-culture starts, thereby providing the tumor antigen-specific T cells. In some embodiments, the antigen-loaded DCs are cultured in a DC maturation medium comprising a toll-like receptor (TLR) agonist. In some embodiments, the DC maturation medium comprises INFγ, MPLA and PGE2. In some embodiments, the antigen-loaded DCs are cultured in the DC maturation medium for about 8 to about 12 days. In some embodiments, the ratio between the population of T cells and the first population of the antigen-loaded DCs is about 20:1. In some embodiments, the population of T cells and the population of antigen-loaded DCs are co-cultured for about 2-3 days. In some embodiments, the ratio between the enriched population of activated T cells and the second population of antigen-loaded DCs is about 1:1. In some embodiments, the enriched population of activated T cells and the second population of antigen-loaded DCs are co-cultured for about 15-20 days (e.g., about 16 days). Exemplary methods are shown in FIGS. 9 and 12.

Figure 15:
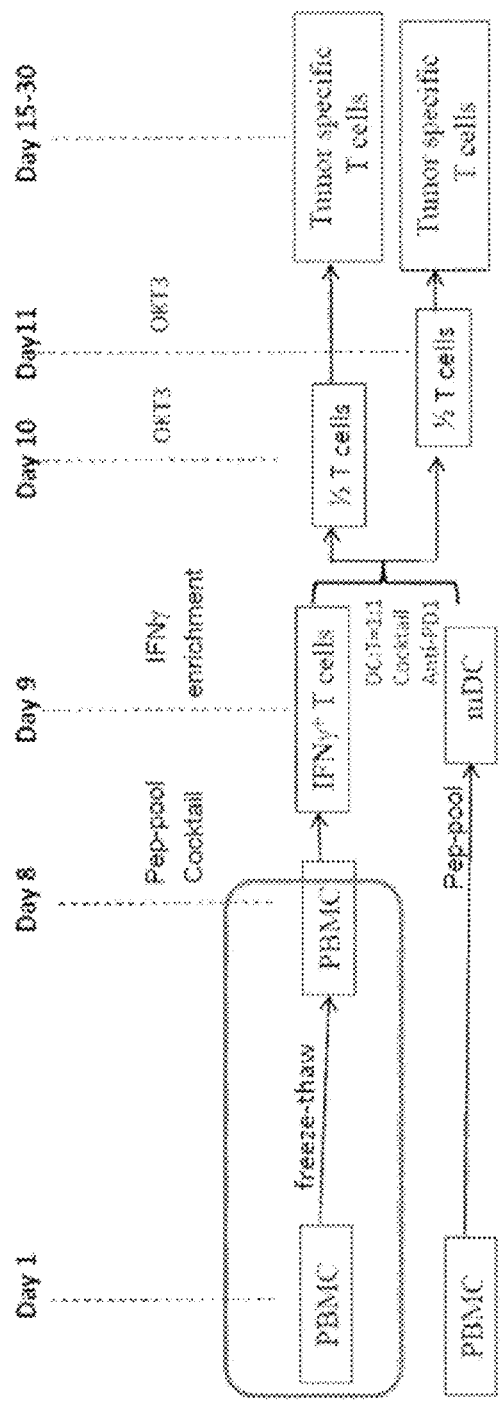
FIG. 15 shows an exemplary method for preparing tumor antigen-specific T cells as described in Example 4.

In some embodiments, there is provided a method of preparing tumor antigen-specific T cells comprising: (a) contacting a population of PBMCs with a plurality of tumor antigen peptides to obtain a population of stimulated PBMCs; (b) isolating an enriched population of activated T cells from the population of stimulated PBMCs using a ligand that specifically recognizes a cytokine (such as IFNγ) to obtain an enriched population of activated T cells; and (c) a co-culture step comprising co-culturing the enriched population of activated T cells and a population of DCs loaded with a plurality of tumor antigen peptides in an initial co-culture medium comprising one or more cytokines (e.g., a plurality of cytokines and an immune checkpoint inhibitor (e.g., anti-PD-1 antibody) to obtain a first co-culture, and adding an anti-CD3 antibody (e.g., OKT3) to the first co-culture about 1 day to about 3 days (e.g., about 1 day or 2 days) after the first co-culture starts, thereby providing the tumor antigen-specific T cells. In some embodiments, the PBMCs are obtained from an individual that has previously received a MASCT. In some embodiments, the PBMCs are obtained from an individual that has clinically benefited from a MASCT. In some embodiments, the PBMCs are from a frozen stock. In some embodiments, the PBMCs are freshly obtained from the individual. In some embodiments, the antigen-loaded DCs are prepared by contacting a population of PBMCs with a plurality of tumor antigen peptides. In some embodiments, the ratio between the enriched population of activated T cells and the population of antigen-loaded DCs is about 1:1. In some embodiments, the enriched population of activated T cells and the population of antigen-loaded DCs are co-cultured for about 7 to about 21 days. An exemplary method is shown in FIG. 15.

Figure 18:
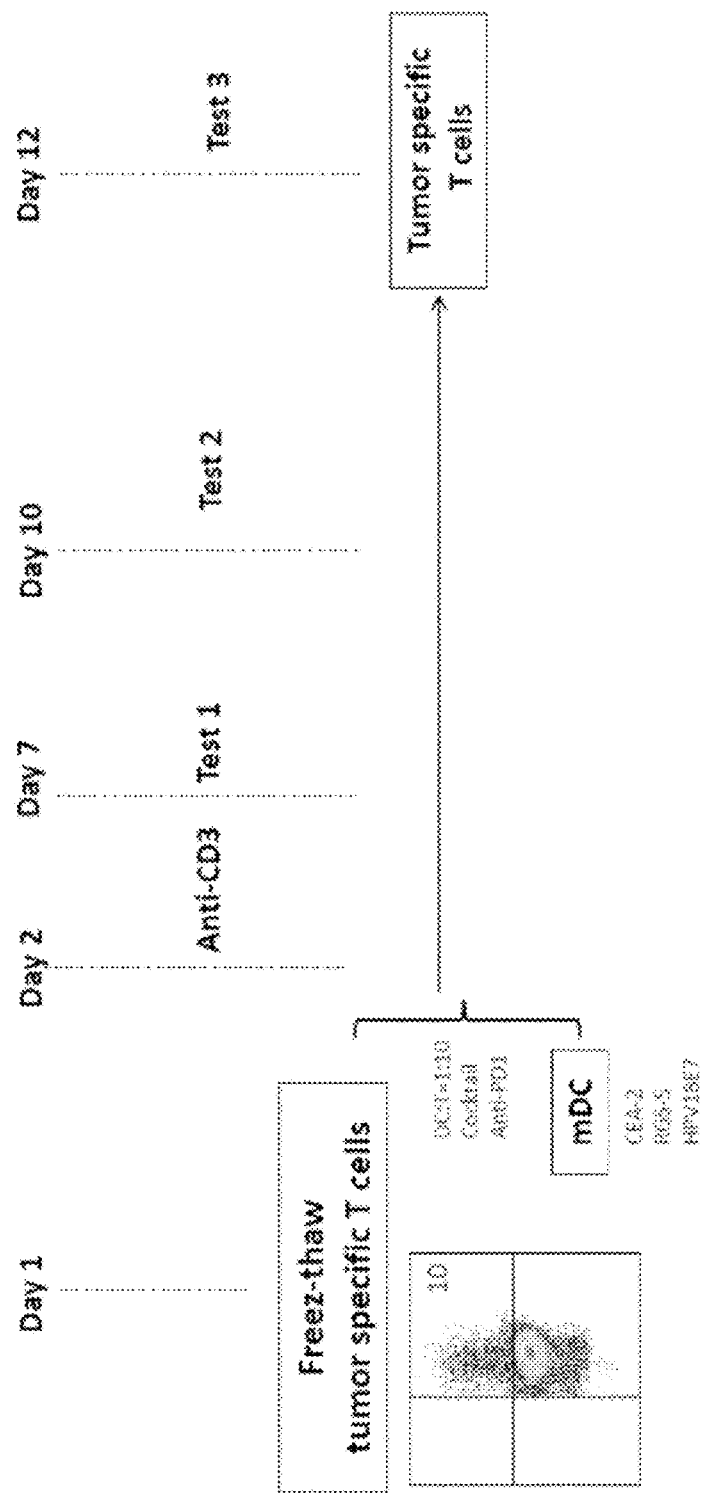
FIG. 18 shows an exemplary method for preparing tumor antigen-specific T cells from a frozen stock of tumor antigen-specific T cells as described in Example 5.

In some embodiments, there is provided a method of preparing tumor antigen-specific T cells, comprising: co-culturing a population of tumor-antigen specific T cells with a population of APCs (e.g., PBMCs or DCs) loaded with a plurality of tumor antigen peptides in a co-culture medium comprising one or more cytokines (e.g., a plurality of cytokines), an immune checkpoint inhibitor (e.g., anti-PD-1) and an anti-CD3 antibody, thereby providing a second population of tumor antigen-specific T cells. In some embodiments, the population of tumor-antigen specific T cells is obtained from a frozen stock of tumor-antigen specific T cells. In some embodiments, the ratio between the population of antigen-loaded APCs and the population of tumor-antigen specific T cells is at least about 1:20. In some embodiments, the population of tumor-antigen specific T cells and the population of antigen-loaded APCs are co-cultured for about 5 to 10 days (e.g., about 8 days). An exemplary method is shown in FIG. 18.

Figure 21A:
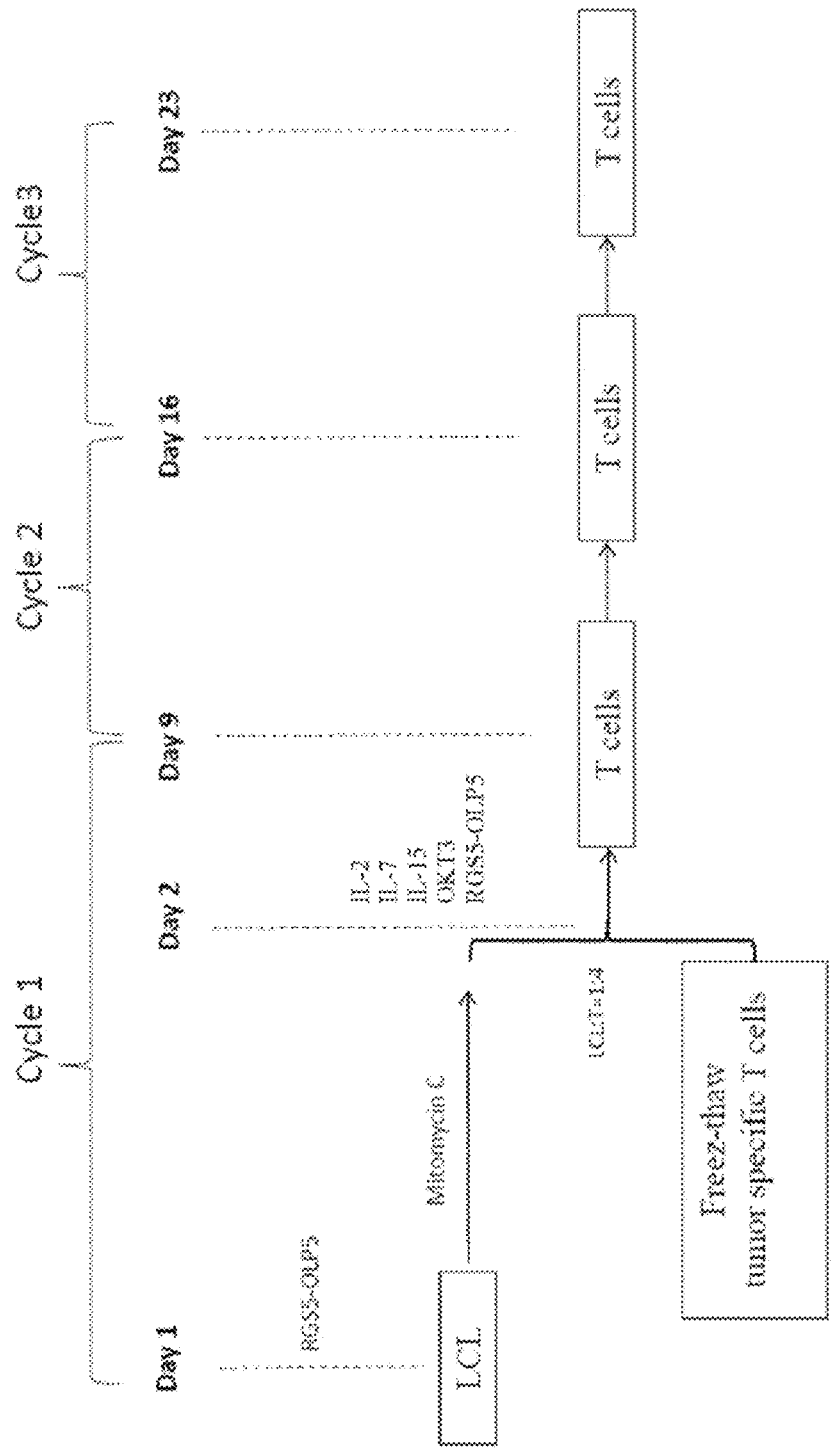
FIGS. 21A-21B show exemplary methods for preparing tumor antigen-specific T cells from a frozen stock of tumor antigen-specific T cells prepared by Method 2 or Method 2m as described in Example 5.
Figure 21B:
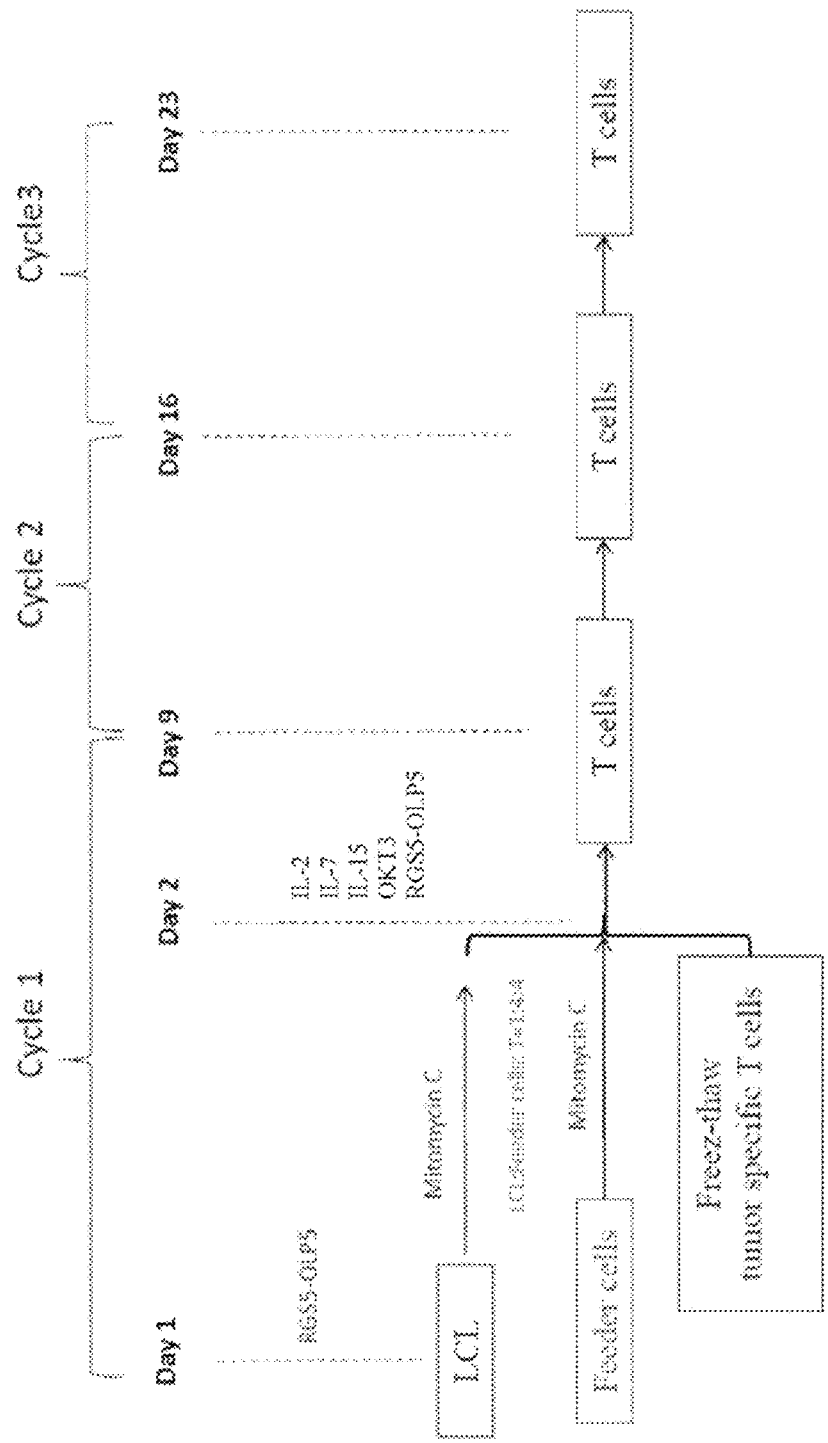

In some embodiments, there is provided a method of preparing tumor antigen-specific T cells, comprising: (a) co-culturing a population of tumor-antigen specific T cells with a first population of APCs (e.g., PBMCs, DCs, or cell line APCs) loaded with one or more tumor antigen peptides for about 5 to 9 days (e.g., about 7 days) in a co-culture medium comprising one or more cytokines (e.g., a plurality of cytokines) and an anti-CD3 antibody to obtain a first population of tumor antigen-specific T cells; and (b) co-culturing the first population of tumor antigen-specific T cells with a second population of APCs loaded with one or more tumor antigen peptides for about 5 to 9 days (e.g., about 7 days), thereby providing a second population of tumor antigen-specific T cells. In some embodiments, the stimulation step is repeated once. In some embodiments, the method further comprises: co-culturing the second population of tumor antigen-specific T cells with a third population of APCs loaded with one or more tumor antigen peptides for about 5 to 9 days (e.g., about 7 days), thereby providing, a third population of tumor antigen-specific T cells. In some embodiments, the APCs are LCL cells with or without feeder cells. In some embodiments, the APCs are DCs. In some embodiments, the APCs are loaded with a single tumor antigen peptide (including a fragment thereof) that elicits specific immune response by the tumor antigen-specific T cells. In some embodiments, the APCs are loaded with a plurality of tumor antigen peptides. In some embodiment, the co-culture medium comprises IL-2 and OKT3. In some embodiments, the co-culture medium comprises IL-2, IL-7, IL-15 and OKT3. In some embodiments, the ratio between the antigen-loaded APCs and the first, second or third population of tumor antigen-specific T cells is about 1:1 to about 1:10 (e.g., about 1:4). Exemplary methods are shown in FIGS. 21A-21B.

It is intended that any of the steps and parameters described herein for preparing the antigen-loaded DCs, the first, second and third co-culturing steps, and the enrichment step, etc., can be combined with each other as if each and every combination is individually described.

Tumor Antigen-Specific T Cells

Further provided by the present application is an isolated population of cells prepared by any embodiment of the methods described herein. Also provided is a frozen population of tumor antigen-specific T cells prepared by any embodiment of the methods described herein. In some embodiments, there is provided a co-culture comprising an enriched population of activated T cells and a population of DCs loaded with one or more tumor antigen peptides. In some embodiments, there is provided a co-culture comprising a thawed population of frozen tumor antigen-specific T cells and a population of DCs loaded with one or more tumor antigen peptides. In some embodiments, the population of T cells and the population of antigen-loaded DCs are derived from the same individual, such as an individual being treated. In some embodiments, the individual has previously received a MASCT. In some embodiments, the individual has clinically benefitted from the MASCT.

In some embodiments, there is provided an isolated population of cells prepared by a method comprising: a) a first co-culturing step, comprising co-culturing a first population of DCs loaded with a plurality of tumor antigen peptides with a population of T cells to obtain a first co-culture comprising activated T cells; b) an enrichment step, comprising subjecting the first co-culture to an enrichment process to obtain an enriched population of activated T cells; and c) a second co-culturing step, comprising co-culturing the enriched population of activated T cells with a second population of DCs loaded with one or more tumor antigen peptides from the plurality of tumor antigen peptides.

The isolated population of cells comprises a high percentage of tumor antigen-specific T cells. In some embodiments, the isolated population of cells comprises at least about any one of 3%, 5%, 6%, 8%, 10%, 15%, 20%, 50%, 60%, 70%, 80%, 90% or higher level of tumor antigen-specific cells. In some embodiments, about any one of 3-10%, 5-15%, 10-15%, 10-20%, 20-50%, 10-50%, 10-70%, 50-90%, or 20%-60% of the cells in the isolated population are tumor antigen-specific T cells.

In some embodiments, the tumor antigen-specific T cells in any embodiment of the isolated population of cells are capable of eliciting specific immune response to the one or more tumor antigen peptides in vivo or ex vivo. In some embodiments, the tumor antigen-specific T cells are capable of increasing cytotoxic T cell activity in a human individual against more than one tumor antigen peptides. In some embodiments, the tumor antigen-specific T cells are character by high expression or secretion level of pro-inflammatory signal molecules, upon stimulation by the one or more tumor antigen peptides. In some embodiments, the expression or secretion level is determined by comparing the expression or secretion level of a molecule (such as a pro-inflammatory signal molecule) of the tumor antigen-specific T cells upon stimulation with the one or more tumor antigen peptides to the expression or secretion level upon stimulation with an irrelevant peptide. In some embodiments, the control expression or secretion level of a molecule is the expression or secretion level of the molecule in a control population of T cells measured under the same assay conditions. In some embodiments, the control population of T cells is a population of T cells induced by one or more irrelevant peptides (such as peptides not corresponding to T cell receptor antigens, or random peptides). In some embodiments, the control expression or secretion level of a molecule is an average or median expression or secretion level of the molecule in a plurality of control populations of T cells. In some embodiments, a high level of expression or secretion of a molecule in the tumor antigen-specific T cells is at least about any of 1.5, 2, 2.5, 3, 4, 5, 10, 20, 50, 100, 1000, or more times the control expression or secretion level.

In some embodiments, upon stimulation with the one or more tumor antigen peptides, the tumor antigen-specific T cells express a plurality of pro-inflammatory molecules, such as IFNγ, TNFα, granzyme B, perforin, or any combination thereof. In some embodiments, at least about any one of 3%, 5%, 10%, 15%, 20%, 30%, 40%, 50%, 60%, 70%, 80%, 90% or higher percentage of tumor antigen-specific T cells that secrete INF-γ upon stimulation with the one or more tumor antigen peptides. In some embodiments, at least about any one of 3%, 5%, 10%, 15%, 20%, 30%, 40%, 50%, 60%, 70%, 80%, 90% or higher percentage of tumor antigen-specific T cells secrete TNF-α upon stimulation with the one of more tumor antigen peptides.

The isolated population of cells described herein can be used to generate specific immune memory in an individual when administered to the individual. In some embodiments, the individual has memory T cells that can elicit specific T cell response against a plurality of tumor antigen peptides after about any of 2 weeks, 1 month, 2 months, 3 months, 4 months, 6 months, 12 months, or more after administration of the isolated population of cells.

The isolated population of cells described herein can also be used to alter immune-inhibitory signals in vivo. In some embodiments, the isolated population of cells reduces immune-inhibitory molecule (such as PD-1) expression frequency on T cells (such as cytotoxic T cells or helper T cells) in an individual when administered to the individual. In some embodiments, the isolated population of cells reduces immune tolerance or immune escape of cancer cells in an individual. Accordingly, there is provided a method of reducing expression frequency of an immune-inhibitory molecule, such as PD-1, in T cells of an individual, comprising administering to the individual an effective amount of any embodiment of the isolated population of cells described herein. Also provided herein is an immunotherapeutic composition comprising any embodiment of the isolated population of cells comprising tumor antigen-specific T cells, and use of any embodiment of the isolated population of cells in the manufacture of a medicament for treating a cancer in an individual.

The isolated population of cells and the co-cultures described in this section may be used for treating cancer, such as solid caner. Immunotherapeutic compositions comprising the isolated population of cells or the co-cultures are useful for treating cancer, preventing tumor progression or metastasis, or reducing cancer immune escape are provided herein. The isolated population of cells and the co-cultures may also be used in the manufacture of a medicament for treating cancer, preventing tumor progression or metastasis, or reducing cancer immune escape.

Co-Culturing

The methods of preparing tumor antigen-specific T cells described herein and the MASCT methods comprise one or more (such as 1, 2, 3, or more) co-culturing steps. In some embodiments, the method comprises a first co-culturing step, comprising co-culturing a population of T cells with a population of DCs loaded with a plurality of tumor antigen peptides. In some embodiments, in the first co-culturing step, the population of T cells is co-cultured with the first population of antigen-loaded DCs for no more than about 7 days, such as about any one of 1, 2, 3, 4, 5, 6, or 7 days. In some embodiments, the population of T cells is co-cultured with the first population of antigen-loaded DCs for about 1-3 days, such as about 2-3 days.

In some embodiments, the first co-culturing step comprises co-culturing a first population of antigen-loaded DCs and the population of T cells in a first co-culture medium comprising one or more cytokines (e.g., a plurality of cytokines) and an immune checkpoint inhibitor. In some embodiments, the first co-culture medium comprises an anti-CD3 antibody. In some embodiments, the first co-culture medium does not comprise an anti-CD3 antibody. In some embodiments, the first co-culturing step comprises co-culturing a first population of antigen-loaded DCs and the population of T cells in a first initial co-culture medium comprising one or more cytokines (e.g., a plurality of cytokines) and an immune checkpoint inhibitor to provide a first co-culture, and adding an anti-CD3 antibody to the first co-culture.

In some embodiments, the method comprises at second co-culturing step, comprising co-culturing an enriched population of activated T cells with a population of DCs loaded with one or more tumor antigen peptides from the plurality of tumor antigen peptides. In some embodiments, in the second co-culturing step, the enriched population of activated T cells and the second population of antigen-loaded DCs are co-cultured for a total of at least about any one of 2, 4, 6, 8, 10, 12, 14, 16, 18, 20, 22, 24, 26, 28, or 30 days. In some embodiments, the enriched population of activated T cells is co-cultured with the second population of antigen-loaded DCs for about 12 days to about 25 days, such as about any one of 12-15, 15-18, 18-21, 15-20, 20-25, 15, 18, 19, 20, 21, or 22 days.

In some embodiments, the enriched population of activated T cells and the second population of antigen-loaded DCs are co-cultured in the presence of the anti-CD3 antibody for at least about any one of 1, 2, 3, 4, 5, 6, 7, 8, 9, 10, 12, 15, 20, 25 or more days. In some embodiments, the enriched population of activated T cells and the second population of antigen-loaded DCs are co-cultured in the presence of the anti-CD3 antibody for about any one of 8-18, 10-20, 1-25, or 12-25 days. In some embodiments, the enriched population of activated T cells and the second population of antigen-loaded DCs are initially co-cultured without an anti-CD3 antibody for about 1-5 days, such as about 1, 2, or 3 days.

In some embodiments, the second co-culturing step comprises co-culturing a second population of antigen-loaded DCs and the enriched population of activated T cells in a second co-culture medium comprising one or more cytokines (e.g., a plurality of cytokines), an immune checkpoint inhibitor. In some embodiments, the second co-culture medium comprises an anti-CD3 antibody. In some embodiments, the second co-culture medium does not comprise an anti-CD3 antibody. In some embodiments, the second co-culturing step comprises co-culturing a second population of antigen-loaded DCs and the enriched population of activated T cells in a second initial co-culture medium comprising one or more cytokines (e.g., a plurality of cytokines) and an immune checkpoint inhibitor to provide a second co-culture; and adding an anti-CD3 antibody to the second co-culture.

In some embodiments, the method of preparing tumor antigen-specific T cells comprises: (1) a first co-culturing step, comprising co-culturing a population of T cells with a first population of DCs loaded with a plurality of tumor antigen peptides, and (2) a second co-culturing step, comprising co-culturing an enriched population of activated T cells with a second population of DCs loaded with one or more tumor antigen peptides from the plurality of tumor antigen peptides.

In some embodiments, the method comprises a third co-culturing step, comprising co-culturing a population of tumor antigen-specific T cells (such as a thawed population of frozen tumor antigen specific T cells) with a population of APCs (e.g., PBMCs or DCs, such as fixed PBMCs) loaded with one or more tumor antigen peptides from the plurality of tumor antigen peptides. In some embodiments, the third co-culturing step is repeated for one or more times (such as 1, 2, 3, 4, 5, 6 or more) times to obtain further populations of tumor antigen-specific T cells. Each further population of tumor antigen-specific T cells may be administered to an individual in need of the treatment In some embodiments, repeating the third co-culturing step comprising co-culturing a portion of the tumor antigen-specific T cells obtained from the third co-culturing step with a second population of antigen-loaded APCs (e.g., PBMCs or DCs, such as fixed PBMCs). In some embodiments, repeating the third co-culturing step comprising adding to the third co-culture a fresh population of antigen-loaded APCs (e.g., PBMCs or DCs, such as fixed PBMCs) at an interval of every about 5-9 days (e.g., about 7 days).

In some embodiments, in the third co-culturing step, the population of tumor antigen-specific T cells and the population of antigen-loaded APCs (e.g., PBMCs or DCs, such as fixed PBMCs) are co-cultured for at least about an one of 2, 4, 6, 8, 10, 12, 14, 16, 18, 20, or 14 days. In some embodiments, the population of tumor antigen-specific T cells and the population of antigen-loaded APCs (e.g., PBMCs or DCs, such as fixed PBMCs) are co-cultured for about 5 days to about 15 days, such as about any one of 5-9, 7-10, 10-12, 12-15, 7, 8, 9, 10, 11, 12, 13, or 15 days.

In some embodiments, the third co-culturing step comprises co-culturing a population of antigen-loaded APCs (e.g., PBMCs or DCs, such as fixed PBMCs) and a population of tumor antigen-specific T cells in a third co-culture medium comprising one or more cytokines (e.g., a plurality of cytokines) and an immune checkpoint inhibitor. In some embodiments, the third co-culture medium does not comprise an anti-CD3 antibody. In some embodiments, the third co-culture medium comprises an anti-CD3 antibody. In some embodiments, the third co-culturing step comprises co-culturing a population of antigen-loaded APCs (e.g., PBMCs or DCs, such as fixed PBMCs) and a population of tumor antigen-specific T cells in a third initial co-culture medium comprising one or more cytokines (e.g., a plurality of cytokines) and an immune checkpoint inhibitor to provide a third co-culture; and adding an anti-CD3 antibody to the third co-culture.

The co-culture medium or the initial co-culture medium for each co-culturing step may be the same or different. Unless indicated otherwise, "co-culture medium" as discussed in the subsection "Co-culturing" includes the first, second and third co-culture medium; "Initial co-culture medium" as discussed in this subsection includes the first, second and third initial co-culture medium. In some embodiments, the co-culture medium (including the initial co-culture medium) comprises one or more (e.g., 1, 2, 3, 4, 5, or more) cytokines. In some embodiments, the co-culture medium (including the initial co-culture medium) comprises a plurality of cytokines (also referred herein as "cytokine cocktail"). Exemplary cytokines include, but are not limited to, IL-2, IL-7, IL-15, IL-21 and the like. In some embodiments, the co-culture medium (including the initial co-culture medium) comprises IL-2. In some embodiments, the co-culture medium (including the initial co-culture medium) comprises IL-2, IL-7, IL-15 and IL-21. In some embodiments, the IL-2 is present at a concentration of at least about any of 50, 100, 200, 300, 400, 500, 600, 700, 800, 900, 1000, 2000, 5000, 6000 or higher IU/ml in the co-culture medium (including the initial co-culture medium). In some embodiments, the IL-2 is present at a concentration of no more than about any one of 1000, 500, 200, 100, 50, 20, or lower IU/ml in the co-culture medium (including the initial co-culture medium). In some embodiments, the first co-culture medium comprises IL-2 at a concentration of no more than about 200 IU/mL (such as about 150, 100 or 50 IU/ml). In some embodiments, the second co-culture medium comprises IL-2 at a concentration of at least about 2000 IU/mL (such as about 3000, 5000, or 6000 IU/mL). In some embodiments, the IL-7 is present at a concentration of at least about any one of 1, 2, 5, 10, 20, 50 or 100 ng/mL in the co-culture medium (including the initial co-culture medium). In some embodiments, the IL-15 is present at a concentration of at least about any one of 1, 2, 5, 10, 20, 50 or 100 ng/mL in the co-culture medium (including the initial co-culture medium). The cytokines may facilitate activation, maturation, and/or proliferation of the T cells, to prime T cells for later differentiation into memory T cells, and/or suppress the percentage of $T_{REG}$ in the co-culture.

In some embodiments, the co-culture medium (including the initial co-culture medium) comprises one or more (such as any of 1, 2, 3, or more) immune checkpoint inhibitors. Any known immune checkpoint inhibitors may be used. In some embodiments, the immune checkpoint inhibitor is a natural or engineered ligand of an inhibitory immune checkpoint molecule, including, for example, ligands of CTLA-4 (e.g., B7.1, B7.2), ligands of TIM-3 (e.g., Galectin-9), ligands of A2a Receptor (e.g., adenosine, Regadenoson), ligands of LAG-3 (e.g., MHC class I or MHC class II molecules), ligands of BTLA (e.g., HVEM, B7-H4), ligands of KIR (e.g., MHC class I or MHC class II molecules), ligands of PD-1 (e.g., PD-L1, PD-L2), ligands of IDO (e.g., NKTR-218, Indoximod, NLG919), and ligands of CD47 (e.g., SIRP-alpha receptor). The immune checkpoint inhibitors may be of any suitable molecular modality, including, but not limited to, small molecules, nucleic acids (such as DNA, RNAi, or aptamer), peptides, or proteins (such as antibodies).

In some embodiments, the immune checkpoint inhibitor is an antibody (such as antagonist antibody) that targets an inhibitory immune checkpoint protein selected from the group consisting of anti-CTLA-4 (e.g., Ipilimumab, Tremelimumab, KAHR-102), anti-TIM-3 (e.g., F38-2E2, ENUM005), anti-LAG-3 (e.g., BMS-986016, IMP701, IMP321, C9B7W), anti-KIR (e.g., Lirilumab and IPH2101), anti-PD-1 (e.g., Nivolumab, Pidilizumab, Pembrolizumab, BMS-936559, atezolizumab, Pembrolizumab, MK-3475, AMP-224, AMP-514, STI-A1110, TSR-042, SHR1210), anti-PD-L1 (e.g., KY-1003 (EP20120194977), MCLA-145, RG7446, BMS-936559, MEDI-4736, MSB0010718C, AUR-012, STI-A010, PCT/US2001/020964, MPDL3280A, AMP-224, Dapirolizumab pegol (CDP-7657), MEDI-4920), anti-CD73 (e.g., AR-42 (OSU-HDAC42, HDAC-42, AR42, AR 42, OSU-HDAC 42, OSU-HDAC-42, NSC D736012, HDAC-42, HDAC 42, HDAC42, NSCD736012, NSC-D736012), MEDI-9447), anti-B7-H3 (e.g., MGA271, DS-5573a, 8H9), anti-CD47 (e.g., CC-90002, TTI-621, VLST-007), anti-BTLA, anti-VISTA, anti-A2aR, anti-B7-1, anti-B7-H4, anti-CD52 (such as alemtazumab), anti-IL-10, and anti-IL-35, anti-TGF-β (such as Fresolumimab). In some embodiments, the antibody is a monoclonal antibody. In some embodiments, the antibody is a full-length antibody. In some embodiments, the antibody is an antigen-binding fragment selected from the group consisting of Fab, Fab', F(ab')₂, Fv, scFv, BiTE, nanobody, and other antigen-binding subsequences of the full length antibody or engineered combinations thereof. In some embodiments, the antibody is a human antibody, a humanized antibody, or a chimeric antibody. In some embodiments, the antibody is a bispecific or multispecific antibody.

In some embodiments, the immune checkpoint inhibitor is an inhibitor of PD-1. In some embodiments, the immune checkpoint inhibitor is an anti-PD-1 antibody. Exemplary anti-PD-1 antibodies include, but are not limited to, Nivolumab, pembrolizumab, pidilizumab, BMS-936559, and atezolizumab, Pembrolizumab, MK-3475, AMP-224, AMP-514, STI-A1110, TSR-042, and SHR-1210. In some embodiments, the immune checkpoint inhibitor is nivolumab (for example, OPDIVO®). In some embodiments, the immune checkpoint inhibitor is Pembrolizumab (for example, KEYTRUDA®). In some embodiments, the immune checkpoint inhibitor is SHR-1210. In some embodiments, the initial co-culture medium comprises IL-2 and an anti-PD-1 antibody (e.g., SHR-1210). In some embodiments, the initial co-culture medium comprises IL-2, IL-7, IL-15, IL-21 and an anti-PD-1 antibody (e.g., SHR-1210).

A suitable concentration of the immune checkpoint inhibitor (e.g., anti-PD-1 antibody) in the co-culture medium (including the initial co-culture medium) include, but are not limited to, at least about any of 1, 2, 5, 10, 15, 20, 25 or more µg/mL. In some embodiments, the immune checkpoint inhibitor (e.g., anti-PD-1 antibody) is present in the co-culture medium (including the initial co-culture medium) is any one of about 1 µg/mL to about 10 µg/mL, about 10 µg/mL to about 20 µg/mL, about 1 µg/mL to about 25 µg/mL, or about 5 µg/mL to about 20 µg/mL.

The anti-CD3 antibody may be present in the co-culture at the time the co-culturing starts, or added to the co-culture after the co-culturing of the antigen-loaded DCs and the T cells, the enriched activated T cells, or the population of tumor antigen-specific T cells starts. In some embodiments, the anti-CD3 antibody is included in the co-culture medium (including the initial co-culture medium). In some embodiments, the initial co-culture medium does not comprise the anti-CD3 antibody.

In some embodiments, the anti-CD3 antibody is added to the second co-culture comprising the enriched population of activated T cells and the second population of antigen-loaded DCs at no more than about any one of 5, 4, 3, 2, or 1 day(s) after the second co-culturing starts. In some embodiments, the anti-CD3 antibody is added to the second co-culture comprising the enriched population of activated T cells and the second population of antigen-loaded DCs about 1, 2, or 3 days after the second co-culturing starts. Any suitable anti-CD3 antibody may be used, including, but not limited to OKT3.

The T cells (e.g., cells, enriched population of activated T cells, or tumor antigen-specific T cells) and antigen-loaded APCs (such as PBMCs or DCs) may be present in the co-cultures at an appropriate ratio in terms of the number of cell. In some embodiments, the ratio between the population of T cells to the first population of antigen-leaded DCs in the first co-culturing step is no more than about any one of 30:1, 25:1, 20:1, 15:1, 10:1, 8:1, or 5:1. In some embodiments, the ratio between the population of T cells to the first population of antigen-loaded DCs in the first co-culturing step is at least about any one of 5:1, 8:1, 10:1, 15:1, 20:1, 25:1, or more. In some embodiments, the ratio between the population of T cells to the first population of antigen-loaded DCs in the first co-culturing step is any one of about 5:1 to about 10:1, about 5:1 to about 20:1, about 10:1 to about 20:1, about 20:1 to about 30:1, or about 5:1 to about 30:1. In some embodiments, the ratio between the enriched population of T cells and the second population of antigen-loaded DCs is at least about any one of 1:1, 2:1, 3:1, 4:1, 5:1, 6:1, 7:1, 8:1, 9:1, or 10:1. In some embodiments, the ratio between the enriched population of T cells and the second population of antigen-loaded DCs is no more than about any one of 10:1, 9:1, 8:1, 7:1, 6:1, 5:1, 4:1. 3:1, 2:1 or 1:1. In some embodiments, the ratio between the enriched population of T cells and the second population of antigen-loaded DCs is any one of about 1:1 to about 20:1, about 1:1 to about 10:1, about 1:1 to about 5:1, about 5:1 to about 10:1, about 10:1 to about 15:1, about 15:1 to about 20:1, about 10:1 to about 20:1, about 1:1 to about 1:3, about 1:1 to about 2:1, or about 2:1 to about 5:1. In some embodiments, the ratio between the population of tumor antigen-specific T cells and the population of antigen-loaded APCs (e.g., PBMCs or DCs, such as fixed PBMCs) is at least about any one of 1:1, 2:1, 3:1, 4:1, 5:1, 6:1, 7:1, 8:1, 9:1, or 10:1. In some embodiments, the ratio between the population of tumor antigen-specific T cells and the population of antigen-loaded APCs (e.g., PBMCs or DCs, such as fixed PBMCs) is no more than about any one of 10:1, 9:1, 8:1, 7:1, 6:1, 5:1, 4:1, 3:1, 2:1 or 1:1. In some embodiments, the ratio between the population of tumor antigen-specific T cells and the population of antigen-loaded APCs (e.g., PBMCs or DCs, such as fixed PBMCs) is any one of about 1:1 to about 20:1, about 1:1 to about 10:1, about 1:1 to about 5:1 about 5:1 to about 10:1, about 10:1 to about 15:1, about 15:1 to about 20:1, about 10:1 to about 20:1, about 1:3 to about 3:1, about 1:1 to about 3:1, about 1:1 to about 2:1, or about 2:1 to about 5:1.

In some embodiments, the T cells and the APCs (e.g., PBMCs or DCs) are derived from the same individual, such as an individual with a cancer (e.g., low to moderate grade cancer). In some embodiments, the T cells, the APCs (e.g., PBMCs or DCs) or both are derived from autologous sources, i.e., from the individual that receives the tumor antigen-specific T cells, the antigen loaded DCs, or both. In some embodiments, the T cell the APCs (e.g., PBMCs, DCs, or cell line APCs) or both are not derived from autologous sources.

In some embodiments, the T cells and/or the APCs (e.g., PBMCs or DCs) are obtained from an individual who has previously received an immunotherapy. In some embodiments, the individual is immunologically responsive to the immunotherapy. "Immunologically responsive" to an immunotherapy means that the individual has developed specific immune response to one or more tumor antigens in response to the immunotherapy. In some embodiments, the T cells and/or the APCs (e.g., PBMCs or DCs) are obtained from an individual who has clinically benefitted from the immunotherapy. An individual who "clinically benefitted" from a therapy has demonstrated a clinical response to the therapy as assessed by a physician. Exemplary clinical responses include, but are not limited to, complete response ("CR"), partial response ("PR"), and stable disease ("SD"). Immunotherapies, include, but are not limited to, immune checkpoint inhibitors, adoptive immune cell therapy (e.g., adoptive T cell therapy, CIK, TIL, CAR-T, and TCR-T therapies), cancer vaccine, oncolytic viruses and combinations thereof. In some embodiments, the T cells and/or the APCs (e.g., PBMCs or DCs) are obtained from an individual who has previously received a MASCT. In some embodiments, the individual is capable of developing a specific immune response against a tumor antigen peptide in the MASCT. Specific immune response against a tumor antigen peptide can be determined using known assays in the art, such as ELISPOT assays. In some embodiments, the individual has clinically benefitted from the MASCT.

The population of T cells used in any embodiment of the methods described herein may be derived from a variety of sources. A convenient source of T cells is from the PBMCs of the human peripheral blood. The population of T cells may be isolated from the PBMCs, or alternatively, a population of PBMCs enriched with T cells (such as by addition of cell specific antibodies and cytokines) can be used in the co-culture. In some embodiments, the population of T cells used in the first co-culturing step is obtained from the peripheral blood mononuclear cells (PBMCs). In some embodiments, the PBMCs are obtained by density gradient centrifugation of a sample of peripheral blood. In some embodiments, the population of T cells used in the first co-culturing step is present in the PBMCs.

In some embodiments, a population of tumor antigen-specific T cells, such as a subpopulation of the tumor antigen-specific T cells prepared using any of the methods described herein, is used in the co-culturing to obtain a further population of tumor antigen-specific T cells. In some embodiments, a subpopulation of a fresh stock of tumor antigen-specific T cells is used to obtain a further population of tumor antigen-specific T cells. In some embodiments, a thawed population of tumor antigen-specific T cells from a frozen stock of the tumor antigen-specific T cells prepared using any of the methods described is used in the co-culturing to obtain a further population of tumor antigen-specific T cells. The frozen stock of tumor antigen-specific T cells may be obtained by freezing (such as flash freezing) tumor antigen-specific T cells prepared by co-culturing an enriched population of activated T cells with a population of antigen-loaded DCs.

In some embodiments, the frozen stock of tumor antigen-specific T cells is stored at about −20° C. to −70° C. In some embodiments, the frozen stock of tumor antigen-specific T cells is stored for at least about any one of 1 month, 3 months, 6 months, 12 months, 2 years, 3 years or more prior to preparing a further population of tumor antigen-specific T cells. In some embodiments, the frozen stock of tumor antigen-specific T cells is store for no more than about any one of 5 years, 4 years, 3 years, 2 years, 1 year or less prior to preparing a further population of tumor antigen-specific T cells. In some embodiments, the frozen stock of tumor antigen-specific T cells is thawed for a single time for use in preparing a further population of tumor antigen-specific T cells. In some embodiments, the frozen stock of tumor antigen-specific T cells is thawed for no more than 3 or 2 times for use in preparing a further population of tumor antigen-specific T cells. In some embodiments, the frozen stock of tumor antigen-specific T cells are aliquoted into a plurality of populations of frozen tumor antigen-specific T cells, wherein each aliquot is thawed once for preparing a further population of tumor antigen-specific T cells.

Enrichment of Activated T cells

The methods of preparing tumor-antigen specific T cells described herein comprise an enrichment step comprising enriching activated T cells from a co-culture comprising a first population of antigen-loaded DCs and a population of T cells. In some embodiments, the method comprises an enrichment step comprising enriching activated T cells from PBMCs stimulated with one or more tumor antigen peptides or fragments thereof, wherein the PBMCs are obtained from an individual that has previously received a MASCT.

In some embodiments, the enrichment process comprises selecting activated T cells based on one or more (such as any one of 1, 2, 3, or more) biomarkers of T cell activation from the co-culture in response to stimulation by one or more tumor antigen peptides or fragments thereof. In some embodiments, APCs (such as PBMCs) loaded with a plurality of tumor antigen peptides are used to stimulate the activated T cells in the co-culture. In some embodiments, the enrichment process comprises isolating activated T cells expressing one or more biomarkers, such as cell surface molecules or secreted molecules, from the co-culture.

In some embodiments, the enrichment process comprises isolating activated T cells expressing or secreting one or more cytokines from the co-culture that has been stimulated by one or more tumor antigen peptides or fragments thereof. In some embodiments, the enrichment step comprises contacting the first co-culture with antigen-loaded PM/ICs to obtain a stimulated co-culture, and isolating an enriched population of activated T cells from the stimulated co-culture using a ligand that specifically recognizes a cytokine. Exemplary cytokines include, but are not limited to, IFNγ and TNFα. Ligands that specifically recognize the cytokine, such as antibodies or receptors for the cytokine, can be used to isolate the enriched population of activated T cells. In some embodiments, the enrichment step comprises contacting the first co-culture with antigen-loaded PBMCs to obtain a stimulated co-culture, and isolating an enriched population of activated T cells from the stimulated co-culture using a ligand that specifically recognizes a cell surface molecule, such as 4-1BB (also known as CD137).

In some embodiments, there is provided a method of enriching activated T cells from a co-culture comprising a population of T cells and a population of DCs loaded with one or more tumor antigen peptides, comprising contacting the co-culture with PBMCs loaded with the one or more tumor antigen peptides to obtain a stimulated co-culture, and isolating an enriched population of activated T cells from the stimulated co-culture using a ligand that specifically recognizes a cytokine or a cell surface molecule. In some embodiments, the cytokine is IFNγ. In some embodiments, the cell surface molecule is 4-1BB.

In some embodiments, the enrichment process comprises isolating activated T cells secreting IFNγ from the co-culture upon stimulation by one or more tumor antigen peptides or fragments thereof. In some embodiments, the enrichment process comprises isolating CD3$^+$IFNγ$^+$ cells from the co-culture upon stimulation by one or more tumor antigen peptides or fragments thereof. In some embodiments, the enrichment process comprises; (1) contacting the co-culture comprising a first population of DCs loaded with one or more tumor antigen peptides or fragments thereof and a population of T cells with the PBMCs loaded with the one or more tumor antigen peptides or fragment thereof for about 10-24 hours (such as about 1 day) to obtain a stimulated co-culture; and (2) isolating activated T cells using a ligand that specifically recognizes IFNγ from the stimulated co-culture. In some embodiments, the first population of antigen-loaded DCs and the population of T cells have been co-cultured for about 1-7 days (such as about 2-3 days) prior to the contacting with the antigen-loaded PBMCs. In some embodiments, the co-culture and the antigen-loaded PBMCs are contacted for at least about any one of 2, 4, 6, 12, 18, 24 or more hours prior to the isolating.

Activated T cells expressing a cytokine (such as IFNγ) can be isolated or enriched from the stimulated co-culture using any known methods in the art. For example, commercial kits are available for isolating T cells that secrete IFNγ, including IFNγ Secretion Assay-Cell Enrichment and Detection Kit from Miltenyi Biotec. In some embodiments, the activated T cells secreting IFNγ are isolated by: (1) contacting, the co-culture with an IFNγ catch reagent that specifically binds to a cell surface antigen on T cells and IFNγ; (2) contacting the IFNγ catch reagent treated co-culture with an anti-IFNγ antibody (e.g., an anti-IFNγ antibody conjugated to R-phycoerthrin or PE); (3) contacting the anti-IFNγ antibody treated co-culture with a magnetic bead comprising a secondary antibody that recognizes the anti-IFNγ antibody (e.g., an anti-PE antibody); and (4) isolating the magnetic beads using a magnetic field (e.g., using a MACS™ separator column), thereby obtaining an enriched population of activated T cells.

In some embodiments, the activated T cells expressing a cell surface biomarker are isolated by: (1) contacting the co-culture with a fluorescently labeled antibody against the cell surface biomarker; and (2) isolating cells bound to the fluorescently labeled antibody from the co-culture by flow cytometry.

PBMC-Based Method

In some embodiments, the method uses PBMC obtained from an individual who has previously received an immunotherapy (e.g., MASCT) to prepare tumor-antigen specific T cells.

In some embodiments, there is provided a method of preparing tumor antigen-specific T cells comprising: a) contacting a first population of PBMCs with a plurality of tumor antigen peptides to provide a population of PBMCs loaded with the plurality of tumor antigen peptides; b) subjecting the population of PBMCs loaded with the plurality of tumor antigen peptides to an enrichment process to provide an enriched population of activated T cells; c) optionally contacting a population of APCs (e.g., PBMCs or DCs) with one or more tumor antigen peptides from the plurality of tumor antigen peptides to provide a population of antigen-loaded APCs; d) a co-culturing step, comprising co-culturing the enriched population of activated T cells with the population of antigen-loaded APCs, thereby obtaining a population of tumor antigen-specific T cells. In some embodiments, the PBMCs are contacted with the plurality of tumor antigen peptides for no more than about 5, 4, 3, 2, or 1 day prior to the enrichment process. In some embodiments, the enrichment process comprises contacting the first co-culture with PBMCs loaded with the plurality of tumor antigen peptides to obtain a stimulated co-culture, and isolating an enriched population of activated T cells from the stimulated co-culture using a ligand that specifically recognizes a cytokine (such as IFNγ) or a cell surface molecule. In some embodiments, the co-culturing step comprises co-culturing the enriched population of activated T cells with the population of antigen-loaded APCs in a co-culture medium comprising one or more cytokines (e.g., a plurality of cytokines), an immune checkpoint inhibitor, and an anti-CD3 antibody. In some embodiments, the co-culturing step comprises co-culturing the enriched population of activated T cells with the population of antigen-loaded APCs in an initial co-culture medium comprising one or more cytokines (e.g., a plurality of cytokines) and an immune checkpoint inhibitor to provide a co-culture, and adding an anti-CD3 antibody to the co-culture. In some embodiments, the anti-CD3 antibody is added to the co-culture at about 1-3 days after the co-culturing starts. In some embodiments, the enriched population of activated T cells and the population of antigen-loaded APCs are co-cultured for a total of about 12-25 days.

In some embodiments, the PBMCs are freshly obtained. In some embodiments, the PBMCs are obtained by thawing a frozen stock of PBMCs. In some embodiments, the PBMCs are autologous, i.e. obtained from the individual being treated. In some embodiments, the peripheral blood from the individual has a low number of DCs or T cells. In some embodiments, the PBMCs are contacted with cytokines, such as IL-2, GM-CSF, or the like, to induce differentiation, maturation, or proliferation of certain cells (such as DCs, T cells, or combination thereof) in the PBMCs concurrently or after the contacting step. In some embodiments, the plurality of tumor antigen peptides is removed after the contacting step.

Antigen Loading of APCs

The methods of preparing tumor-antigen specific T cells described herein and the MASCT methods use APCs (such as PBMCs, dendritic cells, or cell line APCs) loaded with one or more tumor antigen peptides. In some embodiments, the antigen-loaded APCs (e.g., antigen-loaded DCs) are freshly prepared for one or more of the co-culturing steps. In some embodiments, the antigen-loaded APCs (e.g., antigen-loaded DCs) are freshly prepared for each co-culturing step. In some embodiments, the antigen-loaded APCs (e.g., antigen-loaded DCs) are prepared, cultured in a DC maturation medium, and used for one or more co-culturing or stimulation steps. The antigen-loaded DCs used in the first, second and third co-culturing steps may be obtained from a single batch or separate batches of antigen-loaded DCs. Unless indicated otherwise, the features described in this section for the APCs (e.g., DCs) apply to all APCs (e.g., DCs) used in each of the co-culturing steps; and the methods and features described in this section for the antigen-loaded APCs (e.g., DCs) apply to the first population, the second population, and the third population of antigen-loaded DCs and other types of APCs. APCs include, but are not limited to, PBMCs, DCs, B cells, or macrophages. The APCs described herein can be primary cells or derived from cell lines. In some embodiments, the APCs are PBMCs. In some embodiments, the APCs are fixed PBMCs. Fixing PBMCs can destroy the proliferation capacity of the PBMCs, while maintaining the antigen presenting capacity of PBMCs.

The antigen-loaded DCs used in each co-culturing step may be loaded with the same pool of tumor antigen peptides or different pool of tumor antigen peptides. In some embodiments, the first population of DCs in the first co-culturing step is loaded with the same pool of tumor antigen peptides used to load the second population of DCs in the second co-culturing step. In some embodiments, the second population of DCs in the second co-culturing step is loaded with a subset of the pool of tumor antigen peptides used to load the first population of DCs in the first co-culturing step. In some embodiments, the third population of DCs in the third co-culturing step is loaded with a subset of the pool of tumor antigen peptides used to load the first population of DCs in the first co-culturing step and/or the second population of DCs in the second co-culturing step. In some embodiments, the subset of the pool of tumor antigen peptides includes fragments of the tumor antigen peptides and combinations thereof. In some embodiments, a single tumor antigen peptide or fragment thereof is used to load the APCs (such as DCs) used in the second and third co-culturing steps.

In some embodiments, the first population of antigen-loaded DCs used in the first co-culturing step is prepared using the plurality of tumor antigen peptides that the individual used in previous MASCTs. In some embodiments, the first population of antigen-loaded DCs used in the first co-culturing step is prepared using one or more tumor antigen peptides that the individual has specific immune response to in previous MASCTs. In some embodiments, individual tumor antigen peptides from a plurality of tumor antigen peptides or fragments thereof, and combinations thereof are screened (e.g., by ELISPOT) for specific immune response by PBMCs, activated T cells, or tumor antigen-specific T cells derived from an individual to identify one or more tumor antigen peptides (including fragments thereof) for use in subsequent preparation of tumor antigen-specific T cells.

In some embodiments, prior to each co-culturing step, the method of preparing tumor-antigen specific T cells comprises one or more of the following steps: (1) obtaining PBMCs from an individual; (2) obtaining a population of monocytes from the PBMCs; (3) inducing differentiation of the population of monocytes into immature DCs; (4) contacting the immature DCs with one or more tumor antigen peptides to obtain a population of antigen-loaded DCs; and (5) culturing the population of antigen-loaded DCs in a DC maturation medium comprising a TLR agonist (such as MPLA).

In some embodiments, the antigen-loaded DCs are prepared by: (a) contacting a population of DCs with one or more tumor antigen peptides to obtain a population of antigen-loaded DCs, and (b) culturing the population of antigen-leaded DCs in a DC maturation medium comprising a toll-like receptor (TLR) agonist. Exemplary TLR agonists include, but are not limited to, MPLA (monophosphoryl lipid A), Poly I:C, resquimod, gardiquimod, and CL075. Cytokines and other appropriate molecules, such as INFγ and PGE2 (prostaglandin E2) may be further included in the culturing media in the maturation step.

In some embodiments, the antigen-loaded DCs are prepared by: (a) contacting a population of DCs with one or more tumor antigen peptides to obtain a population of antigen-loaded DCs, and (b) culturing the population of antigen-loaded DCs in a DC maturation medium comprising MPLA, INFγ and PGE2.

In some embodiments, the antigen-loaded DCs are prepared by: (a) inducing differentiation of a population of monocytes into immature DCs; (b) contacting a population of immature DCs with one or more tumor antigen peptides to obtain a population of antigen-loaded DCs, and (c) culturing the population of the antigen-loaded DCs in a DC maturation medium comprising MPLA, INFγ and PGE2. In some embodiments, the population of monocytes is obtained from PBMCs.

In some embodiments, the antigen-loaded PBMCs are prepared by contacting a population of PBMCs with one or more tumor antigen peptides. In some embodiments, antigen-loaded cell line APCs are prepared by contacting a population of cell line APCs (e.g., LCL) with one or more tumor antigen peptides.

The DC maturation medium may comprise a suitable concentration of MPLA, INFγ and/or PGE2. In some embodiments, the DC maturation medium comprises MPLA at a concentration of at least about 0.5 μg/mL, such as at least about any one of 1, 2, 3, 4, 5, 6, 7, 8, 9, 10 or more μg/mL. In some embodiments, the DC maturation medium comprises MPLA at a concentration of any one of about 0.5-10, 1-5, 5-10, or 2.5-7.5 μg/mL. In some embodiments the DC maturation medium comprises INFγ at a concentration of at least about 100 IU/mL, such as at least about any one of 150, 200, 250, 300, 400, 500, 600, 800, 1000 or more IU/mL. In some embodiments, the DC maturation medium comprises INFγ at a concentration of about any one of 100-1000, 100-250, 250-500, 500-1000, or 250-750 IU/mL. In some embodiments, the DC maturation medium comprises PGE2 at a concentration of at least about 0.1 µg/mL, such as at least about any one of 0.15, 0.2, 0.25, 0.3, 0.4, 0.5, or more µg/mL. In some embodiments, the DC maturation medium comprises PGE2 at a concentration of about any one of 0.1-0.5, 0.1-0.3, 0.25-0.5 or 0.2-0.4 µg/mL.

The immature DCs loaded with one or more tumor antigen peptides may be induced by TLR agonists to mature for at least about any one of 2, 3, 4, 5, 6, 7, 8, 9, 10, 15, or 20 days. In some embodiments, the DCs loaded with one or more tumor antigen peptides are induced to mature for about 8, 9, 10, 11, or 12 days.

In some embodiments, the antigen-loaded DCs are mature DCs that present one or more tumor antigen peptides. The mature DCs prepared by any of the methods described herein may present at least about any one of 1, 5, 10, 15, 20, 25, 30, 35, 40, 50 or more tumor antigen peptides. Compared to naïve DCs, or DCs that have not been loaded with a plurality of tumor antigen peptides, the multiple-antigen loaded DCs may have enhanced level of presentation for at least about any of 1, 5, 10, 15, 20, 25, 30, 35, 40, 50 or more tumor antigen peptides. In some embodiments, the mature DCs have enhanced level of presentation for more than 10 tumor antigen peptides. In some embodiments, the mature DCs have enhanced level of presentation of about any of 1, 2, 3, 4, 5, 6, 7, 8, 9, 10, 11, 12, 13, 14, or more tumor antigen peptides derived from proteins selected from the group consisting of hTERT, p53, Survivin, NY-ESO-1, CEA, CCND1, RGS5, MMP7, VEGFR1, VEGFR2, MUC1, HER2, MAGE-A1, MAGE-A3, CDCA1, WT1, KRAS, PARP4, MLL3, MTHFR, HBcAg, HBV polymerase, GPC3, SSX, and AFP.

In some embodiments, the antigen-loaded APCs (e.g., DCs or PBMCs) are prepared by pulsing one or more tumor antigen peptides into a population of APCs. In some embodiments, the antigen-loaded DCs are prepared by pulsing one or more tumor antigen peptides into a population of DCs, such as immature DCs, or DCs contained in or derived (such as differentiated) from the PBMCs. As known in the art, pulsing refers to a process of mixing cells, such as APCs (e.g., PBMCs or DCs), with a solution containing antigen peptides, and optionally subsequently removing the antigen peptides from the mixture. The population of DCs may be contacted with one or more tumor antigen peptides for seconds, minutes, or hours, such as about at least any one of 30 seconds, 1 minute, 5 minutes, 10 minutes, 15 minutes, 20 minutes, 30 minutes, 1 hour, 5 hours, 10 hours, 12 hours, 14 hours, 16 hours, 18 hours, 20 hours, 22 hours, 1 day, 2 days, 3 days, 4 days, 5 days, 6 days, one week, 10 days, or more. The concentration of each tumor antigen peptide used in the contacting step may be at least about any one of 0.1, 0.5, 1, 2, 3, 5, or 10 µg/mL. In some embodiments, the concentration of the tumor antigen peptides is about 0.1-200 µg/mL, including for example about any of 0.1-0.5, 0.5-1, 1-10, 10-50, 50-100, 100-150, or 150-200 µg/mL.

In some embodiments, the population of APCs (e.g., DCs or PBMCs) is contacted with one or more tumor antigen peptides in the presence of a composition that facilitates the uptake of the one or more tumor antigen peptides by the APCs (e.g., DCs or PBMCs). In some embodiments, compounds, materials or compositions may be included in a solution of the one or more tumor antigen peptides to facilitate peptide uptake by the APCs (e.g., DCs or PBMCs). Compounds, materials or compositions that facilitate the uptake of the one or more tumor antigen peptides by the APCs (e.g., DCs or PBMCs) include, but are not limited to, lipid molecules and peptides with multiple positively charged amino acids. In some embodiments, more than about any of 50%, 60%, 70% 80%, 90%, or 95% of the tumor antigen peptides are uptaken by the population of APCs (e.g., DCs or PBMCs). In some embodiments, more than about any of 50%, 60%, 70%, 80%, 90%, or 95% of the APCs (e.g., DCs or PBMCs) in the population uptake at least one tumor antigen peptide.

Dendritic cells (such as immature DCs) may be obtained from various sources, including autologous sources, i.e. from the individual receiving the treatment. A convenient source of DCs is the PBMCs from the peripheral blood. For example, monocytes, a type of white blood cells, are abundant in PBMCs, comprising about 5-30% of total PBMCs. Monocytes can be induced to differentiate into DCs, such as immature DCs, using cytokines. In some embodiments, the immature DCs are prepared by obtaining a population of PBMCs, obtaining a population of monocytes from the population of PBMCs, and contacting the population of monocytes with one or more cytokines (e.g., a plurality of cytokines) to obtain a population of immature DCs. Exemplary cytokines that may be used to induce differentiation of monocytes include, but are not limited to, GM-CSF and IL-4, with conditions (such as concentrations, temperature, $CO_2$ level etc.) known in the art.

The adherent fraction of PBMCs contains the majority of monocytes in PBMCs. In some embodiments, the monocytes from the adherent fraction of PBMCs are contacted with cytokines to obtain a population of immature DCs. PBMCs can be conveniently obtained by centrifugation of a sample of peripheral blood, or using apheresis methods to collect from an individual. In some embodiments, the population of PBMCs is obtained by density gradient centrifugation of a sample of human peripheral blood. In some embodiments, the sample is from the individual that receives the multiple-antigen loaded DCs, tumor antigen-specific T cells, or other immunotherapeutic compositions prepared using the multiple-antigen loaded DCs.

Further provided by the present application is an isolated population of DCs prepared by any of the embodiments of the methods described herein. In some embodiments, the isolated population of DCs is capable of eliciting MHC-restricted T cell response in vivo or ex vivo. In some embodiments, the MHC-restricted T cell response is mediated by both MHC class I and MHC class II molecules. In some embodiments, the isolated population of DCs is capable of inducing differentiation and proliferation of tumor antigen-specific T cells.

Tumor Antigen Peptides

The methods described herein and the MASCT methods use one or more tumor antigen peptides to prepare antigen-loaded APCs (such as antigen-loaded DCs), activated T cells and tumor antigen-specific T cells that can trigger specific immune response ex vivo and in vivo. In some embodiments, the plurality or tumor antigen peptides is a plurality of synthetic tumor antigen peptides. In some embodiments, the plurality of tumor antigen peptides is not obtained from a cell sample, such as a lysed cell composition. As used herein, "one or more tumor antigen peptides from the plurality of tumor antigen peptides" refers to a sub-selection or all tumor antigen peptides in the plurality of tumor antigen peptides, including fragments of the tumor antigen peptides and combinations thereof.

In some embodiments, each tumor antigen peptide comprises at least about any one of 1, 2, 3, 4, 5, or 10 epitopes from a single protein antigen (including a neoantigen). In some embodiments, each tumor antigen peptide in the plurality of tumor antigen peptides comprises at least one epitope recognizable by a T cell receptor. In some embodiments, the plurality of tumor antigen peptides comprises at least one tumor antigen peptide that comprises at least 2 epitopes from a single protein antigen. The tumor antigen peptide can be a naturally derived peptide fragment from a protein antigen containing one or more epitopes, or an artificially designed peptide with one or more natural epitope sequences, wherein a linker peptide can optionally be placed in between adjacent epitope sequences. In some preferred embodiments, the epitopes contained in the same tumor antigen peptide are derived from the same protein antigen.

The tumor antigen peptide may contain at least one MHC-I epitope, at least one MHC-II epitope, or both MHC-I epitope(s) and MHC-II epitope(s). In some embodiments, the plurality of tumor antigen peptides comprises at least one peptide comprising an MHC-I epitope. In some embodiments, the plurality of tumor antigen peptides comprises at least one peptide comprising an MHC-II epitope. In some embodiments, at least one tumor antigen peptide in the plurality of tumor antigen peptides comprises both MHC-I and MHC-II epitopes.

Special design strategies can be applied to the sequence of the tumor antigen peptides (including neoantigen peptides) in order to optimize the immune response to DCs loaded with the tumor antigen peptides. Typically, a peptide longer than the exact epitope peptide can increase uptake of the peptide into DCs. In some embodiments, an MHC-I or MHC-II epitope sequence is extended at the N terminus or the C terminus or both termini according to the natural sequence of the protein harboring the epitope to obtain an extended sequence, wherein the extended sequence is amenable for presentation by both class I and class II MHC molecules, and by different subtypes of MHC molecules in different individuals. In some embodiments, the epitope sequence is extended at one or both termini by at least about any one of 1, 2, 3, 4, 5, 6, 7, 8, 9, 10, 12, 15, or 20 amino acid residues to generate the extended epitope. In some embodiments, the peptides comprising an MHC-I or MHC-II epitope further comprise additional amino acids flanking the epitope at the N-terminus, the C-terminus, or both. In some embodiments, each tumor antigen peptide in the plurality of tumor antigen peptides is at least about any one of 10, 15, 20, 25, 30, 35, 40, 45, 50, 60, 70, 80, 90, or 100 amino acids long. Different tumor antigen peptides in the plurality of tumor antigen peptides may have the same length, or different lengths. In some embodiments, the plurality of tumor antigen peptides is each about 20-40 amino acids long.

In some embodiments, the amino acid sequences of one or more epitope peptides used to design a tumor antigen peptide in the present application are based on sequences known in the art or available in public databases, such as the Peptide Database (Vigneron N. et al. *Cancer Immunity;* 13:15 (2013)).

In some embodiments, the amino acid sequences of one or more epitope peptides are predicted based on the sequence of the antigen protein using a bioinformatics tool for T cell epitope prediction. Exemplary bioinformatics tools for T cell epitope prediction are known in the art, for example, See Yang X. and Yu X. (2009) "An introduction to epitope prediction methods and software" *Rev. Med. Virol.* 19(2): 77-96. In some embodiments, the sequence of the antigen protein is known in the art or available in public databases. In some embodiments, the sequence of the antigen protein is determined by sequencing a sample (such as a tumor sample) of the individual being treated.

The present application contemplates tumor antigen peptides derived from any tumor antigens and epitopes known in the art, including neoantigens and neoepitopes, or specially developed or predicted using bioinformatics tools by the inventors.

In some embodiments, the plurality of tumor antigen peptides comprises a first core group of general tumor antigen peptides. In some embodiments, the plurality of tumor antigen peptides further comprises a second group of cancer-type specific antigen peptides. In some embodiments, the plurality of tumor antigen peptides comprises one or more neoantigen peptides. In some embodiments, neoantigen peptides are cancer-type specific antigen peptides. In some embodiments, the plurality of tumor antigen peptides consists of the first core group of general tumor antigen peptides. In some embodiments, the plurality of tumor antigen peptides consists of the first core group of general tumor antigen peptides and the second group of cancer-type specific antigen peptides. In some embodiments, the plurality of tumor antigen peptides consists of neoantigen peptides only. In some embodiments, the plurality of tumor antigen peptides comprises a first core group of general tumor antigen peptides and one or more neoantigen peptides. In some embodiments, the plurality of tumor antigen peptides comprises a first core group of general tumor antigen peptides, a second group of cancer-type specific antigen peptides, and one or more neoantigen peptides.

In some embodiments, the plurality of tumor antigen peptides comprises a first core group of general tumor antigen peptides. In some embodiments, the plurality of tumor antigen peptides further comprises a second group of cancer-type specific antigen peptides. In some embodiments, the plurality of tumor antigen peptides comprises one or more neoantigen peptides. In some embodiments, neoantigen peptides are cancer-type specific antigen peptides. In some embodiments, the plurality of tumor antigen peptides consists of the first core group of general tumor antigen peptides. In some embodiments, the plurality of tumor antigen peptides consists of the first core group of general tumor antigen peptides and the second group of cancer-type specific antigen peptides. In some embodiments, the plurality of tumor antigen peptides consists of neoantigen peptides only. In some embodiments, the plurality of tumor antigen peptides comprises a first core group of general tumor antigen peptides and one or more neoantigen peptides. In some embodiments, the plurality of tumor antigen peptides comprises a first core group of general tumor antigen peptides, a second group of cancer-type specific antigen peptides, and one or more neoantigen peptides.

The first core group of general tumor antigen peptides is derived from tumor antigens commonly overexpressed by a variety of cancers of different types. Therefore, the first core group of general tumor antigen peptides is useful to prepare dendritic cells and/or activated T cells for treating individuals with different cancer types. For example, in some embodiments, the first core group of general tumor antigen peptides is useful for methods described herein for treating a variety of cancers, such as lung cancer, colon cancer, gastric cancer, prostate cancer, melanoma, lymphoma, pancreatic cancer, ovarian cancer, breast cancer, glioma, esophageal cancer, nasopharyngeal carcinoma, cervical cancer, renal carcinoma, or hepatocellular carcinoma. Exemplary tumor antigen peptides of the first core group include, but are not limited to, peptides derived from hTERT, p53, Survivin, NY-ESO-1, CEA, CCND1, MET, MUC1, Her2, MAGEA1, MAGEA3, WT-1, RGS5, MMP7, VEGFR (such as VEGFR1 and VEGFR2), and CDCA1. The first core group may comprise peptides derived from at least about any one of 1, 2, 5, 10, 15, 20, 25, 30, 40, 50, 60, 70, 80 or more tumor antigens. The first core group may comprise at least about any one of 1, 2, 5, 10, 15, 20, 25, 30, 40, 50, 60, 70, 80 or more general tumor antigen peptides. In some embodiments, the first core group comprises more than one general tumor antigen peptides. In some embodiments, the first core group comprises about 10 to about 20 general tumor antigen peptides.

The second group of cancer-type specific antigen peptides is derived from tumor antigens that are overexpressed only in one or a limited number of cancer types. Therefore, the second group of cancer-type specific antigen peptides is useful to prepare dendritic cells and/or activated T cells for treating individuals with a particular type of cancer. Exemplary cancer-type specific antigen peptides for treating hepatocellular carcinoma (HCC) include, but are not limited to, peptides derived from SSX, AFP, and GPC3. In some embodiments, one or more cancer—specific antigen peptide is a virus-specific antigen peptide derived from a virus that can induce cancer, or relates to cancer development in the individual when infecting the individual. In some embodiments, the virus-specific antigen peptide is specific to the subtype of the virus infecting the individual. Exemplary virus-specific antigen peptides for treating an HCC patient with concurrent infection of HBV include, but are not limited to, peptides derived from HBV core antigen (HBcAg), and HBV DNA polymerase. In some embodiments, the second group comprises virus-specific antigen peptides derived from HBV antigens, wherein the method is to treat hepatocellular carcinoma in an individual. In some embodiments, the second group comprises virus-specific antigen peptides derived from HPV antigens, wherein the method is to treat cervical cancer in an individual. In some embodiments, the second group comprises virus-specific antigen peptides derived from EBV antigen, wherein the method is to treat nasopharyngeal carcinoma in an individual. The second group of cancer-type specific antigen peptides may comprise peptides derived from at least about any one of 1, 5, 10, 15, 20, 25, 30, 40, 50 or more cancer-type specific antigens. The second group of cancer-type specific antigen peptides may comprise at least about any one of 1, 2, 5, 10, 15, 20, 25, 30, 40, 50 or more cancer-type specific antigen peptides. In some embodiments, the second group comprises more than one cancer-type specific antigen peptides. In some embodiments, the second group comprises about 1 to about 10 cancer-type specific antigen peptides. In some embodiments, the type of cancer targeted by the cancer-type specific antigen peptides is selected from the group consisting essentially of hepatocellular carcinoma, cervical cancer, nasopharyngeal carcinoma, endometrial cancer, colorectal cancer, breast cancer, endometrial cancer, and lymphoma.

In some embodiments, the plurality of tumor antigen peptides comprises one or more (such as any of 1, 2, 3, 4, 5, 6, 7, 8, 9, 10 or more) neoantigen peptides. In some embodiments, the plurality of tumor antigen peptides consists of neoantigen peptides. In some embodiments, the plurality of tumor antigen peptides comprises neoantigen peptides and no general tumor antigen peptides. In some embodiments, the plurality of tumor antigen peptides comprises one or more general tumor antigen peptides and one or more neoantigen peptides. In some embodiments, the plurality of tumor antigen peptides comprises one or more general tumor antigen peptides, one or more cancer-type specific antigen peptides, and one or more neoantigen peptides. The neoantigen peptides are derived from neoantigens. Neoantigens are newly acquired and expressed antigens present in tumor cells of the individual, such as the individual being treated for cancer. In some embodiments, neoantigens are derived from mutant protein antigens that are only present in cancer cells, but absent in normal cells. Neoantigens may be uniquely present in the tumor cells (such as all tumor cells or a portion of tumor cells) of the individual being treated for cancer, or present in individuals having similar types of cancer as the individual being treated. In some embodiments, the neoantigen is a clonal neoantigen. In some embodiments, the neoantigen is a subclonal neoantigen. In some embodiments, the neoantigen is present in at least about any of 10%, 20%, 30%, 40%, 50%, 60%, 70%, 80%, 90%, 95% or more tumor cells in the individual. In some embodiments, the neoantigen peptide comprises an MHC-I restricted neoepitope. In some embodiments, the neoantigen peptide comprises an MHC-II restricted neoepitope. In some embodiments, the neoantigen peptide is designed to facilitate presentation of the neoepitope by both class I and class II MHC molecules, for example, by extending the neoepitope at both the N- and the C-termini. Exemplary neoantigen peptides include, but are not limited to, neoepitope derived from mutant KRAS (e.g., $KRAS^{G12A}$), PARP4 (e.g., $PARP4^{T1170I}$), MLL3 (e.g., $MLL3^{C988F}$), and MTHFR (e.g., $MTHFR^{A222V}$).

Neoantigen peptides can be selected based on the genetic profile of one or more tumor sites of the individual being treated, and neoantigens are not expressed in normal tissues. In some embodiments, the genetic profile of the tumor sample comprises sequence information of the full genome. In some embodiments, the genetic profile of the tumor sample comprises sequence information of the exome. In some embodiments, the genetic profile of the tumor sample comprises sequence information of cancer-associated genes.

Neoantigen peptides suitable for use in the present application may be derived from any mutant proteins, such as those encoded by mutant cancer-associated genes, in the tumor cells. In some embodiments, the neoantigen peptide comprises a single neoepitope derived from a cancer-associated gene. In some embodiments, the neoantigen peptide comprises more than one (such as 2, 3, or more) neoepitope derived from a cancer-associated gene. In some embodiments, the neoantigen peptide comprises more than one (such as 2, 3, or more) neoepitope derived from more than one (such as 2, 3, or more) cancer-associated genes. In some embodiments, the plurality of tumor antigens comprises a plurality of neoantigen peptides derived from a single cancer-associated gene. In some embodiments, the plurality of tumor antigens comprises a plurality of neoantigen peptides derived from more than one (such as any of 2, 3, 4, 5, or more) cancer-associated genes.

Cancer-associated genes are genes that are overexpressed in cancer cells, but expressed at low levels in normal cells. Exemplary cancer-associated genes include, but are not limited to, ABL1, AKT1, AKT2, AKT3, ALK, ALOX12B, APC, AR, ARAF, ARID1A, ARID1B, ARID2, ASXL-1, ATM, ATRX, AURKA, AURKB, AXL, B2M, BAP1, BCL2, BCL2L1, BCL2L12, BCL6, BCOR, BCORL1, BLM, BMPR1A, BRAF, BRCA1, BRCA2, BRD4, BRIP1, BUB1B, CADM2, CARD11, CBL, CBLB, CCND1, CCND2, CCND3, CCNE1, CD274, CD58, C179B, CDC73, CDH1, CDK1, CDK2, CDK4, CDK5, CDK6, CDK9, CDKN1A, CDKN1B, CDKN1C, CDKN2A, CDKN2B, CDKN2C, CEBPA, CHEK2, CIITA, CREBBP, CRKL, CRLF2, CRTC1, CRTC2, CSF1R, CSF3R, CTNNB1, CUX1, CYLD, DDB2, DDR2, DEPDC5, DICER1, DIS3, DMD, DNMT3A, EED, EGFR, EP300, EPHA3, EPHA5, EPHA7, ERBB2, ERBB3, ERBB4, ERCC2, ERCC3, ERCC4, ERCC5, ESR1, ETV1, ETV4, ETV5, ETV6, EWSR1, EXT1, EXT2, EZH2, FAM46C, FANCA, FANCC, FANCD2, FANCE, FANCF, FANCG, FAS, FBXW7, FGFR1, FGFR2, FGFR3, FGFR4, FH, FKBP9, FLT3, FLT4, FUS, GATA3, GATA4, GATA6, GLI1, GLI2, GLI3, GNA11, GNAQ, GNAS, GNB2L1, GPC3, GSTM5, H3F3A, HNF1A, HRAS, ID3, IDH1, IDH2, IGF1R, IKZF1, IKZF3, INSIG1, JAK2, JAK3, KCNIP1, KDM5C, KDM6A, KDM6B, KDR, KEAP1, KIT, KRAS, LINC00894, LMO1, LMO2, LMO3, MAP2K1, MAP2K4, MAP3K1, MAPK1, MCL1, MDM2, MDM4, MECOM, MEF2B, MEN1, MET, MITF, MLH1, MLL (KMT2A), MLL2 (KTM2D), MPL, MSH2, MSH6, MTOR, MUTYH, MYB, MYBL1, MYC, MYCL1 (MYCL), MYCN, MYD88, NBN, NEGR1, NF1, NF2, NFE2L2, NFKBIA, NFKBIZ, NKX2-1, NOTCH1, NOTCH2 NPM1, NPRL2, NPRL3, NRAS, NTRK1, NTRK2, NTRK3, PALB2, PARK2, PAX5, PBRM1, PDCD1LG2, PDGFRA, PDGFRB, PHF6, PHOX2B, PIK3C2B, PIK3CA, PIK3R1, PIM1, PMS 1, PMS2, PNRC1, PRAME, PRDM1, PRF1, PRKAR1A, PRKCI, PRKCZ, PRKDC, PRPF40B, PRPF8, PSMD13, PTCH1, PTEN, PTK2, PTPN11, PTPRD, OKI, RAD21, RAF1, RARA, RBI, RB1, RBL2, RECQL4, REL, RET, RFWD2, RHEB, RHPN2, ROS1, RPL26, RUNX1, SBDS, SDHA, SDHAF2, SDHB, SDHC, SDHD, SETBP1, SETD2, SF1, SF3B1, SH2B3, SLITRK6, SMAD2, SMAD4, SMARCA4, SMARCB1, SMC1A, SMC3, SMO, SOCS1, SOX2, SOX9, SQSTM1, SRC, SRSF2, STAG1, STAG2, STAT3, STAT6, STK11, SUFU, SUZ12, SYK, TCF3, TCF7L1, TCF7L2, TERC, TERT, TET2, TLR4, TNFAIP3, TP53, TSC1, TSC2, U2AF1, VHL, WRN, WT1, XPA, XPC, XPO1, ZNF217, ZNF708, and ZRSR2.

In some embodiments, the plurality of tumor antigen peptides comprises at least one (such as at least about any of 1, 2, 3, 4, 5, 6, 7, 8, 9, 10, 11, 12, 13, 14, 15 or more) tumor antigen peptide each comprising one or more epitopes encoded by a cancer-associated gene selected from the group consisting of hTERT, p53, Survivin, NY-ESO-1, CEA, CCND1, RGS5, MMP7, VEGFR1, VEGFR2, MUC1, HER2, MAGE-A1, MAGE-A3, CDCA1, WT1, KRAS, PARP4, MLL3, MTHFR, HBcAg, HBV polymerase, GPC3, SSX, and AFP. In some embodiments, the plurality of tumor antigen peptides comprises at least 10 tumor antigen peptides. In some embodiments, the plurality of tumor antigen peptides comprises tumor antigen peptides derived from hTERT, p53, Survivin, NY-ESO-1, CEA, CCND1, MUC1, Her2, MAGEA1, MAGEA3, WT-1, RGS5, VEGFR1, VEGFR2, and CDCA1.

In some embodiments, the one or more tumor antigen peptides is present in a composition having at least about any one of 95%, 96%, 97%, 98%, 99%, 99.9% or higher percentage of the tumor antigen peptides. In some embodiments, the purity of the one or more tumor antigen peptides is at least about 98%. In some embodiments, the solubility of the one or more tumor antigen peptides in the medium for pulsing the tumor antigen peptides into the DCs is at least about any one of 80%, 85%, 90%, 95%, 98%, 99%, 99.9% or higher. In some embodiments, the one or more tumor antigen peptides is about 100% soluble in the medium for pulsing the tumor antigen peptides into the APCs.

MASCT

In some embodiments, the T cells, PBMCs, and DCs used in the methods of preparing tumor antigen-specific peptides described herein are obtained from an individual that has previously received a MASCT. In some embodiments, the individual has developed specific response to the plurality of tumor antigen peptides used in the methods of preparing tumor antigen-specific peptides described herein, for example, as determined by ELISPOT.

As used herein, "MASCT" or "Multiple Antigen Specific Cell Therapy" refers to methods of adoptive T cells therapy comprising administering to an individual an effective amount of activated T cells prepared by co-culturing a population of T cells with a population of DCs loaded with a plurality of tumor antigen peptides. MASCT methods have been described, for example, in International Patent Application Publication No. WO2016145578A1 and International Patent Application No. PCT/CN2018/081338, the contents of which are incorporated herein by reference in their entirety. First-generation MASCT, precision MASCT, PBMC-based MASCT, customized MASCT, neoantigen-based MASCT, improved MASCT, and combination therapy with MASCT (e.g., immune checkpoint inhibitor and MASCT) are all within the scope of MASCT of the present application. Any suitable features and parameters for preparation of antigen-loaded DCs, preparation of activated T cells, enrichment steps, and co-culturing steps described in the present application or in International Patent Applications WO2016145578A1 and PCT/CN2018/081338 may be combined in a MASCT treatment.

The individual may have received a single type of MASCT, or a combination of different types of MASCT, for example, customized MASCT and improved MASCT. The individual may have received one or more cycles of the MASCT. In some embodiments, the individual has received at least about any one of 2, 5, 10, 15, 20 or more cycles of MASCT. In some embodiments, the individual has received MASCT over at least about any one of 3 months, 6 months, 9 months, 12 months, 2 years, 3 years or longer.

In some embodiments, the MASCT comprises administering to the individual an effective amount of activated T cells, wherein the activated T cells are prepared by co-culturing a population of T cells with a population of antigen presenting cells such as DCs) loaded with a plurality of tumor antigen peptides. In some embodiments, the activated T cells are administered intravenously. In some embodiments, the activated T cells are administered for at least three times. In some embodiments, the individual has previously been administered an effective amount of antigen presenting cells loaded with the plurality of tumor antigen peptides. In some embodiments, the method comprises administering to the individual an effective amount of antigen presenting cells (such as DCs) loaded with the plurality of tumor antigen peptides. In some embodiments, the antigen presenting cells are administered about 7 days to about 21 days (such as about 7 days to about 14 days, or about 14 days to about 21 days) prior to the administration of the activated T cells. In some embodiments, the antigen presenting cells are administered for at least three times. In some embodiments, the antigen presenting cells are administered subcutaneously, intradermally or intravenously. In some embodiments, the activated T cells and the population of antigen presenting cells are from the same individual. In some embodiments, the activated T cells and/or the population of antigen presenting cells are from the individual being treated. In some embodiments, the population of antigen presenting cells is a population of DCs, B cells, or macrophages. In some embodiments, the antigen presenting cells are DCs. In some embodiments, the MASCT further comprises administering to the individual an effective amount of an immune checkpoint inhibitor. In some embodiments, the activated T cells and the immune checkpoint inhibitor are administered simultaneously, such as in the same composition. In some embodiments, the activated T cells and the immune checkpoint inhibitor are administered sequentially.

In some embodiments, the MASCT comprises: (a) administering to the individual an effective amount of DCs loaded with a plurality of tumor antigen peptides; (b) co-culturing a population of DCs loaded with the plurality of tumor antigen peptides and a population of T cells to obtain a population of activated T cells; and (c) administering to the individual an effective amount of the activated T cells. In some embodiments, the interval between the administration of the DCs and the administration of the activated T cells is about 7 days to about 21 days (such as about 7 days to about 14 days, about 14 days to about 21 days, about 10 days or about 14 days). In some embodiments, the DCs loaded with the plurality of tumor antigen peptides are administered subcutaneously. In some embodiments, the DCs loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of DCs loaded with the plurality of tumor antigen peptides for about 7 days to about 21 days (such as about 7 days to about 10 days, about 10 days to about 15 days, about 15 days to about 21 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with one or more cytokines (such as a plurality of cytokines, e.g., IL-2, IL-7, IL-15, IL-21, or any combination thereof) and optionally an anti-CD3 antibody. In some embodiments, the population of T cells is contacted with an immune checkpoint inhibitor (such as an inhibitor of PD-1, PD-L1, or CTLA-4) prior to and/or during the co-culturing. In some embodiments, the population of DCs loaded with the plurality of tumor antigen peptides is prepared by contacting a population of DCs with the plurality of tumor antigen peptides. In some embodiments, the population of T cells and the population of DCs are derived from the same individual. In some embodiments, the population of T cells, the population of DCs, the population of PBMCs, or any combination thereof is derived from the individual being treated. In some embodiments, the MASCT further comprises administering to the individual an effective amount of an immune checkpoint inhibitor. In some embodiments, the activated T cells and the immune checkpoint inhibitor are administered simultaneously, such as in the same composition. In some embodiments, the activated T cells and the immune checkpoint inhibitor are administered sequentially.

In some embodiments, the MASCT comprises: (a) inducing differentiation of a population of monocytes into a population of DCs; (b) contacting the population of DCs with a plurality of tumor antigen peptides to obtain a population of DCs to loaded with the plurality of tumor antigen peptides; (c) administering to the individual an effective amount of the DCs loaded with the plurality of tumor antigen peptides; (d) co-culturing the population of DCs loaded with the plurality of tumor antigen peptides and a population of non-adherent PBMCs to obtain the population of activated T cells; and (e) administering to the individual an effective amount of the activated T cells, wherein the population of monocytes and the population of non-adherent PBMCs are obtained from a population of PBMCs. In some embodiments, the interval between the administration of the DCs and the administration of the activated T cells is about 7 days to about 21 days (such as about 7 days to about 14 days, about 14 days to about 21 days, about 10 days or about 14 days). In some embodiments, the DCs loaded with the plurality of tumor antigen peptides are administered subcutaneously. In some embodiments, the DCs loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, about 14 days to about 21 days, or about 10 days). In some embodiments, the co-culturing further comprises contacting the activated T cells with one or more cytokines (e.g., a plurality of cytokines, such as IL-2, IL-7, IL-15, IL-21, or any combination thereof) and optionally an anti-CD3 antibody. In some embodiments, the population of non-adherent PBMCs is contacted with an immune checkpoint inhibitor (such as an inhibitor of PD-1, PD-L1, or CTLA-4) prior to and/or during the co-culturing. In some embodiments, the population of PBMCs is obtained from the individual being treated. In some embodiments, the MASCT further comprises administering to the individual an effective amount of an immune checkpoint inhibitor. In some embodiments, the activated T cells and the immune checkpoint inhibitor are administered simultaneously, such as in the same composition. In some embodiments, the activated T cells and the immune checkpoint inhibitor are administered sequentially.

In some embodiments, the MASCT comprises: contacting a population of peripheral blood mononuclear cells (PBMCs) with a plurality of tumor antigen peptides to obtain a population of activated PBMCs, and administering to the individual an effective amount of the activated PBMCs. In some embodiments, the population of PBMCs is contacted with the plurality of tumor antigen peptides in the presence of a composition that facilitates the uptake of the plurality of tumor antigen peptides by antigen press cells (such as DCs) in the PBMCs. In some embodiments, the population of PBMCs is contacted with the plurality of tumor antigen peptides in the presence of an immune checkpoint inhibitor, such as an inhibitor of PD-1, PD-L1, CTLA-4, IDO, TIM-3, BTLA, VISTA, and LAG-3. In some embodiments, the population of activated PBMCs is contacted with IL-2. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the MASCT further comprises administering to the individual an effective amount of an immune checkpoint inhibitor. In some embodiments, the activated T cells and the immune checkpoint inhibitor are administered simultaneously, such as in the same composition. In some embodiments, the activated T cells and the immune checkpoint inhibitor are administered sequentially.

In some embodiments, the MASCT comprises: (a) co-culturing a population of DCs loaded with a plurality of tumor antigen peptides and a population of T cells in an initial co-culture medium comprising one or more cytokines (e.g., a plurality of cytokines) and an immune checkpoint inhibitor to provide a co-culture; b) adding an anti CD3 antibody to the co-culture at about 3 to 7 days after the co-culturing starts, thereby obtaining the population of activated T cells; and (c) administering to the individual an effective amount of the activated T cells. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 µg/mL. In some embodiments, the anti-CD3 antibody is added to the co-culture at about 5 days after the co-culturing starts. In some embodiments, the population of DCs loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of DCs and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of DCs loaded with the plurality of tumor antigen peptides. In some embodiments, the DCs loaded with the plurality of tumor antigen peptides are administered for at least three times. In some embodiments, the DCs loaded with the plurality of tumor antigen peptides are administered subcutaneously, intradermally or intravenously.

In some embodiments, the MASCT comprises: a) contacting a population of DCs with a plurality of tumor antigen peptides to obtain a population of DCs loaded with the plurality of tumor antigen peptides; b) culturing the population of DCs loaded with the plurality of tumor antigen peptides in a DC maturation medium comprising MPLA; c) co-culturing the population of DCs loaded with the plurality of tumor antigen peptides and a population of T cells, thereby obtaining the population of activated T cells; and d) administering to the individual an effective amount of the activated T cells. In some embodiments, step c) comprises co-culturing the population of DCs loaded with the plurality of tumor antigen peptides and a population of T cells in a co-culture medium comprising an interleukin cocktail, an immune checkpoint inhibitor and an anti-CD3 antibody. In some embodiments, the population of DCs loaded with the plurality of tumor antigen peptides and the population of T cells are co-cultured for at least about 10 days in the presence of the anti-CD3 antibody. In some embodiments, the DC maturation medium comprises INFγ and MPLA. In some embodiments, the DC maturation medium further comprises PGE2. In some embodiments, the MPLA is present in the DC maturation medium at a concentration of at least about 0.5 µg/mL. In some embodiments, the INFγ is present in the DC maturation medium at a concentration of at least about 100 IU/mL. In some embodiments, the PGE2 is present in the DC maturation medium at a concentration of at least about 0.1 µg/mL. In some embodiments, the plurality of cytokines comprises IL-2, IL-7, IL-15 and IL-21. In some embodiments, the IL-2 is present in the co-culture medium at a concentration of at least about 500 IU/mL. In some embodiments, the immune checkpoint inhibitor is an anti-PD-1 antibody. In some embodiments, the anti-PD-1 antibody is present in the co-culture medium at a concentration of at least about 10 µg/mL. In some embodiments, the population of DCs loaded with the plurality of tumor antigen peptides and the population of T cells are co-cultured for at least about 10 days in the presence of the anti-CD3 antibody. In some embodiments, the population of T cells is present in a population of PBMCs. In some embodiments, the population of DCs and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of DCs loaded with the plurality of tumor antigen peptides. In some embodiments, the DCs loaded with the plurality of tumor antigen peptides are administered for at least three times. In some embodiments, the DCs loaded with the plurality of tumor antigen peptides are administered subcutaneously, intradermally or intravenously.

In some embodiments, the MASCT comprises: a) contacting a population of DCs with a plurality of tumor antigen peptides to obtain a population of DCs loaded with the plurality of tumor antigen peptides; b) co-culturing the population of DCs loaded with the plurality of tumor antigen peptides and a population of T cells in an initial co-culture medium comprising one or more cytokines (e.g., a plurality of cytokines) and an immune checkpoint inhibitor to provide a co-culture; c) adding an anti-CD3 antibody to the co-culture at about 3 to 7 days after the co-culturing starts, thereby obtaining the population of activated T cells and d) administering to the individual an effective amount of the activated T cells. In some embodiments, step (a) further comprises culturing the population of DCs loaded with the plurality of tumor antigen peptides in a DC maturation medium comprising a toll-like receptor (TLR) agonist. In some embodiments, the TLR agonist is selected from the group consisting of MPLA, Poly I:C, resquimod, gardiquimod, and CL075. In some embodiments, the DC maturation medium comprises PGE2. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 µg/mL. In some embodiments, the anti-CD3 antibody is added to the co-culture at about 5 days after the co-culturing starts. In some embodiments, the population of DCs loaded with the plurality of tumor antigen peptides and the population of T cells are co-cultured for at least about 10 days in the presence of the anti-CD3 antibody. In some embodiments, the population of DCs and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of DCs loaded with the plurality of tumor antigen peptides. In some embodiments, the DCs loaded with the plurality of tumor antigen peptides are administered for at least three times. In some embodiments, the DCs loaded with the plurality of tumor antigen peptides are administered subcutaneously, intradermally or intravenously.

In some embodiments, the MASCT comprises: a) contacting a population of DCs with a plurality of tumor antigen peptides to obtain a population of DCs loaded with the plurality of tumor antigen peptides; b) culturing the population of DCs loaded with the plurality of tumor antigen peptides in a DC maturation medium comprising MPLA; c) co-culturing the population of DCs loaded with the plurality of tumor antigen peptides and a population of T cells in an initial co-culture medium comprising one or more cytokines (e.g., a plurality of cytokines) and an immune checkpoint inhibitor to provide a co-culture; d) adding an anti-CD3 antibody to the co-culture, thereby obtaining the population of activated T cells; and e) administering to the individual an effective amount of the activated T cells. In some embodiments, the anti-CD3 antibody is added to the co-culture when the co-culturing starts. In some embodiments, the anti-CD3 antibody is added to the co-culture after the co-culturing starts. In some embodiments, the DC maturation medium comprises INFγ and MPLA. In some embodiments, the DC maturation medium further comprises PGE2. In some embodiments, the MPLA is present in the DC maturation medium at a concentration of at least about 0.5 μg/mL. In some embodiments, the INFγ is present in the DC maturation medium at a concentration of at least about 100 IU/mL. In some embodiments, the PGE2 is present in the DC maturation medium at a concentration of at least about 0.1 μg/mL. In some embodiments, the plurality of cytokines comprises IL-2, IL-7, IL-15 and IL-21. In some embodiments, the IL-2 is present in the initial co-culture medium at a concentration of at least about 500 IU/mL. In some embodiments, the immune checkpoint inhibitor is an anti-PD-1 antibody. In some embodiments, the anti-PD-1 antibody is present in the initial co-culture medium at a concentration of at least about 10 μg/mL. In some embodiments, the population of DCs loaded with the plurality of tumor antigen peptides and the population of T cells are co-cultured for at least about 10 days in the presence of the anti-CD3 antibody. In some embodiments, the population of DCs and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of DCs loaded with the plurality of tumor antigen peptides. In some embodiments, the DCs loaded with the plurality of tumor antigen peptides are administered for at least three times. In some embodiments, the DCs loaded with the plurality of tumor antigen peptides are administered subcutaneously, intradermally or intravenously.

In some embodiments, the MASCT comprises: a) contacting a population of DCs with a plurality of tumor antigen peptides to obtain a population of DCs loaded with the plurality of tumor antigen peptides; b) culturing the population of DCs loaded with the plurality of tumor antigen peptides in a DC maturation medium comprising MPLA, INFγ and PGE2; c) co-culturing the population of DCs loaded with the plurality of tumor antigen peptides and a population of T cells in an initial co-culture medium comprising one or more cytokines (such as IL-2 or a plurality of cytokines comprising IL-2, IL-7, IL-15 and IL-21) and an anti-PD-1 antibody to provide a co-culture; d) adding an anti-CD3 antibody to the co-culture at about 3 to 7 days (e.g., about 5 days) after the co-culturing starts, thereby obtaining the population of activated T cells; and e) administering to the individual an effective amount of the activated T cells. In some embodiments, the MPLA is present in the DC maturation medium at a concentration of at least about 0.5 μg/mL. In some embodiments, the INFγ is present in the DC maturation medium at a concentration of at least about 100 IU/mL. In some embodiments, the PGE2 is present in the DC maturation medium at a concentration of at least about 0.1 μg/mL. In some embodiments, the IL-2 is present in the initial co-culture medium at a concentration of at least about 500 IU/mL. In some embodiments, the anti-PD-1 antibody is present in the initial co-culture medium at a concentration of at least about 10 μg/mL. In some embodiments, the population of DCs loaded with the plurality of tumor antigen peptides and the population of T cells are co-cultured for at least about 10 days in the presence of the anti-CD3 antibody. In some embodiments, the population of DCs and the population of T cells are obtained from the individual being treated. In some embodiments, the activated T cells are administered to the individual for at least three times. In some embodiments, the activated T cells are administered intravenously. In some embodiments, the method further comprises administering to the individual an effective amount of DCs loaded with the plurality of tumor antigen peptides. In some embodiments, the DCs loaded with the plurality of tumor antigen peptides are administered for at least three times. In some embodiments, the DCs loaded with the plurality of tumor antigen peptides are administered subcutaneously, intradermally or intravenously.

Generally, dosages, schedules, and routes of administration of the activated T cells and the population of DCs loaded with the plurality of tumor antigen peptides described herein may be determined according to the size and condition of the individual, and according to standard pharmaceutical practice. Exemplary routes of administration include intravenous, intra-arterial, intraperitoneal, intrapulmonary, intravesicular, intramuscular, intra-tracheal, subcutaneous, intraocular, intrathecal, or transdermal. In some embodiments, the DCs loaded with the plurality of tumor antigen peptides are administered subcutaneously. In some embodiments, the activated T cells are administered intravenously.

The dose of the cells administered to an individual may vary according to, for example, the particular type of cells being administered, the route of administration, and the particular type and stage of cancer being treated. The amount should be sufficient to produce a desirable response, such as a therapeutic response against cancer, but without severe toxicity or adverse events. In some embodiments, the amount of the activated T cells or the DCs to be administered is a therapeutically effective amount. In some embodiments, the amount of the cells (such as multiple-antigen loaded DCs, or the activated T cells) is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same individual prior to treatment or compared to the corresponding activity in other individuals not receiving the treatment. Standard methods can be used to measure the magnitude of this effect, such as in vitro assays with purified enzyme, cell-based assays, animal models, or human testing.

In some embodiments, the antigen-loaded dendritic cells are administered at a dose at least about, any one of $1\times10^5$, $5\times10^5$, $1\times10^6$, $1.5\times10^6$, $2\times10^6$, $3\times10^6$, $4\times10^6$, $5\times10^6$, $6\times10^6$, $7\times10^6$, $8\times10^6$, $9\times10^6$, $1\times10^7$ or $5\times10^7$ cells/individual. In some embodiments, the antigen-loaded dendritic cells are administered at a dose about arty one of $1\times10^5$-$5\times10^5$, $5\times10$-$1\times10^6$, $1\times10^6$-$2\times10^6$, $2\times10^6$-$3\times10^6$, $3\times10^6$-$4\times10^6$, $4\times10^6$-$5\times10^6$-$6\times10^6$, $5\times10^6$-$6\times10^6$, $6\times10^6$-$7\times10^6$, $7\times10^6$-$8\times10^6$, $8\times10^6$-$1\times10^8$, $1\times10^6$-$3\times10^6$, $3\times10^6$-$5\times10^6$, $5\times10^6$-$7\times10^6$, $2\times10^6$-$2\times10^7$, $5\times10^6$-$2\times10^7$, or $1\times10^6$-$2\times10^7$ cells/individual. In some embodiments, the antigen-loaded dendritic cells are administered at a dose of at least about $1\times10^6$ cells/individual. In some embodiments, the antigen-loaded dendritic cells are administered at a dose of about $1.5\times10^6$ to about $1.5\times10^7$ cells/individual.

In some embodiments, the antigen-loaded dendritic cells are administered at a dose at least about any one of $1\times10^4$, $2.5\times10^4$, $5\times10^4$, $1\times10^5$, $2\times10^5$, $2\times10^5$, $2.5\times10^5$, $4\times10^5$, $6\times10^5$, $8\times10^5$, $1\times10^6$, $2\times10^6$ or $1\times10^7$ cells/kg. In some embodiments, the antigen-loaded dendritic cells are administered at a dose about any one of $1\times10^4$-$5\times10^4$, $5\times10^4$-$1\times10^5$, $1\times10^5$-$2\times10^5$, $2\times10^5$-$4\times10^5$, $4\times10^5$-$6\times10^5$, $6\times10^5$-$8\times10^5$, $8\times10^5$-$1\times10^6$, $1\times10^6$-$2\times10^6$, $2\times10^6$-$1\times10^7$, $1\times10^4$-$1\times10^5$, $1\times10^5$-$1\times10^6$, $1\times10^6$-$1\times10^7$, $1\times10^4$-$1\times10^6$, or $1\times10^5$-$1\times10^7$ cells/kg. In some embodiments, the antigen-loaded dendritic cells are administered at a dose of at least about $2\times10^5$ cells/kg. In some embodiments, the antigen-loaded dendritic cells are administered at a dose of about $2.5\times10^4$ to about $2.5\times10^5$ cells/kg.

In some embodiments, the activated T cells are administered at a dose of at least about any one of $1\times10^8$, $5\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $1.5\times10^{10}$, $2\times10^{10}$, or $5\times10^{10}$ cells individual. In some embodiments, the activated T cells are administered at a close of about any one of $1\times10^8$-$5\times10^8$, $5\times10^8$-$1\times10^9$, $1\times10^9$-$5\times10^9$, $5\times10^9$-$1\times10^{10}$, $3\times10^9$-$7\times10^9$, $1\times10^{10}$-$2\times10^{10}$, or $1\times10^9$-$1\times10^{10}$ cells/individual. In some embodiments, the activated T cells are administered at a dose of at least about $3\times10^9$ cells/individual. In some embodiments, the activated T cells are administered at a dose of about $1\times10^9$ to about $1\times10^{10}$ cells/individual.

In some embodiments, the activated T cells are administered at a dose of at least about any one of $1\times10^7$, $2\times10^7$, $4\times10^7$, $6\times10^7$, $8\times10^7$, $1\times10^8$, $2\times10^8$, $4\times10^8$, $6\times10^8$, $8\times10^8$, $1\times10^9$ cells/kg. In some embodiments, the activated T cells are administered at a dose of about any one of $1\times10^7$-$1\times10^8$, $1\times10^7$-$5\times10^7$, $2\times10^7$-$4\times10^7$, $5\times10^7$-$1\times10^8$, $1\times10^8$-$2\times10^8$, $5\times10^7$-$1\times10^8$, $1\times10^8$-$2\times10^8$, $2\times10^8$-$5\times10^8$, $1\times10^8$-$1\times10^9$, or $1\times10^7$-$1\times10^9$ cells/kg. In some embodiments, the activated T cells are administered at a dose of at least about $6\times10^7$ cells/kg. In some embodiments, the activated T cells are administered at a dose of about $1.5\times10^7$ to about $2\times10^8$ cells/kg.

In some embodiments, the MASCT is particularly suitable for an individual with a low total mutation load in the cancer of the individual. In some embodiments, the MASCT is particularly suitable for an individual with a low mutation load in the cancer-associated genes in the cancer of the individual. In some embodiments, the MASCT is particularly suitable for an individual with a low mutation load in immune genes related to T cell response in the cancer of the individual. In some embodiments, the MASCT is particularly suitable for an individual with a low mutation load in the MHC genes in the cancer of the individual. The mutation load may be mutation load in all cancer cells, or a subset of cancer cells, such as a primary or metastatic tumor site, for example, cells in a tumor biopsy sample.

In some embodiments, a low mutation load of one or more genes is a low number of mutations accumulated on the one or more genes. In some embodiments, a total number of no more than about any of 500, 400, 300, 200, 100, 50, 40, 30, 20, 10, 5 or fewer mutations indicate a low mutation load.

In some embodiments, no more than about any of 50, 40, 30, 25, 20, 15, 14, 13, 12, 11, 10, 9, 8, 7, 6, 5, 4, 3, 2 or 1 mutations in the one or more MHC genes indicate a low mutation load of the one or more MHC genes. In some embodiments, a low mutation load of one or more genes is a low ratio between the number of mutations accumulated on the one or more genes (such as MHC genes) and the total number of mutations in a selected set of genes (such as cancer-associated genes) or the full genome.

In some embodiments, the one or more MHC genes comprise MHC class I genes (or loci). In some embodiments, the one or more MHC genes comprise MHC class II genes (or loci). In some embodiments, wherein the individual is a human individual, the one or more MHC genes are selected front the group consisting of HLA-A, HLA-B, HLA-C and B2M.

Exemplary mutations include, but are not limited to, deletion, frameshift, insertion, indel, missense mutation, nonsense mutation, point mutation, copy number variation, single nucleotide variation (SNV), silent mutation, splice site mutation, splice variant, gene fusion, and translocation. In some embodiments, the copy number variation of the MHC gene is caused by structural rearrangement of the genome, including deletions, duplications, inversion, and translocation of a chromosome or a fragment thereof. In some embodiments, the mutations in the one or more MHC genes are selected from point mutations, frameshift mutations, gene fusions, and copy number variations. In some embodiments, the mutations are in the protein-coding region of the MHC genes. In some embodiments, the mutation is a nonsynonymous mutation. In some embodiments, the mutation is not a polymorphism. In some embodiments, the mutation is present in normal cells of the individual. In some embodiments, the mutation is not present in normal cells of the individual. In some embodiments, the mutation affects the physiochemical or functional properties, such as stability or binding affinity, of the MHC molecule encoded by the affected gene. In some embodiments, the mutation results in an irreversible deficiency in the molecule. In some embodiments, the mutation reduces the binding affinity of the MHC molecule to T cell epitopes and/or T cell receptors. In some embodiments, the mutation is a loss-of-function mutation. In some embodiments, the mutation results in reversible deficiency in the MHC molecule. In some embodiments, the mutation does not affect the binding, affinity of the MHC molecule to T cell epitopes and/or T cell receptors. In some embodiments, the mutation is a somatic mutation. In some embodiments, the mutation is a germline mutation.

The mutations counted towards the mutation load may be present in all cancer cells or in a subset of cancer cells. In some embodiments, the mutations are present in all cancer cells in the individual. In some embodiments, the mutations are present in all cancer cells of a tumor site. In some embodiments, the mutations are clonal. In some embodiments, the mutations are subclonal. In some embodiments, the mutations are present in at least about any of 10%, 20%, 30%, 40%, 50%, 60%, 70%, 80%, 90%, 95%, or more cancer cells of the individual.

The mutations in certain genes and/or in certain domains or positions of the one or more MHC genes may have more profound influence on the clinical response of the individual to the treatment methods described herein. For example, loss-of-function mutations may occur in the leader peptide sequence, a3 domain (which binds the CD8 co-receptor of T cells), a1 peptide binding domain, or a2 peptide binding domain of the HLA molecule, see, for example, Shukla S. et al. *Nature Biotechnology* 33, 1152-1158 (2015), incorporated herein by reference. Mutations in B2M (β2-macroglobulin) gene may also promote tumor escape phenotypes. See, for example, Monica B et al. *Cancer Immunol. Immu.*, (2012) 61: 1359-1371. In some embodiments, presence of any number (such as 1, 2, 3, 4, 5, or more) of mutations in the functional regions of the one or more MHC genes, such as the leader peptide sequence, a1 domain, a2 domain, or a3 domain, indicates a high mutation load. In some embodiments, presence of any number (such as 1, 2, 3, 4, 5, or more) loss-of-function mutations in the one or more MHC genes (such as HLA-A, HLA-B or HLA-C genes in human individuals) indicates a high mutation load. In some embodiments, a low mutation load in the one or more MHC genes comprises no mutation in the functional regions, including leader peptide sequence, a1 domain (for example, residues in direct contact with the CD8 co-receptor), a2 domain, and a3 domain (for example, residues in direct contact with the epitope), of the one or more MHC genes (such as HLA-A, HLA-B or HLA-C genes). In some embodiments, presence of any number of mutations (such as loss-of-function mutations) in the B2M gene indicates a high imitation load. In some embodiments, a low mutation load in the one or more MHC genes comprises no mutation in the B2M gene.

The mutation load of one or more genes (such as MHC genes) may be determined by any known methods in the art, including, but not limited to, genomic DNA sequencing, exome sequencing, or other DNA sequencing-based methods using Sanger sequencing or next generation sequencing platforms; polymerase chain reaction assays; in situ hybridization assays; and DNA microarrays.

In some embodiments, the mutation load of the one or more MHC genes is determined by sequencing a tumor sample from the individual. In some embodiments, the sequencing is next generation sequencing. In some embodiments, the sequencing is full genome sequencing. In some embodiments, the sequencing is exome sequencing, such as whole exome sequencing ("WES"). In some embodiments, the sequencing is RNA sequencing. In some embodiments, the sequencing is targeted sequencing of candidate genes, such as cancer-associated genes plus HLA genes. For example, ONCOGXONE™ Plus (Admera Health), are available to sequence cancer-associated genes and HLA loci with high sequencing depth. In some embodiments, the same sequencing data can be used to determine the mutation load of the one or more MHC genes and to identify neoantigens in the individual.

In some embodiments, the tumor sample is a tissue sample. In some embodiments, the tumor sample is a tumor biopsy sample, such as fine needle aspiration of tumor cells or laparoscopy obtained tumor cells (such as including tumor stroma). In some embodiments, the tumor sample is freshly obtained. In some embodiments, the tumor sample is frozen. In some embodiments, the tumor sample is a Formaldehyde Fixed-Paraffin Embedded (FFPE) sample. In some embodiments, the tumor sample is a cell sample. In some embodiments, the tumor sample comprises a circulating metastatic cancer cell. In some embodiments, the tumor sample is obtained by sorting circulating tumor cells (CTCs) from blood. In some embodiments, nucleic acids (such as DNA and/or RNA) are extracted from the tumor sample for the sequencing analysis. In some embodiments, the sequencing data of the tumor sample is compared to the sequencing data of a reference sample, such as a sample of a healthy tissue from the same individual, or a sample of a healthy individual, to identify mutations and determine mutation load in the tumor cells. In some embodiments, the sequencing data of the tumor sample is compared to the reference sequences from a genome database to identify mutations and determine mutation load in the tumor cells.

Any of the MASCT methods may comprise using one or more neoantigen peptides in the plurality of tumor antigen peptides. In some embodiments, the MASCT further comprises the steps of selecting the individual for the method of treating based on having one or more (such as at least 5) neoantigens in the individual, and/or the steps of (i) identifying a neoantigen of the individual; and (ii) incorporating a neoantigen peptide derived from the neoantigen in the plurality of tumor antigen peptides for use in the treatment method.

In some embodiments, the MASCT comprises: (a) identifying a neoantigen of the individual; (b) incorporating a neoantigen peptide in a plurality of tumor antigen peptides, wherein the neoantigen peptide comprises a neoepitope in the neoantigen; (c) optionally administering an effective amount of DCs loaded with the plurality of tumor antigen peptides; (d) preparing a population of activated T cells by co-culturing the antigen-loaded DCs with a population of T cells; and (e) administering to the individual an effective amount of activated T cells, wherein the individual has one or more neoantigens.

The individual may have any number (such as at least ti bout any one of 1, 2, 4, 5, 6, 7, 8, 9, 10, 11, 12, 13, 14, 15, 20, 50, 100 or more) of neoantigens in order to benefit from the MASCT method using a plurality of tumor antigen peptides comprising a neoantigen peptide. In some embodiments, the MASCT method is particularly suitable for an individual having at least about any one of 4, 5, 6, 7, 8, 10, 15, 20, 50, 100 or more neoantigens. In some embodiments, the neoantigen comprises one or more neoepitopes. In some embodiments, the MASCT method is particularly suitable for an individual having at least about any one of 4, 5, 6, 7, 8, 10, 15, 20, 50, 100 or more neoepitopes. In some embodiments, the T cell epitopes are MHC-I restricted epitopes. In some embodiments, the neoepitope has a higher affinity to the MHC molecules of the individual than the corresponding wildtype T cell epitope. In some embodiments, the neoepitope has higher affinity to a model T cell receptor than the corresponding wildtype T cell epitope. In some embodiments, the neoantigen (or neoepitope) is a clonal neoantigen. In some embodiments, the neoantigen (or neoepitope) is a subclonal neoantigen. In some embodiments, the neoantigen (or neoepitope) is present in at least about any one of 10%, 20%, 30%, 40%, 50%, 60%, 70%, 80%, 90%, 95% or more tumor cells in the individual.

The MASCT can be used in monotherapy as well as in combination therapy with another agent. For example, any of the treatment methods described herein may be combined with administration of one or more (such as any of 1, 2, 3, 4, or more) immune checkpoint inhibitors. In some embodiments, the immune checkpoint inhibitor is selected from the group consisting of inhibitors of PD-1, PD-L1, CTLA-4, IDO, TIM-3, BTLA, VISTA, and LAG-3.

In some embodiments, the immune checkpoint inhibitor is an inhibitor of PD-1. In some embodiments, the immune checkpoint inhibitor is an anti-PD-1 antibody. Exemplary anti-PD-1 antibodies include, but are not limited to, Nivolumab, pembrolizumab, pidilizumab, BMS-936559, and atezolizumab, Pembrolizumab, MK-3475, AMP-224, AMP-514, STI-A1110, and TSR-042. In some embodiments, the immune checkpoint inhibitor is nivolumab (for example, OPDIVO®). In some embodiments, the immune checkpoint inhibitor is Pembrolizumab (for example, KEYTRUDA®). In some embodiments, the immune checkpoint inhibitor is SHR-1210.

In some embodiments, the immune checkpoint inhibitor is an inhibitor of PD-L1. In some embodiments, the immune checkpoint inhibitor is an anti-PD-L1 antibody. Exemplary anti-PD-L1 antibodies include, but are not limited to, KY-1003, MCLA-145, RG7446, BMS935559, MPDL3280A, MEDI4736, Avelumab, or STI-A1010.

In some embodiments, the immune checkpoint inhibitor is an inhibitor of CTLA-4. In some embodiments, the immune checkpoint inhibitor is an anti-CTLA-4 antibody. Exemplary anti-CTLA-4 antibodies include, but are not limited to, Ipilimumab, Tremelimumab, and KAHR-102. In some embodiments, the immune checkpoint inhibitor is Ipilimumab (for example, YERVOY®).

In some embodiments, the activated T cells and the immune checkpoint inhibitor are administered simultaneously. In some embodiments, the activated T cells and the immune checkpoint inhibitor are administered in a single composition. In some embodiments, the immune checkpoint inhibitor is present in the first, second or third co-culture. In some embodiments, the activated T cells and the immune checkpoint inhibitor are admixed prior to (such as immediately prior to) the administration. In some embodiments, the activated T cells and the immune checkpoint inhibitor are administered simultaneously via separate compositions.

In some embodiments, the activated T cells and the immune checkpoint inhibitor are administered sequentially. In some embodiments, the immune checkpoint inhibitor is administered prior to the administration of the activated T cells. In some embodiments, the immune checkpoint inhibitor is administered after the administration of the activated T cells.

Exemplary routes of administration of the immune checkpoint inhibitor include, but are not limited to, intratumoral, intravesical, intramuscular, intraperitoneal, intravenous, intra-arterial, intracranial, intrapleural, subcutaneous, and epidermal routes, or be delivered into lymph glands, body spaces, organs or tissues known to contain such live cancer cells. In some embodiments, the immune checkpoint inhibitor is administered intravenously. In some embodiments, the immune checkpoint inhibitor is administered by infusion. In some embodiments, the immune checkpoint inhibitor is infused over at least about any of 10 minutes, 30 minutes, 1 hour, 2 hours, 4 hours, 6 hours, or more. In some embodiments, the immune checkpoint inhibitor is administered via the same administration route as the activated T cells. In some embodiments, the immune checkpoint inhibitor is administered via a different administration route as the activated T cells.

Suitable dose of the immune checkpoint inhibitor include, but are not limited to, about any one of 1 mg/m$^2$, 5 mg/m$^2$, 10 mg/m$^2$, 20 mg/m$^2$, 50 mg/m$^2$, 100 mg/m$^2$, 200 mg/m$^2$, 300 mg/m$^2$, 400 mg/m$^2$, 500 mg/m$^2$, 750 mg/m$^2$, 1000 mg/m$^2$, or more. In some embodiments, the dose of immune checkpoint inhibitor is any one of about 1 to about 5 mg/m$^2$, about 5 to about 10 mg/m$^2$, about 10 to about 20 mg/m$^2$, about 20 to about 50 mg/m$^2$, about 50 to about 100 mg/m$^2$, about 100 mg/m$^2$ to about 200 mg/m$^2$, about 200 to about 300 mg/m$^2$, about 300 to about 400 mg/m$^2$, about 400 to about 500 mg/m$^2$, about 500 to about 750 mg/m$^2$, or about 750 to about 1000 mg/m$^2$. In some embodiments, the dose of immune checkpoint inhibitor is about any one of 1 µg/kg, 2 µg/kg, 5 µg/kg, 10 µg/kg, 20 µg/kg, 50 µg/kg, 0.1 mg/kg, 0.2 mg/kg, 0.3 mg/kg 0.4 mg/kg, 0.5 mg/kg, 1 mg/kg, 2 mg/kg, 5 mg/kg, 10 mg/kg, 20 mg/kg, 50 mg/kg, 100 mg/kg, or more. In some embodiments, the dose of the immune checkpoint inhibitor is any one of about 1 µg/kg to about 5 µg/kg, about 5 µg/kg to about 10 µg/kg, about 10 µg/kg to about 50 µg/kg, about 50 µg/kg to about 0.1 mg/kg, about 0.1 mg/kg to about 0.2 mg/kg, about 0.2 mg/kg to about 0.3 mg/kg, about 0.3 mg/kg to about 0.4 mg/kg, about 0.4 mg/kg to about 0.5 mg/kg, about 0.5 mg/kg to about 1 mg/kg, about 1 mg/kg to about 5 mg/kg, about 5 mg/kg to about 10 mg/kg, about 10 mg/kg to about 20 mg/kg, about 20 mg/kg to about 50 mg/kg, about 50 mg/kg to about 100 mg/kg, or about 1 mg/kg to about 100 mg/kg.

In some embodiments, the immune checkpoint inhibitor is administered daily. In some embodiments, the immune checkpoint inhibitor is administered is administered at least about any one of 1×, 2×, 3×, 4×, 5×, 6×, or 7× (i.e., daily) a week. In some embodiments, the immune checkpoint inhibitor is administered weekly. In some embodiments, the immune checkpoint inhibitor is administered weekly without break; weekly, two out of three weeks; weekly three out of four weeks; once every two weeks; once every 3 weeks; once every 4 weeks; once every 6 weeks; once every 8 weeks, monthly, or every two to 12 months. In some embodiments, the intervals between each administration are less than about any one of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, the immune checkpoint inhibitor is administered once every 3 months. In some embodiments, there is no break in the dosing schedule. In some embodiments, the interval between each administration is no more than about a week. In some embodiments, the immune checkpoint inhibitor is administered with the same dosing schedule as the activated T cells. In some embodiments, the immune checkpoint inhibitor is administered with a different dosing schedule as the activated T cells.

In some embodiments, the immune checkpoint inhibitor is administered in every MASCT treatment cycle. For example, the immune checkpoint inhibitor may be administered about any of 1, 2, 3, 4, 5, 6, or more times every MASCT treatment cycle. In some embodiments, the immune checkpoint inhibitor is not administered in every MASCT treatment cycle. For example, the immune checkpoint inhibitor may be administered about once every 1, 2, 3, 4, 5, or more MASCT treatment cycles.

The administration of the immune checkpoint inhibitor can be over an extended period of time, such as from about a month up to about seven years. In some embodiments, the immune checkpoint inhibitor is administered over a period of at least about any one of 1, 2, 3, 4, 5, 6, 7, 8, 9, 10, 11, 12, 18, 24, 30, 36, 48, 60, 72, or 84 months. In some embodiments, the immune checkpoint inhibitor is administered for a single time. In some embodiments, the immune checkpoint inhibitor is administered repeatedly. In some embodiments, the immune checkpoint inhibitor is administered repeatedly until disease progression.

The number of neoantigens may be combined with other biomarkers or selection criteria to select an individual for any one of the MASCT methods described herein. In some embodiments, the MASCT method is particularly suitable for an individual with a low mutation load (such as in one or more MHC genes) in the cancer cells, and/or have at least about any of 4, 5, 6, 7, 8, 10 or more neoantigens (such as neoantigens with high affinity MHC-I restricted neoepitopes).

Any number (such as any of 1, 2, 3, 4, 5, 6, 7, 8, 9, 10, or more) of neoantigen peptides may be designed based on the neoantigens of the individual and to be incorporated in the plurality of tumor antigen peptides for use in any of the treatment methods described herein. In some embodiments, the plurality of tumor antigen peptides comprises a single neoantigen peptide. In some embodiments, the plurality of tumor antigen peptides comprises a plurality of neoantigen peptides. Each neoantigen peptide may comprise one or more neoepitopes from a neoantigen of the individual. In some embodiments, the neoepitope is a T cell epitope. Methods of designing a neoantigen peptide based on a neoantigen are described in the section "Plurality of tumor antigen peptides."

The neoantigens in the individual may be identified using any known methods in the art. In some embodiments, the neoantigen is identified based on the genetic profile of a tumor sample from the individual. Each neoantigen comprises one or more neoepitopes. In some embodiments, the one or more neoepitopes in the neoantigen are identified based on the genetic profile of the tumor sample. Any known genetic profiling methods, such as next generation sequencing (NGS) methods, microarrays, or proteomic methods may be used to provide the genetic profile of the tumor sample.

In some embodiments, the neoantigen is identified by sequencing a tumor sample from the individual. In some embodiments, the sequencing is next generation sequencing. In some embodiments, the sequencing is full-genome sequencing. In some embodiments, the sequencing is exome sequencing, such as whole exome sequencing ("WES"). In some embodiments, the sequencing is RNA sequencing. In some embodiments, the sequencing is targeted sequencing of candidate genes, such as cancer-associated genes. Many commercial NGS cancer panels, for example, ONCOGXONE™ Plus (Admera Health), are available to sequence cancer-associated genes with high sequencing depth.

In some embodiments, the tumor sample is a tissue sample. In some embodiments, the tumor sample is a tumor biopsy sample, such as fine needle aspiration of tumor cells or laparoscopy obtained tumor cells (such as including tumor stroma). In some embodiments, the tumor sample is freshly obtained. In some embodiments, the tumor sample is frozen. In some embodiments, the tumor sample is a Formaldehyde Fixed-Paraffin Embedded (FFPE) sample. In some embodiments, the tumor sample is a cell sample. In some embodiments, the tumor sample comprises a circulating metastatic cancer cell. In some embodiments, the tumor sample is obtained by sorting circulating tumor cells (CTCs) from blood. In some embodiments, nucleic acids (such as DNA and/or RNA) are extracted from the tumor sample for the sequencing analysis. In some embodiments, proteins are extracted from the tumor sample for the sequencing analysis.

In some embodiments, the genetic profile of the tumor sample is compared to the genetic profile of a reference sample, such as a sample of a healthy tissue from the same individual, or a sample of a healthy individual, to identify candidate mutant genes in the tumor cells. In some embodiments, the genetic profile of the tumor sample is compared to the reference sequences from a genome database to identify candidate mutant genes in the tumor cells. In some embodiments, the candidate mutant genes are cancer-associated genes. In some embodiments, each candidate mutant gene comprises one or more mutations, such as non-synonymous substitutions, indel (insertion or deletion), or gene fusion, which may give rise to a neoantigen. Common Single Nucleotide Polymorphisms (SNPs) are excluded from the candidate mutations.

In some embodiments, neoepitopes in neoantigens are identified from the candidate mutant proteins. In some embodiments, the neoepitopes are predicted in silico. Exemplary bioinformatics tools for T cell epitope prediction are known in the art, for example, see Yang X. and Yu X. (2009) "An introduction to epitope prediction methods and software" Rev. Med. Virol. 19(2): 77-96. Factors considered in the T cell epitope prediction algorithms include, but are not limited to, MHC subtype of the individual, sequence-derived physiochemical properties of the T cell epitope, MHC binding motifs, proteasomal cleavage pattern, transporter associated with antigen processing (TAP) transport efficiency, MHC binding affinity, peptide-MHC stability, and T-cell receptor binding affinity. In some embodiments, the neoepitope is an MHC-I restricted epitope. In some embodiments, the neoepitope is an MHC-II restricted epitope.

In some embodiments, the neoepitope has high affinity to the MHC molecules of the individual. In some embodiments, the method further comprises determining the MHC subtype of the individual, for example, from the sequencing data, to identify one or more MHC molecules of the individual. In some embodiments, the method further comprises determining the affinity of the neoepitope to an MHC molecule, such as an MHC class I molecule. In some embodiments, the method comprises determining the affinity of the neoepitope to one or more MHC (such as MHC class I) molecules of the individual. In some embodiments, the affinity of the neoepitope to one or more MHC molecules of the individual is compared to the affinity of the corresponding wildtype epitope to the one or more MHC molecules of the individual. In some embodiments, the neoepitope is selected for having a higher (such as at least about any of 1.5, 2, 5, 10, 15, 20, 25, 50, 100, or more times) affinity to the one or more MHC molecules (such as MHC-I molecules) of the individual than the corresponding wildtype epitope. In some embodiments, the MHC binding affinity is predicted in silico using any known tools or methods in the art. In some embodiments, the MHC binding affinity is determined experimentally, such as using an in vitro binding assay.

In some embodiments, the MASCT further comprises determining the affinity of the complex comprising the neoepitope and an MHC molecule (such as an MHC class I molecule of the individual) to a T cell receptor. In some embodiments, the affinity of the complex comprising the neoepitope and the MHC molecule to the cell receptor is compared to that of the complex comprising the corresponding wildtype epitope and the MHC molecule. In some embodiments, the MHC molecule is from the individual. In some embodiments, the T cell receptor is on the surface of one or more T cells of the individual. In some embodiments, the neoepitope is selected for having a higher (such as at least about any one of 1.5, 2, 5, 10, 15, 20, 25, 50, 100, or more times) affinity in a complex comprising the neoepitope and an MHC molecule to a T cell receptor model than the corresponding wildtype epitope. In some embodiments, the TCR binding affinity is predicted in silico using any known tools or methods in the art. In some embodiments, the TCR binding affinity is determined experimentally, for example, by determining the T cell response against the neoepitope.

In some embodiments, the neoantigen (or the neoepitope) is identified further based on the expression level of the neoantigen (or the neoepitope) in the tumor sample. Expression level of the neoantigen (or the neoepitope) may determined using any methods for quantification of mRNA or protein levels known in the art, such as RT-PCR, antibody-based assays, mass spectrometry. In some embodiments, the expression level of the neoantigen (or the neoepitope) is determined from the sequencing data of the tumor sample.

In some embodiments, the neoantigen (or the neoepitope) is expressed in the tumor cells at a level of at least about any one of 10, 20, 50, 100, 200, 500, 1000, 2000, 5000, $10^4$, or more copies per cell. In some embodiments, the neoantigen (or the neoepitope) is expressed at a level of more than about any one of 1.5, 2, 5, 10, 20, 50, 100, or more times than the corresponding wildtype protein (or the corresponding wildtype epitope) in the tumor cells.

In some embodiments, the neoantigen peptide is selected or identified by the steps comprising (a) sequencing a tumor sample from the individual to identify a neoantigen; (b) identifying a neoepitope in the neoantigen; optionally (c) determining the MHC subtype of the individual (e.g., using the sequencing data) to identify an MHC molecule of the individual; optionally (d) determining the affinity of the neoepitope to the MHC molecule of the individual; optionally (e) determining the affinity of the complex comprising the neoepitope and the MHC molecule to a T cell receptor; and (f) obtaining a peptide comprising the neoepitope to provide the neoantigen peptide. In some embodiments, the neoepitope has higher affinity to the MHC molecule (such as MHC-I molecule) of the individual and/or higher affinity in the complex comprising the neoepitope and the MHC molecule to the TCR as compared to the complex comprising the corresponding wildtype T cell epitope and the MHC molecule. In some embodiments, the neoepitope is extended at the N terminus or the C terminus or both termini according to the natural sequence of the neoantigen harboring the epitope to obtain an extended sequence, wherein the extended sequence is amenable for presentation by both class I and class II MEC molecules. Any of the treatment methods described herein using one or more neoantigen peptides may further comprise any one or more of the neoantigen selection/identification steps.

III. Methods of Treatment

The present application provides cell-based immunotherapy methods of treating cancer in an individual, comprising administering to the individual an effective amount of the tumor antigen-specific T cells prepared using any one of the methods described in Section II. In some embodiments, the method further comprises administering to the individual an effective amount of antigen-loaded DCs. In some embodiments, the method is used as a maintenance therapy for a previous MASCT received by the individual.

In some embodiments, there is provided a method of treating a cancer in an individual, comprising administering to the individual an effective amount of tumor antigen-specific T cells, wherein the tumor antigen-specific T cells are prepared by steps comprising: a) a first co-culturing step, comprising co-culturing a first population of DCs loaded with a plurality of tumor antigen peptides with a population of T cells to obtain a first co-culture comprising activated T cells; b) an enrichment step, comprising subjecting the first co-culture to an enrichment process to obtain an enriched population of activated T cells; and c) a second co-culturing step, comprising co-culturing the enriched population of activated T cells with a second population of DCs loaded with one or more tumor antigen peptides from the plurality of tumor antigen peptides to obtain a population of tumor antigen-specific T cells. In some embodiments, there is provided a method of treating a cancer in an individual, comprising: a) a first co-culturing step, comprising co-culturing a first population of DCs loaded with a plurality of tumor antigen peptides with a population of T cells to obtain a first co-culture comprising activated T cells; b) an enrichment step, comprising subjecting the first co-culture to an enrichment process to obtain an enriched population of activated T cells; and c) a second co-culturing step, comprising co-culturing the enriched population of activated T cells with a second population of DCs loaded with one or more tumor antigen peptides from the plurality of tumor antigen peptides to obtain a population of tumor antigen-specific T cells; and d) administering to the individual an effective amount of the tumor antigen-specific T cells. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody). In some embodiments, the ratio between the enriched population of activated T cells and the second population of antigen-loaded DCs is about 1:1 to about 20:1 (e.g., about 1:1 or about 2:1). In some embodiments, the population of cells in the first co-culturing step is present in a population of PBMCs. In some embodiments, the enrichment step comprises contacting the first co-culture with antigen-loaded APCs (e.g., PBMCs) to obtain a stimulated co-culture, and isolating an enriched population of activated T cells using a ligand that specifically recognizes a cytokine (such as IFNγ) or a cell surface molecule. In some embodiments, the enriched population of activated T cells and the second population of antigen-loaded DCs are co-cultured for about 12 to 25 days. In some embodiments, the method comprises co-culturing the second population of antigen-loaded DCs with time population of T cells in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the method further comprises administering to the individual an effective amount of antigen-loaded DCs. In some embodiments, the antigen-loaded DCs are administered subcutaneously.

In some embodiments, there is provided a method of treating a cancer in an individual, comprising administering to the individual an effective amount of tumor antigen-specific T cells, wherein the tumor antigen-specific T cells are prepared by steps comprising: a) contacting a first population of DCs with a plurality of tumor antigen peptides to obtain a first population of DCs loaded with a plurality of tumor antigen peptides; b) a first co-culturing step, comprising co-culturing the first population of DCs loaded with the plurality of tumor antigen peptides with a population of T cells to obtain a first co-culture comprising activated T cells; c) an enrichment step, comprising subjecting the first co-culture to an enrichment process to obtain an enriched population of activated T cells; d) contacting a second population of dendritic cells with one or more tumor antigen peptides from the plurality of tumor antigen peptides to obtain a second population of DCs loaded with one or more tumor antigen peptides from the plurality of tumor antigen peptides; and e) a second co-culturing step, comprising co-culturing the enriched population of activated T cells with the second population of DCs loaded with one or more tumor antigen peptides from the plurality of tumor antigen peptides in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells. In some embodiments, there is provided a method of treating a cancer in an individual, comprising: a) contacting a first population of DCs with a plurality of tumor antigen peptides to obtain a first population of DCs loaded with a plurality of tumor antigen peptides; b) a first co-culturing step, comprising co-culturing the first population of DCs loaded with the plurality of tumor antigen peptides with a population of T cells to obtain a first co-culture comprising activated T cells; c) an enrichment step, comprising subjecting the first co-culture to an enrichment process to obtain an enriched population of activated T cells; d) contacting a second population or dendritic cells with one or more tumor antigen peptides from the plurality of tumor antigen peptides to obtain a second population of DCs loaded with one or more tumor antigen peptides from the plurality of tumor antigen peptides; and e) a second co-culturing step, comprising co-culturing the enriched population of activated T cells with the second population of DCs loaded with one or more tumor antigen peptides from the plurality of tumor antigen peptides in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells; and f) administering to the individual an effective amount of the tumor antigen-specific T cells. In some embodiments, the first co-culturing step is carried out for no more than about 7 days (such as about 1-3 days, e.g., about 3 days) prior to the enrichment step. In some embodiments, the ratio between the population of T cells to the first population of antigen-loaded DCs is no more than about 30:1 (e.g., about 20:1, 15:1 or 10:1). In some embodiments, the first population of antigen-loaded DCs and the population of T cells are co-cultured in a first co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody). In some embodiments, the ratio between the enriched population of activated T cells and the second population of antigen-loaded DCs is about 1:1 to about 20:1 (e.g., about 1:1 or about 2:1). In some embodiments, the population of T cells in the first co-culturing step is present in a population of PBMCs. In some embodiments, the enrichment step comprises contacting the first co-culture with antigen-loaded APCs (e.g., PBMCs) to obtain a stimulated co-culture, and isolating an enriched population of activated T cells using ligand that specifically recognizes a cytokine (such as IFNγ) or a cell surface molecule. In some embodiments, the enriched population of activated T cells and the second population of antigen-loaded DCs are co-cultured for about 12 to 25 days. In some embodiments, the method comprises co-culturing the second population of antigen-loaded DCs with the population of T cells in an initial second co-culture medium comprising an immune checkpoint inhibitor and optionally one or more cytokines (e.g., IL-2 or a plurality of cytokines) to provide a second co-culture; and adding an anti-CD3 antibody (e.g., OKT3) and optionally one or more cytokines (e.g., IL-2 or a plurality of cytokines) to the second co-culture to obtain a population of tumor antigen-specific T cells. In some embodiments, the anti-CD3 antibody is added to the second co-culture no more than about 3 days (e.g., about 2 days) after the second co-culturing step starts. In some embodiments, the one or more cytokines is added to the second co-culture no more than about 3 days (e.g., about 2 days) after the second co-culturing step starts. In some embodiments, the method further comprises administering to the individual an effective amount of antigen-loaded DCs. In some embodiments, the antigen-loaded DCs are administered subcutaneously.

In some embodiments, there is provided a method of treating a cancer in an individual, comprising administering to the individual an effective amount of tumor antigen-specific T cells, wherein the tumor antigen-specific T cells are prepared by: co-culturing a population of tumor antigen-specific T cells (e.g., from a frozen stock) with a population of APCs (e.g., PBMCs or DCs) loaded with one or more tumor antigen peptides, wherein the tumor antigen-specific T cells is prepared by any one of the methods described herein for preparing tumor antigen-specific T cells. In some embodiments, the population of APCs and the population of tumor antigen-specific T cells are derived from the individual being treated. In some embodiments, the tumor antigen-specific T cells are administered intravenously. In some embodiments, the method further comprises administering to the individual an effective amount of antigen-loaded DCs. In some embodiments, the antigen-loaded DCs are administered subcutaneously.

In addition to the administration step(s), some embodiments of the treatment method further comprise one or more of the following cell preparation steps: 1) obtaining PBMCs from the individual; 2) obtaining a population of DCs from the PBMCs (e.g., by inducing differentiation of a population of monocytes from the PBMCs); 3) obtaining a population of T cells front the PBMCs; 4) preparing a population of DCs loaded with one or more tumor antigen peptides; 5) inducing maturation of the population of antigen-loaded DCs in a DC maturation medium; 6) co-culturing a first population of antigen-loaded DCs and a population of T cells; 7) subjecting the co-culture comprising the first population of antigen-loaded DCs and the population of T cells to an enrichment process to provide an enriched population of activated T cells; 8) co-culturing a second population of antigen-loaded DCs and an enriched population of activated T cells; 9) freezing a population of tumor antigen-specific T cells; 10) thawing a population of tumor antigen-specific T cells; and 11) co-culturing a population of APCs (e.g., PBMCs or DCs) loaded with one or more tumor antigen peptides with a thawed population of tumor antigen-specific T cells from a frozen stock.

Thus, in some embodiments, there is provided a method of treating a cancer in an individual, comprising: (a) obtaining a population of PBMCs from the individual; (b) obtaining a first population of DCs from the population of PBMCs; (c) contacting the first population of DCs with a plurality of tumor antigen peptides to obtain a first population of antigen-loaded DCs; (d) culturing the first population of antigen-loaded DCs in a DC maturation medium comprising MPLA, INFγ and PGE2; (e) optionally administering an effective amount of the antigen-loaded DCs to the individual; (f) a first co-culturing step, comprising co-culturing the first population of antigen-loaded DCs and a population of T cells (e.g., in the presence of PBMCs) in a co-culture medium comprising one or more cytokines (such as a plurality of cytokines, e.g., IL-2, IL-7, IL-15 and IL-21) and an immune checkpoint inhibitor (e.g., anti-PD-1 antibody) to provide a first co-culture comprising activated T cells; (g) an enrichment step, comprising contacting the first co-culture with APCs (e.g., PBMCs) loaded with the plurality of tumor antigen peptides to obtain a stimulated co-culture, and isolating an enriched population of activated T cells from the stimulated co-culture using a ligand that specifically recognizes a cytokine (e.g., IFNγ) or a cell surface molecule; (h) optionally contacting a second population of DCs with one or more tumor antigen peptides from the plurality of tumor antigen peptides to obtain a second population of antigen-loaded DCs; (i) a second co-culturing step, comprising co-culturing the enriched population of activated T cells with the second population of antigen-loaded DCs in an initial co-culture medium comprising one or more cytokines (such as IL-2 or a plurality of cytokines, e.g., IL-2, IL-7, IL-15 and IL-21) and an immune checkpoint inhibitor (e.g., anti-PD-1 antibody) to provide a second co-culture, and adding an anti-CD3 antibody (e.g., OKT3) to the second co-culture to provide tumor antigen-specific T cells; and (j) administering an effective amount of the tumor antigen-specific T cells to the individual. In some embodiments, the first population and second population of DCs and the population of T cells are obtained from the individual being treated. In some embodiments, the tumor antigen-specific T cells are administered intravenously. In some embodiments, the antigen-loaded DCs are administered subcutaneously. In some embodiments, the method further comprises freezing a population of the tumor antigen-specific T cells to obtain a frozen stock, co-culturing a population of thawed tumor antigen-specific T cells from the frozen stock with a third population of DCs loaded with one or more tumor antigen peptides from the plurality of tumor antigen peptides to provide a second population of tumor antigen-specific T cells, and administering an effective amount of the second population of tumor antigen-specific T cells.

The methods described herein are suitable for treating various cancers, including liquid and solid cancers. In some embodiments, the cancer is selected from the group consisting of hepatocellular carcinoma, cervical cancer, lung cancer, colorectal cancer, lymphoma, renal carcinoma, breast cancer, pancreatic cancer, gastric cancer, esophageal cancer, ovarian cancer, prostate cancer, nasopharyngeal carcinoma, melanoma, endometrial cancer, and brain cancer. The methods are applicable to cancers of all stages, including early stage, advanced stage and metastatic cancer.

In some embodiments, the method reduces the severity of one or more symptoms associated with the cancer by at least about any of 10%, 20%, 30%, 40%, 50%, 60%, 70% 80%, 90%, 95% or 100% compared to the corresponding symptom in the same individual prior to treatment or compared to the corresponding symptom in other individuals not receiving the treatment method. In some embodiments, the method delays progression of the cancer.

In some embodiments, the method is for treating hepatocellular carcinoma (HCC). In some embodiments, the HCC is early stage HCC, non-metastatic HCC, primary HCC, advanced HCC, locally advanced HCC, metastatic HCC, HCC in remission, or recurrent HCC. In some embodiments, the HCC is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve all lobes of the liver and/or has spread involve other organs (e.g., lung, lymph nodes, bone). In some embodiments, the HCC is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the HCC is, according to AJCC (American Joint Commission on Cancer) staging criteria, stage T1, T2, T3, or T4 HCC. In some embodiments, the HCC is any one of liver cell carcinomas, fibrolamellar variants of HCC, and mixed hepatocellularcholangiocarcinomas. In some embodiments, the HCC is caused by Hepatitis B Virus (HBV) infection.

In some embodiments, the method is for treating lung cancer. In some embodiments, the lung cancer is a non-small cell lung cancer (NSCLC). Examples of NCSLC include, but are not limited to, large-cell carcinoma (e.g., large-cell neuroendocrine carcinoma, combined large-cell neuroendocrine carcinoma, basaloid carcinoma, lymphoepithelioma-like carcinoma, clear cell carcinoma, and large-cell carcinoma with rhabdoid phenotype), adenocarcinoma (e.g., acinar, papillary (e.g., bronchioloalveolar carcinoma, non-mucinous, mucinous, mixed mucinous and nonmucinous and indeterminate cell type) solid adenocarcinoma with mucin, adenocarcinoma with mixed subtypes, well-differentiated fetal adenocarcinoma, mucinous (colloid) adenocarcinoma, mucinous cystadenocarcinoma, signet ring adenocarcinoma, and clear cell adenocarcinoma), neuroendocrine lung tumors, and squamous cell carcinoma (e.g., papillary, clear cell, small cell, and basaloid). In some embodiments, the NSCLC may be, according to TNM classifications, a stage T tumor (primary tumor), a stage N tumor (regional lymph nodes), or a stage M tumor (distant metastasis).

In some embodiments, the lung cancer is a carcinoid (typical or atypical), adenosquamous carcinoma, cylindroma, or carcinoma of the salivary gland (e.g., adenoid cystic carcinoma or mucoepidermoid carcinoma). In some embodiments, the lung cancer is a carcinoma with pleomorphic, sarcomatoid, or sarcomatous elements (e.g., carcinomas with spindle and/or giant cells, spindle cell carcinoma, giant cell carcinoma, carcinosarcoma, or pulmonary blastoma). In some embodiments, the lung cancer is small cell lung cancer (SCLC; also called oat cell carcinoma). The small cell lung cancer may be limited-stage, extensive stage or recurrent small cell lung cancer. In some embodiments, the individual may be a human who has a gene, genetic mutation, or polymorphism suspected or shown to be associated with lung cancer (e.g., SASH1, LATS1, IGF2R, PARK2, KRAS, PTEN, Kras2, Krag, PasI, ERCC1, XPD, IL8RA, EGFR, $\alpha_1$-AD, EPHX, MMP1, MMP2, MMP3, MMP12, IL1β, RAS, and/or AKT) or has one or more extra copies of a gene associated with lung cancer.

In some embodiments, the method is for treating cervical cancer. In some embodiments, the cervical cancer is early stage cervical cancer, non-metastatic cervical cancer, locally advanced cervical cancer, metastatic cervical cancer, cervical cancer in remission, unresectable cervical cancer, cervical cancer in an adjuvant setting, or cervical cancer in a neoadjuvant setting. In some embodiments, the cervical cancer is caused by human papillomavirus (HPV) infection. In some embodiments, the cervical cancer may be, according to TNM classifications, a stage T tumor (primary tumor), a stage N tumor (regional lymph nodes), or a stage M tumor (distant metastasis). In some embodiments, the cervical cancer is any of stage 0, stage I (Tis, N0, M0), stage IA (T1a, N0, M0), wage IB (T1b, N0, M0), stage IIA (T2a, N0, M0), stage IIB (T2b, N0, M0), stage IIIA (T3a, N0, M0), stage IIIB (T3b, N0, M0, or T1-3, N1, M0) stage IVA (T4, N0, M0), or stage IVB (T1-T3, N0, M1) cervical cancer. In some embodiments, the cervical cancer is cervical squamous cell carcinoma, cervical adenonocarcinoma, or adenosquamous carcinoma.

In some embodiments, the method is for treating breast cancer. In some embodiments, the breast cancer is early stage breast cancer, non-metastatic breast cancer, locally advanced breast cancer, metastatic breast cancer, hormone receptor positive metastatic breast cancer, breast cancer in remission, breast cancer in an adjuvant setting, ductal carcinoma in situ (DCIS), invasive ductal carcinoma (IDC), or breast cancer in a neoadjuvant setting. In some embodiments, the breast cancer is hormone receptor positive metastatic breast cancer. In some embodiments, the breast cancer (which may be HER2 positive or HER2 negative) is advanced breast cancer. In some embodiments, the breast cancer is ductal carcinoma in situ. In some embodiments, the individual may be a human who has a gene, genetic mutation, or polymorphism associated with breast cancer (e.g., BRCA1, BRCA2, ATM, CHEK2, RAD51, AR, DIRAS3, ERBB2, TP53, AKT, PTEN, and/or PI3K) or has one or more extra copies of a gene (e.g., one or more extra copies of the HER2 gene) associated with breast cancer.

In some embodiments, the method is for treating pancreatic cancer. In some embodiments, the pancreatic cancer includes, but is not limited to, serous microcystic adenoma intraductal papillary mucinous neoplasm, mucinous cystic neoplasm, solid pseudopapillary neoplasm, pancreatic adenocarcinoma, pancreatic ductal carcinoma, or pancreatoblastoma. In some embodiments, the pancreatic cancer is any of early stage pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, recurrent pancreatic cancer, pancreatic cancer in an adjuvant setting, or pancreatic cancer in a neoadjuvant setting.

In some embodiments, the method is for treating ovarian cancer. In some embodiments, the ovarian cancer is ovarian epithelial cancer. Exemplary ovarian epithelial cancer histological classifications include: serous cystomas (e.g., serous benign cystadenomas, serous cystadenomas with proliferating activity of the epithelial cells and nuclear abnormalities but with no infiltrative destructive growth, or serous cystadenocarcinomas), mucinous cystomas (e.g., mucinous benign cystadenomas, mucinous cystadenomas with proliferating activity of the epithelial cells and nuclear abnormalities but with no infiltrative destructive growth, or mucinous cystadenocarcinomas), endometrioid tumors (e.g., endometrioid benign cysts, endometrioid tumors with proliferating activity of the epithelial cells and nuclear abnormalities but with no infiltrative destructive growth, or endometrioid adenocarcinomas), clear cell (mesonephroid) tumors (e.g., benign clear cell tumors, clear cell tumors with proliferating activity of the epithelial cells and nuclear abnormalities but with no infiltrative destructive growth, or clear cell cystadenocarcinomas), unclassified tumors that cannot be allotted to one of the above groups, or other malignant tumors. In various embodiments, the ovarian epithelial cancer is stage I (e.g., stage IA, IB or IC), stage II (e.g., stage IIA, IIB, or IIC), stage III (e.g., stage IIIA, IIIB, or IIIC), or stage IV. In some embodiments, the individual may be a human who has a gene, genetic mutation, or polymorphism associated with ovarian cancer (e.g., BRCA1 or BRCA2) or has one or more extra copies of a gene associated with ovarian cancer (e.g., one or more extra copies of the HER2 gene). In some embodiments, the ovarian cancer is an ovarian germ cell tumor. Exemplary histologic subtypes include dysgerminomas or other germ cell tumors (e.g., endodermal sinus tumors such as hepatoid car intestinal tumors, embryonal carcinomas, olyembryomas, choriocarcinomas, teratomas, or mixed form tumors). Exemplary teratomas are immature teratomas, mature teratomas, solid teratomas, and cystic teratomas (e.g., dermoid cysts such as mature cystic teratomas, and dermoid cysts with malignant transformation). Some teratomas are monodermal and highly specialized, such as struma ovarii, carcinoid, struma ovarii and carcinoid, or others (e.g., malignant neuroectodermal and ependymomas). In some embodiments, the ovarian germ cell tumor is stage I (e.g., stage IA, IB, or IC), stage II (e.g., stage IIA, IIB, or IIC), stage III (e.g., stage IIIA, IIIB, or IIIC), or stage IV.

The treatment methods described herein in some embodiments are not applicable to patients with cancers of T-cell origin, such as T-cell lymphoma.

Several viruses are related to cancer in humans. For example, Hepatitis B virus (HBV) can cause chronic infection of the liver, increasing an individual's chance of liver cancer, or hepatocellular carcinoma (HCC). Human papilloma viruses (HPVs) are group of more than 150 related viruses, which cause papilloma, or warts, when they infect and grow in skin or mucous membranes, such as the mouth, throat, or vagina. Several types of HPV (including types 16, 18, 31, 33, 39, 45, 51, 52, 56, 58, 59 and 6) are known to cause cervical cancer. HPVs also play a role in inducing or causing other cancers of the genitalia, and are linked to some cancers of the mouth and throat Epstein-Barr virus (EBV) is a type of herpes virus, which chronically infects and remains latent in B lymphocytes. EBV infection increases an individual's risk of developing nasopharyngeal carcinoma and certain types of fast-growing lymphomas such as Burkitt lymphoma. EBV is also linked to Hodgkin lymphoma and some cases of gastric cancer. In addition to causing cancer or increasing risk of developing cancer, viral infections, such as infections with HBV, HPV, and EBV, may result in damage to tissues or organs, which can increase the disease burden of an individual suffering from a cancer, and contribute to cancer progression. It is known in the art that the human body can be induced to mount effective and specific immune response, including cytotoxic T cell response, against several cancer-related viruses, such as HBV, HPV and EBV, including their various subtypes. Therefore, in some embodiments, there is provided a method of treating a virus-related cancer in an individual, comprising administering to the individual an effective amount of tumor antigen-specific T cells, wherein the tumor antigen-specific T cells are prepared using any one of the methods of preparing tumor antigen-specific T cells described herein, wherein the plurality of tumor antigen peptides comprise one or more tumor antigen peptides derived from the virus. In some embodiments, the cancer is HBV-related hepatocellular carcinoma, HPV-related cervical cancer, or EBV-related nasopharyngeal carcinoma.

The methods described herein can be used for any one or more of the following purposes: alleviating one or more symptoms of cancer, delaying progression of cancer, shrinking cancer tumor size, disrupting (such as destroying) cancer stroma, inhibiting cancer tumor growth, prolonging overall survival, prolonging disease-free survival, prolonging time to cancer disease progression, preventing or delaying cancer tumor metastasis, reducing (such as eradiating) preexisting cancer tumor metastasis, reducing incidence or burden of preexisting cancer tumor metastasis preventing recurrence of cancer, and/or improving clinical benefit of cancer.

In some embodiments, there is provided a method of inhibiting cancer cell proliferation (such as tumor growth) in an individual, comprising administering to the individual an effective amount of tumor antigen-specific T cells prepared using any one of the methods of preparing tumor antigen-specific T cells described herein. In some embodiments, the method further comprises administering to the individual an of amount of an effective amount of antigen-loaded DCs. In some embodiments, at least about 10% (including for example at least about any of 20%, 30%, 40%, 60%, 70%, 80%, 90%, or 100%) cell proliferation is inhibited.

In some embodiments, there is provided a method of inhibiting tumor metastasis in an individual, comprising administering to the individual an effective amount of tumor antigen-specific T cells prepared using any one of the methods of preparing tumor antigen-specific T cells described herein. In some embodiments, the method further comprises administering to the individual an effective amount of an effective amount of antigen-loaded DCs. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided.

In some embodiments, there is provided a method of reducing tumor size in an individual, comprising administering to the individual an effective amount of tumor antigen-specific T cells prepared using any one of the methods of preparing tumor antigen-specific T cells described herein. In some embodiments, the method further comprises administering to the individual an effective amount of an effective amount of antigen-loaded DCs. In some embodiments, the tumor size is reduced at least about 10% (including for example at least about any of 20%, 30%, 40%, 60%, 70%, 80%, 90%, or 100%).

In some embodiments, there is provided a method of prolonging progression-free survival of cancer in an individual, comprising administering to the individual an effective amount of tumor antigen-specific T cells prepared using any one the methods of preparing tumor antigen-specific T cells described herein. In some embodiments, the method further comprises administering to the individual an effective amount of an effective amount of antigen-loaded DCs. In some embodiments, the method prolongs the time to disease progression by at least any of 1, 2, 3, 4, 5, 6, 7, 8, 9, 10, 11, or 12 weeks.

In some embodiments, there is provided a method of prolonging survival of an individual having cancer, comprising administering to the individual an effective amount of tumor antigen-specific T cells prepared using any one of the methods of preparing tumor antigen-specific T cells described herein. In some embodiments, the method further comprises administering to the individual an effective amount of an effective amount of antigen-loaded DCs. In some embodiments, the method prolongs the time to disease progression by at least about any one of 1, 2, 3, 4, 5, 6, 7, 8, 9, 10, 11, or 12 weeks. In some embodiments, the method prolongs the survival of the individual by at least about arty one of 1, 2, 3, 4, 5, 6, 7, 8, 9, 10, 11, 12, 18, or 24 months.

In some embodiments, there is provided a method of reducing adverse effects (AEs) and severe adverse effects (SAEs) in an individual having cancer, comprising administering to the individual an effective amount of tumor antigen-specific T cells prepared using any one of the methods of preparing tumor antigen-specific T cells described herein. In some embodiments, the method further comprises administering to the individual an effective amount of antigen-loaded DCs.

In some embodiments, the method is predictive of and/or results in an objective response (such as a partial response or complete response). In some embodiments, the method is predictive of and/or results in improved quality of life.

Some cancer immunotherapies are associated with immune-related adverse events (irAEs) in additional to common adverse events generally associated with other cancer therapies. IrAEs are usually mechanistically related to either on-target T-cell toxicity against target antigens that are expressed in normal, non-tumor tissue, so called on-target off-tumor effect, or off-target effects such as breaking of self-tolerance or epitope cross-reaction. IrAEs can lead to severe symptoms and conditions on the dermatologic, gastrointestinal, endocrine, hepatic, ocular, neurologic, and other tissues or organs. Typical irAEs reported for cancer immunotherapy methods known in the art include fatal immune-mediated dermatitis, pneumonia, colitis, lymphocytic hypophysitis, pancreatitis, lymphadenopathy, endocrine disorders, CNS toxicity, and the like. In some embodiments, the treatment method is associated with low incidence of adverse events, such as irAEs. In some embodiments, less than about any one of 50%, 40%, 30%, 20%, 10%, 5%, 4%, 3%, 2%, or 1% of individuals experience irAEs, such as irAEs of Grade 2-5.

Generally, dosages, schedules, and routes of administration of the tumor antigen-specific T cells and the population of DCs loaded with the plurality of tumor antigen peptides may be determined according to the size and condition of the individual, and according to standard pharmaceutical practice. Exemplary routes of administration include intravenous, intra-arterial, intraperitoneal, intrapulmonary, intravesicular, intramuscular, intra-tracheal, subcutaneous, intraocular, intrathecal, or transdermal. In some embodiments, the DCs loaded with the plurality of tumor antigen peptides are administered subcutaneously. In some embodiments, the tumor antigen-specific T cells are administered intravenously.

The dose of the cells administered to an individual may vary according to, for example, the particular type of cells being administered, the route of administration, and the particular type and stage of cancer being treated. The amount should be sufficient to produce a desirable response, such as a therapeutic response against cancer, but without severe toxicity or adverse events. In some embodiments, the amount of the tumor antigen-specific T cells or the DCs to be administered is a therapeutically effective amount. In some embodiments, the amount of the cells (such as multiple-antigen loaded DCs, or the tumor antigen-specific T cells) is an amount sufficient to decrease the size of a tumor, decrease the number of cancer cells, or decrease the growth rate of a tumor by at least about an of 10%, 20%, 30%, 40%, 50%, 60%, 70%, 80%, 90%, 95% or 100% compared to the corresponding tumor size, number of cancer cells, or tumor growth rate in the same individual prior to treatment or compared to the corresponding activity in other individuals not receiving the treatment. Standard methods can be used to measure the magnitude of this effect, such as in vitro assays with purified enzyme, cell-based assays, animal models, or human testing.

In some embodiments, the tumor antigen-specific T cells are administered at a dose of at least about any one of $1\times10^8$, $5\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $1.5\times10^{10}$, $2\times10^{10}$, or $5\times10^{10}$ cells/individual. In some embodiments, the tumor antigen-specific T cells are administered at a dose of about any one of $1\times10^8$-$5\times10^8$, $5\times10^8$-$1\times10^9$, $1\times10^9$-$5\times10^9$, $5\times10^9$-$1\times10^{10}$, $3\times10^9$-$7\times10^9$, $1\times10^{10}$-$2\times10^{10}$, or $1\times10^9$-$1\times10^{10}$ cells/individual. In some embodiments, the tumor antigen-specific T cells are administered at a dose of at least about $3\times10^9$ cells/individual. In some embodiments, the tumor antigen-specific T cells are administered at a dose of about $1\times10^9$ to about $1\times10^{10}$ cells/individual.

In some embodiments, the tumor antigen-specific T cells are administered at a dose of at least about any one of $1\times10^7$, $2\times10^7$, $4\times10^7$, $6\times10^7$, $8\times10^7$, $1\times10^8$, $4\times10^8$, $6\times10^8$, $8\times10^8$, $1\times10^9$ cells/kg. In some embodiments, the tumor antigen-specific T cells are administered at a dose of about any one of $1\times10^7$-$1\times10^8$, $1\times10^7$-$5\times10^7$, $2\times10^7$-$4\times10^7$, $5\times10^7$-$1\times10^8$, $1\times10^8$-$2\times10^8$, $5\times10^7$-$1\times10^8$, $1\times10^8$-$2\times10^8$, $2\times10^8$-$5\times10^8$, $1\times10^8$-$1\times10^9$, or $1\times10^7$-$1\times10^9$ cells/kg. In some embodiments, the tumor antigen-specific T cells are administered at a dose of at least about $6\times10^7$ cells/kg. In some embodiments, the tumor antigen-specific T cells are administered at a dose of about $1.5\times10^7$ to about $2\times10^8$ cells/kg.

In some embodiments, a stabilizing agent or an excipient, such as human albumin, is used together with the tumor antigen-specific T cells, and/or the antigen-loaded DCs The dosage and dosing schedule of the cells in the treatment method may be adjusted over the course of the treatment, based on the judgment of the administering physician. In some embodiments, the tumor antigen-specific T cells are administered without administering the antigen-loaded DCs. In some embodiments, the tumor antigen-specific T cells are administered at least about any one of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 1 month, after the DCs loaded with the plurality of tumor antigen peptides are administered. In some embodiments, the tumor antigen-specific T cells are administered concurrently with the DCs. In some embodiments, the tumor antigen-specific T cells are administered about 14-21 days after the DCs are administered. In some embodiments, the tumor antigen-specific T cells are administered about 14 days after the DCs are administered.

The treatment method may comprise a single treatment, or repeated treatments. In some embodiments, the tumor antigen-specific T cells are administered for at least about any one of 1, 2, 3, 4, 5, 6, 7, 8, 9, 10, or more than 10 times. In some embodiments, the tumor antigen-specific T cells are administered at least 3 times. In some embodiments, the DCs are administered for at least about any one of 1, 2, 3, 4, 5, 6, 7, 8, 9, 10, or more than 10 times. In some embodiments, the DCs are administered at least 3 times. In some embodiments, one or more cell (such as antigen-loaded dendritic cell or tumor antigen-specific T cells) preparation steps are repeated prior to the repeated administration of the DCs, the tumor antigen-specific T cells, or both. In some embodiments, the treatment method is repeated once per week, once 2 weeks, once 3 weeks, once 4 weeks, once per month, once per 2 months, once per 3 months, once per 4 months, once per 5 months, once per 6 months, once per 7 months, once per 8 months, once per 9 months, or once per year. In some embodiments, the interval between each administration of the DCs, or the tumor antigen-specific T cells is about any one of 1 week to 2 weeks, 2 weeks to 1 month, 2 weeks to 2 months, 1 month to 2 months, 1 month to 3 months, 3 months to 6 months, or 6 months to a year. In some embodiments, the interval between each administration of the DCs or the tumor antigen-specific T cells is about 0.5 to about 5 months, such as about 2 weeks to about 2 months, or about 2 months to about 5 months. In some embodiments, all steps of the treatment method are repeated once per month during the first 6 months of treatment, every two months for the second 6 months of treatment, and every half a year after first 12 months of treatment if the individual has stable disease. In some embodiments, the repeated treatment comprises preparing a further population of tumor antigen-specific T cells using a frozen stock of previously prepared tumor antigen-specific T cells, and administering an effective amount of the further population of tumor antigen-specific T cells to the individual. Any embodiment of the treatment method described herein can be combined with any other embodiment of the treatment method during the full course of a repeated treatment.

The treatment method provided herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radio-frequency ablation or the like, in an adjuvant setting or a neoadjuvant setting. In some embodiments, the treatment method is used as a first therapy. In some embodiments, there exists no other approved anti-cancer therapy for the individual. In some embodiments, the treatment method is used as a second therapy, wherein the individual has previously received resection, radio-frequency ablation, chemotherapy, radiation therapy, or other types of cancer therapy. In some embodiments, the individual has progressed or has not been able to tolerate standard anti-cancer therapy. In some embodiments, the individual receives other types of cancer therapy prior to, concurrently with, or after receiving the treatment method described herein. For example, the treatment method described herein may precede or follow the other cancer therapy (such as chemotherapy, radiation, surgery or combination thereof) by intervals ranging from minutes, days, weeks to months. In some embodiments, the interval between the first and the second therapy is such that the tumor antigen-specific T cells and the other cancer therapy (such as chemotherapy, radiation, surgery, or combination thereof) would be able to exert an advantageously combined effect on the individual. In some embodiments, the treatment method described herein is used in conjunction with other cancer therapy (such as chemotherapy, radiation, surgery, or combination thereof) treat cancer in an individual. The combination therapy methods described herein may be performed alone or in conjunction with another therapy, such as surgery, radiation, gene therapy, immunotherapy, bone marrow transplantation, stem cell transplantation, hormone therapy, targeted therapy, cryotherapy, ultrasound therapy, photodynamic therapy, chemotherapy or the like. Additionally, a person having a greater risk of developing a proliferative disease may receive treatments to inhibit and/or delay the development of the disease.

The methods described herein for treating cancer can be used in monotherapy as well as in combination therapy with another agent. For example, any of the treatment methods described herein may be combined with administration of one or more (such as any of 1, 2, 3, 4, or more) immune checkpoint inhibitors. In some embodiments, the immune checkpoint inhibitor is selected from the group consisting of inhibitors of PD-1, PD-L1, CTLA-4, IDO, TIM-3, BTLA, VISTA, and LAG-3

In some embodiments, the immune checkpoint inhibitor is an inhibitor of PD-1. In some embodiments, the immune checkpoint inhibitor is an anti-PD-1 antibody. Exemplary anti-PD-1 antibodies include, but are not limited to, Nivolumab, pembrolizumab, pidilizumab, BMS-936559, and atezolizumab, Pembrolizumab, MK-3475, AMP-224, AMP-514, STI-A1110, and TSR-042. In some embodiments, the immune checkpoint inhibitor is nivolumab (for example, OPDIVO®). In some embodiments, the immune checkpoint, inhibitor is Pembrolizumab (for example, KEYTRUDA®). In some embodiments, the immune checkpoint inhibitor is SHR-1210.

In some embodiments, the immune checkpoint inhibitor is an inhibitor of PD-L1. In some embodiments, the immune checkpoint inhibitor is an anti-PD-L1 antibody. Exemplary anti-PD-L1 antibodies include, but are not limited to, KY-1003, MCLA-145, RG7446, BMS935559, MPDL3280A, MEDI4736, Avelumab, or STI-A1010.

In some embodiments, the immune checkpoint inhibitor is all inhibitor of CTLA-4. In some embodiments, the immune checkpoint inhibitor is an anti-CTLA-4 antibody. Exemplary anti-CTLA-4 antibodies include, but are not limited to, Ipilimumab, Tremelimumab, and KAHR-102. In some embodiments, the immune checkpoint inhibitor is Ipilimumab (for example, YERVOY®).

In some embodiments, the tumor antigen-specific T cells and the immune checkpoint inhibitor are administered simultaneously. In some embodiments, the tumor antigen-specific cells and the immune checkpoint inhibitor are administered in a single composition. In some embodiments, the immune checkpoint inhibitor is present in the first, second or third co-culture. In some embodiments, the tumor antigen-specific T cells and the immune checkpoint inhibitor are admixed prior to (such as immediately prior to) the administration. In some embodiments, the tumor antigen-specific T cells and the immune checkpoint inhibitor are administered simultaneously via separate compositions.

In some embodiments, the tumor antigen-specific T cells and the immune checkpoint inhibitor are administered sequentially. In some embodiments, the immune checkpoint inhibitor is administered prior to the administration of the tumor antigen-specific T cells. In some embodiments, the immune checkpoint inhibitor is administered after the administration of the tumor antigen-specific T cells.

Exemplary routes of administration of the immune checkpoint inhibitor include, but are not limited to, intratumoral, intravesical, intramuscular, intraperitoneal, intravenous, intra-arterial, intracranial, intrapleural, subcutaneous, and epidermal routes, or be delivered into lymph glands, body spaces, organs or tissues known to contain such live cancer cells. In some embodiments, the immune checkpoint inhibitor is administered intravenously. In some embodiments, the immune checkpoint inhibitor is administered by infusion. In some embodiments, the immune checkpoint inhibitor is infused over at least about any of 10 minutes, 30 minutes, 1 hour, 2 hours, 4 hours, 6 hours, or more. In some embodiments, the immune checkpoint inhibitor is administered via the same administration route as the tumor antigen-specific T cells. In some embodiments, the immune checkpoint inhibitor is administered via a different administration route as the tumor antigen-specific T cells.

Suitable dose of the immune checkpoint inhibitor include, but are not limited to, about any one of 1 mg/m$^2$, 5 mg/m$^2$, 10 mg/m$^2$, 20 mg/m$^2$, 50 mg/m$^2$, 100 mg/m$^2$, 200 mg/m$^2$, 300 mg/m$^2$, 400 mg/m$^2$, 500 mg/m$^2$, 750 mg/m$^2$, 1000 mg/m$^2$, or more. In some embodiments, the dose of immune checkpoint inhibitor is any one of about 1 to about 5 mg/m$^2$, about 5 to about 10 mg/m$^2$, about 10 to about 20 mg/m$^2$, about 20 to about 50 mg/m$^2$, about 50 to about 100 mg/m$^2$, about 100 mg/m$^2$ to about 200 mg/m$^2$, about 200 to about 300 mg/m$^2$, about 300 to about 400 mg/m$^2$, about 400 to about 500 mg/m$^2$, about 500 to about 750 mg/m$^2$, or about 750 to about 1000 mg/m$^2$. In some embodiments, the dose of immune checkpoint inhibitor is about any one of 1 µg/kg, 2 µg/kg, 5 µg/kg, 10 µg/kg, 20 µg/kg, 50 µg/kg, 0.1 mg/kg, 0.2 mg/kg, 0.3 mg/kg, 0.4 mg/kg, 0.5 mg/kg, 1 mg/kg, 2 mg/kg, 5 mg/kg, 10 mg/kg, 20 mg/kg, 50 mg/kg, 100 mg/kg, or more. In some embodiments, the dose of the immune checkpoint inhibitor is any one of about 1 µg/kg to about 5 µg/kg, about 5 µg/kg to about 10 µg/kg, about 10 µg/kg, to about 50 µg/kg, about 50 µg/kg to about 0.1 mg/kg, about 0.1 mg/kg to about 0.2 mg/kg, about 0.2 mg/kg to about 0.3 mg/kg, about 0.3 mg/kg to about 0.4 mg/kg, about 0.4 mg/kg to about 0.5 mg/kg, about 0.5 mg/kg to about 1 mg/kg, about 1 mg/kg to about 5 mg/kg, about 5 mg/kg to about 10 mg/kg, about 10 mg/kg to about 20 mg/kg, about 20 mg/kg to about 50 mg/kg, about 50 mg/kg to about 100 mg/kg, or about 1 mg/kg to about 100 mg/kg.

In some embodiments, the immune checkpoint inhibitor is administered daily. In some embodiments, the immune checkpoint inhibitor is administered is administered at least about any one of 1×, 2×, 3×, 4×, 5×, 6×, or 7× (i.e., daily) a week. In some embodiments, the immune checkpoint inhibitor is administered weekly. In some embodiments, the immune checkpoint inhibitor is administered weekly without break; weekly, two out of three weeks; weekly three out of four weeks; once every two weeks; once every 3 weeks; once every 4 weeks; once every 6 weeks; once every 8 weeks, monthly, or every two to 12 months. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, the immune checkpoint inhibitor is administered once every 3 months. In some embodiments, there is no break in the dosing schedule. In some embodiments, the interval between each administration is no more than about a week. In some embodiments, the immune checkpoint inhibitor is administered with the same dosing schedule as the tumor antigen-specific T cells. In some embodiments, the immune checkpoint inhibitor is administered with a different dosing schedule as the tumor antigen-specific T cells.

In some embodiments, the immune checkpoint inhibitor is administered in every tumor antigen-specific T cell treatment cycle. For example, the immune checkpoint inhibitor may be administered about any of 1, 2, 3, 4, 5, 6, or more times every tumor antigen-specific T cell treatment cycle. In some embodiments, the immune checkpoint inhibitor is not administered in every tumor antigen-specific T cell treatment cycle. For example, the immune checkpoint inhibitor may be administered about once every 1, 2, 3, 4, 5, or more tumor antigen-specific T cell treatment cycles.

The administration of the immune checkpoint inhibitor can be over an extended period of time, such as from about a month up to about seven years. In some embodiments, the immune checkpoint inhibitor is administered over a period of at least about any one of 1, 2, 3, 4, 5, 6, 7, 8, 9, 10, 11, 12, 18, 24, 30, 36, 48, 60, 72, or 84 months. In some embodiments, the immune checkpoint inhibitor is administered for a single time. In some embodiments, the immune checkpoint inhibitor is administered repeatedly. In some embodiments, the immune checkpoint inhibitor is administered repeatedly until disease progression.

Previous Immunotherapy

In some embodiments, the treatment method described herein is particularly suitable for an individual who has previously received an immunotherapy. In some embodiments, the individual is immunologically responsive to the immunotherapy. "Immunologically responsive" means that the immunotherapy has triggered specific immune response in the individual to cancer or a cancer-related virus. In some embodiments, the individual had clinical response, e.g., complete response, partial response, or stable disease, to the immunotherapy. In some embodiments, the individual has relapsed after receiving the immunotherapy. In some embodiments, the immunotherapy is selected from the group consisting of an immune checkpoint inhibitor, an adoptive immune cell therapy, a cancer vaccine, an oncolytic virus and combinations thereof.

Thus, in some embodiments, there is provided a method of treating a cancer in an individual, comprising: (a) optionally administering an effective amount of antigen-loaded DCs; and (b) administering to the individual an effective amount of tumor antigen-specific T cells, wherein the tumor antigen-specific T cells are prepared by any one of the methods of preparing tumor antigen-specific T cells described above in Section II, and wherein the individual has previously received an immunotherapy (such as an immune checkpoint inhibitor, an adoptive immune cell therapy, a cancer vaccine, an oncolytic virus, or a combination thereof). In some embodiments, the individual is immunologically responsive to the immunotherapy.

In some embodiments, there is provided a method of treating a cancer in an individual, comprising: (a) selecting an individual who has previously received an immunotherapy (such as an immune checkpoint inhibitor, an adoptive immune cell therapy, a cancer vaccine, an oncolytic virus, or a combination thereof) for the method; (b) optionally administering an effective amount of antigen-loaded DCs; and (c) administering to the individual an effective amount of tumor antigen-specific T cells, wherein the tumor antigen-specific T cells are prepared by any one of the methods of preparing tumor antigen-specific. T cells described above in Section II. In some embodiments, the individual is immunologically responsive to the immunotherapy.

In some embodiments, there is provided a method of treating a cancer in an individual, comprising: (a) optionally administering an effective amount of antigen-loaded DCs; and (b) administering to the individual an effective amount of tumor antigen-specific T cells, wherein the tumor antigen-specific T cells are prepared by any one of the methods of preparing tumor antigen-specific T cells described above in Section II, and wherein the individual is selected for treatment based on having previously received an immunotherapy (such as an immune checkpoint inhibitor, an adoptive immune cell therapy, a cancer vaccine, an oncolytic virus, or a combination thereof). In some embodiments, the individual is immunologically responsive to the immunotherapy. In some embodiments, the individual has not previously received an immunotherapy.

In some embodiments, the individual is capable of developing an antigen-specific immune response against a tumor antigen. Specific immune response against one or more tumor antigen peptides may be determined using any known methods in the art, for example, by measuring levels of cytotoxic factor (such as perforin or granzyme B), or cytokine release (such as IFNγ or TNFα) from T cells (or PBMCs) after stimulation by the individual tumor antigen peptide. An antibody-based assay, such as ELISPOT, may be used to quantify the cytotoxic factor, or cytokine (such as IFNγ) levels. The individual capable of developing an antigen-specific immune response against a tumor antigen may or may not have previously received an immunotherapy.

Thus, in some embodiments, there is provided a method of treating a cancer in an individual, comprising: (a) optionally administering an effective amount of antigen-loaded DCs; and (b) administering to the individual an effective amount of tumor antigen-specific T cells, wherein the tumor antigen-specific T cells are prepared by any one of the methods of preparing tumor antigen-specific T cells described above in Section II, and wherein the individual is capable of developing an antigen-specific immune response against a tumor antigen based on an ELISPOT assay using the tumor antigen and a PBMC sample from the individual.

In some embodiments, there is provided a method of treating a cancer in an individual, comprising: (a) performing an ELISPOT assay using a tumor antigen and a PBMC sample from the individual; (b) selecting an individual for the method if the ELISPOT assay indicates that the individual is capable of developing an antigen-specific immune response against the tumor antigen; (c) optionally administering an effective amount of DCs loaded with one or more tumor antigen peptides derived from the tumor antigen, and (d) administering to the individual an effective amount of tumor antigen-specific T cells, wherein the tumor antigen-specific T cells are prepared by any one of the methods of preparing tumor antigen-specific T cells described above in Section II.

In some embodiments, there is provided a method of treating a cancer in an individual, comprising: (a) optionally administering an effective amount of antigen-loaded DCs; and (b) administering to the individual an effective amount of tumor antigen-specific T cells, wherein the tumor antigen-specific T cells are prepared by any one of the methods of preparing tumor antigen-specific T cells described above in Section II, and wherein the individual is selected for treatment based on an ELISPOT assay using a tumor antigen and an PBMC sample from the individual that indicates the individual is capable of developing an antigen-specific immune response against the tumor antigen.

Monitoring After Treatment

Any of the treatment methods described herein and the MASCT methods may further comprise a monitoring step after the individual receives the treatment. Post-treatment monitoring may be beneficial for adjusting the treatment regimen of the individual to optimize treatment outcome.

For example, the plurality of tumor antigen peptides described herein may be adjusted or customized based on the specific immune response of the individual against each of the plurality of tumor antigen peptides and/or the clinical response of the individual to the tumor antigen-specific T cells in order to provide a plurality of customized tumor antigen peptides, which may be used for repeated treatments. In some embodiments, tumor antigen peptides that do not elicit a strong specific immune response can be removed from the antigen peptide pool for future preparations of the pulsed DCs or tumor antigen-specific T cells.

Specific immune response against one or more tumor antigen peptides may be determined using any known methods in the art, for example, by measuring levels of cytotoxic factor (such as perforin or granzyme B), or cytokine release (such as IFNγ or TNFα) from T cells (or PBMCs) after stimulation by the individual tumor antigen peptide. An antibody-based assay, such as ELISPOT, may be used to quantify the cytotoxic factor, or cytokine (such as IFNγ) levels. In some embodiments, the cytokine (such as IFNγ) release level from T cells (or PBMCs) in response to a tumor antigen peptide is normalized to a reference, such as a baseline cytokine release level, or a nonspecific cytokine release level of from T cells (or PBMCs) in response to an irrelevant peptide, to provide a cytokine (such as IFNγ) fold change value. In some embodiments, a cytokine (such as IFNγ) fold change value of more than about any one of 1.2, 1.5, 2, 2.5, 3, 4, 5, 6, 8, 10, or more in an ELISPOT assay indicate strong specific immune response against the tumor antigen peptide. In some embodiments, a tumor antigen peptide with a cytokine (such as IFNγ) fold change value of less than about any one of 10, 8, 6, 5, 4, 3, 2.5, 2, 1.5, 1.2 or less in an ELISPOT assay is removed from the plurality of tumor antigen peptides to provide a plurality of customized tumor antigen peptides for future treatments.

Clinical response of the individual to the treatment methods described herein may be assessed by known methods in the art by a physician, such as by imaging methods, blood tests, biomarker assessment, and biopsy. In some embodiments, the clinical response is monitored by determining the number of circulating tumor cells (CTC) in the individual before and after receiving the tumor antigen-specific T cells. In some embodiments, the CTCs have detached from a primary tumor and circulate in a bodily fluid. In some embodiments, the CTCs have detached from a primary tumor and circulate in the bloodstream. In some embodiments, the CTCs are an indication of metastasis. CTC numbers can be determined by a variety of methods known in the art, including, but not limited to, CellSearch method, Epic Science method, isoflux, and maintrac. In some embodiments, the number of single CTCs, including specific subtypes of CTCs, in a blood sample of the individual is determined. In some embodiments, a number of more than about any of 10, 20, 50, 100, 150, 200, 300 or more of single CTCs per mL of the blood sample in the individual after receiving the treatment indicates an increased risk of metastasis, and/or poor clinical response to the treatment method. In some embodiments, an increased number (such as at least about any one of 1.5, 2, 3, 4, 5, 10, or more fold increase) of single CTCs of the individual after receiving the treatment compared to before receiving the treatment indicates poor clinical response to the treatment method. In some embodiments, the number of CTC clusters in a blood sample of the individual is determined. In some embodiments, detection of at least about any of 1, 5, 10, 50, 100, or more CTC clusters in a blood sample of the individual after receiving the treatment indicates an increased risk of metastasis, and/or poor clinical response to the treatment. In some embodiments, an increased number (such as at least about any one of 1.5, 2, 3, 4, 5, 10, or more fold increase) of CTC clusters of the individual after receiving the treatment compared to before receiving the treatment indicates poor clinical response to the treatment.

V. Compositions, Kits and Articles of Manufacture

The present application further provides kits, compositions (such as pharmaceutical compositions), and articles of manufacture for use in any embodiment of the treatment methods and the tumor antigen-specific T cell preparation methods described herein.

In some embodiments, there is provided a kit useful for cancer immunotherapy, comprising at least 10 tumor antigen peptides. A person skilled in the art may use any combinations of tumor antigen peptides from the first core group and optionally any combinations of cancer-type specific antigen peptides from the second group, and/or neoantigen peptides to load a population of DCs, which can further be used to prepare tumor antigen-specific T cells useful for treating cancer in an individual.

The kit may contain additional components, such as containers, reagents, culturing media, cytokines, immune checkpoint inhibitors, TLR agonists, buffers, antibodies, and the like to facilitate execution of any embodiment of the treatment methods or cell preparation methods described herein. For example, in some embodiments, the kit further comprises a peripheral blood collection and storage apparatus, which can be used to collect an individual's peripheral blood. In some embodiments, the kit further comprises containers and reagents for density gradient centrifugation of peripheral blood, which can be used to isolate PBMCs from a sample of human peripheral blood. In some embodiments, the kit further comprises culturing media, cytokines, or buffers for obtaining DCs from peripheral blood. In some embodiments, the kit further comprises culturing media, TLR agonists (e.g., MPLA), IFNγ, PGE2, reagents and buffers for loading the plurality of tumor antigen peptides into DCs. In some embodiments, the kit further comprises cytokines (e.g., IL-2, IL-7, IL-15 and IL-21), immune checkpoint inhibitors (e.g., anti-PD1 antibody) anti-CD3 antibody, buffers, or culturing media for co-culturing T cells, enriched activated T cells, or tumor antigen-specific T cells with antigen-loaded APCs (e.g., DCs). In some embodiments, the kit further comprises antibodies, magnetic beads, and columns for enriching activated T cells expressing a cytokine (e.g., IFNγ). In some embodiments, the kit further comprises containers, buffers, and reagents for freezing and storing tumor antigen-specific T cells. In some embodiments, the kit further comprises reagents for determining the mutation load (such as in one or more MHC genes) in cancer cells. In some embodiments, the kit further comprises an immune checkpoint inhibitor for combination therapy with the treatment method. In some embodiments, the kit further comprises reagents for identifying a neoantigen (such as by sequencing) a tumor sample. In some embodiments, the kit further comprises an ELISPOT assay for assessing specific immune response against one or more tumor antigen peptides.

The kits of the present application are in suitable packaging. Suitable packaging include, but is not limited to, vials, bottles, jars, flexible packaging (e.g., Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions may also comprise instructions relating to the use of the tumor antigen peptides (and optionally additional components described above). In some embodiments, the kit further comprises an instructional manual, such as a manual describing a protocol of an embodiment of the treatment methods, or an embodiment of the cell preparation methods as described herein. The instructions may also include information on dosage, dosing schedule, and routes of administration of the DCs and/or the tumor antigen-specific T cells prepared using the kit for the intended treatment. In some embodiments, the kit further comprises instructions for selecting an individual for the treatment method. In some embodiments, the kit further comprises instructions for determining the mutation load of cancer cells, and/or determining the number of neoantigens in an individual. In some embodiments, the kit further comprises instructions for administering an immune checkpoint inhibitor in combination with the treatment method, including, for example, information on dosage, dosing schedule, and route of administration of the immune checkpoint inhibitor. In some embodiments, the kit further comprises instructions for identifying a neoantigen (such as by sequencing) in a tumor sample. In some embodiments, the kit further comprises instructions for monitoring an individual after receiving the treatment.

The containers may be unit doses, bulk packages (e.g., multi-dose packages) or sub-unit doses. For example, kits may be provided that contain sufficient tumor antigen peptides as disclosed herein to prepare sufficient tumor antigen-specific T cells and/or antigen-loaded APCs (such as DCs) to provide effective treatment of an individual for an extended period, such as any of 3 weeks, 6 weeks, 9 weeks, 3 months, 4 months, 5 months, 6 months, 8 months, 9 months, 1 year or more.

Kits may also include multiple unit doses of tumor antigen peptides and instructions for use and packaged in quantities sufficient for storage and use in pharmacies, for example, hospital pharmacies and compounding pharmacies.

Further provided are kits, compositions (such as pharmaceutical compositions), and articles of manufacture of any one of the isolated population of cells (such as DCs, or tumor antigen-specific T cells) described herein.

The isolated population of cells described herein may be used in pharmaceutical compositions or formulations, by combining the isolated population of cells described with a pharmaceutically acceptable carrier, excipients, stabilizing agents and/or other agents, which are known in the art, for use in the methods of treatment, methods of administration, and dosage regimens described herein. In some embodiments, human albumin is used as a pharmaceutically acceptable carrier.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid, lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. The final form may be sterile and may also be able to pass readily through an injection device such as a hollow needle. The proper viscosity may be achieved and maintained by the proper choice of solvents or excipients.

The pharmaceutical compositions described herein may include other agents, excipients, or stabilizers to improve properties of the composition. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. In some embodiments, the pharmaceutical composition is formulated to have a pH in the range of about 4.5 to about 9.0, including for example pH ranges of about any one of 5.0 to about 8.0, about 6.5 to about 7.5, or about 6.5 to about 7.0. In some embodiments, the pharmaceutical composition can also be made to be isotonic with blood by the addition of a suitable tonicity modifier, such us glycerol.

In some embodiments, the isolated cell composition (such as pharmaceutical compositions) suitable for administration to a human. In some embodiments, the compositions (such as pharmaceutical compositions) is suitable for administration to a human by parenteral administration. Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as ampules and vials, and can be stored in a condition requiring only the addition of the sterile liquid excipient methods of treatment, methods of administration, and dosage regimens described herein (i.e., water) for injection, immediately prior to use. In some embodiments, the compositions (such as pharmaceutical compositions) is contained in a single-use vial, such as a single-use sealed vial. In some embodiments, each single-use vial contains about $10^9$ tumor antigen-specific T cells. In some embodiments, each single-use vial contains enough tumor antigen-specific T cells to be expanded to about $10^9$ tumor antigen-specific T cells. In some embodiments, the composition (such as pharmaceutical composition) is contained in a multi-use vial. In some embodiments, the composition (such as pharmaceutical composition) is contained in bulk in a container.

Also provided are unit dosage forms comprising the isolated cell compositions (such as pharmaceutical compositions) and formulations described herein. These unit dosage forms can be stored in a suitable packaging in single or multiple unit dosages and may also be further sterilized and sealed. In some embodiments, the composition (such as pharmaceutical composition) also includes one or more other compounds (or pharmaceutically acceptable salts thereof) that are useful for treating cancer.

The present application further provides kits comprising any of the isolated population of cells, compositions (such as pharmaceutical compositions), formulations, unit dosages, and articles of manufacture described herein for use in the methods of treatment, methods of administration, and dosage regimens described herein. Kits described herein include one or more containers comprising the tumor antigen-specific T cells.

VI. Exemplary Embodiments

Among the embodiments provided herein are:
1. A method of preparing a population of tumor antigen-specific T cells, the method comprising:
a) a first co-culturing step, comprising co-culturing a first population of dendritic cells loaded with a plurality of tumor antigen peptides with a population of T cells to obtain a first co-culture comprising activated T cells;

b) an enrichment step, comprising subjecting the first co-culture to an enrichment process to obtain an enriched population of activated T cells; and c) a second co-culturing step, comprising co-culturing the enriched population of activated T cells with a second population of dendritic cells loaded with one or more tumor antigen peptides from the plurality of tumor antigen peptides to obtain a population or tumor antigen-specific T cells.

2. The method of embodiment 1, wherein the first co-culturing step is carried out for about 1 to about 3 days prior to the enrichment step.

3. The method of embodiment 1 or 2, wherein the ratio between the population of T cells to the first population of dendritic cells loaded with the plurality of tumor antigen peptides is no more than about 30:1.

4. The method of any one of embodiments 1-3, wherein the first population of dendritic cells loaded with the plurality of tumor antigen peptides and the population of T cells are co-cultured in a first co-culture medium comprising one or more cytokines and an immune checkpoint inhibitor.

5. The method of embodiment 4, wherein the first co-culture medium comprises IL-2, IL-7, IL-15 and IL-21 and an anti-PD-1 antibody.

6. The method of embodiment 4, wherein the first co-culture medium comprises IL-2 and an anti-PD-1 antibody.

7. The method of any one of embodiments 1-6, wherein the enrichment step comprises contacting the first co-culture with antigen presenting cells (APCs) loaded with the plurality of tumor antigen peptides to obtain a stimulated co-culture, and isolating from the stimulated co-culture an enriched population of activated T cells using a ligand that specifically recognizes a cytokine.

8. The method of embodiment 7, wherein the cytokine is IFNγ.

9. The method of any one of embodiments 1-8, wherein the ratio between the enriched population of activated T cells and the second population of dendritic cells loaded with one or more tumor antigen peptides from the plurality of tumor antigen peptides is about 1:1 to about 20:1.

10. The method of any one of embodiments 1-9, wherein the enriched population of activated T cells and the second population of dendritic cells loaded with one or more tumor antigen peptides from the plurality of tumor antigen peptides are co-cultured for about 12 to 25 days.

11. The method of one of embodiments 1-10, wherein the second co-culturing step comprises co-culturing the second population of dendritic cells loaded with one or more tumor antigen peptides from the plurality of tumor antigen peptides with the enriched population of activated T cells in an initial second co-culture medium comprising an immune checkpoint inhibitor and optionally one or more cytokines to provide a second co-culture; and adding an anti-CD3 antibody to the second co-culture to obtain a population of tumor antigen-specific T cells.

12. The method of embodiment 11, wherein the anti-CD3 antibody is added to the second co-culture no more than about 3 days after the second co-culturing step starts.

13. The method of embodiment 12, wherein the anti-CD3 antibody is added to the second co-culture at about 2 days after the second co-culturing step starts.

14. The method of any one of embodiments 11-13, wherein the anti-CD3 antibody is OKT3.

15. The method of any one of embodiments 11-14, wherein the second co-culturing step comprises adding one or more cytokines to the second co-culture.

16. The method of embodiment 15, wherein the one or more cytokines comprise IL-2.

17. The method of embodiment 15 or 16, wherein the one or more cytokines is added to the second co-culture no more than about 3 days (e.g., about 2 days) after the second co-culturing step starts.

18. The method of any one of embodiments 11-17, wherein the initial second co-culture medium comprises IL-2 and an anti-PD-1 antibody.

19. The method of any one of embodiments 11-18, wherein the initial second co-culture medium comprises IL-2, IL-7, IL-15 and IL-21 and an anti-PD-1 antibody.

20. The method of any one of embodiments 1-19, further comprising a third co-culturing step comprising co-culturing a population of the tumor antigen-specific T cells with a population of antigen presenting cells (APCs) loaded with one or more tumor antigen peptides from the plurality of tumor antigen peptides to obtain a second population of tumor antigen-specific T cells.

21. The method of embodiment 20, wherein the APCs are PBMCs or dendritic cells.

22. The method of embodiment 20 or 21, wherein the ratio between the population of tumor antigen-specific T cells and the population of APCs loaded with one or more tumor antigen peptides from the plurality of tumor antigen peptides is about 1:1 to about 20:1.

23. The method of any one of embodiments 20-22, wherein the population of tumor antigen-specific T cells and the population of APCs loaded with one or more tumor antigen peptides from the plurality of tumor antigen peptides are co-cultured for about 5 to 9 days.

24. The method of any one of embodiments 20-23, wherein the population of tumor antigen-specific T cells and the population of APCs loaded with one or more tumor antigen peptides from the plurality of tumor antigen peptides are co-cultured in a third co-culture medium comprising one or more cytokines and an anti-CD3 antibody.

25. The method of embodiment 24, wherein the third co-culture medium comprises IL-2 and OKT3.

26. The method of embodiment 25, wherein the third co-culture medium comprises IL-2, IL-7, IL-15 and OKT3.

27. The method of any one of embodiments 20-26, the third co-culturing step is repeated.

28. The method of any one of embodiments 20-27, wherein the population of the tumor antigen-specific T cells is obtained from a frozen stock of the tumor antigen-specific T cells.

29. The method of any one of embodiments 1-28, wherein the first co-culturing step further comprises contacting a population of dendritic cells with a plurality of tumor antigen peptides to obtain the first population of dendritic cells loaded with the plurality of tumor antigen peptides, and/or the second co-culturing step further comprises contacting a population of dendritic cells with one or more tumor antigen peptides from the plurality of tumor antigen peptides to obtain the second population of dendritic cells loaded with one or more tumor antigen peptides from the plurality of tumor antigen peptides.

30. The method of embodiment 29, wherein the first co-culturing step further comprises culturing the first population of dendritic cells loaded with the plurality of tumor antigen peptides in a DC maturation medium comprising a toll-like receptor (TLR) agonist, and/or the second co-culturing step further comprises culturing the second population of dendritic cells loaded with one or more tumor antigen peptides from the plurality of tumor antigen peptides in a DC maturation medium comprising a toll-like receptor (TLR) agonist.

31. The method of embodiment 30, wherein the DC maturation medium comprises INFγ, MPLA and PGE2.
32. The method of any one of embodiments 29-31, wherein the population of dendritic cells is obtained by inducing differentiation of a population of monocytes from PBMCs
33. The method of any one of embodiments 1-32, wherein the population of T cells in the first co-culturing step is present in a population of PBMCs.
34. The method of any one of embodiments 29-33, wherein the population of dendritic cells and the population of T cells are obtained from the same individual.
35. The method of any one of claims 1-34, wherein the plurality of tumor antigen peptides comprises a neoantigen peptide, optionally wherein the plurality of tumor antigen peptides consists of neoantigen peptides.
36. The method of any one of embodiments 1-35, wherein the plurality of tumor antigen peptides is a plurality of synthetic tumor antigen peptides.
37. The method of any one of embodiments 1-36, wherein the plurality of tumor antigen peptides is not obtained from a cell sample.
38. An isolated population of cells prepared using the method of any one of embodiments 1-37.
39. The isolated population of cells of embodiment 38, comprising at least about 3% of tumor antigen-specific T cells that secrete INF-γ upon stimulation with one or more tumor antigen peptides from the plurality of tumor antigen peptides.
40. The isolated population of cells of embodiment 38 or 39, comprising at least about 3% of tumor antigen-specific T cells that secrete TNF-α upon stimulation with one or more tumor antigen peptides from the plurality of tumor antigen peptides.
41. A method of treating a cancer in an individual, composing administering to the individual an effective amount of the tumor antigen-specific T cells prepared by the method of any one of embodiments 1-37.
42. The method of embodiment 41, further comprising freezing a population of the tumor antigen-specific T cells to obtain a frozen stock, co-culturing a thawed population of tumor antigen-specific T cells from the frozen stock with a population of dendritic cells loaded with one or more tumor antigen peptides from the plurality of tumor antigen peptides to provide a second population of tumor antigen-specific T cells, and administering an effective amount of the second population of tumor antigen-specific T cells.
43. The method of embodiment 41 or 42, wherein the tumor antigen-specific T cells are administered intravenously.
44. The method of any one of embodiments 41-43, wherein the individual is a human individual.
45. The method of embodiment 44, wherein the individual has previously received an immunotherapy.
46. The method of embodiment 45, wherein the individual is immunologically responsive to the immunotherapy.
47. The method of embodiment 45 or 46, wherein the immunotherapy is selected from the group consisting of an immune checkpoint inhibitor, an adoptive immune cell therapy, a cancer vaccine, an oncolytic virus and combinations thereof.
48. The method of embodiment 47, wherein the individual is capable of developing a specific immune response against a tumor antigen peptide.
49. The method of embodiment 47 or 48, wherein the individual has clinically benefited from a Multiple-Antigens Stimulating Cellular Therapy (MASCT) comprising administering to the individual an effective amount of activated T cells prepared by co-culturing a population of T cells with a population of dendritic cells loaded with the plurality of tumor antigen.

EXAMPLES

The examples below are intended to be purely exemplary of the present application and should therefore not be considered to limit the invention in any way. The following examples and detailed description are offered by way of illustration and not by way of limitation.

Example 1

Specific Immune Response Against Tumor Antigen Peptides in a Patient Treated with MASCT Patient W J, female, was diagnosed with cervical cancer with vascular invasion at age 41, and was tested positive with Human Papilloma Virus (HPV) DNA. She underwent curative resection, and a five-month chemo-radio therapy. The patient took a second HPV DNA test, and was confirmed to be negative in serum HPV DNA. The clinical history and response of this patient is summarized in FIG. 1.

About two years after the curative resection and chemo-radio therapy, the patient was diagnosed to have metastasis tumor on the right sacroiliac joint bone according to Magnetic Resonance Imaging (MRI) and Emission Computed Tomography (ECT). The patient then received ten local radiotherapy treatments, followed by three MASCT treatment, administered one per month. The MASCT treatment used PBMCs from the patient's own peripheral blood to prepare dendritic cells pulsed with a pool of 18 antigen peptides, including a core group of 12 tumor-associated antigen peptides, as well as a cervical cancer-specific group of 6 antigen peptides derived from viral proteins of HPV. Briefly, monocytes from the patient's PBMCs were differentiated into immature DCs and then pulsed with multiple synthetic peptide antigens including tumor-associated antigens and HPV antigens. The immature DCs were further stimulated by TLR ligands to differentiate into mature DCs (mDCs). Half of mDCs were subcutaneous injected to the patient. Maintaining T cells were prepared by culturing non-adherent PBMCs with anti-CD3 antibody (e.g., OKT3), and IL2. The other half of mDCs was co-cultured with the maintaining T cells for another 7-9 days before infusion. The patient was confirmed to have HLA-A2 serotype (HLA-A0201$^+$).

After four MASCT treatments, the patient's ECT results showed that the right sacroiliac joint bone metastasis was reduced, and no metastasis was detected, indicating positive treatment outcome of MASCT. The patient received four additional MASCT treatments administered with an interval of about 1 month or 2 months. After a total of 8 MASCT treatments, a sample of the patient's PBMC was obtained and tested with an ELISPOT assay to determine whether the patient had a therapeutically effective MHC-restricted T cell response to the antigen peptide pool and each of the antigen peptides within the pool. The ELISPOT results demonstrated enhanced T-cell response to the cervical carcinoma antigen peptide pool, and individual antigen peptides within both the core group of tumor-specific antigen peptides (such as hTERT, p53, CEA, and RGS5), and the cervical cancer-specific group of tumor antigen peptides (such as HPV-3 and HPV-5). The patient's ECT after a total of 8 MASCT showed further reduction of the right sacroiliac joint bone metastasis, and no new metastasis sites, indicating that the MASCT treatment regimen was successful in reducing tumor burden in the patient and in preventing tumor progression and further metastasis.

Based on the patient's specific immune response, the antigen peptide pool was customized to provide a patient-specific antigen peptide pool by saving the responsive peptides that had induced specific responses and removing the non-responsive peptides that did not induce specific responses. The patient was further treated with four cycles of MASCT prepared using the patient-specific antigen peptide pool (referred herein as "precise MASCT"). After the four precise MASCT, The patient's ECT showed no development of the right sacroiliac joint bone metastasis, and no new metastasis sites.

Figure 2A:
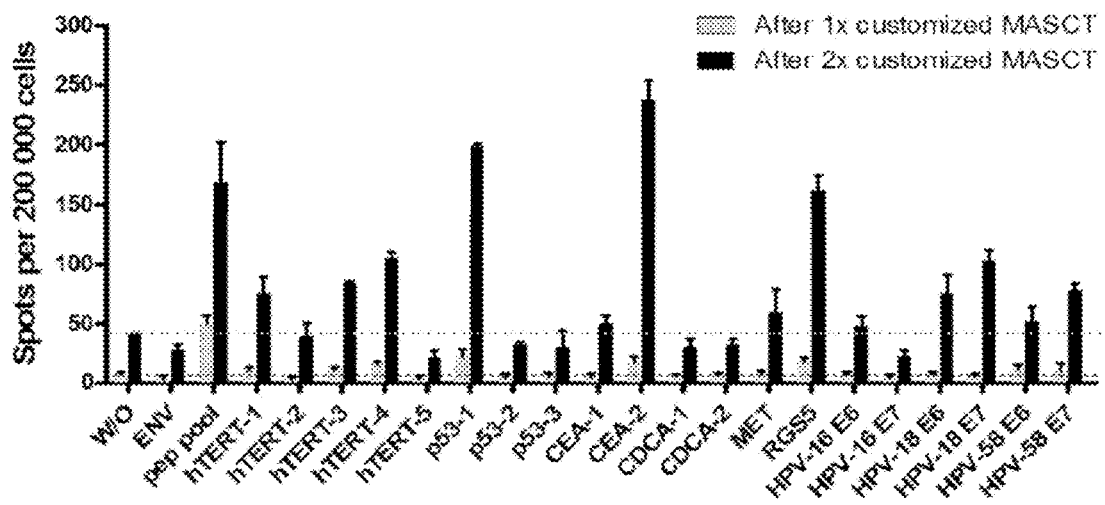
FIGS. 2A-2B show specific immune response by the patient's PBMCs against the cervical carcinoma antigen peptide pool (pep pool), and each tumor antigen peptide in the pool after customized MASCT treatments as determined by ELISPOT. W/O=response without stimulation with any antigen peptide. ENV refers to experiment with an irrelevant peptide. The dotted line indicates a threshold of no elevated immune response as measured by spots per 200,000 cells which reflect IFNγ secretion levels.
Figure 2B:
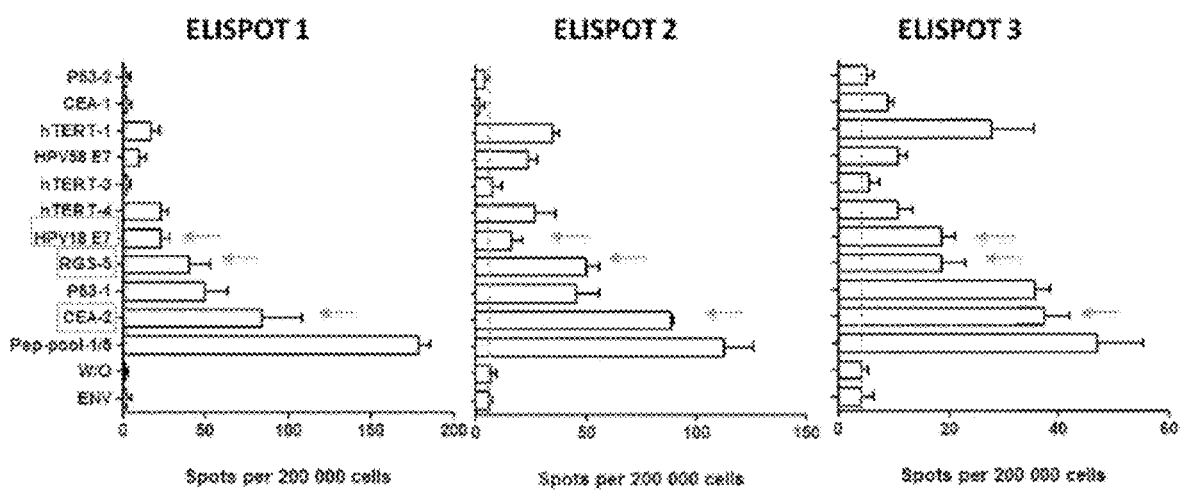

The antigen peptide pool was further adjusted based on the specific immune response of the patient, and the patient was treated with four cycles of a $2^{nd}$ precise MASCT using the further adjusted peptide antigen pool. After the second four cycles of precise MASCT, the patient was evaluated as having stable disease (SD). The patient-specific antigen peptide pool elicited enhanced specific responses as demonstrated by the ELISPOT assay (FIG. 2A). In particular, HPV18-E7 peptide, CEA peptide, and RGS5 peptide consistently yielded the strongest specific response (FIG. 2B).

Example 2

Preparation of Tumor Antigen-Specific T Cells from PBMCs of a Patient Treated with MASCT PBMC samples from the patient in Example 1 were obtained and used as the starting material to prepare tumor antigen-specific T cells in this example.

Cells Preparation

FIG. 3 provides an overview of the protocol used in this example. Briefly, on Day 1, peripheral blood mononuclear cells (PBMCs) from the patient were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed with a peptide pool comprising three tumor antigen peptides derived from CEA, RGS5, and HPV18-E7 (1 µg/mL/peptide), and then cultured in a DC maturation medium to differentiate into mature DCs. On Day 8, PBMCs containing T cells were co-cultured with antigen-loaded mature DCs at a ratio between the T cells and the mature antigen-loaded DCs of about 20:1, and the co-culture medium contained a cytokine cocktail and an anti-PD-1 antibody. On Day 13, an anti-CD3 antibody was added to the co-culture. On Day 20, the co-culture was stimulated with PBMCs pulsed with the peptide pool. On Day 21, an IFNγ secretion assay-cell enrichment and detection kit (Miltenyi Biotec) was used to isolate a population of IFNγ$^+$ T cells. On Day 22, the IFNγ$^+$ T cells were co-cultured with antigen-loaded mature DCs at a ratio between the T cells and the antigen-loaded mature DCs of about 2:1 in a medium containing a cytokine cocktail, an anti-PD-1 antibody, and an anti-CD3 antibody from Day 22 to Day 31-35 to obtain tumor antigen-specific T cells.

Proliferation Assay

Cell proliferation was assessed using cell samples from Day 1 (PBMCs), Day 8 (start of co-culture), Day 21 (before IFNγ enrichment and after IFNγ enrichment), and Days 27, 29, 31, 34 and 35 (co-culture of IFNγ$^+$ T cells with antigen-loaded mature DCs). The numbers of cells in each sample were counted.

Figure 4:
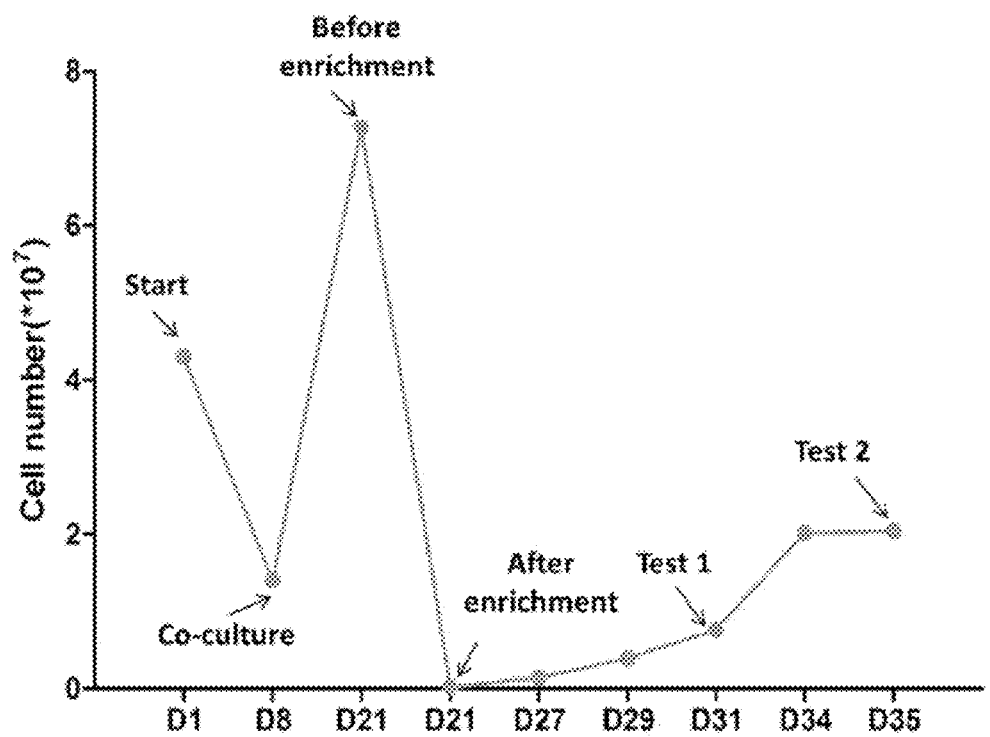
FIG. 4 shows cell proliferation at various time points in the preparation of tumor antigen-specific T cells.

As shown in FIG. 4, the initial co-culture of antigen-loaded mature DCs and T cells yielded a small number of IFNγ$^+$ T cells (Day 21). In the co-culture of enriched IFNγ$^+$ T cells and antigen-loaded mature DCs, the number of cells continued to increase until Day 34, at which time point the total number of cells in the co-culture plateaued at about $2 \times 10^7$.

IFNγ Production by Tumor Antigen-Specific T Cells

Various co-culture samples were each plated (T cells $1 \times 10^6$ cells/well; PBMCs: $2.5 \times 10^5$ cells/well) in AIM-V medium and stimulated with 2 µg/mL of the peptide pool for 4 hours. The IFNγ production levels by tumor antigen-specific T cells in each sample were detected by intracellular cytokine staining and FACS analysis. Cell samples incubated with 10 µg/mL irrelevant peptide were used as negative controls.

Antibodies for cell surface (e.g., anti-human CD3-FITC) or intracellular cytokine (e.g., anti-human IFNγ-APC) staining were obtained from BD Biosciences. Intracellular cytokine staining was performed by fixing and permeabilizing cells with cytofix/cytoperm (BD Biosciences). Flow cytometry was performed using FACS CantoII (BD Biosciences) flow cytometers and data was analyzed with the Flowjo program.

Figure 5:
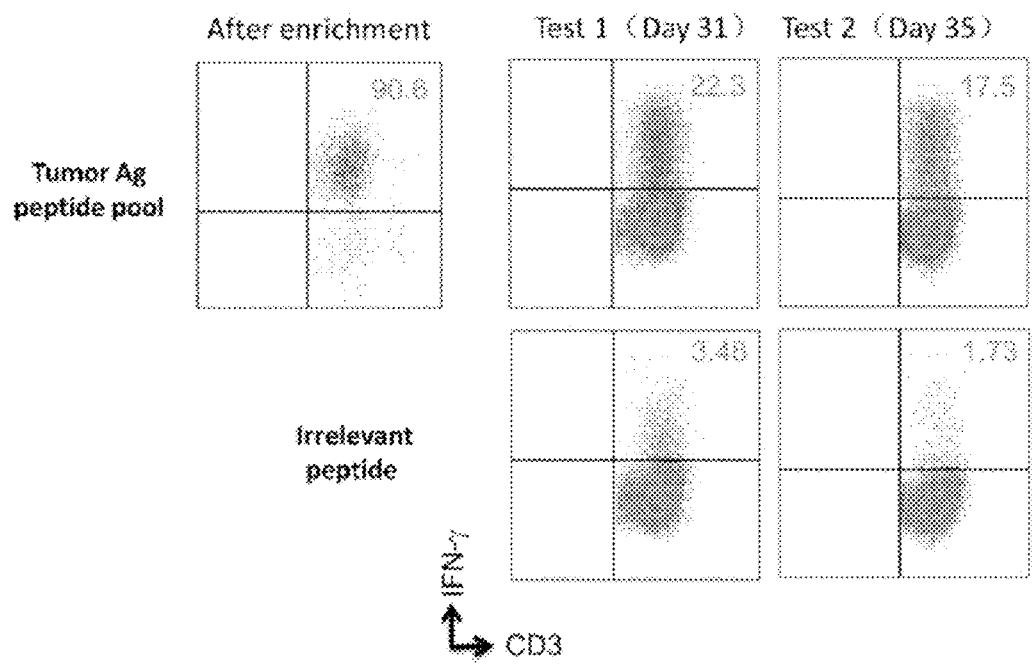
FIG. 5 shows the percentages of IFNγ$^+$CD3$^+$ tumor antigen-specific T cells in various co-culture samples.

FIG. 5 shows the percentages of tumor antigen-specific T cells in the cell samples as determined by assessing IFNγ$^+$ CD3$^+$ cells in response to stimulation by the tumor antigen peptide pool. After the enrichment step, the percentage of tumor antigen-specific T cells in the cell sample reached 90.6%. However, on Day 31, the co-culture contained about 22.3% tumor antigen-specific T cells that responded to stimulation by the tumor antigen peptide pool. On Day 35, the co-culture contained about 17.5% tumor antigen-specific T cells that produced IFNγ in response to stimulation by the tumor antigen peptide pool. Non-specific T cells that produced IFNγ in response to stimulation by irrelevant peptides only constituted about 1.73% and 3.48% of the co-cultures on Days 31 and 35 respectively.

Example 3

Preparation of Tumor Antigen-Specific T Cells from PBMCs of a Patient Treated with MASCT PBMC samples from the patient in Example 1 were obtained and used as the starting material to prepare tumor antigen-specific T cells in this example.

Method 2

Cells Preparation

FIG. 6 provides an overview of the protocol of exemplary "Method 2". Briefly, on Day 1, peripheral blood mononuclear cells (PBMCs) from the patient were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed with a peptide pool comprising three tumor antigen peptides derived from CEA, RGS5, and HPV18-E7 (1 µg/mL/peptide), and then cultured in a DC maturation medium to differentiate into mature DCs. On Day 8, PBMCs containing T cells were co-cultured with antigen-loaded mature DCs at a ratio between the cells and the mature antigen-loaded DCs of about 15:1, and the co-culture medium contained a cytokine cocktail and an anti-PD-1 antibody. On Day 11, the co-culture was stimulated with PBMCs pulsed with the peptide pool. On Day 12, an IFNγ secretion assay-cell enrichment and detection kit (Miltenyi Biotec) was used to isolate a population of IFNγ$^+$ T cells. On Day 12, the IFNγ$^+$ T cells were co-cultured with antigen-loaded mature DCs at a ratio between the T cells and the antigen-loaded mature DCs of about 2:1 in a medium containing a cytokine cocktail, an anti-PD-1 antibody, and an anti-CD3 antibody from Day 12 to Day 25-35 to obtain tumor antigen-specific T cells.

Proliferation Assay

Cell proliferation was assessed using cell samples from Day 1 (PBMCs), Day 8 (start of co-culture), Day 11 (before IFNγ enrichment and after IFNγ enrichment), and Days 17, 21, 25, 27, 31 and 32 (co-culture of IFNγ$^+$ T cells antigen-loaded mature DCs) by methods described in Example 2.

Figure 7:
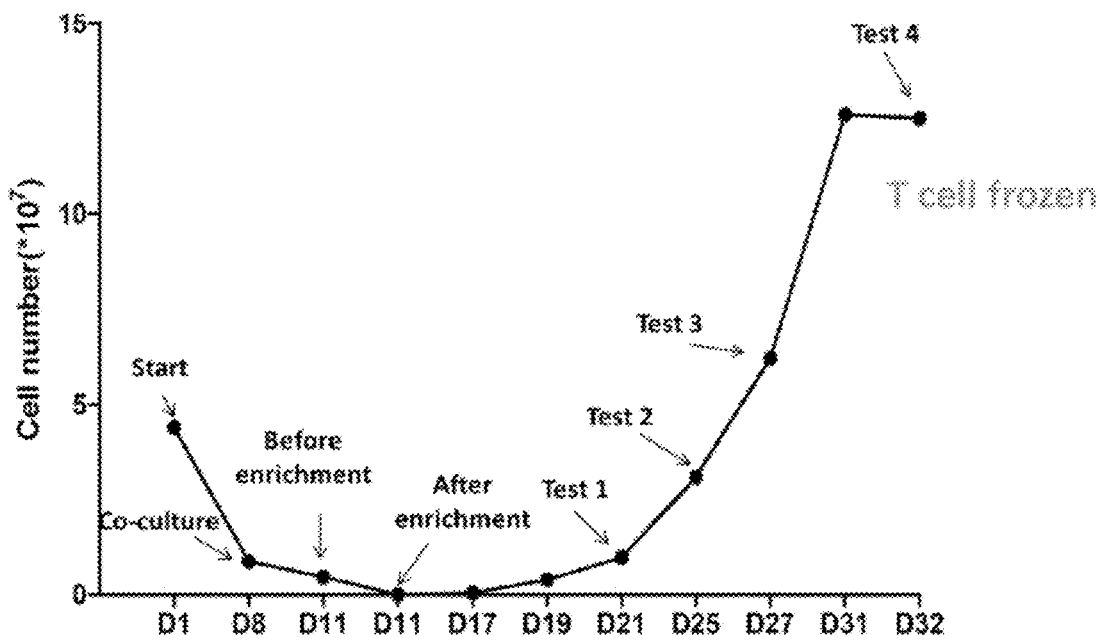
FIG. 7 shows cell proliferation at various time points in the preparation of tumor antigen-specific T cells.

As shown in FIG. 7, the initial co-culture of antigen-loaded mature DCs and T cells yielded a small number of IFNγ$^+$ T cells (Day 11). In the co-culture of enriched IFNγ$^+$ T cells and antigen-loaded mature DCs, the number of cells continued to increase rapidly until Day 31, at which time point the total number of cells in the co-culture plateaued at more than $10^8$.

IFNγ Production by Tumor Antigen-Specific T Cells

Figure 8A:
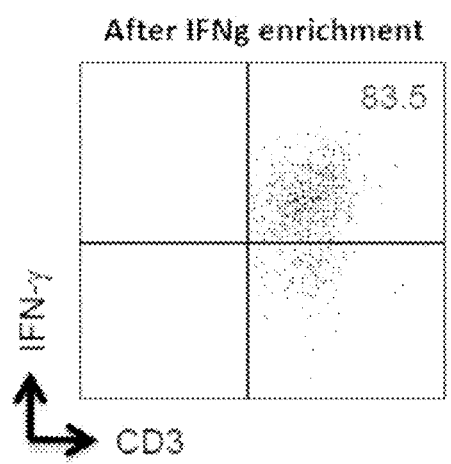
FIGS. 8A-8B shows the percentages of IFNγ$^+$CD3$^+$ tumor antigen-specific T cells in various co-culture samples.
Figure 8B:
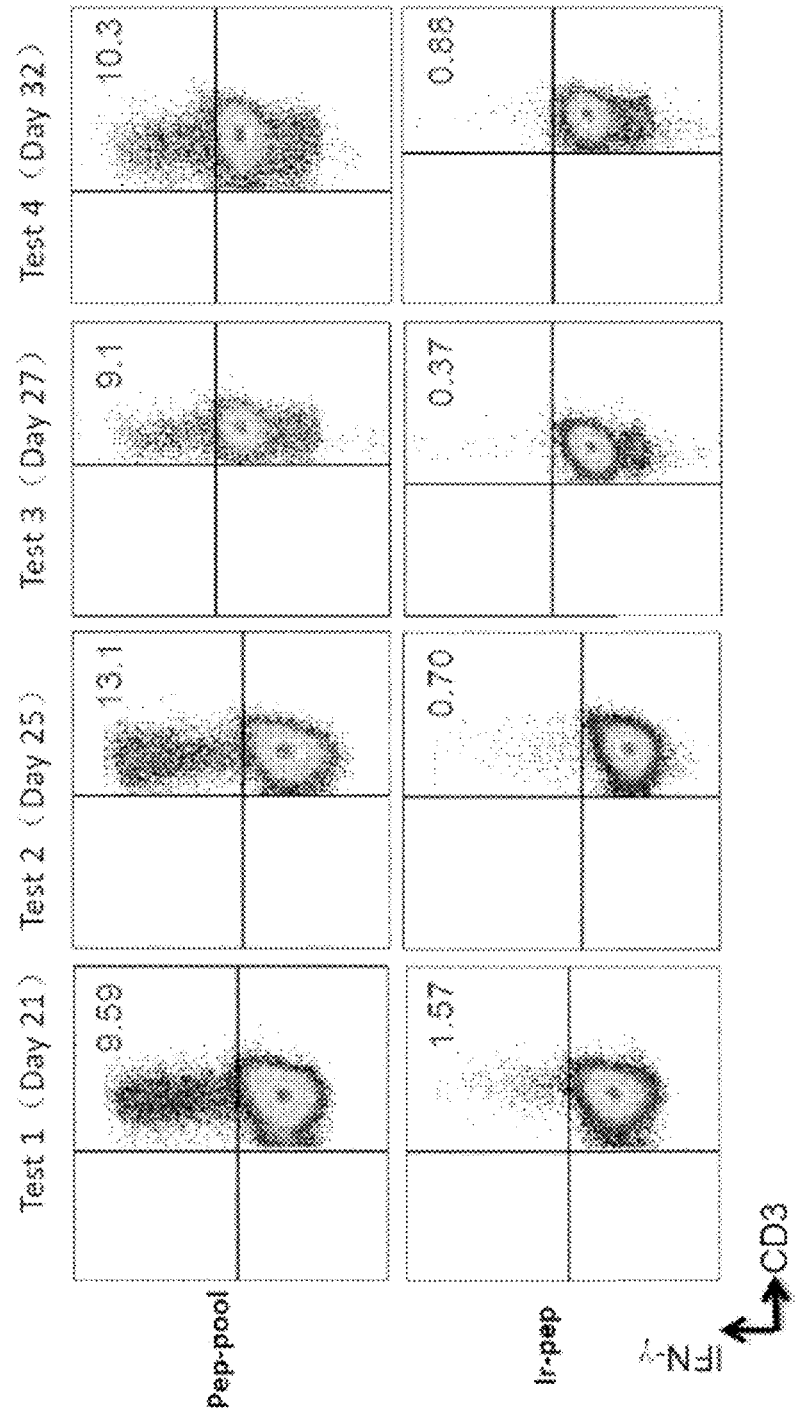

The IFNγ production levels by tumor antigen-specific T cells in various co-culture samples were determined by methods described in Example 2. FIGS. 8A-8B show the percentages of tumor antigen-specific T cells in the cell samples as determined by assessing IFNγ$^+$CD3$^+$ cells in response to stimulation by the tumor antigen peptide pool. After the enrichment step, the percentage of tumor antigen-specific T cells in the cell sample reached 83.5%. From Day 21 to Day 32, the co-cultures contained about 10% tumor antigen-specific T cells that produced IFNγ in response to stimulation by the tumor antigen peptide pool. Non-specific T cells that produced IFNγ in response to stimulation by irrelevant peptides constituted less than 1% in the co-cultures on Days 25-32.

Optimization of Method 2 ("Method 2m")

Cells Preparation

FIG. 9 provides an overview of the protocols of exemplary "Method 2m". Briefly, on Day 1, peripheral blood mononuclear cells (PBMCs) from the patient were obtained by density gradient centrifugation on Lymphoprep (Nycomed Pharma Oslo, Norway). The adherent monocytes were continued to be cultured in AIM-V medium with 1000 GM-CSF and 500 U/mL, IL-4 to differentiate into immature dendritic cells (DCs). The resulting immature DCs were pulsed with a peptide pool comprising three tumor antigen peptides derived from CEA, RGS5, and HPV18-E7 peptide), and then cultured in a DC maturation medium to differentiate into mature DCs. On Day 8, PBMCs containing T cells were co-cultured with antigen-loaded mature DCs at a ratio between the T cells and the mature antigen-loaded DCs of about 20:1, and the co-culture medium contained a cytokine cocktail and an anti-PD-1 antibody. On Day 11, the co-culture was stimulated with PBMCs pulsed with the peptide pool. On Day 12, an IFNγ secretion assay-cell enrichment and detection kit (Miltenyi Biotec) was used to isolate a population of IFNγ$^+$ T cells. Meanwhile, the antigen-loaded mature DCs were cultured in the DC maturation medium. On Day 12, the IFNγ$^+$ T cells were co-cultured with antigen-loaded mature DCs at a ratio between the T cells and the antigen-loaded mature DCs of about 1:1 in a medium containing a cytokine cocktail, an anti-PD-1 antibody. On Day 13 or 14, an anti-CD3 antibody (OKT3) was added to the co-culture, which was continued to be cultured to Day 30 to obtain tumor antigen-specific T cells.

Proliferation Assay

Cell proliferation was assessed using cell samples from Day 1 (PBMCs), Day 9 (start of co-culture), Day 12 (before IFNγ enrichment), Day 12 (after IFNγ enrichment), and Days 22 and 30 (co-culture of IFNγ$^+$ T cells with antigen-loaded mature DCs) by methods described in Example 2.

Figure 10:
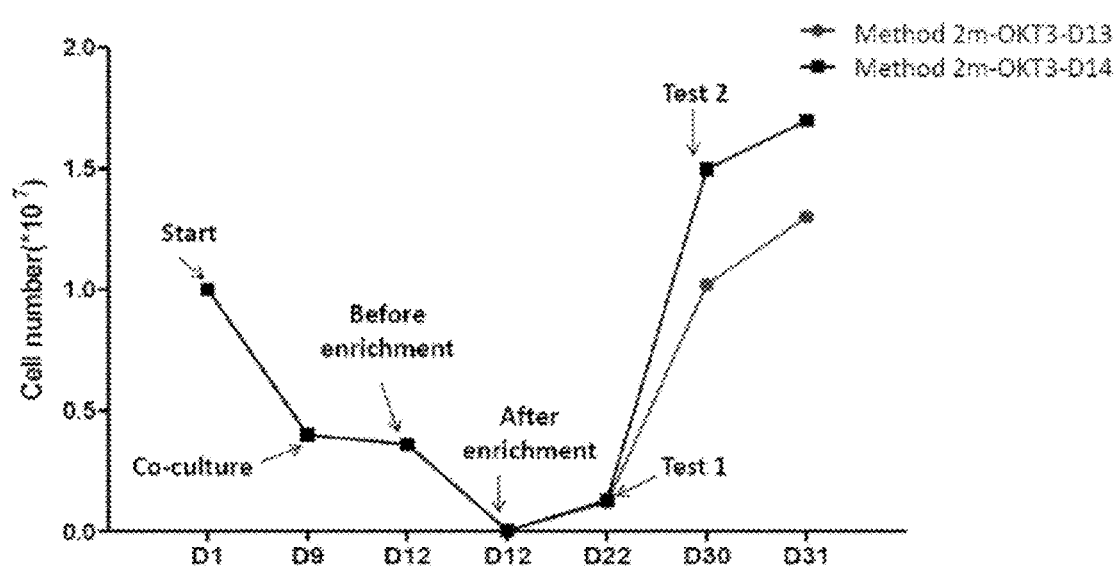
FIG. 10 shows cell proliferation at various time points in the preparation of tumor antigen-specific T cells.

As shown in FIG. 10, the initial co-culture of antigen-loaded mature DCs and T cells yielded a small number of IFNγ$^+$ T cells (Day 12). In the co-culture of enriched IFNγ$^+$ T cells and antigen-loaded mature DCs, the number of cells continued to increase rapidly until Day 31. The method with anti-CD3 antibody added on Day 14 resulted in a higher level of cell proliferation.

IFNγ Production by Tumor Antigen-Specific T Cells

Figure 11A:
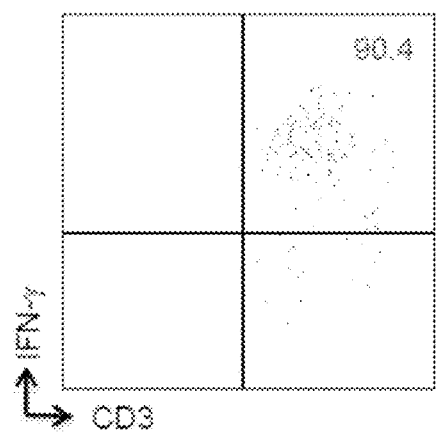
FIGS. 11A-11B show the percentages of IFNγ$^+$CD3$^+$ tumor antigen-specific T cells in various co-culture samples.
Figure 11B:
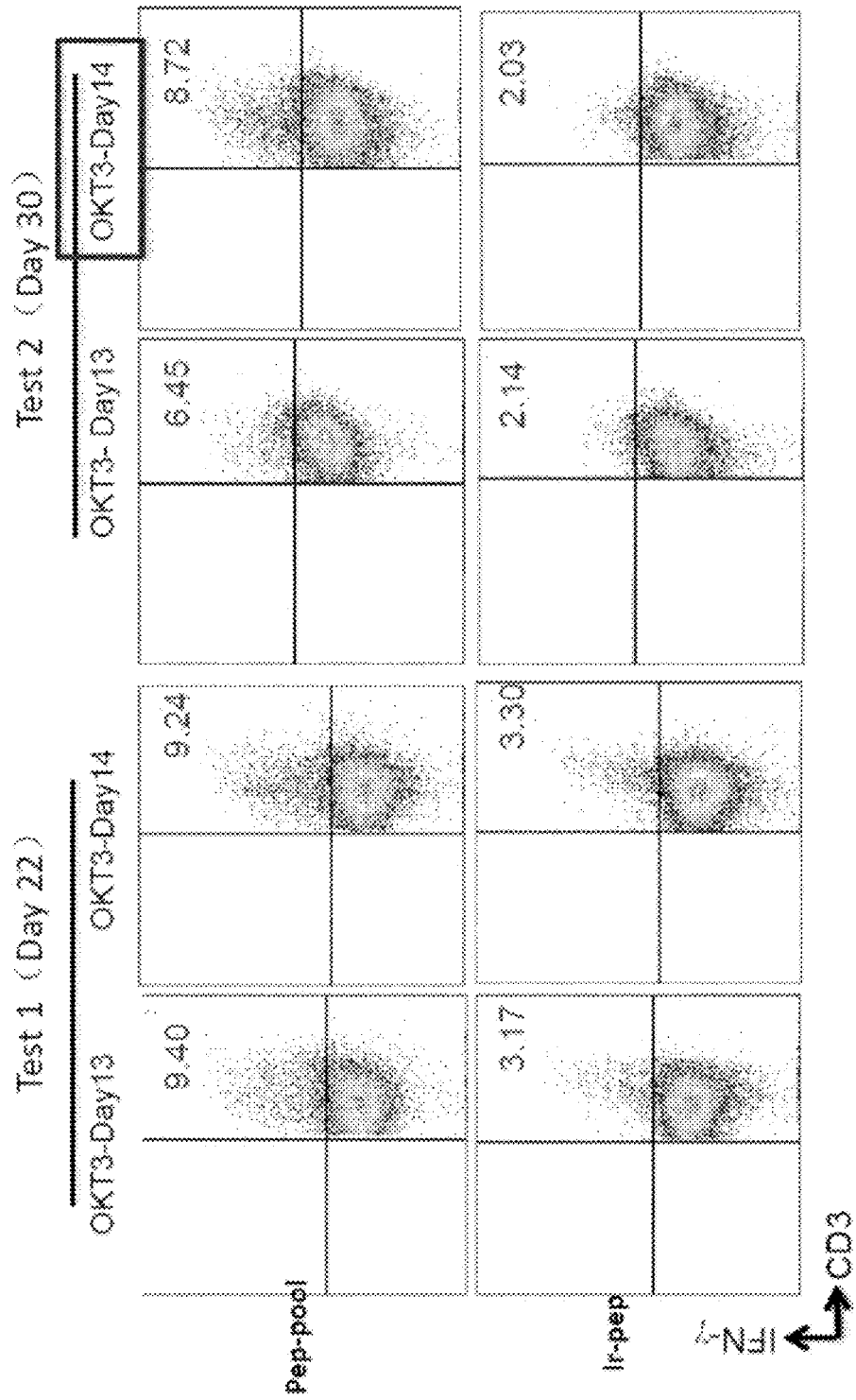
Figure 11C:
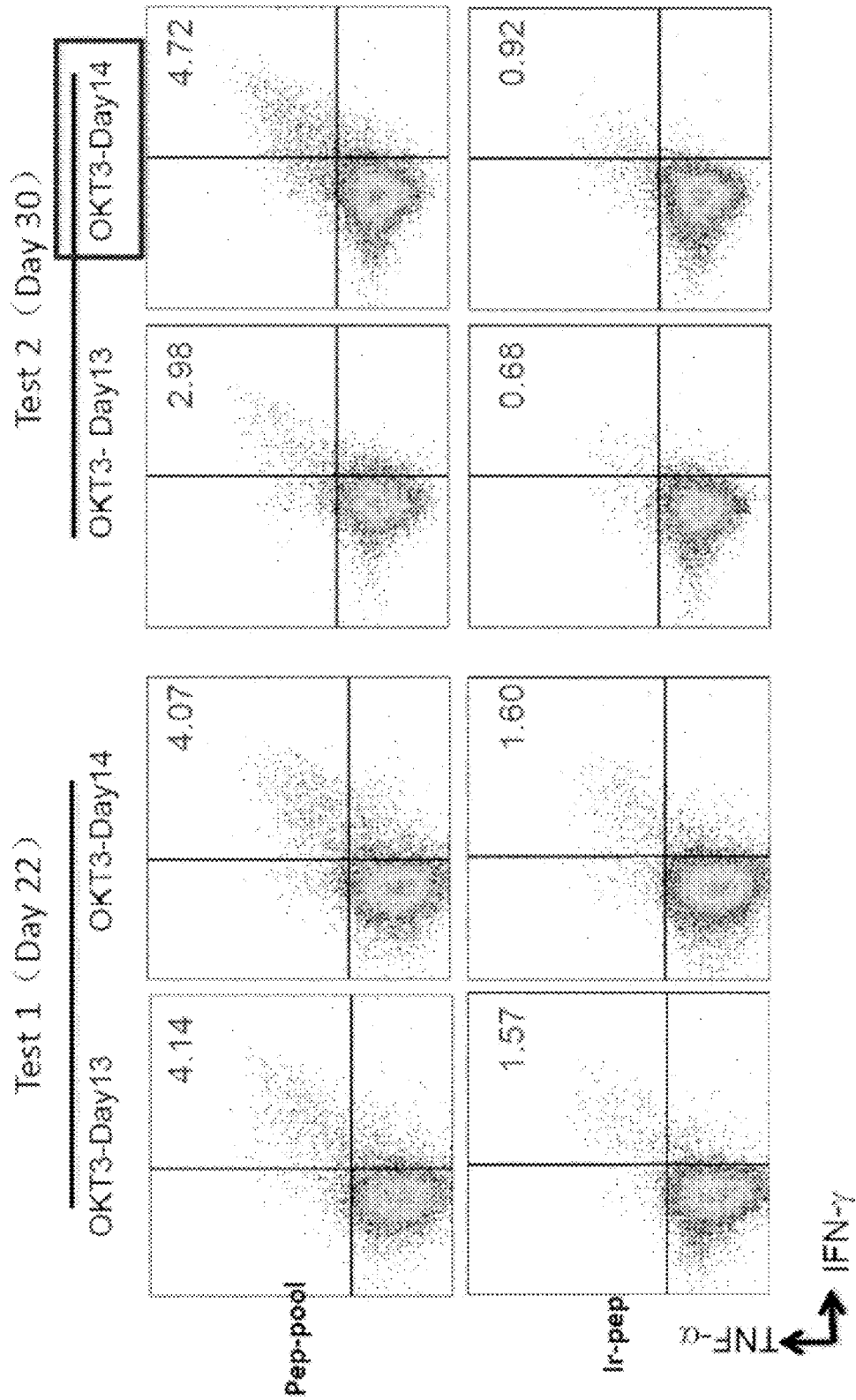
FIG. 11C shows the percentages of IFNγ$^+$TNFα$^+$ tumor antigen-specific T cells in various co-culture samples.

The IFNγ production levels by tumor antigen-specific T cells in various co-culture samples were determined by methods described in Example 2. FIGS. 11A-11B show the percentages of tumor antigen-specific T cells in the cell samples as determined by assessing IFNγ$^+$CD3$^+$ cells in response to stimulation by the tumor antigen peptide pool. After the enrichment step, the percentage of tumor antigen-specific T cells in the cell sample reached 90.4%. From Day 22 to Day 30, the co-cultures contained about 6-10% tumor antigen-specific T cells that produced IFNγ in response to stimulation by the tumor antigen peptide pool. The method with anti-CD3 antibody added on Day 14 yielded a higher percentage of IFNγ$^+$CD3$^+$ cells. Consistent results were obtained by assessing IFNγ$^+$TNFα$^+$ cells (FIG. 11C).

Optimization of Method 2m

Cells Preparation

FIG. 12 provides an overview of the protocols of exemplary "Method 2m". Briefly, on Day 1, peripheral blood mononuclear cells (PBMCs) from the patient were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 differentiate into immature dendritic cells (DCs). The resulting immature DCs were pulsed with a peptide pool comprising three tumor antigen peptides derived from CEA, RGS5, and HPV18-E7 (1 µg/mL/peptide), and then cultured in a DC maturation medium to differentiate into mature DCs. On Day 9, PBMCs containing T cells were co-cultured with antigen-loaded mature DCs at a ratio between the T cells and the mature antigen-loaded DCs of about 20:1, and the co-culture medium contained a cytokine cocktail and an anti-PD-1 antibody. On Day 11, the co-culture was stimulated with PBMCs pulsed with the peptide pool. On Day 12, an IFNγ secretion assay-cell enrichment and detection kit (Miltenyi Biotec) was used to isolate a population of IFNγ$^+$ T cells. Meanwhile, the antigen-loaded mature DCs were cultured in the DC maturation medium. On Day 12, the IFNγ$^+$ T cells were co-cultured with antigen-loaded mature DCs at a ratio between the T cells and the antigen-loaded mature DCs of about 1:1 in a medium containing a cytokine cocktail, an anti-PD-1 antibody. On Day 13, 14, or 15, an anti-CD3 antibody (OKT3) was added to the co-culture, which was continued to be cultured to Day 30 to obtain tumor antigen-specific T cells.

Proliferation Assay

Cell proliferation was assessed using cell samples from Day 1 (PBMCs), Day 9 (start of co-culture), Day 12 (before IFNγ enrichment), Day 12 (after IFNγ enrichment), and Days 19 and 31 (co-culture of IFNγ+ T cells with antigen-loaded mature DCs) by methods described in Example 2.

Figure 13:
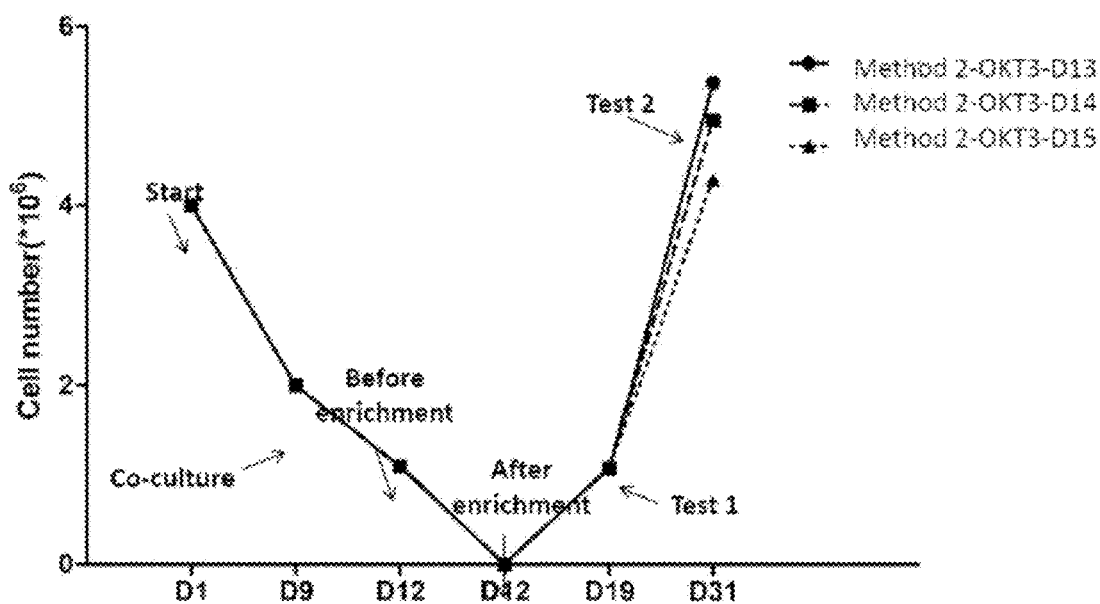
FIG. 13 shows cell proliferation at various time points in the preparation of tumor antigen-specific T cells.

As shown in FIG. 13, the initial co-culture of antigen-loaded mature DCs and T cells yielded a small number of IFNγ+ T cells (Day 12). In the co-culture of enriched IFNγ+ T cells and antigen-loaded mature DCs, the number of cells continued to increase rapidly until Day 31. The method with anti-CD3 antibody added on Day 14 resulted in the highest level of cell proliferation.

IFNγ Production by Tumor Antigen-Specific T Cells

Figure 14A:
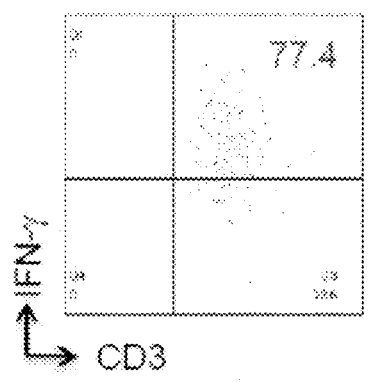
FIGS. 14A-14C show the percentages of IFNγ$^+$CD3$^+$ tumor antigen-specific T cells in various co-culture samples.
Figure 14B:
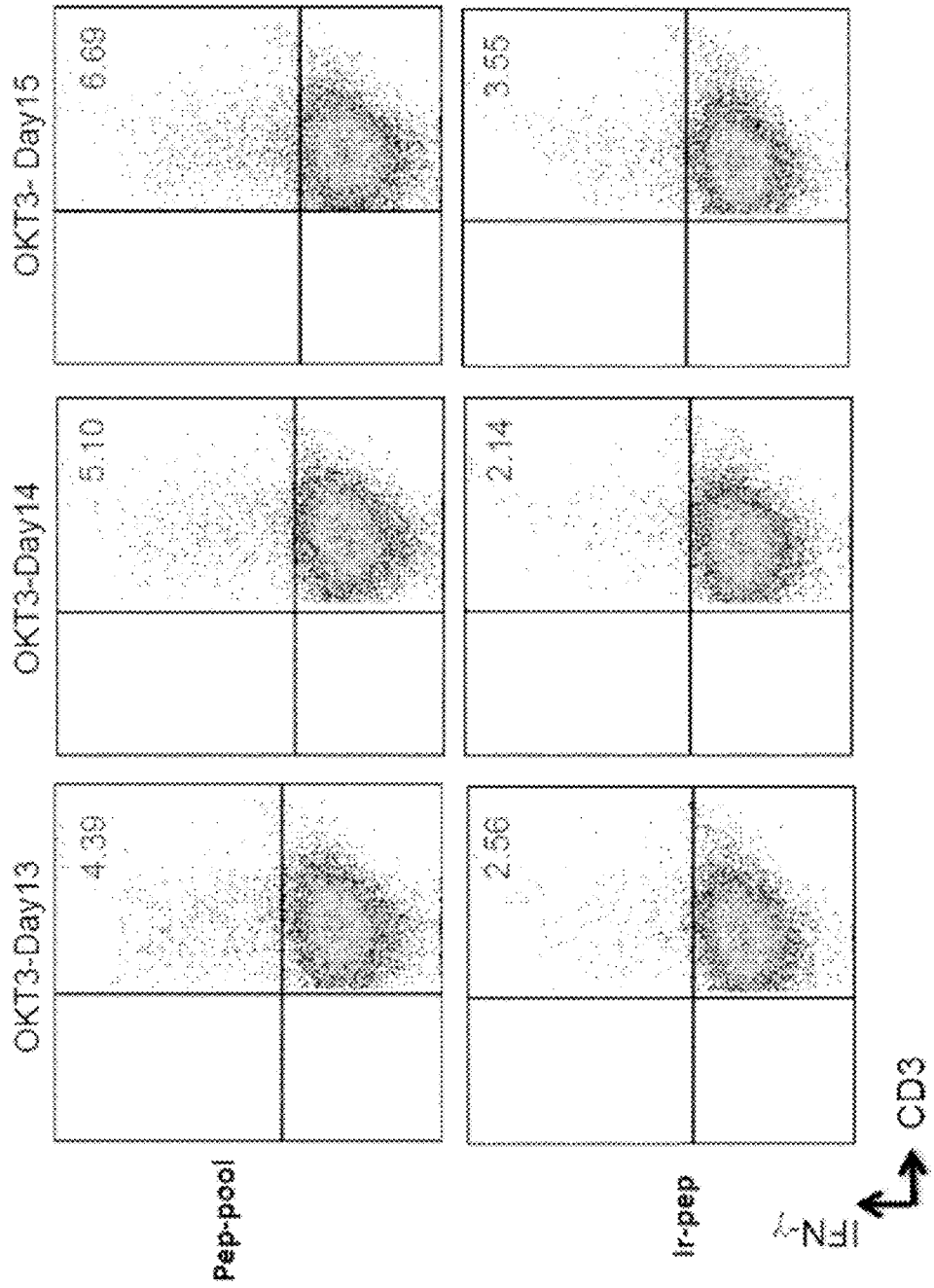
Figure 14C:
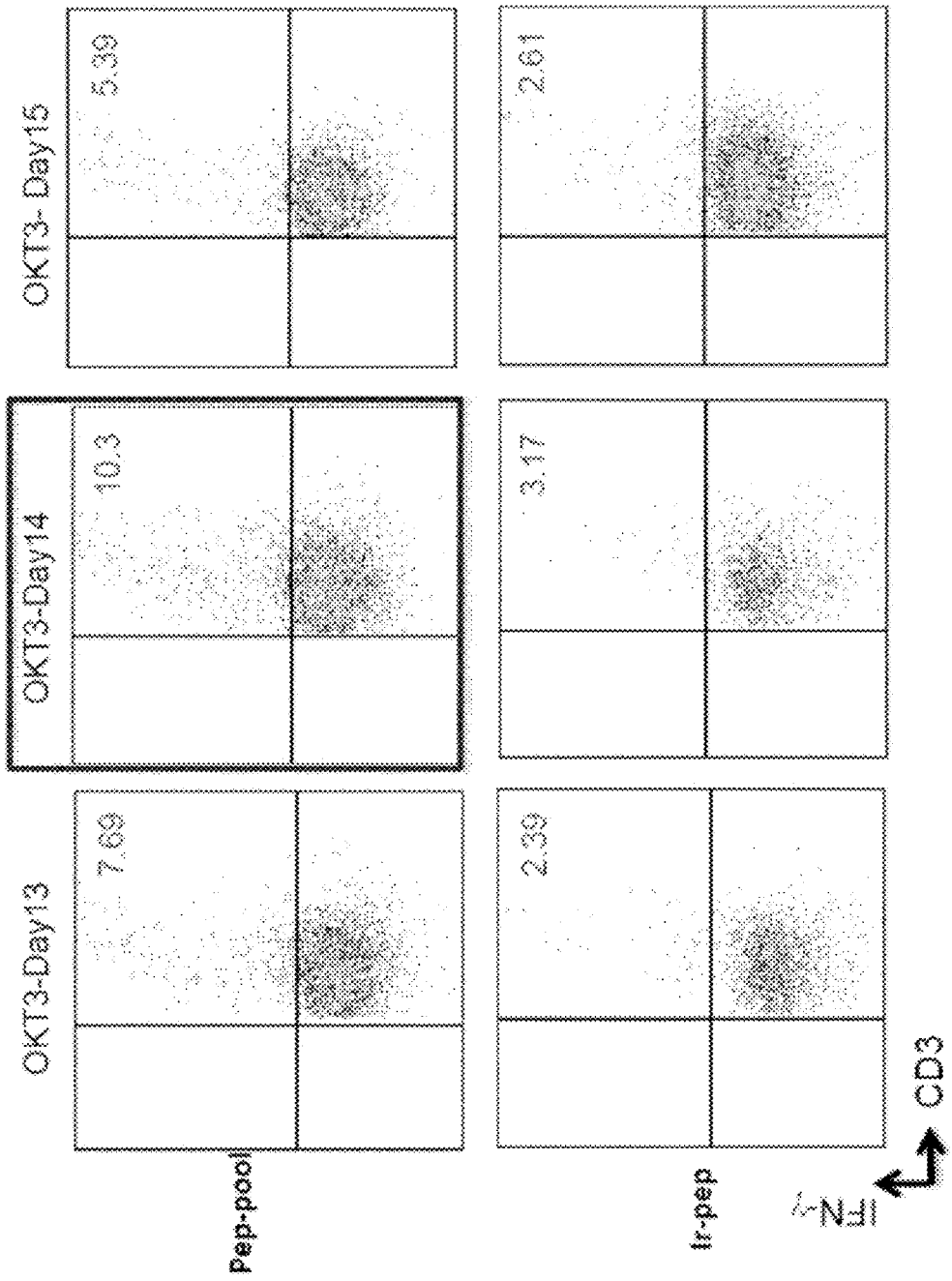

The IFNγ production levels by tumor antigen-specific T cells in various co-culture samples were determined by methods described in Example 2. FIGS. 14A-14C show the percentages of tumor antigen-specific T cells in the cell samples as determined by assessing IFNγ+CD3+ cells in response to stimulation by the tumor antigen peptide pool. After the enrichment step, the percentage of tumor antigen-specific T cells in the cell sample reached 77.4%. The method with anti-CD3 antibody added on Day 14 yielded the highest percentage of IFNγ+CD3+ cells.

Figure 24:
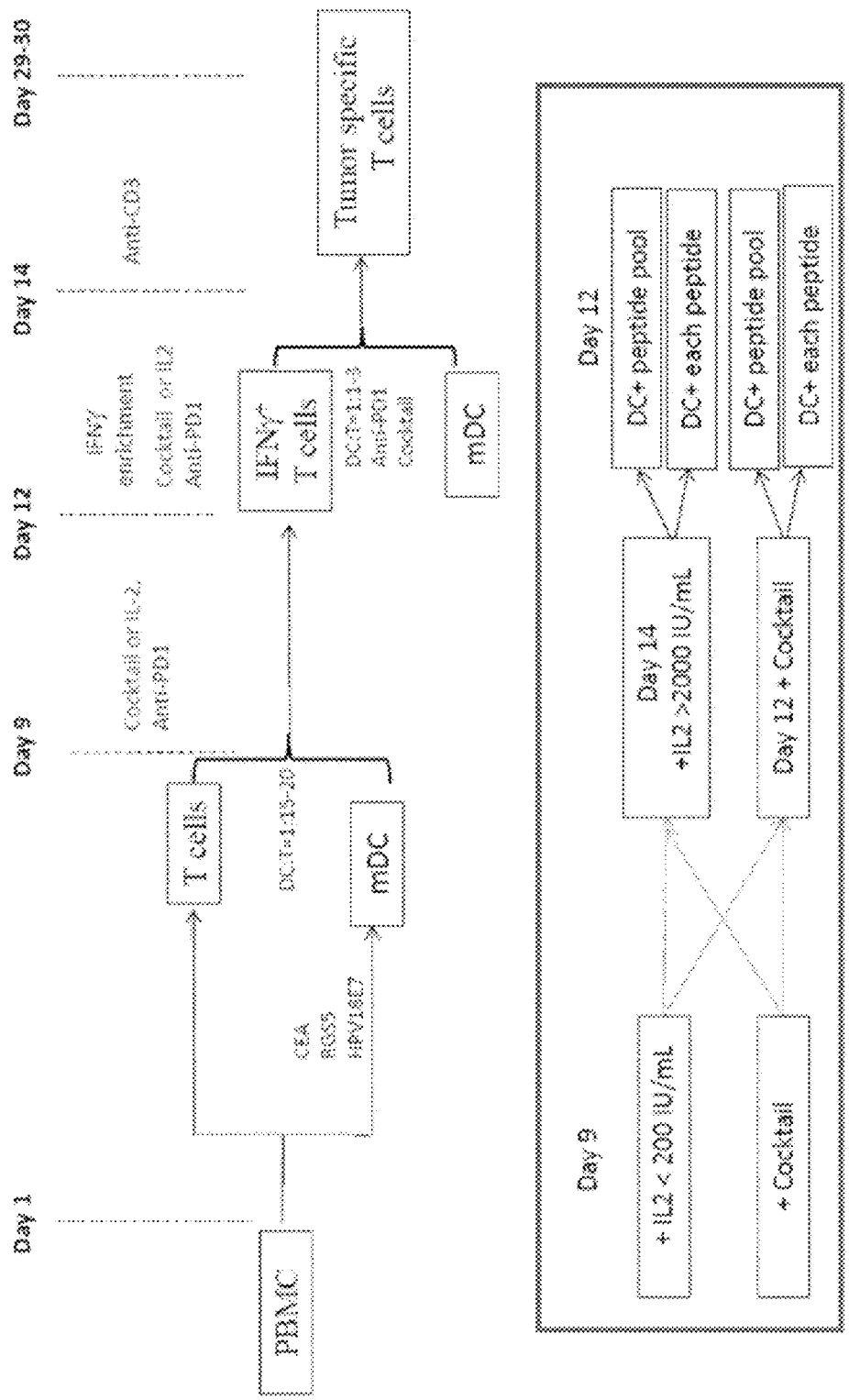
FIG. 24 shows exemplary methods for preparing tumor antigen-specific T cells as described in Example 3.

Comparison of Cytokine Cocktail v. IL-2 and Antigen Peptide Pool v. Single Antigen Peptide Cells Preparation FIG. 24 provides an overview of protocols that compare addition of cytokine cocktail v. IL-2 alone, and stimulation with DC loaded with a pool of antigen peptides v. a single antigen peptide. Briefly, on Day 1, peripheral blood mononuclear cells (PBMCs) from the patient were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (PCs). The resulting immature DCs were pulsed with a peptide pool comprising three tumor antigen peptides derived from CEA, RGS5, and HPV18-E7 (1 μg/mL/peptide), and then cultured in a DC maturation medium to differentiate into mature DCs. On Day 9, PBMCs containing T cells were co-cultured with antigen-loaded mature DCs at a ratio between the T cells and the mature antigen-loaded DCs of about 15:1 to about 20:1, and the co-culture medium contained a cytokine cocktail or IL-2 (no more than about 200 U/mL) and an anti-PD-1 antibody. On Day 11, the co-culture was stimulated with PBMCs pulsed with the peptide pool or each individual peptide. On Day 12, an IFNγ secretion assay-cell enrichment and detection kit (Miltenyi Biotec) was used to isolate a population of IFNγ+ T cells. Meanwhile, the antigen-loaded mature DCs were cultured in the DC maturation medium. The IFNγ+ T cells were co-cultured with antigen-loaded mature DCs at a ratio between the T cells and the antigen-loaded mature DCs of about 1:1 to about 3:1 in a medium containing a cytokine cocktail added on Day 12 or IL-2 alone (at least about 2000 IU/mL) added on Day 14, and an anti-PD-1 antibody. On Day 14, an anti-CD3 antibody (OKT3) was added to the co-culture, which was continued to be cultured to Day 29-30 to obtain tumor antigen-specific T cells.

Proliferation Assay and IFNγ Production by Tumor Antigen-Specific T Cells

Cell proliferation was assessed using cell samples from Day 1 (PBMCs), Day 9 (start of co-culture), Day 12 (before IFNγ enrichment), Day 12, (after IFNγ enrichment), and Days 19, 24 and 29 (co-culture of IFNγ+ T cells with antigen-loaded mature DCs) by methods described in Example 2.

Figure 25A:
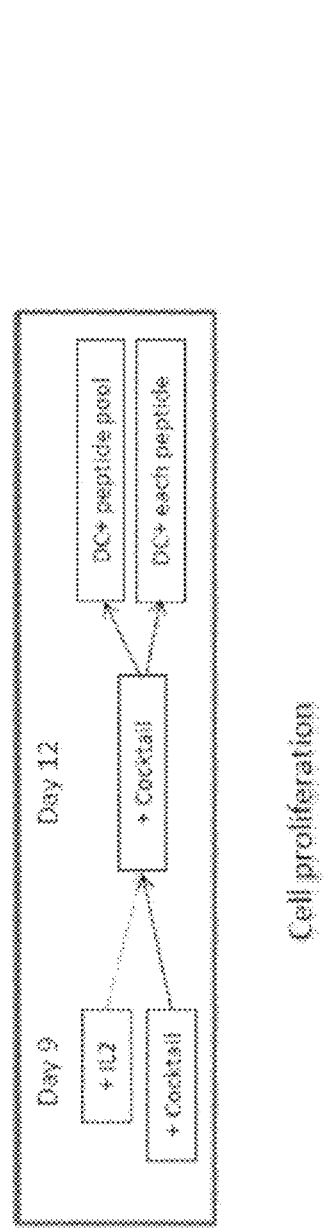
FIG. 25A shows cell proliferation at various time points in the preparation of tumor antigen-specific T cells.
Figure 25A:
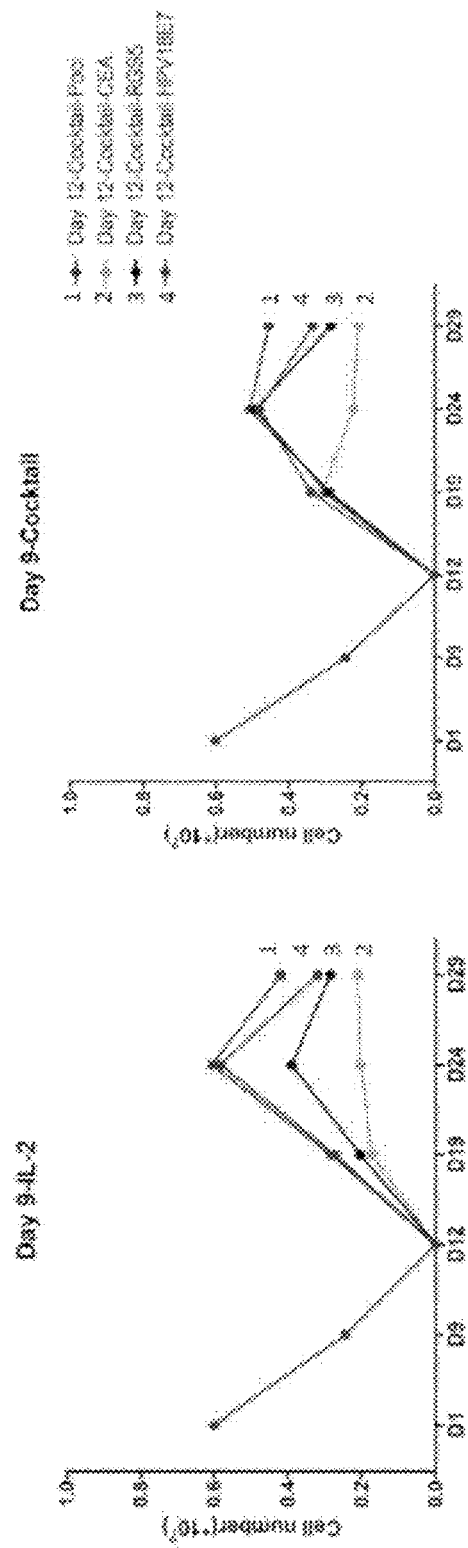

As shown in FIG. 25A, the initial co-culture of antigen-loaded mature DCs and T cells yielded a small number of IFNγ+ T cells (Day 12). In the co-culture of enriched IFNγ+ T cells and antigen-loaded mature DCs, the number of cells continued to increase rapidly until Day 29.

Figure 25B:
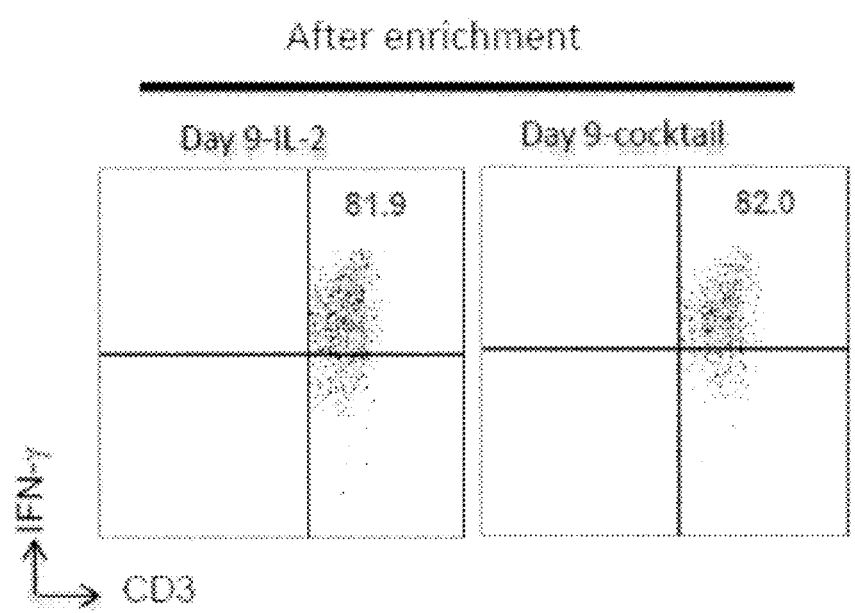
FIG. 25B shows the percentages IFNγ$^+$CD3$^+$ tumor antigen-specific T cells before and after the enrichment step.

The IFNγ production levels by tumor antigen-specific T cells in various co-culture samples were determined by methods described in Example 2. As shown in FIG. 25B, similar percentage of IFNγ+ T cells were obtained after the enrichment step on Day 12 with the cytokine cocktail or IL-2 only added to the co-culture on Day 9.

Table 1 below compares the percentages of tumor-specific T cells in the cell samples on Day 19 (Test 1) and Day 29 (Test 2) as determined by assessing IFNγ+CD3+ and IFNγ+TNFα+ cells in response to stimulation by the tumor antigen peptide pool or individual antigen peptides. Protocols with cytokine cocktail or IL-2 alone added on Day 9 and co-culture with DCs pulsed with tumor antigen pool or single tumor antigen yield comparable results in terms of T cell proliferation and percentages of tumor-specific T cells.

TABLE 1

Percentages of Tumor-specific T cells in Cell Samples.

| Tumor-specific T cells | b | Test 1 | | | | Test 2 | | | |
|---|---|---|---|---|---|---|---|---|---|
| | | Pool | CEA | RGS5 | HPV18E7 | Pool | CEA | RGS5 | HPV18E7 |
| Day 9 IL-2 | | | | | | | | | |
| CD3+ IFNγ+ (%) | Pool | 9.40 | 0.36 | 2.47 | 6.74 | 8.97 | 0.63 | 2.60 | 5.30 |
| | CEA | 13.90 | 0.27 | 6.69 | 5.46 | 6.66 | 0.70 | 3.64 | 3.29 |
| | RGS5 | 9.44 | 0.54 | 3.00 | 5.89 | 5.86 | 0.59 | 2.40 | 3.39 |
| | HPV18E7 | 12.65 | 0.50 | 4.44 | 6.05 | 7.16 | 1.31 | 2.50 | 4.39 |
| IFNγ+ TNFα+ (%) | Pool | 4.15 | 0.16 | 1.08 | 4.07 | 5.32 | 0.52 | 2.40 | 3.94 |
| | CEA | 8.96 | 0.21 | 4.25 | 4.07 | 3.76 | 0.64 | 1.85 | 2.69 |
| | RGS5 | 6.38 | 0.29 | 1.36 | 4.61 | 3.81 | 0.37 | 1.66 | 2.80 |
| | HPV18E7 | 7.90 | 0.44 | 2.85 | 3.65 | 4.69 | 0.91 | 1.92 | 2.90 |
| Day 9 Cocktail | | | | | | | | | |
| CD3+ IFNγ+ (%) | Pool | 9.96 | 0.68 | 1.82 | 5.72 | 8.13 | 2.51 | 3.80 | 4.30 |
| | CEA | 11.21 | 0.79 | 5.37 | 5.71 | 5.86 | 0.71 | 2.86 | 4.26 |

TABLE 1-continued

Percentages of Tumor-specific T cells in Cell Samples.

| Tumor-specific T cells | b | Test 1 a | | | | Test 2 | | | |
|---|---|---|---|---|---|---|---|---|---|
| | | Pool | CEA | RGS5 | HPV18E7 | Pool | CEA | RGS5 | HPV18E7 |
| | RGS5 | 9.09 | 0.20 | 2.25 | 5.44 | 8.79 | 1.37 | 4.35 | 6.38 |
| | HPV18E7 | 12.08 | 1.16 | 6.09 | 4.16 | 9.73 | 1.87 | 4.93 | 3.83 |
| IFNγ+ TNFα+ | Pool | 5.33 | 0.56 | 0.89 | 3.54 | 4.07 | 1.06 | 1.91 | 2.42 |
| (%) | CEA | 6.96 | 0.62 | 3.51 | 3.67 | 2.84 | 0.69 | 0.42 | 2.71 |
| | RGS5 | 5.67 | 0.50 | 1.59 | 4.00 | 5.06 | 0.08 | 1.29 | 3.62 |
| | HPV18E7 | 6.48 | 0.69 | 3.84 | 2.30 | 4.63 | 0.62 | 2.56 | 2.52 | a: stimulation/testing conditions
b: culturing conditions

Figure 26A:
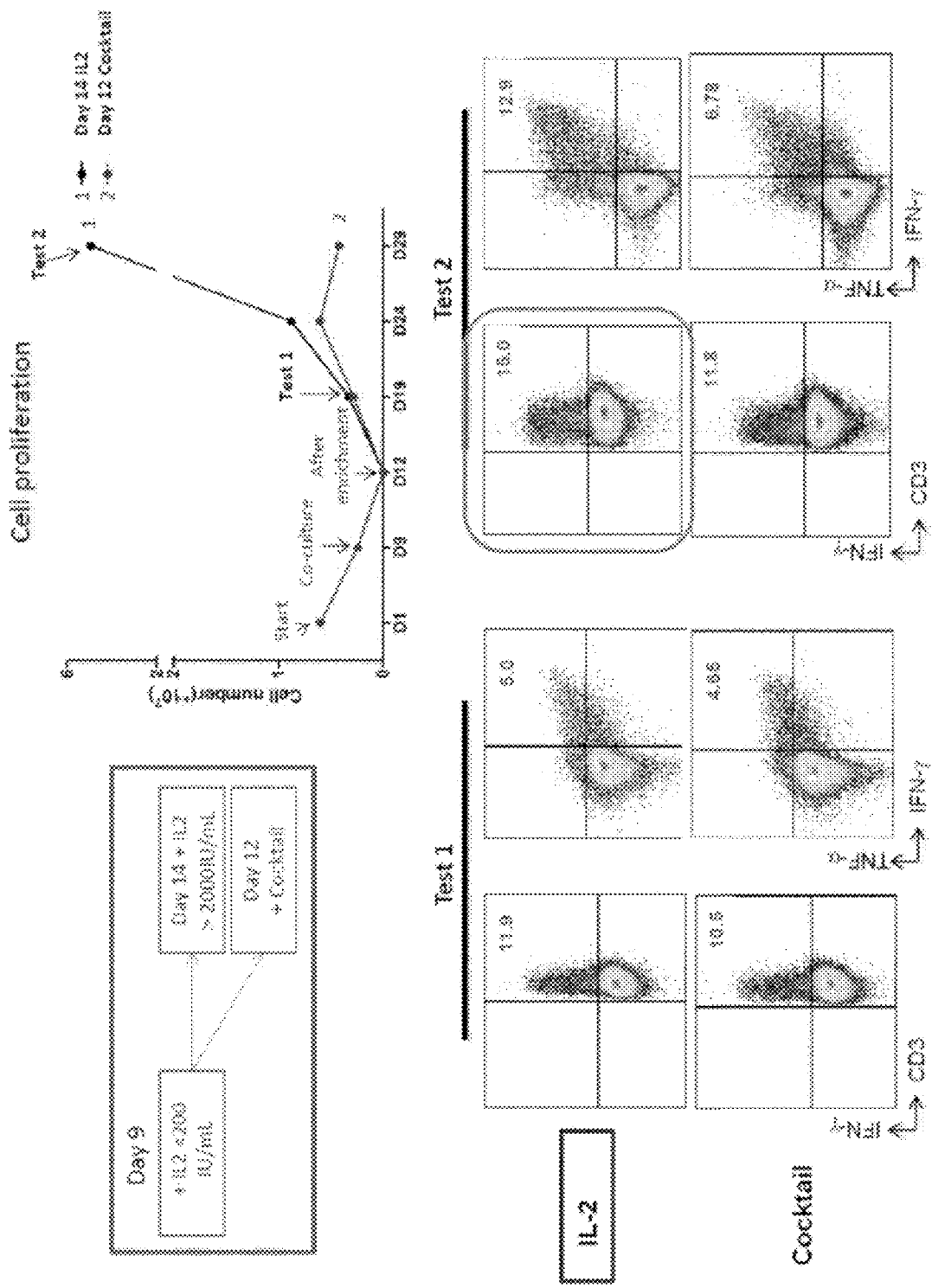
FIGS. 26A-26B show cell proliferation and percentages of tumor antigen-specific T cell populations in various co-culture samples.
Figure 26B:
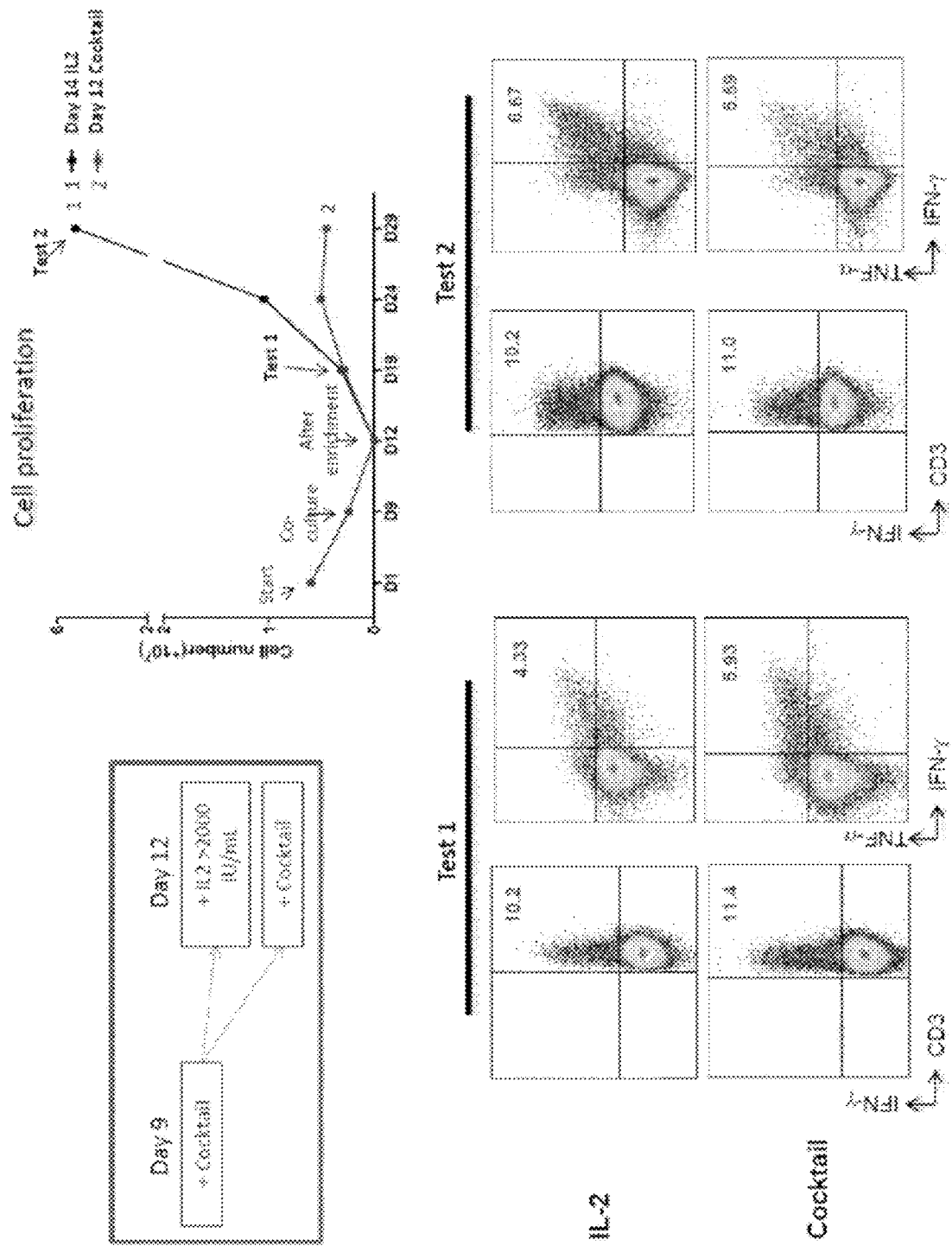

FIGS. 26A-26B compare T cell numbers and percentages of tumor antigen-specific T cells in various co-culture samples using protocols with IL-2 or cytokine cocktail added on Days 9 and 12. The protocol with IL-2 added on Day 9, co-culture with DCs pulsed with the tumor antigen peptide pool on Day 12 and IL-2 added on Day 14 yielded the highest percentage of tumor-antigen-specific T cells on Days 19 and 29.

Example 4

Preparation of Tumor Antigen-Specific T Cells from PBMCs of a Patient Treated with MASCT A frozen stock or PBMC samples from the patient in Example 1 were used as the starting material to prepare tumor antigen-specific T cells in this example. Fresh PBMCs could be used instead of the frozen PBMCs in this example.
Cells Preparation FIG. 15 provides an overview of the protocol used in this example. Briefly, on Day 1, peripheral blood mononuclear cells (PBMCs) from the patient were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed with a peptide pool comprising three tumor antigen peptides derived from CEA, RGS5, and HPV18-E7 (1 μg/mL/peptide), and then cultured in a DC maturation medium to differentiate into mature DCs. On Day 8, PBMCs were stimulated with the peptide pool. On Day 9, an IFNγ secretion assay-cell enrichment and detection kit (Miltenyi Biotec) was used to isolate a population of IFNγ+ T cells from the stimulated PBMCs. On Day 9, the IFNγ+ T cells were co-cultured with antigen-loaded mature DCs at a ratio between the T cells and the antigen-loaded mature DCs of about 1:1 in a medium containing a cytokine cocktail and an anti-PD-1 antibody. An anti-CD3 antibody (OKT3) was added to the co-culture on Day 10 or Day 11, which was continued to be cultured to Day 15-30 to obtain tumor antigen-specific T cells.
Proliferation Assay Cell proliferation was assessed using cell samples from Day 1 (PBMCs), Day 9 (before IFNγ enrichment and after IFNγ enrichment), and Days 19, 27 and 28 (co-culture of IFNγ+ T cells with antigen-loaded mature DCs) by methods described in Example 2.

Figure 16:
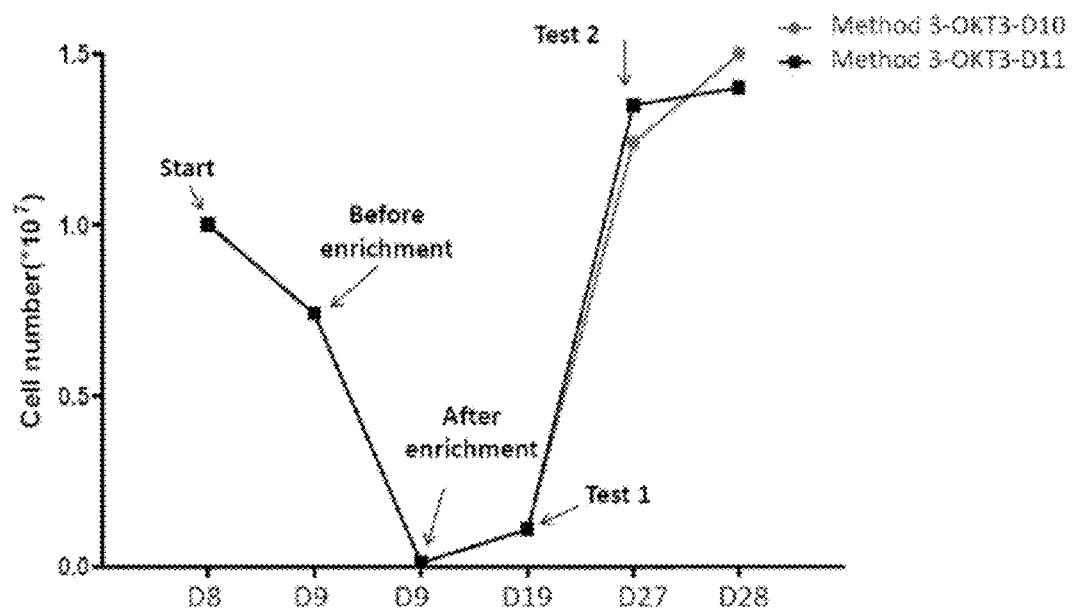
FIG. 16 shows cell proliferation at various time points in the preparation of tumor antigen-specific T cells.
Figure 17A:
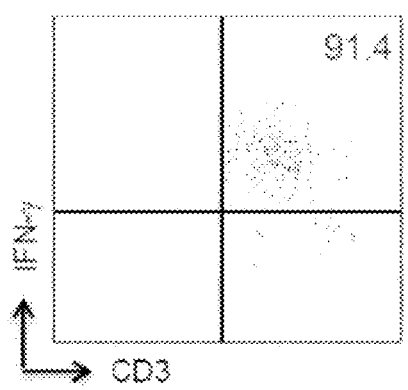
FIGS. 17A-17B show the percentages of IFNγ$^+$CD3$^+$ tumor antigen-specific T cells in various co-culture samples.
Figure 17B:
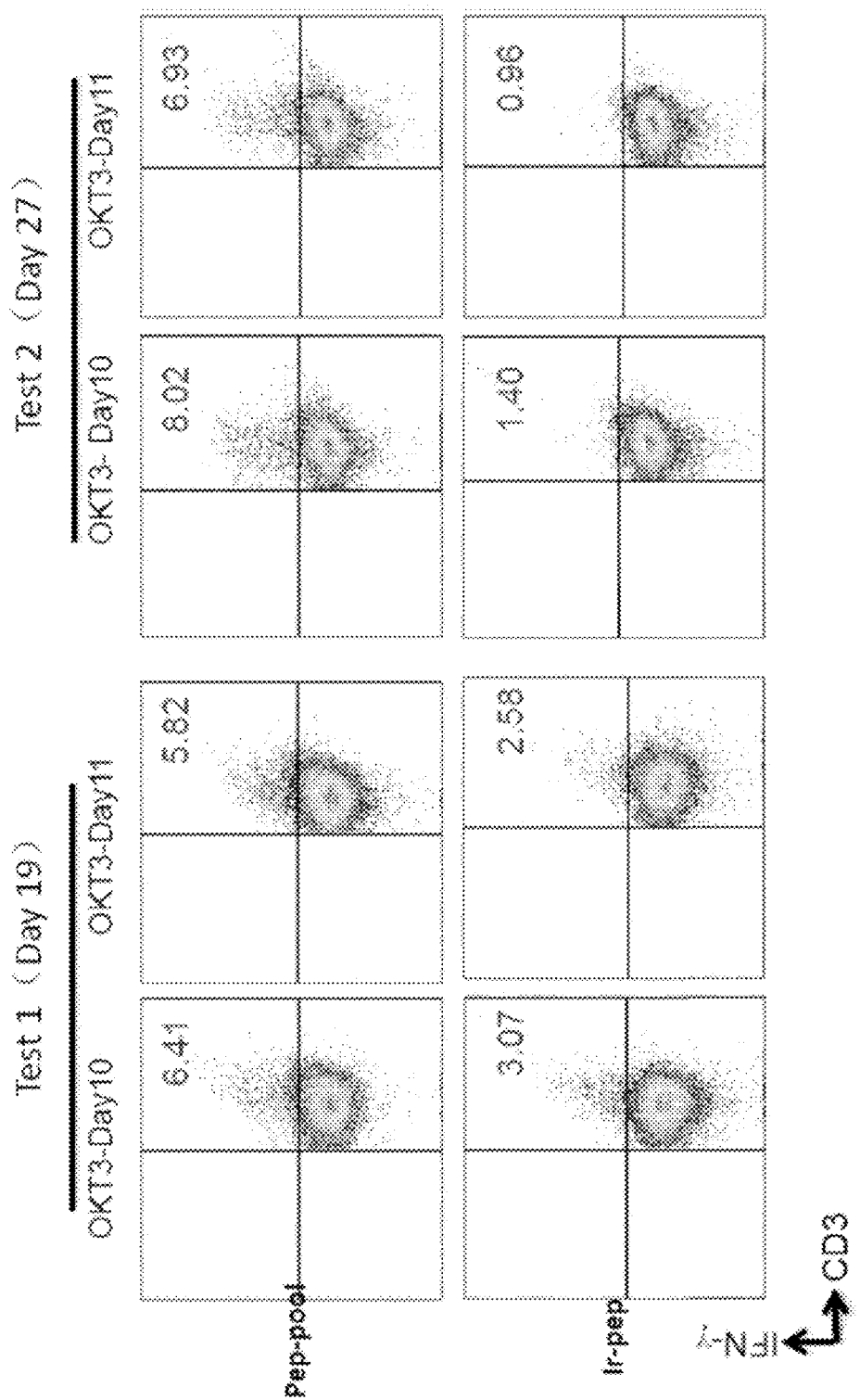
Figure 17C:
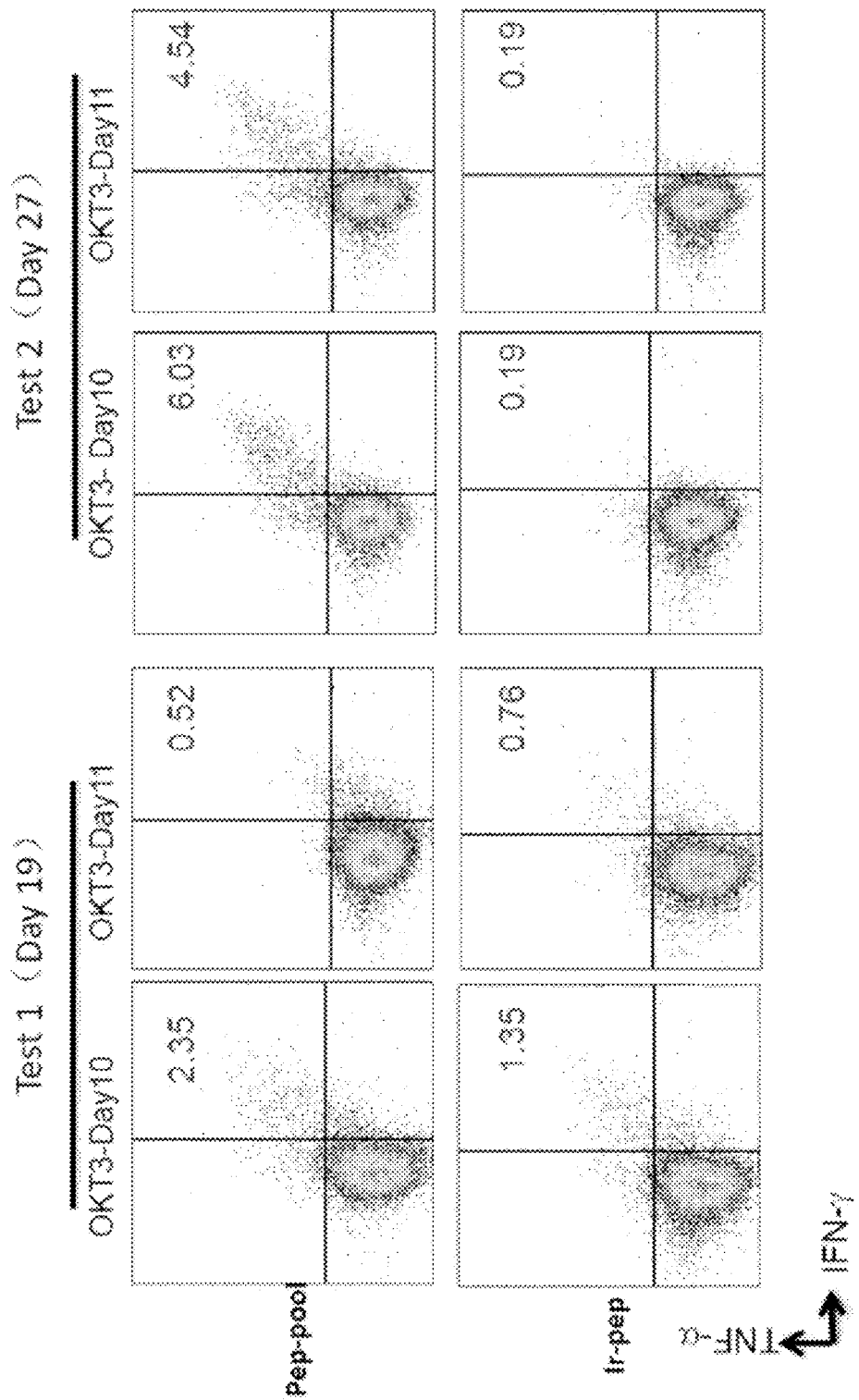
FIG. 17C shows the percentages of IFNγ$^+$TNFα$^+$ tumor antigen-specific T cells in various co-culture samples.

As shown in FIG. 16, the initial co-culture of antigen-loaded mature DCs and T cells yielded a small number of IFNγ+ T cells (Day 9). In the co-culture of enriched IFNγ+ T cells and antigen-loaded mature DCs, the number of cells continued to increase rapidly until Day 28, at which time point the total number of cells in the co-culture plateaued at more than $10^7$.
IFNγ Production by Tumor Antigen-Specific T Cells The IFNγ production levels by tumor antigen-specific T cells in various co-culture samples were determined by methods described in Example 2. FIGS. 17A-17B show the percentages of tumor antigen-specific T cells in the cell samples as determined by assessing IFNγ+CD3+ cells in response to stimulation by the tumor antigen peptide pool. After the enrichment step, the percentage of tumor antigen-specific T cells in the cell sample reached 91.4%. On Day 27, the co-culture in which the anti-CD3 antibody was added on Day 10 yielded the highest percentage of IFNγ+CD3+ cells. Consistent results were obtained by assessing IFNγ+ TNFα+ cells (FIG. 17C).

Example 5

Preparation of Tumor Antigen-Specific T Cells from Frozen Stock of Tumor Antigen-Specific T Cells A frozen stock of tumor antigen-specific T cells prepared using Method 2 was used in this example to prepare a further population of tumor specific T cells.
Cells Preparation FIG. 18 provides an overview of the protocol used in this example. Briefly, a sample of the co-culture containing tumor antigen-specific T cells on Day 32 using Method 2 described in Example 3 was frozen to provide a frozen stock of tumor antigen-specific T cells. On Day 1 of this experiment, a sample of the frozen stock of tumor antigen-specific T cells was thawed, and co-cultured with freshly prepared antigen-loaded mature DCs in a co-culture medium comprising a cocktail of cytokines, an anti-PD-1 antibody, and an anti-CD3 antibody until Day 12. The ratio between the tumor antigen-specific T cells and the antigen-loaded mature DCs was about 10:1.
Proliferation Assay Cell proliferation was assessed using cell samples from Days 1, 4, 7, 10 and 12 of the co-culture by methods described in Example 2.

Figure 19:
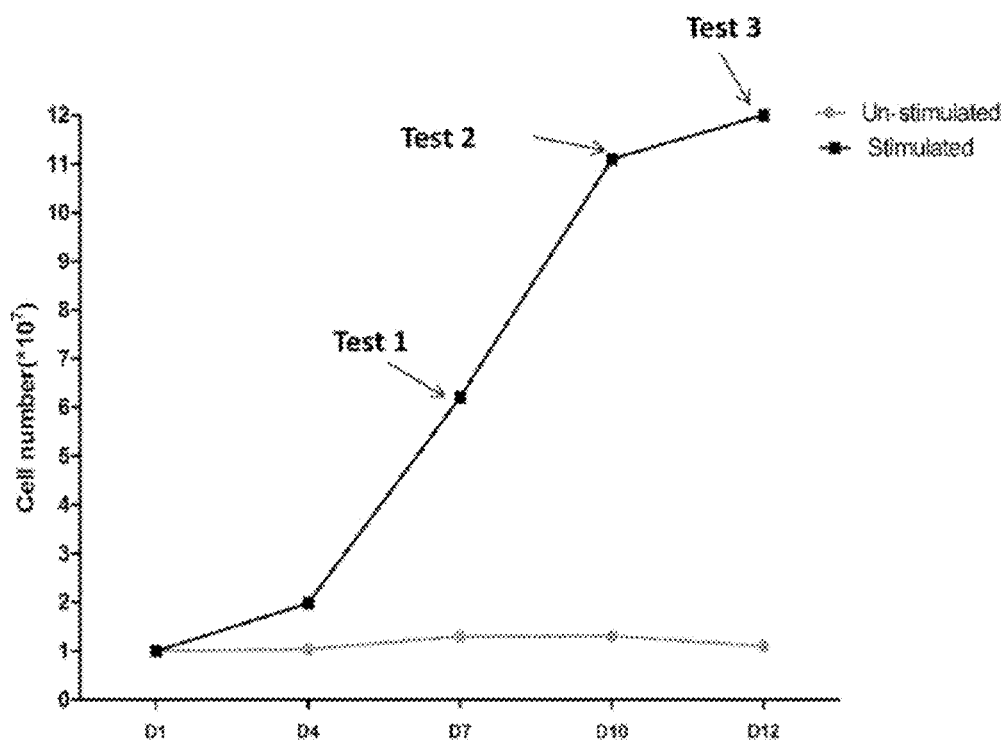
FIG. 19 shows cell proliferation at various time points in the preparation of tumor antigen-specific T cells.

As shown in FIG. 19, cells continued to proliferate when a thawed population of frozen tumor antigen-specific T cells was co-cultured with antigen-loaded mature DCs ("stimulated" curve), while no cell proliferation was observed in a thawed population of frozen tumor antigen-specific T cells without stimulation by antigen-loaded mature DCs ("unstimulated" curve). On Day 12 of the co-culturing, the total number of cells exceeded about $10^8$.

Cytokine Production by Tumor Antigen-Specific T Cells

The IFNγ production levels by tumor antigen-specific T cells in various co-culture samples were determined by methods described in Example 2.

Figure 20A:
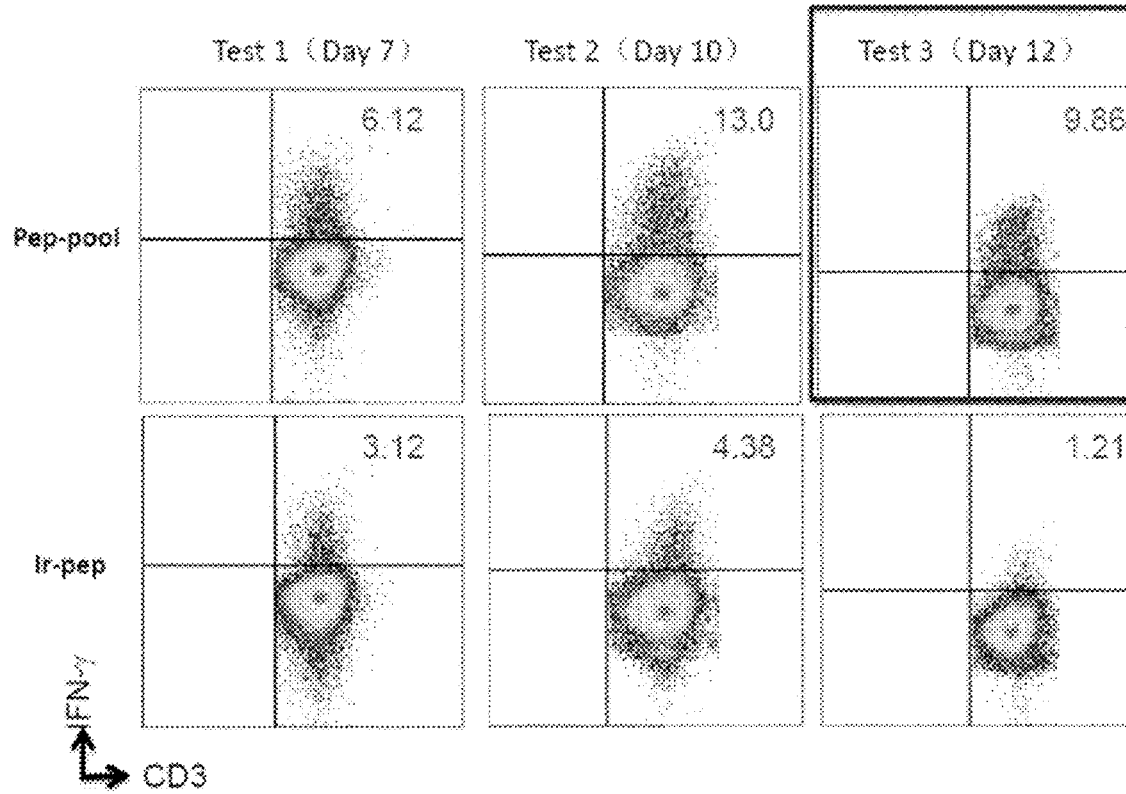
FIG. 20A shows the percentages of IFNγ$^+$CD3$^+$ tumor antigen-specific T cells in various co-culture samples.

FIG. 20A shows the percentages of tumor antigen-specific T cells in the cell samples as determined by assessing IFNγ$^+$CD3$^+$ cells in response to stimulation by the tumor antigen peptide pool. From Day 7 to Day 12, the co-culture contained about 10% tumor antigen-specific T cells that produced IFNγ in response to stimulation by the tumor antigen peptide pool. Non-specific T cells that produced IFNγ in response to stimulation by irrelevant peptides constituted only about 1.21% of the co-culture on Day 12.

Figure 20B:
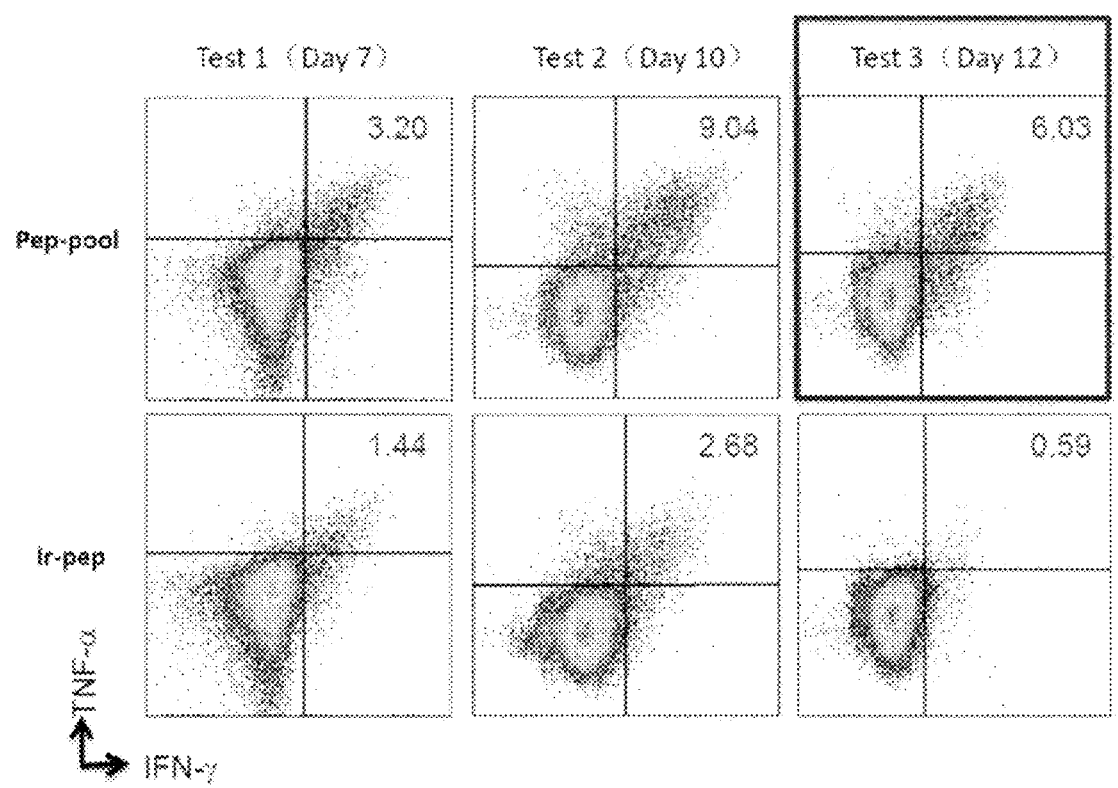
FIG. 20B shows the percentages of IFNγ$^+$TNFα$^+$ tumor antigen-specific T cells in various co-culture samples.

FIG. 20B shows the percentages of tumor antigen-specific T cells in the cell samples as determined by assessing TNF-α$^+$IFNγ$^+$ cells in response to stimulation by the tumor antigen peptide pool. The results are consistent with the measurements based on IFNγ$^+$CD3$^+$ cells. On Day 10, the co-culture contained about 9.04% tumor antigen-specific T cells that produced both TNF-α and IFNγ in response to stimulation by the minor antigen peptide pool. Nonspecific T cells that produced both TNF-α and IFNγ in response to stimulation by irrelevant peptides constituted about 2.68% on Day 10.

Example 6

Preparation of Tumor Antigen-Specific T Cells from Frozen Stock of Tumor Antigen-Specific T Cells A frozen stock of tumor antigen-specific T cells prepared using Method 2 or Method 2m was used in this example to prepare a further population of tumor antigen-specific T cells.

Cells Preparation

FIGS. 21A-21B provide an overview of the protocols used in this example. Briefly, a sample of the co-culture containing tumor antigen-specific T cells on Day 32 using Method 2 or on Day 30 using Method 2m described in Example 3 was frozen to provide a frozen stock of tumor antigen-specific T cells. On Day 1 of this experiment, a sample of the frozen stock of tumor antigen-specific T cells was thawed, and co-cultured with LCL cells (an APC cell line) loaded with RGS5-OLP5 (1 μg/mL) in a co-culture medium comprising a cocktail of cytokines (IL-2, IL-7, IL-15), an anti-CD3 antibody (OKT-3) and RGS5-OLP5 until Day 9, with or without feeder cells. The ratio between the tumor antigen-specific T cells and the antigen-loaded LCL cells was about 4:1. The ratio between the tumor antigen-specific T cells, the feeder cells, and the antigen-loaded LCL cells was about 4:4:1. On Days 9 and 16, the cycles were repeated by co-culturing the tumor antigen-specific T cells with antigen-loaded LCL cells with or without the presence of feeder cells.

PBMCs and dendritic cells may be used in place of the LCL cells to provide antigen-loaded APCs. The APCs may be loaded with a single tumor antigen peptide, an epitope fragment of a single tumor antigen peptide, a pool of tumor antigen peptides, or a pool of epitope fragments of rumor antigen peptides.

Proliferation Assay

Cell proliferation was assessed using cell samples from Days 1, 9, 16 and 23 of the co-culture by methods described in Example 2.

Figure 22:
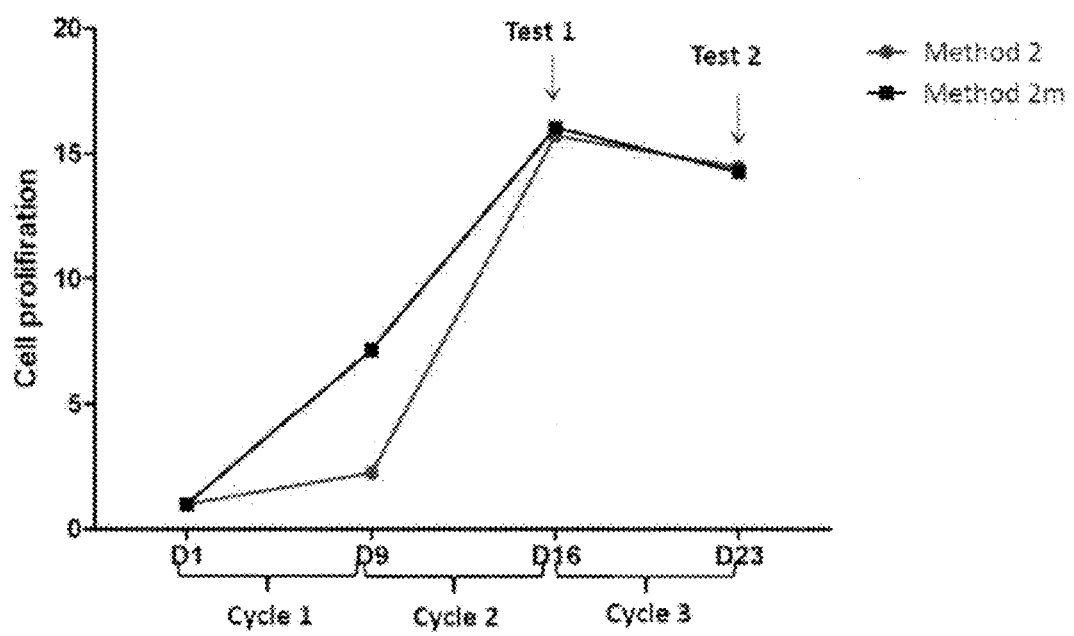
FIG. 22 shows cell proliferation at various time points in the preparation of tumor antigen-specific T cells.

As shown in FIG. 22, cells continued to proliferate when a thawed population of frozen tumor antigen-specific T cells was co-cultured with antigen-loaded LCL cells with or without feeder cells until Day 16. The total cell numbers decreased by Day 23.

Cytokine Production by Tumor Antigen-Specific T Cells

The IFNγ production levels by tumor antigen-specific cells in various co-culture samples were determined by methods described in Example 2.

Figure 23A:
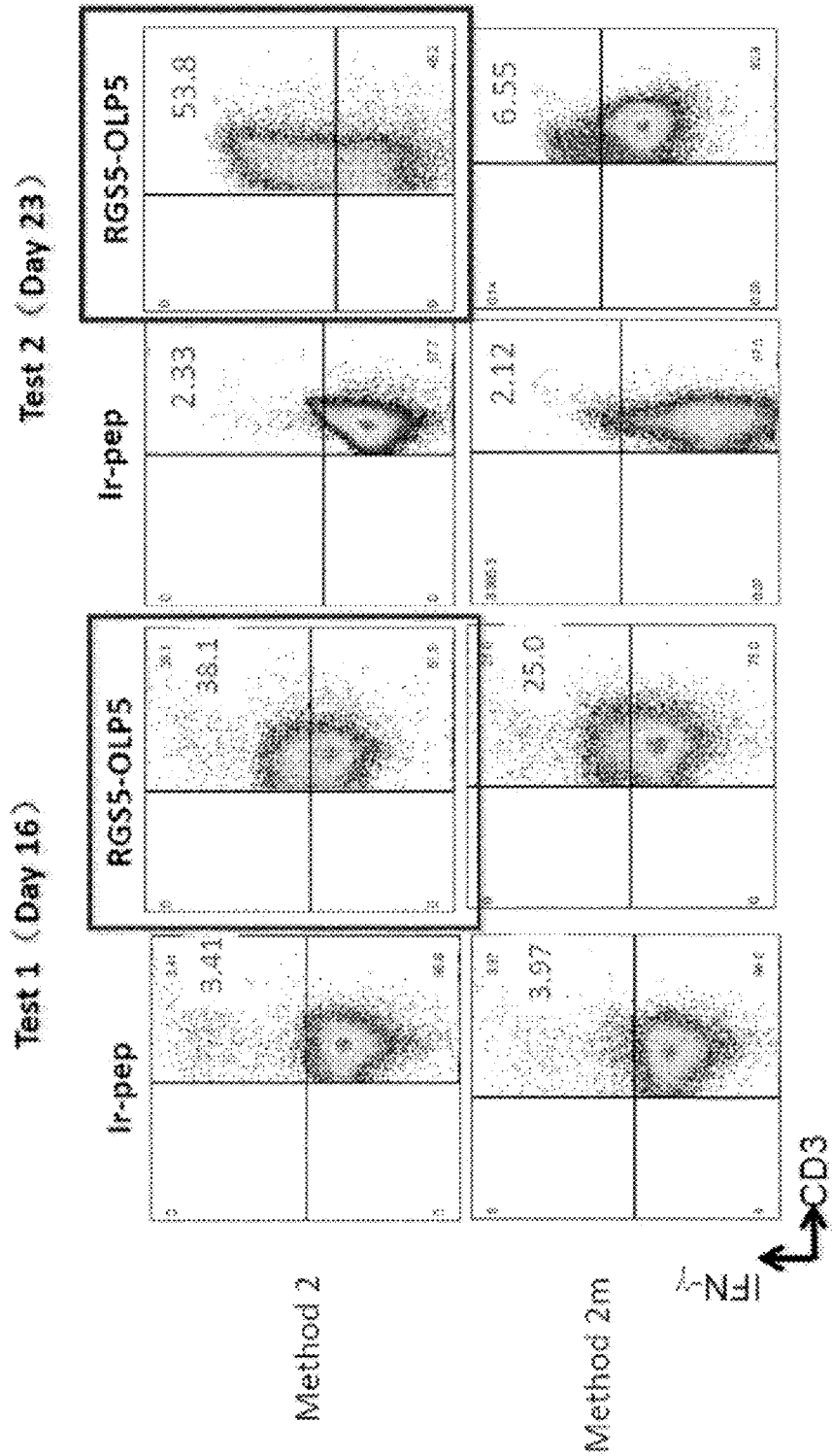
FIG. 23A shows the percentages of IFNγ$^+$CD3$^+$ tumor antigen-specific T cells in various co-culture samples.
Figure 23B:
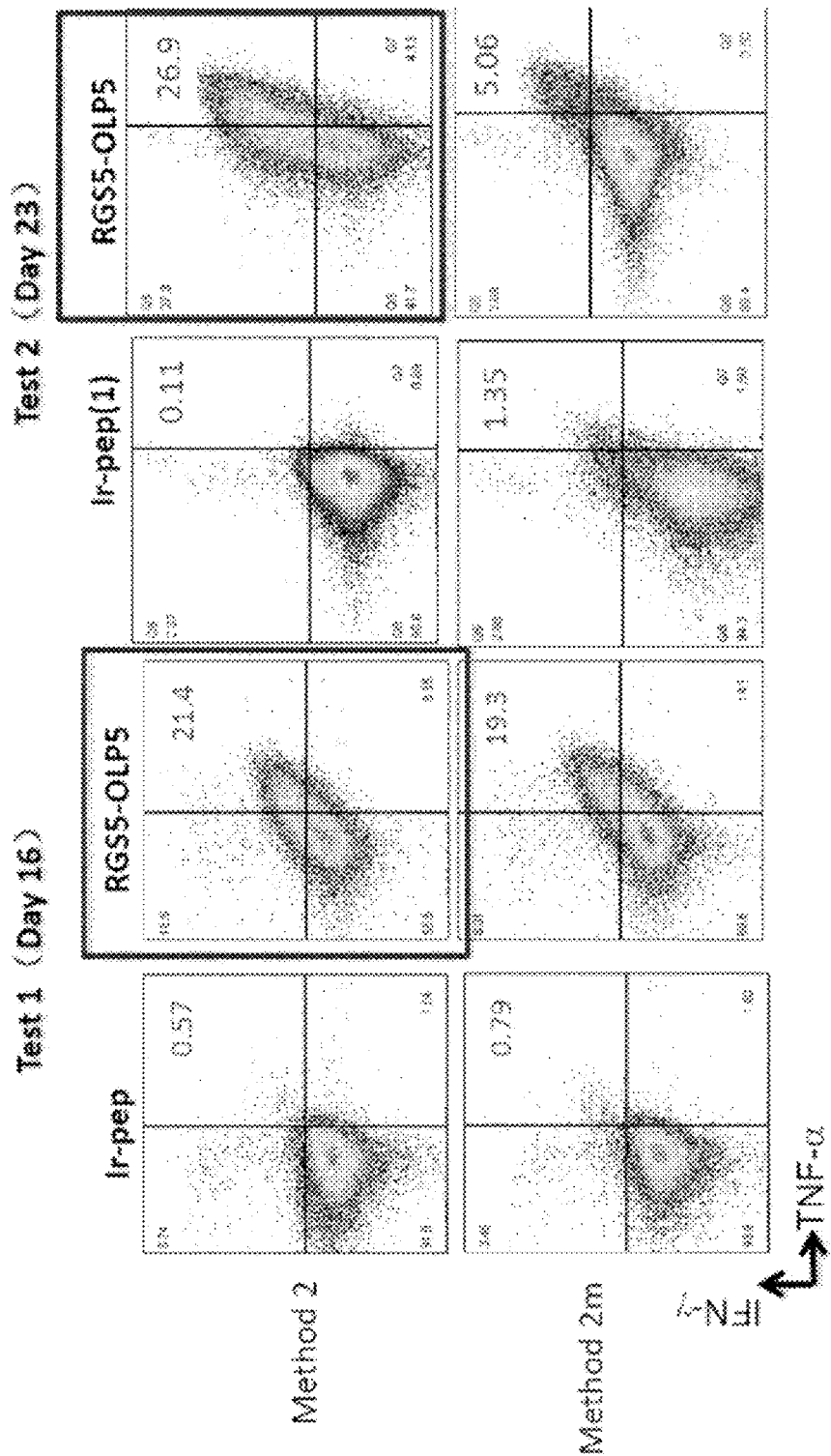
FIG. 23B shows the percentages of IFNγ$^+$TNFα$^+$ tumor antigen-specific T cells in various co-culture samples.

FIG. 23A shows the percentages of tumor antigen-specific T cells in the cell samples as determined by assessing IFNγ$^+$CD3$^+$ cells in response to stimulation by the RGS5-OLP5 peptide. On Day 16 the co-culture derived from a frozen stock of tumor antigen-specific T cells using Method 2m contained about 38.6% tumor antigen-specific T cells that produced IFNγ in response to stimulation by the RGS5-OLP5 peptide. Notably, on Day 23, the co-culture derived from a frozen stock of tumor antigen-specific T cells using Method 2m contained about 53.8% tumor antigen-specific T cells that produced IFNγ in response to stimulation by the RGS5-OLP5 peptide. The co-cultures derived from a frozen stock of tumor antigen-specific T cells using Method 2 yielded lower percentages of tumor antigen-specific T cells that produced IFNγ in response to stimulation by the RGS5-OLP5 peptide on Day 16 and Day 23. Consistent results were obtained by assessing IFNγ$^+$TNFα$^+$ cells (FIG. 23B). These results suggest that repeated stimulation of the tumor antigen-specific T cells with APCs loaded with a tumor antigen peptide could enhance percentage of T cells that specifically respond to the tumor antigen peptide.

Example 7

Two-Round Tumor Specific T Cell Amplification from a Patient Treated with MASCT

Figure 27:
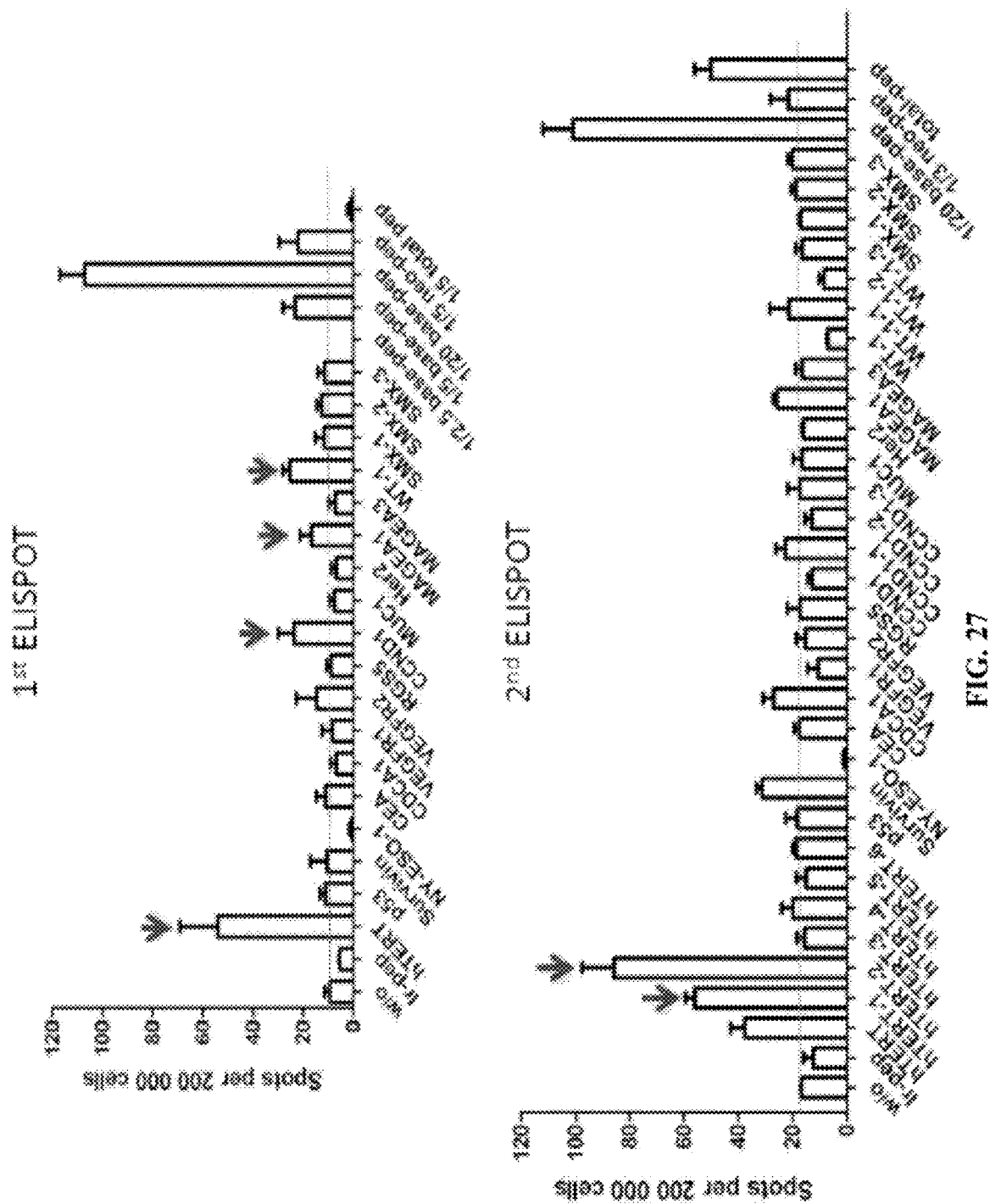
FIG. 27 shows specific immune response by the patient's PBMCs against the tumor antigen peptide pools, and each tumor antigen peptide in the pool after MASCT treatments as determined by ELISPOT assays. Percentages indicate reduced peptide concentration. For example, ½₀ base-pep indicates a pool of general tumor antigen peptides at 20 times dilution.

Patient SMZ was diagnosed with metastatic lung cancer, and received 5 cycles of unproved MASCT treatment (see, PCT/CN2018/081338 and PCT/CN2019/080535) with activated T cells prepared using DCs loaded with a pool of general tumor antigen peptides (hTERT, p53, Survivin, NY-ESO-1, CEA, CDCA1, VEGFR1, VEGFR2, RGS5, CCND1, MUC1, Her2, MAGEA1, MAGEA3, WT-1) and neoantigen peptides (SMX-1, SMX-2 and SMX-3). The top panel of FIG. 27 shows antigen-specific cell response by the patient's PBMC sample after the 5$^{th}$ cycle of improved MASCT in an ELISPOT assay. Four tumor antigens, hTERT, CCND1, MAGE-A1 and WT-1, in particular, induced strong immune response. The patient was subsequently treated with an additional cycle (cycle 6) of improved MASCT. The bottom panel of FIG. 27 shows antigen-specific T cell response by the patient's PBMC sample after the 6$^{th}$ cycle of improved MASCT in an ELISPOT assay. In the ELISPOT assay, single peptides from each of the tumor antigen peptide sub-pools corresponding to antigens hTERT, CCND1, MAGE-A1, and WT-1, were used to detect antigen-specific immune responses and to identify immune-dominant tumor antigen peptides. Peptides hTERT-1 and hTERT-2 showed particularly strong immune response.

PBMC samples from Patient SMZ were obtained to prepare tumor specific T cells using a two-round protocol.

Round 1

Figure 28:
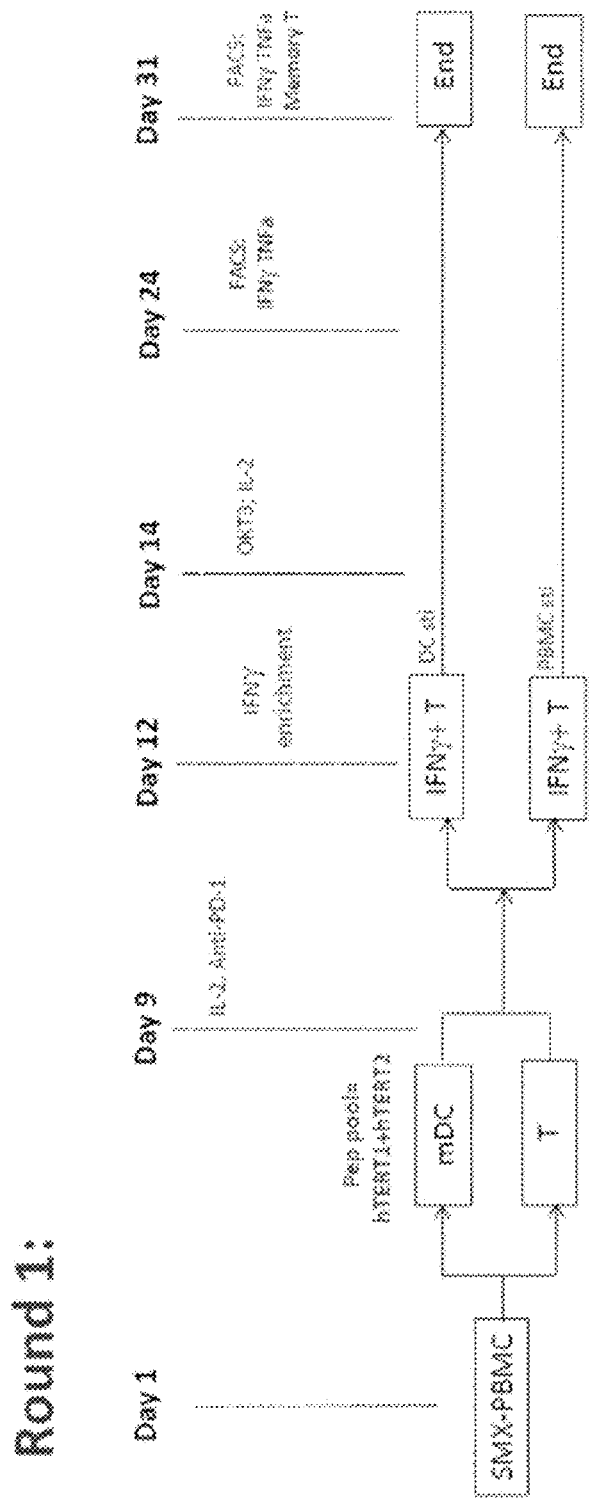
FIG. 28 shows Round 1 protocol of an exemplary two-round methods for preparing tumor antigen-specific T cells using PBMCs from Patient SMZ.

FIG. 28 provides an overview of the protocol for Round 1 of tumor-specific T cells preparation used in this example. Briefly, on Day 1, peripheral blood mononuclear cells (PBMCs) from the patient were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed with a peptide pool comprising two tumor antigen peptides derived from hTERT (i.e., hTERT1 and hTERT2, 1 μg/mL/peptide), and then cultured in a DC maturation medium to differentiate into mature DCs. On Day 8, PBMCs were stimulated with the peptide pool. On Day 9, an IFNγ secretion assay-cell enrichment and detection kit (Miltenyi Biotec) was used to isolate a population of IFNγ$^+$ T cells from the stimulated PBMCs. On Day 9, the IFNγ$^+$ T cells were co-cultured with antigen-loaded mature DCs in a medium containing IL-2 and an anti-PD-1 antibody. On Day 11, the co-culture was stimulated with PBMCs pulsed with the peptide pool or each individual peptide. On Day 12, an IFNγ secretion assay-cell enrichment and detection kit (Miltenyi Biotec) was used to isolate a population of IFNγ$^+$ T cells. Meanwhile, the antigen-loaded mature DCs ("DC sti") or PBMCs ("PBMC sti") were prepared and co-cultured with the IFNγ$^+$ T cells. On Day 14, an anti-CD3 antibody (OKT3) and IL-2 (at least about 2000 IU/mL) were added to the co-culture, which was continued to be cultured to Day 31 to obtain tumor antigen-specific T cells.

Figure 29A:
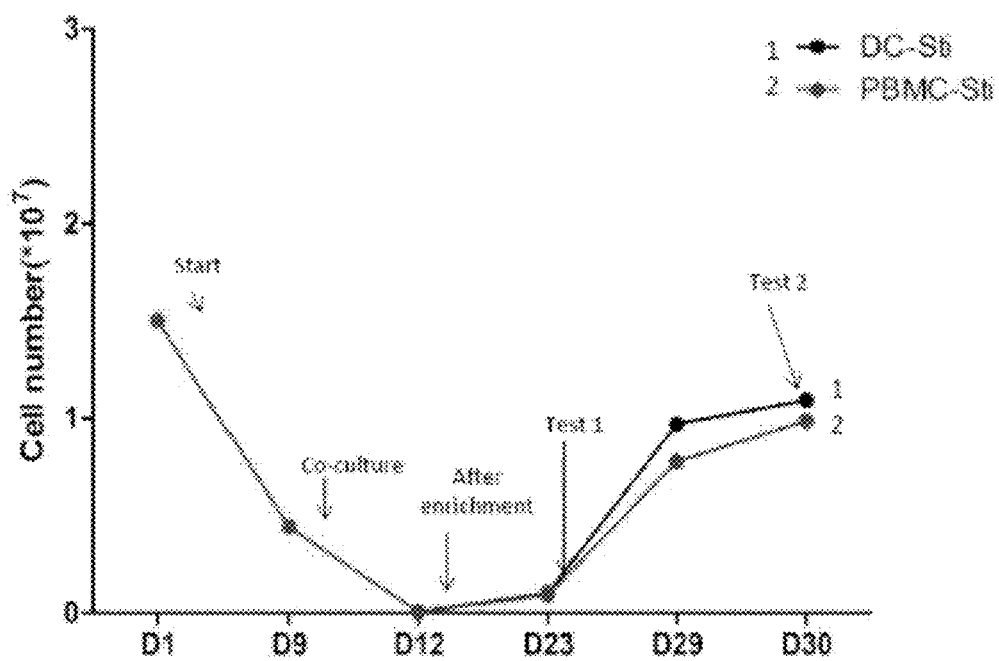
FIG. 29A shows cell proliferation at various time points in Round 1.

Cell proliferation was assessed using cell samples from Day 1 (PBMCs), Day 9 (before IFNγ enrichment), Day 12 (after IFNγ enrichment), and Days 23, 29 and 30 (co-culture of IFNγ$^+$ T cells with antigen-loaded DCs or PBMCs) by methods described in Example 2. As shown in FIG. 29A, protocols with antigen-loaded DCs or PBMCs yielded similar T cell proliferation results.

Figure 29B:
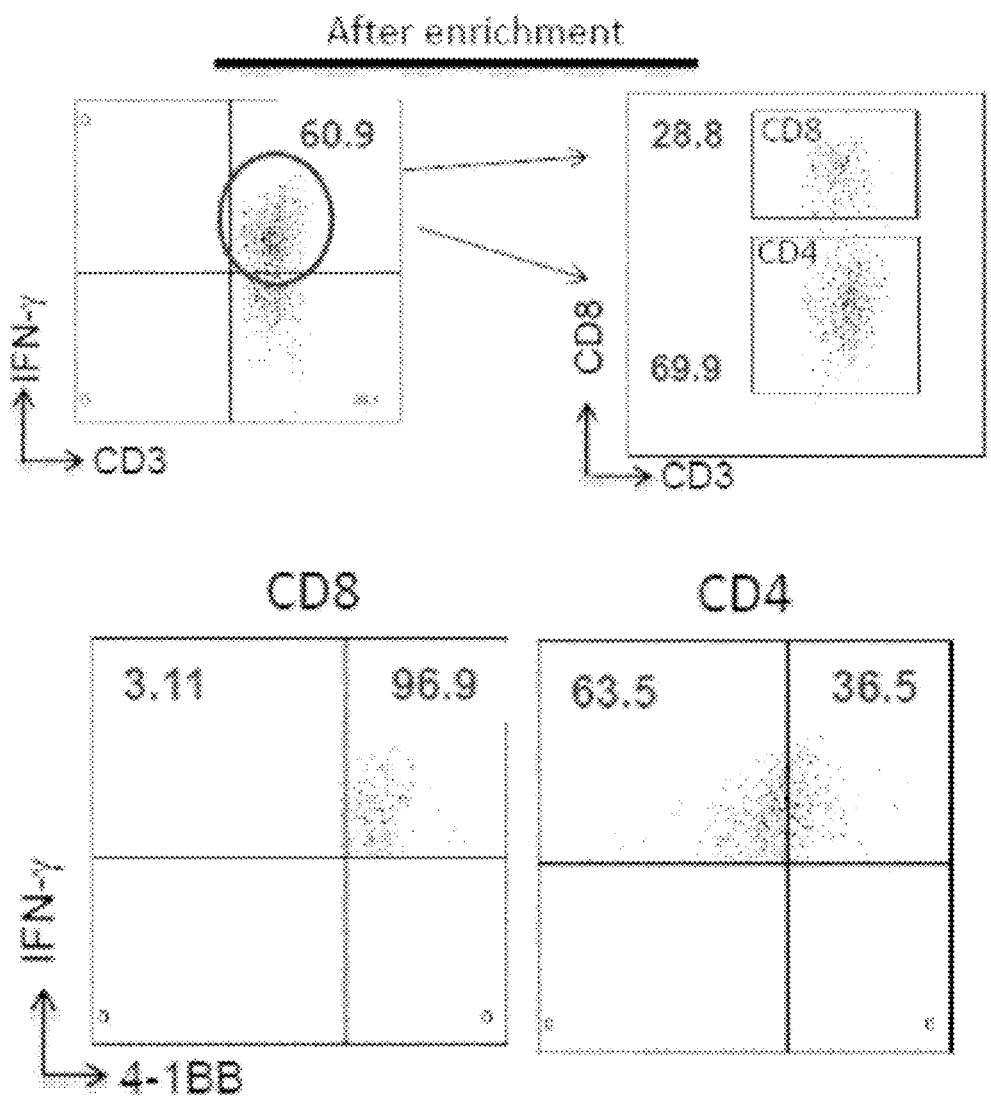
FIG. 29B shows percentages of IFNγ$^+$CD3$^+$ tumor antigen-specific T cell populations after the enrichment step.
Figure 30A:
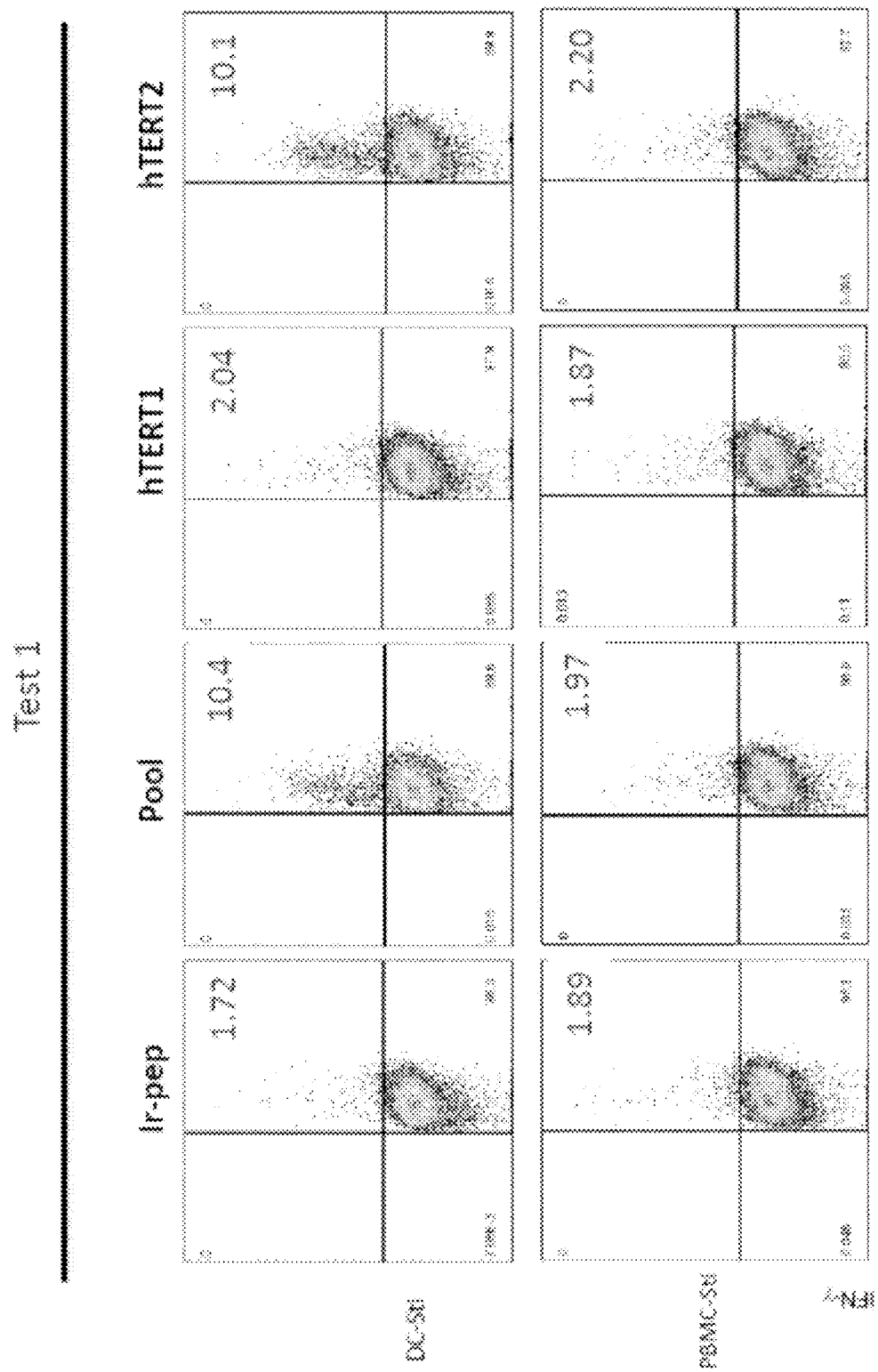
FIGS. 30A-30E shows percentages of tumor antigen-specific T cell populations in various co-culture samples of Round 1.
Figure 30B:
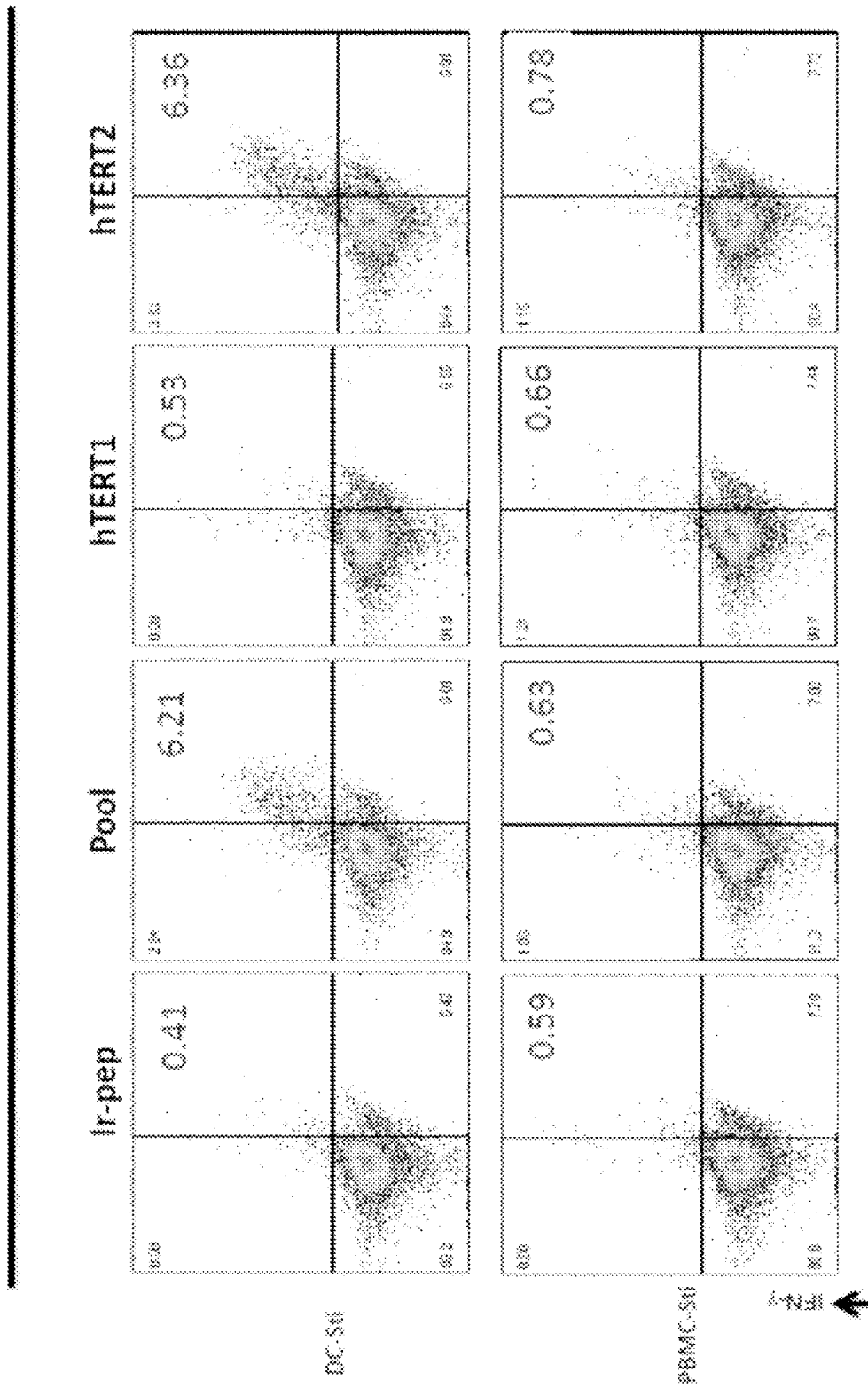
Figure 30C:
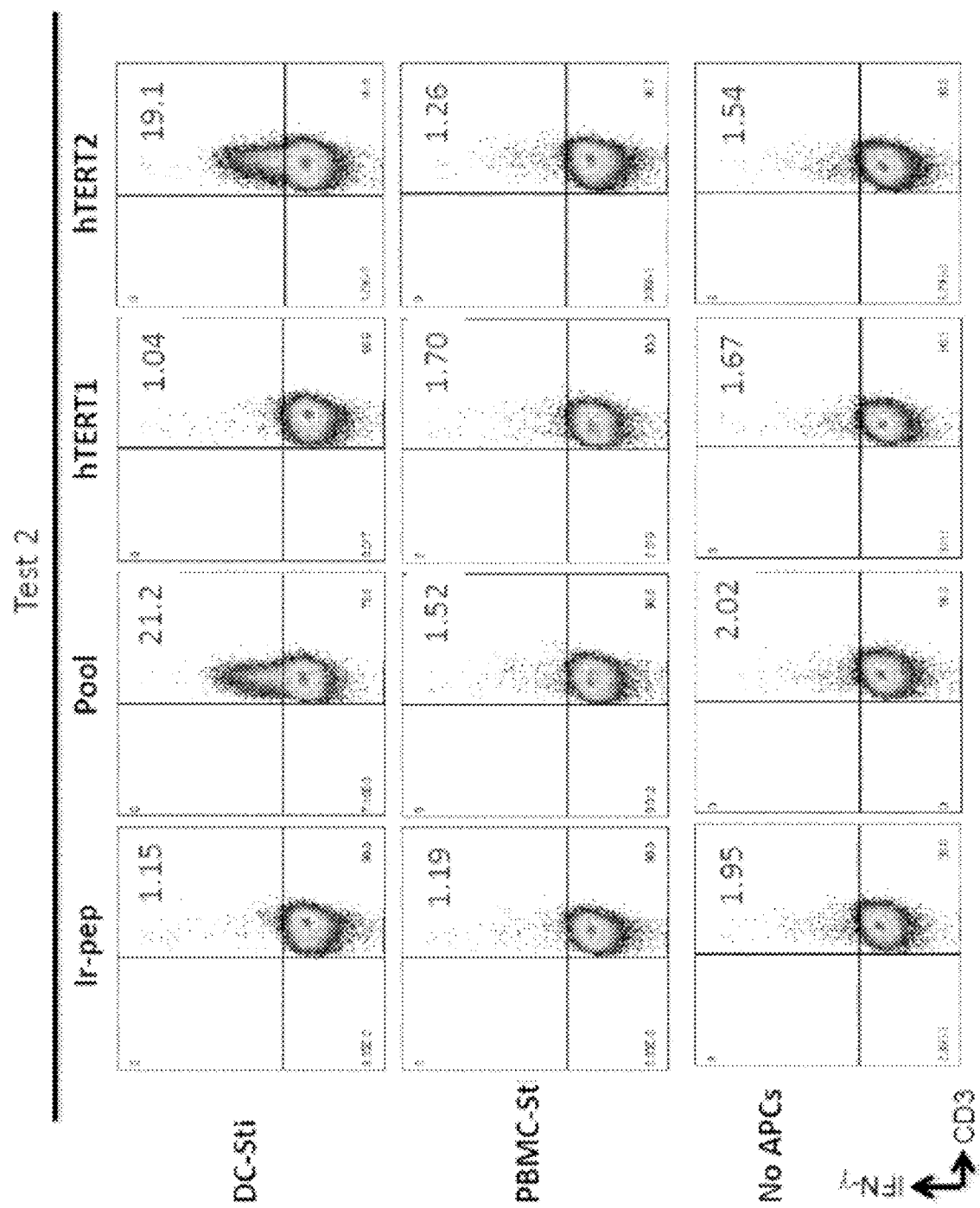
Figure 30D:
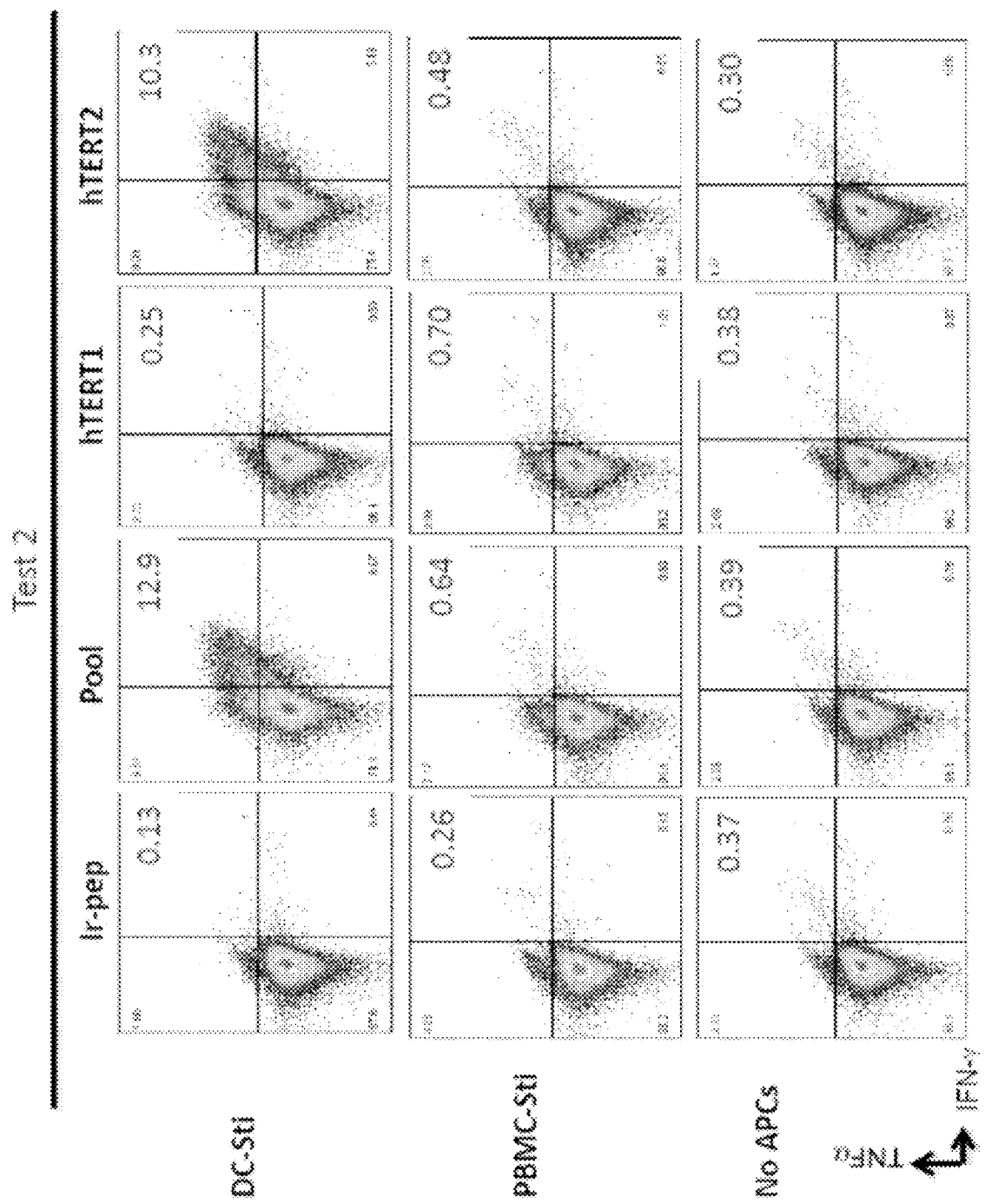
Figure 30E:
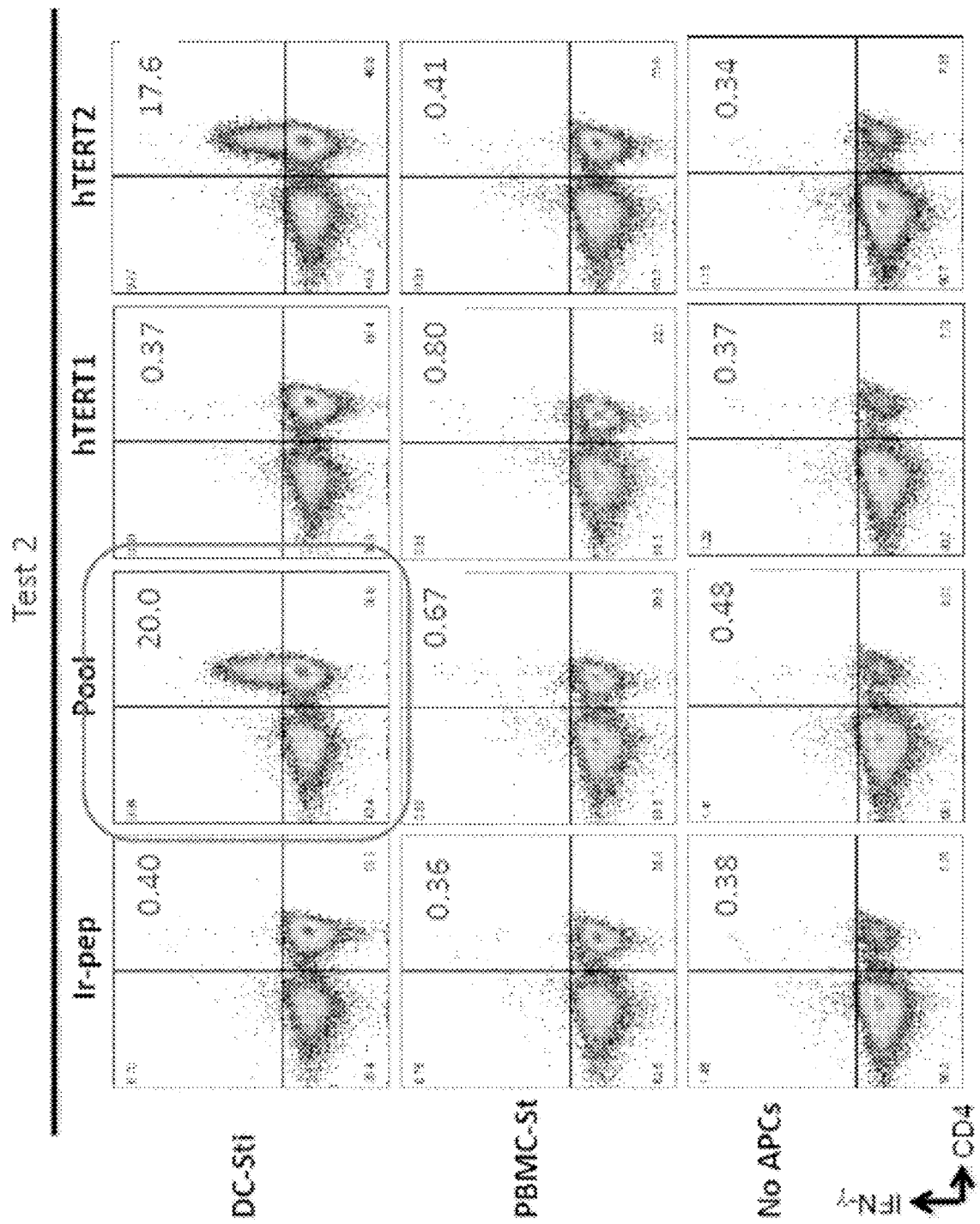
Figure 30F:
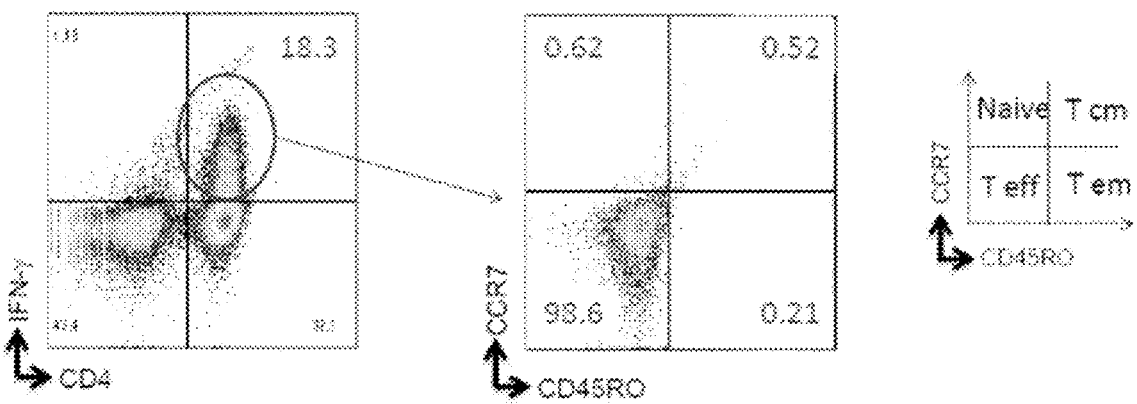
FIG. 30F shows effector T cell populations in IFNγ$^+$CD4$^+$ tumor antigen-specific T cells obtained at the end of Round 1.

The IFNγ production levels by tumor antigen-specific T cells in various co-culture samples were determined by methods described in Example 2. FIG. 29B shows percentages of various T cell populations after the enrichment step. FIGS. 30A-30E compare the percentages of various tumor-specific T cell populations in the cell samples on Days 23 and 30 as determined by assessing IFNγ$^+$CD3$^+$, IFNγ$^+$CD4$^+$ and IFNγ$^+$TNFα$^+$ cells in response to stimulation by the tumor antigen peptide pool or individual antigen peptides. Co-culture with antigen-loaded DCs yielded the highest percentages of tumor-specific T cells. As shown in FIG. 30F, 98.6% of the IFNγ$^+$CD4$^+$ cells in the sample on Day 30 are CCR7$^-$CD45RO$^-$ effector T cells.

Round 2

Figure 31:
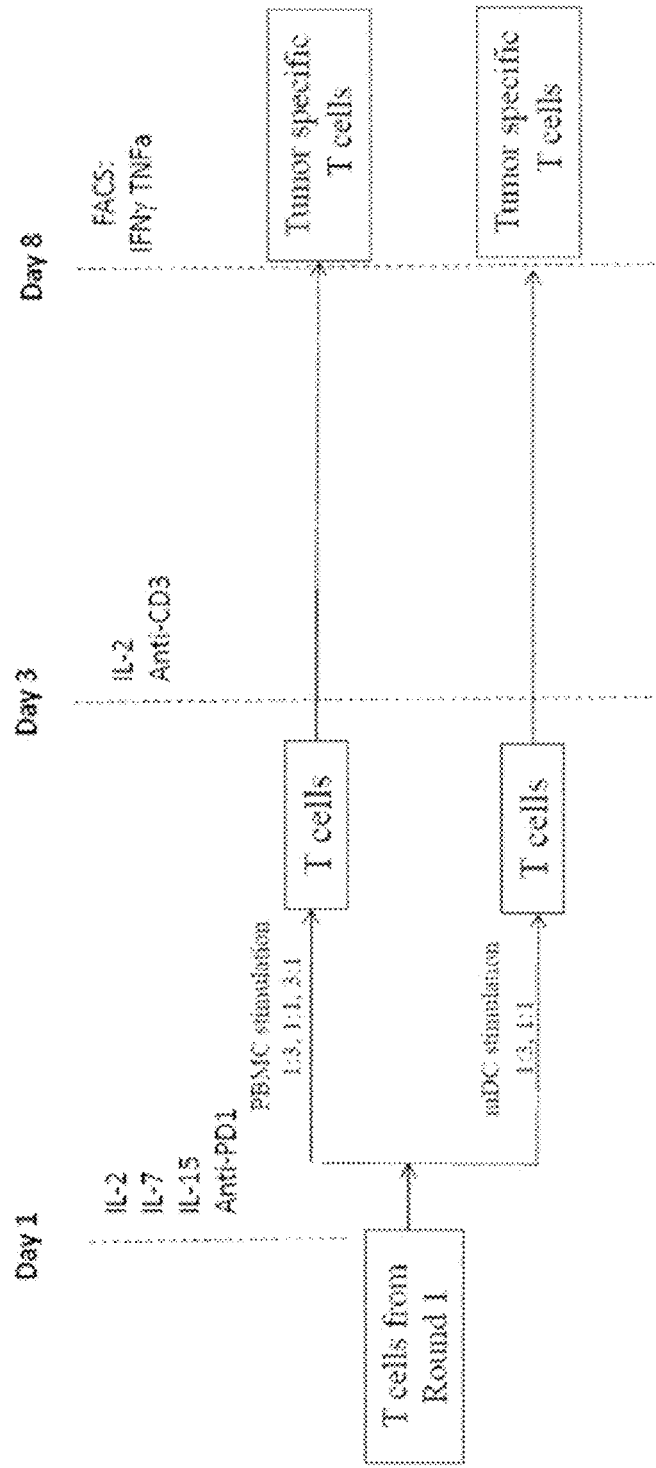
FIG. 31 shows Round 2 protocol of an exemplary two-round methods for preparing tumor antigen-specific T cells using PBMCs from Patient SMZ.

FIG. 31 provides an overview of the protocol for Round 2 of tumor-specific T cells preparation used in this example. Briefly, on Day 1, tumor-specific T cells from Round 1 were cultured in a medium comprising a cytokine cocktail (IL-2, IL-7, and IL-15) and an anti-PD-1 antibody. PBMCs or mature DCs loaded with the hTERT-2 peptide were prepared. The tumor-specific T cells and the antigen-loaded DCs or PBMCs were co-cultured at a ratio between T cells and PBMCs of 1:3, 1:1 or 3:1 or at a ratio between T cells and DCs of 3:1 and 1:1. On Day 3, an anti-CD3 antibody (OKT3) and IL-2 were added to the co-culture, which was continued to be cultured to Day 8 to obtain tumor antigen-specific T cells.

Figure 32A:
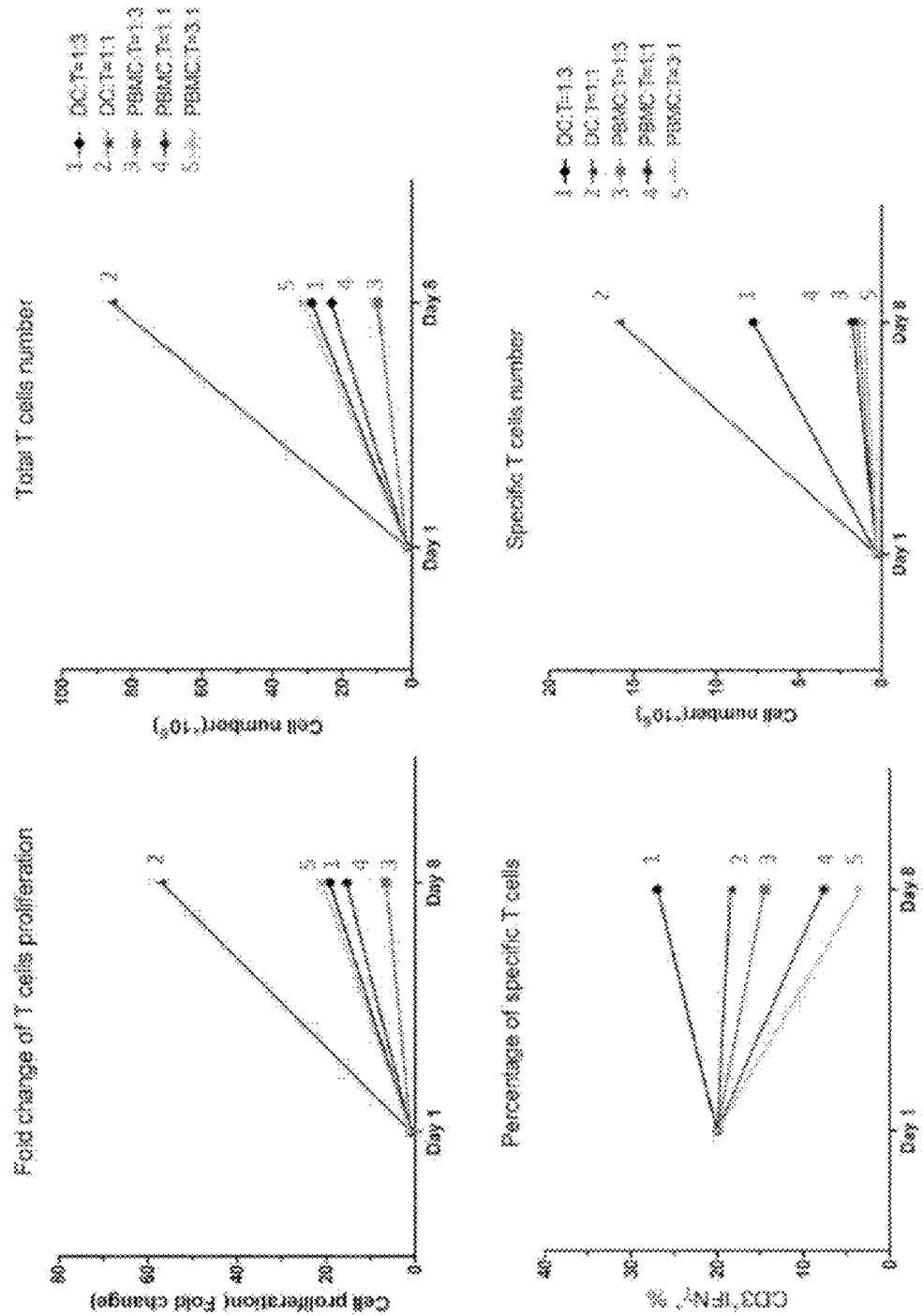
FIG. 32A shows number of T cells and tumor-specific T cells at various time points in Round 2.

Cell proliferation was assessed using cell samples from Day 1 (round 1 tumor specific T cells), and Day 8 (co-culture of IFNγ$^+$ T cells with antigen-loaded DCs or PBMCs) by methods described in Example 2. The IFNγ production levels by tumor antigen-specific T cells in various co-culture samples were determined by methods described in Example 2. As shown in FIG. 32A, co-culture with antigen-loaded DCs yielded the highest number of T cells and highest percentage of tumor-specific T cells on Day 8.

Figure 32B:
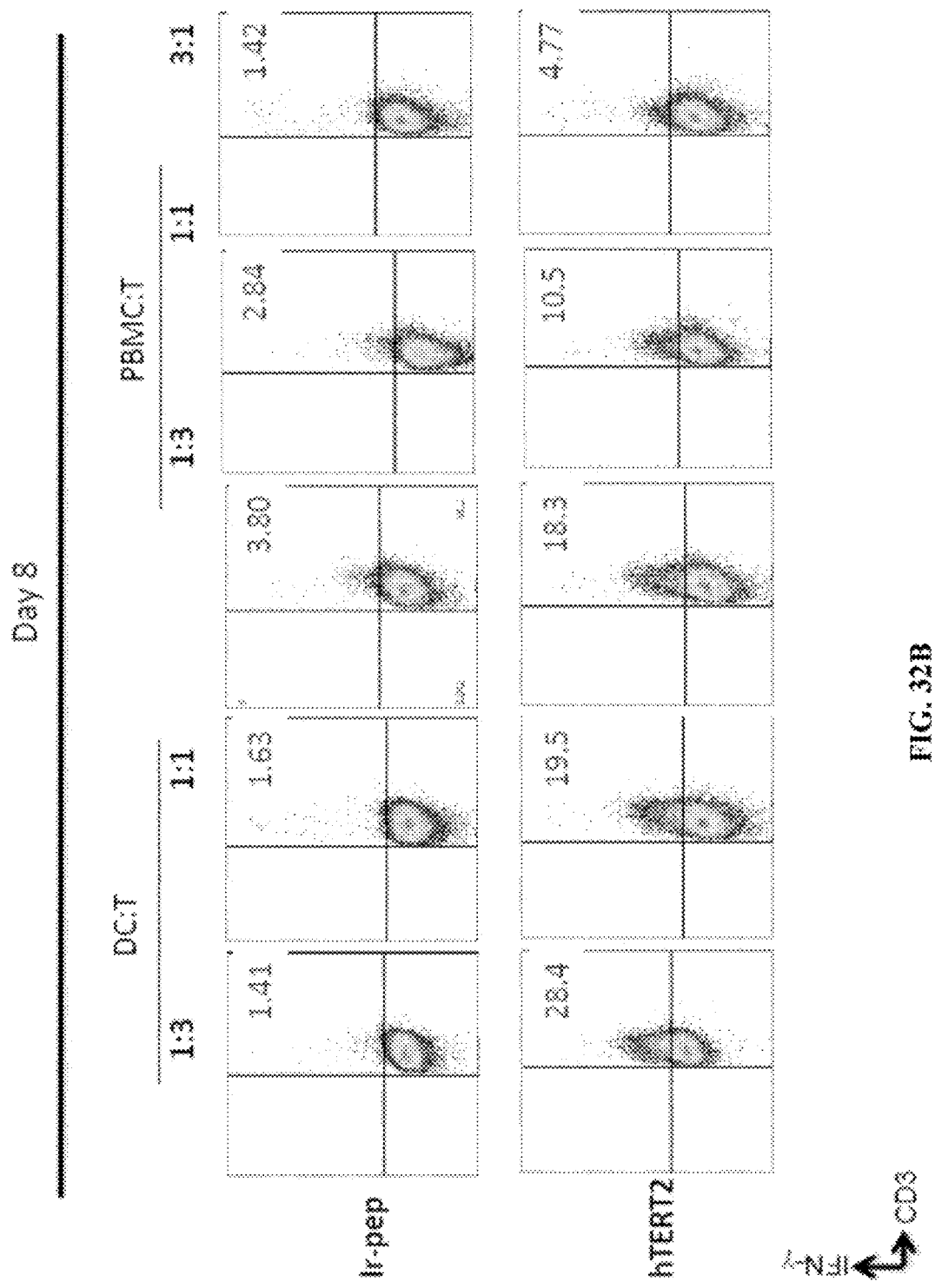
FIGS. 32B-32C show percentages of tumor antigen-specific T cell populations in various co-culture samples of Round 2.
Figure 32C:
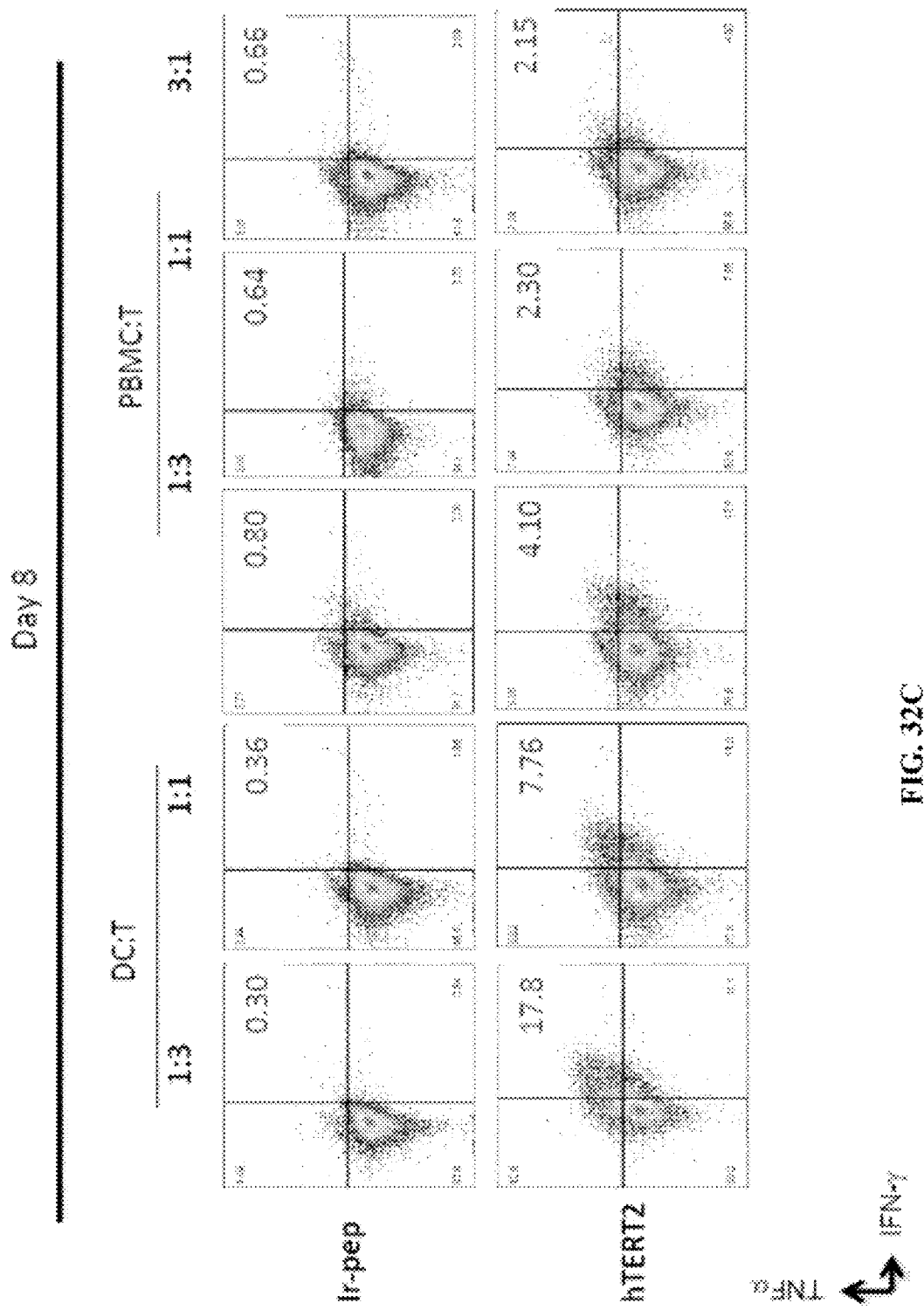

FIGS. 32B-32C compare the percentages of various tumor-specific T cell populations in the cell samples on Day 8 as determined by assessing IFNγ$^+$CD3$^+$ and IFNγ$^+$TNFα$^+$ cells in response to stimulation by the hTERT2 antigen peptide. Co-culture with antigen-loaded DCs with a ratio between DCs to T cells of 3:1 yielded the highest percentages of tumor-specific T cells.

Figure 33:
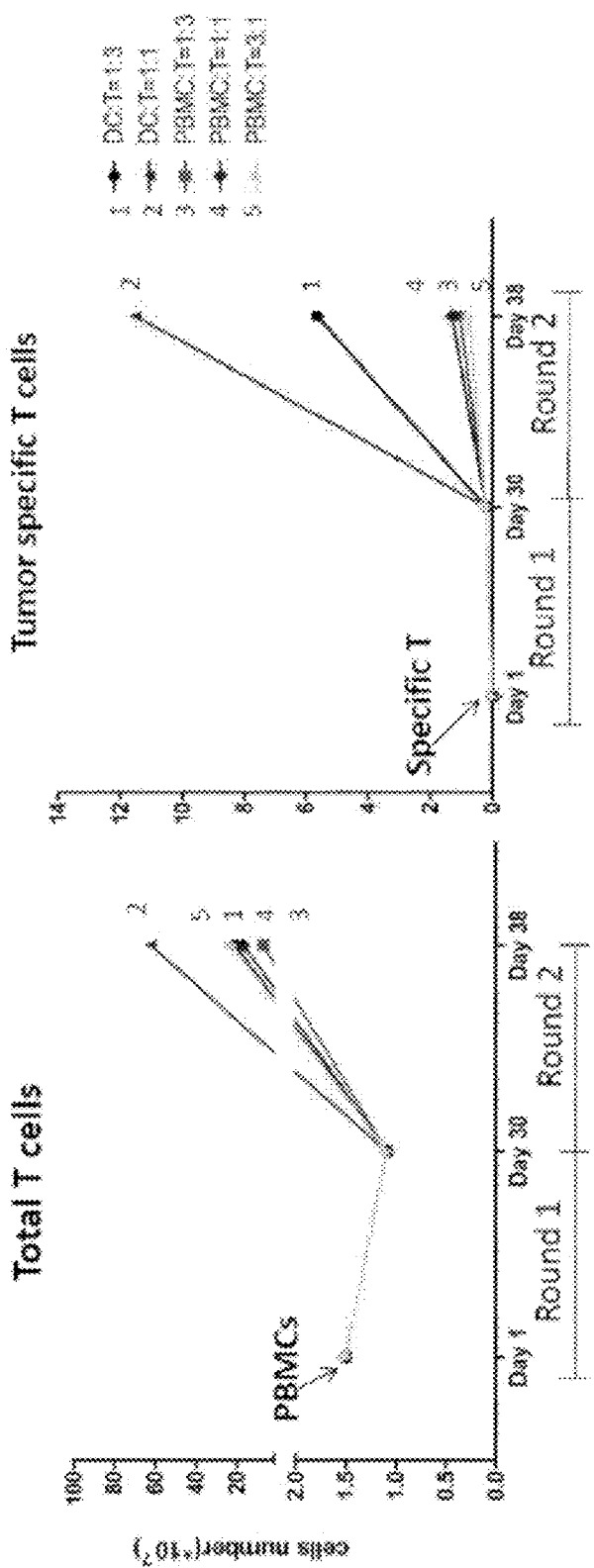
FIG. 33 show number of T cells and tumor antigen-specific T cells at various time points of Round 1 and Round 2.

FIG. 33 shows the number of T cells and tumor-specific T cells on Day 1 and Day 30 of Round 1, and on Day 38, i.e., Day 8 of Round 2. The two-round protocols are effective in amplifying tumor-specific T cells. Stimulation by antigen-loaded DCs in Round 2 yielded the higher number of T cells and higher percentage tumor-specific T cells than stimulation by antigen-loaded PBMCs. The tumor-specific T cells obtained at the end of Round 1 are effector T cells.

The invention claimed is:

1. A method of treating a cancer in an individual, comprising: a) a first co-culturing step, comprising co-culturing a first population of dendritic cells loaded with a plurality of tumor antigen peptides with a population of T cells to obtain a first co-culture comprising activated T cells;
   b) an enrichment step, comprising contacting the first co-culture with antigen presenting cells (APCs) loaded with the plurality of tumor antigen peptides to obtain a stimulated co-culture, and isolating from the stimulated co-culture an enriched population of activated T cells using a ligand that specifically recognizes a cytokine expressed by the activated T cells; and
   c) a second co-culturing step, comprising co-culturing the enriched population of activated T cells with a second population of dendritic cells loaded with one or more tumor antigen peptides from the plurality of tumor antigen peptides to obtain a population of tumor antigen-specific T cells; and
   d) administering to the individual an effective amount of the tumor antigen-specific T cells, wherein the individual has previously received an immunotherapy.

2. The method of claim 1, wherein the first co-culturing step is carried out for 1 to 3 days prior to the enrichment step.

3. The method of claim 1, wherein the ratio between the population of cells to the first population of dendritic cells loaded with the plurality of tumor antigen peptides is no more than 30:1.

4. The method of claim 1, wherein the first population of dendritic cells loaded with the plurality of tumor antigen peptides and the population of T cells are co-cultured in a first co-culture medium comprising one or more cytokines and an immune checkpoint inhibitor.

5. The method of claim 1, wherein the cytokine is IFN.

6. The method of claim 1, wherein the ratio between the enriched population of activated T cells and the second population of dendritic cells loaded with one or more tumor antigen peptides from the plurality of tumor antigen peptides is 1:1 to 20:1.

7. The method of claim 1, wherein the enriched population of activated T cells and the second population of dendritic cells loaded with one or more tumor antigen peptides from the plurality of tumor antigen peptides are co-cultured for 12 to 25 days.

8. The method of claim 1, wherein the second co-culturing step comprises co-culturing the second population of dendritic cells loaded with one or more tumor antigen peptides from the plurality of tumor antigen peptides with the enriched population of activated T cells in an initial second co-culture medium comprising an immune checkpoint inhibitor and optionally one or more cytokines to provide a second co-culture; and adding an anti-CD3 antibody and optionally one or more cytokines to the second co-culture to obtain a population of tumor antigen-specific T cells.

9. The method of claim 8, wherein the anti-CD3 antibody and optionally one or more cytokines are added to the second co-culture no more than 3 days after the second co-culturing step starts.

10. The method of claim 1, further comprising a third co-culturing step comprising co-culturing a population of the tumor antigen-specific T cells with a population of antigen presenting cells (APCs) loaded with one or more tumor antigen peptides from the plurality of tumor antigen peptides to obtain a second population of tumor antigen-specific T cells.

11. The method of claim 10, wherein the APCs are peripheral blood mononuclear cells (PBMCs) or dendritic cells.

12. The method of claim 10, wherein the ratio between the population of tumor antigen-specific T cells and the population of APCs loaded with one or more tumor antigen peptides from the plurality of tumor antigen peptides is 1:1 to 20:1.

13. The method of claim 10, wherein the population of tumor antigen-specific T cells and the population of APCs loaded with one or more tumor antigen peptides from the plurality of tumor antigen peptides are co-cultured for 5 to 9 days.

14. The method of claim 10, wherein the population of tumor antigen-specific T cells and the population of APCs loaded with one or more tumor antigen peptides from the plurality of tumor antigen peptides are co-cultured in a third co-culture medium comprising one or more cytokines and an anti-CD3 antibody.

15. The method of claim 10, wherein the third co-culturing step is repeated.

16. The method of claim 10, wherein the population of the tumor antigen-specific T cells is obtained from a frozen stock of the tumor antigen-specific T cells.

17. The method of claim 1, wherein the immunotherapy is selected from the group consisting of an immune checkpoint inhibitor, an adoptive immune cell therapy, a cancer vaccine, an oncolytic virus and combinations thereof.

18. The method of claim 17, wherein the individual is capable of developing a specific immune response against a tumor antigen peptide.

19. The method of claim 1, wherein the immunotherapy the individual has previously received is a Multiple-Antigen Stimulating Cellular Therapy (MASCT) comprising administering to the individual an effective amount of activated T cells prepared by co-culturing a population of T cells with a population of dendritic cells loaded with the plurality of tumor antigen, and wherein the individual has clinically benefited from the MASCT.

20. The method of claim 1, wherein the tumor antigen-specific T cells are administered intravenously.

* * * * *